US009090901B2

(12) United States Patent
Taramino et al.

(10) Patent No.: US 9,090,901 B2
(45) Date of Patent: Jul. 28, 2015

(54) PLANTS WITH ALTERED ROOT ARCHITECTURE, RELATED CONSTRUCTS AND METHODS INVOLVING GENES ENCODING LEUCINE RICH REPEAT KINASE (LLRK) POLYPEPTIDES AND HOMOLOGS THEREOF

(75) Inventors: Graziana Taramino, Wilmington, DE (US); Stephen M. Allen, Wilmington, DE (US); Stanley Luck, Wilmington, DE (US); Xiaomu Niu, Johnston, IA (US); Hajime Sakai, Newark, DE (US); Scott V. Tingey, Wilmington, DE (US); Dwight Tomes, Grimes, IA (US)

(73) Assignees: E I DU PONT DE NEMOURS AND COMPANY, Wilmington, DE (US); PIONEER HI BRED INTERNATIONAL INC, Johnston, IA (US)

( * ) Notice: Subject to any disclaimer, the term of this patent is extended or adjusted under 35 U.S.C. 154(b) by 559 days.

(21) Appl. No.: 13/347,850

(22) Filed: Jan. 11, 2012

(65) Prior Publication Data
US 2012/0110700 A1 May 3, 2012

Related U.S. Application Data

(63) Continuation of application No. 12/274,412, filed on Nov. 20, 2008, now abandoned.

(60) Provisional application No. 61/041,281, filed on Apr. 1, 2008, provisional application No. 60/989,161, filed on Nov. 20, 2007.

(51) Int. Cl.
*C12N 15/63* (2006.01)
*C12N 15/82* (2006.01)
*C07K 14/415* (2006.01)

(52) U.S. Cl.
CPC .......... *C12N 15/8241* (2013.01); *C07K 14/415* (2013.01); *C12N 15/8201* (2013.01)

(58) Field of Classification Search
None
See application file for complete search history.

(56) References Cited

U.S. PATENT DOCUMENTS

| 6,344,601 | B1 | 2/2002 | Chua et al. |
|---|---|---|---|
| 2004/0034888 | A1 | 2/2004 | Liu et al. |
| 2004/0106531 | A1 | 12/2004 | Kanno et al. |
| 2005/0059154 | A1 | 3/2005 | Beeckman et al. |
| 2006/0123505 | A1 | 6/2006 | Kikuchi et al. |
| 2006/0141495 | A1 | 6/2006 | Wu |
| 2007/0011783 | A1 | 1/2007 | Liu et al. |
| 2005/0057473 | A1 | 3/2009 | Hsu |
| 2013/0305398 | A1* | 11/2013 | Coffin .......................... 800/260 |

FOREIGN PATENT DOCUMENTS

| JP | 2005185101 | 7/2005 |
|---|---|---|
| WO | 9909151 | 2/1999 |
| WO | 0004761 | 2/2000 |
| WO | 0129240 | 4/2001 |
| WO | 03008540 | 1/2003 |
| WO | 2007124312 | 11/2007 |

OTHER PUBLICATIONS

McConnell et al, Nature 411 (6838):709-713, 2001.*
Bowie et al, Science 247:1306-1310, 1990.*
Kano-Murakami et al (1993, FEBS 334:365-368).*
Lopez-Bucio et al., Current Opinion in Plant Biology. The Role of Nutrient Availability in Regulating Root Architecture, vol. 6, p. 280-287, 2003.
Malamy, J.E., Plant, Cell and Environment. Intrinsic and Environmental Response Pathways that Regulate Root System Architecture, vol. 28, p. 67-77, 2005.
Hochholdinger et al., Annals of Botany. Genetic Dissection of Root Formation in Maize (*Zea mays*) Reveals Root-Type Specific Developmental Programmes, vol. 93, p. 359-368, 2004.
Weigel et al., Plant Physiology. Activation Tagging in *Arabidopsis*, vol. 122, p. 1003-1013, 2000.
National Center for Biotechnology Information, General Identifier No. 115455429, Accession No. NP_001051315, Feb. 14, 2008, Ohyanagi et al., The Rice Annotation Project Database (RAP-DB) hub for *Oryza sativa*.
National Center for Biotechnology Information, General Identifier No. 125600990, Accession No. EAZ40566, Feb. 5, 2009, Yu et al., The Genomes of *Oryza sativa*: A History of Duplications.
National Center for Biotechnology Information, General Identifier No. 115438737, Accession No. NP_001043648, Feb. 14, 2008, Ohyanagi et al., The Rice Annotation Project Database (RAP-DB) hub for *Oryza sativa*.
Bao Yiqun et al., Plant Journal. Reduced Expression of Alpha-Tubulin Genes in *Arabidopsis thaliana* Specifically Affects Root Growth and morphology, Root Hair Development and Root Gravitropism, vol. 28(2), p. 145-157, 2001.
Schnabel Elise et al., Plant Molecular Biology. The Medicago Truncatula SUNN Gene Encodes a CLV1-like Leucine-Rich Repeat Receptor Kinase that Regulates Nodule Number and Root Length, vol. 58(6), p. 809-822, 2005.
Jones et al., Plant Journal. Analysis of the Root-Hair Morphogenesis Transcriptome Reveals the molecular Identity of Six Genes with Roles in Root-Hair Development in *Arabidopsis*, vol. 45(1); p. 83-100, 2006.
Nodine et al., Developmental Cell. RPK1 and TOAD2 are Two Receptor-Like Kinases Redundantly Required for *Arabidopsis* Embryonic Pattern Formation, vol. 12(6), p. 943-956, 2007.
Osakabe et al., Plant Cell. Leucine-Rich Repeat Receptor-Like Kinasel is a Key Membrane-Bound Regulator of Abscisic Acid Early Signaling in *Arabidopsis*, vol. 17(4), p. 1105-1119, 2005.
Sun et al., Plant Journal. Xa26, A Gene Conferring Resistance to *Xanthomonas* oryzae pv. Oryzae in Rice; Encodes an LRR Receptor Kinase-Like Protein, vol. 37(4), p. 517-527, 2004.

* cited by examiner

*Primary Examiner* — Stuart F Baum

(57) ABSTRACT

Isolated polynucleotides and polypeptides and recombinant DNA constructs particularly useful for altering root structure of plants, compositions (such as plants or seeds) comprising these recombinant DNA constructs, and methods utilizing these recombinant DNA constructs. The recombinant DNA construct comprises a polynucleotide operably linked to a promoter functional in a plant, wherein said polynucleotide encodes a polypeptide useful for altering plant root architecture.

4 Claims, 21 Drawing Sheets

| SEQ ID NO | 330 | 340 | 350 | 360 | 370 | 380 | 390 | 400 | |
|---|---|---|---|---|---|---|---|---|---|
| SEQ ID NO 15.pro | GGIPESVTALPRLRVLWVPRAGLECTLPSNWGRCSNLEMVNLGGNLLSGAIPRDLGQCSNLKFLNLSSRLSGLLDKDLC | | | | | | | | 381 |
| SEQ ID NO 17.pro | GGIPEDTIATLEKLRMLWAPRATLEGELPGNWSSCQSLEMINLGENIFSCGIPKGLIVECENLKFLNISMKFTGSVDSSLP | | | | | | | | 375 |
| SEQ ID NO 19.pro | | | | | | | | | 229 |
| SEQ ID NO 22.pro | | | | | MG- | | | | 141 |
| SEQ ID NO 23.pro | GGIPESVTALPKLRMLWAPRAGFENIPSNWGRCHSLEMVNLAENLLSGVIPRELGQCSNLKFLNLSSMKLSGSIDNGLC | | | | | | | | 372 |
| SEQ ID NO 24.pro | GGIPDAVVALPKLRVLMAPRATLEGELPRNWSACQSLEMINLGENIFSGGIPNGLIVECSSHLKFLNISSNKLTGAIDPSLT | | | | | | | | 382 |
| SEQ ID NO 36.pro | ----SLR------------QTQIP------------IYSKELPIDRVGGRSL-----AQTHEREQPSLP | | | | | | | | 90 |

| SEQ ID NO | 410 | 420 | 430 | 440 | 450 | 460 | 470 | 480 | |
|---|---|---|---|---|---|---|---|---|---|
| SEQ ID NO 15.pro | PHCMTVFDVSGNELSGSIPACVNF-RVC-TSHLVLDKMSSSYSSFLNSKTLQELPSVFCNSGECSVVYENFAKNNLEGHLT | | | | | | | | 459 |
| SEQ ID NO 17.pro | VPCMDVFDVSGNQLSGSLPVFMSKKNCLSSQAPRDDLVSEYSSFFTYQALAGFMSSPSPLDAHLTSYHSFSRNNFTGPVT | | | | | | | | 455 |
| SEQ ID NO 19.pro | | | | | | | | | 229 |
| SEQ ID NO 22.pro | | | | | | | | | 141 |
| SEQ ID NO 23.pro | PHCIAVFDVSRNELSGTIPACAN-KGC-TPQL-DDDMPSRYPSFFMSKAAQPSSGYCKSGNCSVVYHNFANNNLGCHLT | | | | | | | | 449 |
| SEQ ID NO 24.pro | VPCMDVFDVSGNRFSGAMPVF-EQKGCPSSQLPFDDLVSEYSSFSYQALAGFRSSSFVLGTDLTSYHSFAQNNFTGPVK | | | | | | | | 461 |
| SEQ ID NO 36.pro | PP-------------------------------DKYANREPAGA-- | | | | | | | | 103 |

| SEQ ID NO | 490 | 500 | 510 | 520 | 530 | 540 | 550 | 560 | |
|---|---|---|---|---|---|---|---|---|---|
| SEQ ID NO 15.pro | SLPESADREGNKTSYVFVVDHNNFSGSIDSTILEQCSNLIKGLIVVSFRDNKISGQITAEFSRKCSAIRAIDIAGNQTSGMM | | | | | | | | 539 |
| SEQ ID NO 17.pro | SIPLATEKLGMQGSYAFLADGNHLGGQLQPSIFDKCNSSRGLVFEISNNLISGAIPTDIGSLCSSLLVLGVAGNQLSGMI | | | | | | | | 535 |
| SEQ ID NO 19.pro | | | | | | | | | 229 |
| SEQ ID NO 22.pro | | | | | | | | | 141 |
| SEQ ID NO 23.pro | SLPFSADREGNKILYAFHVDYNNFTGSLHEILLAQCNNVEGLIVSFRDNKISGGLIEEMSTKCSAIRADLAGNRITGVM | | | | | | | | 529 |
| SEQ ID NO 24.pro | SLPLAADKLGMQGSYAFLADGNMIAGQIQPDIFSKCNSSRGFIVDVSNNLITGGIPVEIGSLVVLGVAGNQLSGLI | | | | | | | | 541 |
| SEQ ID NO 36.pro | | | | | | | | | 103 |

| SEQ ID NO | 570 | 580 | 590 | 600 | 610 | 620 | 630 | 640 | |
|---|---|---|---|---|---|---|---|---|---|
| SEQ ID NO 15.pro | PDNVGLLGALVKMDMSRNFLEGQIPASFKDEKSLKFLSLAGNNISGRIPSCLGQLRSLRVLDLSSNLSLAGEIPNNLVTLG | | | | | | | | 619 |
| SEQ ID NO 17.pro | PSSIGELISYLISLDLSRNRLGGVIPTSVKNLLIHLQRLSLAQNLLNGTIPPDINQLHALKVLDLSSNLLMGMIFDALADLR | | | | | | | | 615 |
| SEQ ID NO 19.pro | -VRMDLSRNLLHGRLPSGLAQLKNLRFLSLSGNNFSGELPS---------------------VALT | | | | | | | | 273 |
| SEQ ID NO 22.pro | --------------LEKLEILDLKGNNFIGGI---------R | | | | | | | | 160 |
| SEQ ID NO 23.pro | PGNIGLLSALVKMDISRNLLEGQIPSSFKELKSLKFLSLAENNLSGTIPSCLGKLRSLEVLDLSSNLSGKIPRNLVTLT | | | | | | | | 609 |
| SEQ ID NO 24.pro | PTSIGQLNYLISLDLSRNHLGGEIPTSVKNLPNLERLSLGHNFLNGTIPTEINQLYSLKVLDLSSNLTGEIPGALADLR | | | | | | | | 621 |
| SEQ ID NO 36.pro | -------AVGHLAISKSS- | | | | | | | | 114 |

```
                    970         980         990         1000        1010        1020        1030        1040
                    |           |           |           |           |           |           |           |
SEQ ID NO 15.pro    LGNSETHATTGVAGTFGYVAPEYAMTCRVSDKADVYSYGVVLLELISDKKALDPSFSPYGNGFNIVAWACMLLQKGRARE 1011
SEQ ID NO 17.pro    LGNSETHATTGVAGTFGYVAPEYAMTCRVSDKADVYSYGVVLMELISDKKALDPSFSPYGNGFNIVAWACMLLRQGRARE 1010
SEQ ID NO 19.pro    LRNSETHATTDVAGTFGYVAPEYAMTCRVSDKADVYSYGVVLLELISDKKALDPSFSPYGNGFNIVSWAVRLIQRGRVRE 547
SEQ ID NO 22.pro    LGTSQSHVTTGVAGTFGYVAPEYAMTCRVSEKADVYSYGIVLLELISDKRALDPSFSSHENGFNIVSWAHMMLSQGKAKE 489
SEQ ID NO 23.pro    LGNSETHATTGVAGTFGYVAPEYAMTCRVSDKADVYSYGVVLLELISDKKALDPSFSPYGNGFNIVAWACMLLQKGRARE 998
SEQ ID NO 24.pro    LGNSETHATTGVAGTFGYVAPEYANTGMLNEKSDVYSFGVLLLETVTGRNPVD--YSRSSNEVNLVEWLKTMVANRRAEE 1016
SEQ ID NO 36.pro    LGSDKSHITTRVMGTFGYVAPEYANTGMLNEKSDVYSFGVLLLETVTGRNPVD--YSRSSNEVNLVEWLKTMVANRRAEE 417

1050        1060        1070        1080        1090        1100        1110        1120
                    |           |           |           |           |           |           |           |
SEQ ID NO 15.pro    FFIEGLMDVAPHDDLVEIHLGIKCTVDSLSSRPTMKQVVRRLKELRPPSY.                                 1063
SEQ ID NO 17.pro    FFIDGLMDVGPHDDLVETIHLAVICTADSLSIRPTMKQVVQRLKQLQPPIREHR.                            1065
SEQ ID NO 19.pro    FFVEGLMEKAPHDDLVEFINIAVRCTQESIASRPTMKHVLRCLRELRPPSY.                               599
SEQ ID NO 22.pro    VFTTGLMETGPPDDLVEVIHLALKCTVDSLSIRPTMKQAVRLLKRIQPS---RL.                            541
SEQ ID NO 23.pro    FFIEGLMDVAPHDDLVEIHLGIKCTVDSLSSRPTMKQVVRRLKELRPPS-Y                                1049
SEQ ID NO 24.pro    FFIDGLMDVGPHDDLVETIHLAVMCTVDSLSVRPTMKQVVQRLKQLQPPIREH--------------                1069
SEQ ID NO 36.pro    VADPSLEARPSIRALKRALLVALRCVDPDSEKRPKMGQVVRMLESEEVPYREDRRNRRSRTGSMDIESIAEGSNSAEFGK   497

1130
                    |
SEQ ID NO 15.pro                                                                                       1063
SEQ ID NO 17.pro                                                                                       1065
SEQ ID NO 19.pro                                                                                       599
SEQ ID NO 22.pro                                                                                       541
SEQ ID NO 23.pro                                                                                       1049
SEQ ID NO 24.pro    ----------R                                                                        1070
SEQ ID NO 36.pro    KVERTGSSISDRSQP.                                                                   513
```

Fig. 17

**Modified Hoagland's solutions -
16X concentrations for semi-hydroponics maize growth.**

| Nutrient | 1 mM KNO$_3$ | 2 mM KNO$_3$ | 3 mM KNO$_3$ | 4 mM KNO$_3$ |
|---|---|---|---|---|
| KNO$_3$ | 16 mM | 32 mM | 48 mM | 64 mM |
| KCl | 48 mM | 32 mM | 16 mM | ------ |
| KH$_2$PO$_4$ | 11 mM | 11 mM | 11 mM | 11 mM |
| MgSO$_4$ | 16 mM | 16 mM | 16 mM | 16 mM |
| CaCl$_2$·2H$_2$O | 16 mM | 16 mM | 16 mM | 16 mM |
| Sprint 330 | 1.6 g/L | 1.6 g/L | 1.6 g/L | 1.6 g/L |
| H$_3$BO$_3$ | 24 μM | 24 μM | 24 μM | 24 μM |
| 5 mM MnCl$_2$·4H$_2$O | 8 μM | 8 μM | 8 μM | 8 μM |
| 5 mM ZnSO$_4$·7 H$_2$O | 8 M | 8 μM | 8 μM | 8 μM |
| 0.5 mM CuSO$_4$·5 H$_2$O | 800 nM | 800 nM | 800 nM | 800 nM |
| 0.5 mM H$_2$MoO$_4$·H$_2$O | 800 nM | 800 nM | 800 nM | 800 nM |

Dilute 16X with tap water and determine the pH of the final mixture.
Add 3-12 mL H$_2$SO$_4$ if the pH is above 6.5.
Optimum pH is 5.0 - 5.5

Fig. 18

The effect of different nitrate concentrations on the growth and development of Gaspe Bay Flint derived maize lines (see Example 10C).

| [nitrate] | root (g dwt) | shoot (g dwt) | total vegetative (g dwt) | ear & husk (g dwt) | tassel (g dwt) | tiller # | tiller (g dwt) |
|---|---|---|---|---|---|---|---|
| 1 week after emergence | | | | | | | |
| 1 mM | 0.070a | 0.105b | 0.175b | | | | |
| 2 mM | 0.073a | 0.137ab | 0.209ab | | | | |
| 3 mM | 0.056a | 0.120ab | 0.176ab | | | | |
| 4 mM | 0.074a | 0.157a | 0.231a | | | | |
| 2 weeks after emergence | | | | | | | |
| 1 mM | 0.331ab | 0.544c | 0.875c | | | | |
| 2 mM | 0.266b | 0.951b | 1.217b | | | | |
| 3 mM | 0.352a | 1.171a | 1.523a | | | | |
| 4 mM | 0.303ab | 1.209a | 1.512a | | | | |
| 3 weeks after emergence | | | | | | | |
| 1 mM | 0.757a | 1.283b | 2.040b | 0.379c | 0.239c | 0.8c | 0.080b |
| 2 mM | 0.785a | 2.033a | 2.819a | 0.718a | 0.363bc | 2.3 | 0.506a |
| 3 mM | 0.664a | 1.911a | 2.574a | 0.451bc | 0.403ab | 2.8ab | 0.441a |
| 4 mM | 0.845a | 2.129a | 2.974a | 0.650ab | 0.506a | 3.3a | 0.688a |
| 4 weeks after emergence | | | | | | | |
| 1 mM | 0.842b | 2.010b | 2.852b | 1.318b | 0.677b | * | * |
| 2 mM | 1.493a | 3.772a | 5.265a | 3.130a | 1.018a | * | * |
| 3 mM | 1.232ab | 3.563a | 4.795a | 3.060a | 0.875ab | * | * |
| 4 mM | 1.010b | 2.943a | 3.952a | 2.787a | 0.891ab | * | * |

* Tillers removed 3 weeks after emergence
Means with similar letters are not different by protected Least Significant Difference (LSD) (0.05)

SEQUENCE LISTING

<160> NUMBER OF SEQ ID NOS: 37

<210> SEQ ID NO 1
<211> LENGTH: 18444
<212> TYPE: DNA
<213> ORGANISM: artificial sequence
<220> FEATURE:
<223> OTHER INFORMATION: vector

<400> SEQUENCE: 1

```
catgaatcaa acaaacatac acagcgactt attcacacga gctcaaatta caacggtata      60
tatcctgccg tcgacaacca tggtctagac aggatcccg ggtaccgagc tcgaatttgc      120
aggtcgactg cgtcatccct tacgtcagtg gagatatcac atcaatccac ttgctttgaa     180
gacgtggttg gaacgtcttc tttttccacg atgctcctcg tgggtggggg tccatctttg    240
ggaccactgt cggcagaggc atcttgaacg atagcctttc ctttatcgca atgatggcat    300
ttgtaggtgc caccttcctt ttctactgtc cttttgatga agtgacagat agctgggcaa    360
tggaatccga ggaggtttcc cgatattacc ctttgttgaa aagtctcaat tgcccttt    420 tcttctgaga ctgttgcgtc atcccttacg tcagtggaga tatcacatca atccacttgc    480
tttgaagacg tggttggaac gtcttctttt tccacgatgc tcctcgtggg tggggtcca    540 tctttgggac cactgtcggc agaggcatct tgaacgatag cctttccttt atcgcaatga    600
tggcatttgt aggtgccacc ttccttttct actgtccttt tgatgaagtg acagatagct    660
gggcaatgga atccgaggag gtttcccgat attacccttt gttgaaaagt ctcagttaac    720
ccgcgatcct gcgtcatccc ttacgtcagt ggagatatca catcaatcca cttgctttga    780
agacgtggtt ggaacgtctt ctttttccac gatgctcctc gtgggtgggg gtccatcttt    840
gggaccactg tcggcagagg catcttgaac gatagccttt cctttatcgc aatgatggca    900
tttgtaggtg ccaccttcct tttctactgt ccttttgatg aagtgacaga tagctgggca    960
atggaatccg aggaggtttc ccgatattac cctttgttga aaagtctcaa ttgccctttg   1020
gtcttctgag actgttgcgt catccttac gtcagtggag atatcacatc aatccacttg    1080
ctttgaagac gtggttggaa cgtcttcttt tccacgatg ctcctcgtgg gtggggtcc    1140 atctttggga ccactgtcgg cagaggcatc ttgaacgata gcctttcctt tatcgcaatg    1200
atggcatttg taggtgccac cttccttttc tactgtcctt tgatgaagt gacagatagc    1260 tgggcaatgg aatccgagga ggtttcccga tattaccctt tgttgaaaag tctcagttaa    1320
cccgcaattc actggccgtc gttttacaac gtcgtgactg ggaaaaccct ggcgttaccc    1380
```

```
aacttaatcg ccttgcagca catcccccctt tcgccagctg gcgtaatagc gaagaggccc    1440
gcaccgatcg cccttcccaa cagttgcgca gcctgaatgg cgaatggatc gatccgtcga    1500
tcgaccaaag cggccatcgt gcctcccccac tcctgcagtt cgggggcatg gatgcgcgga   1560
tagccgctgc tggtttcctg gatgccgacg gatttgcact gccggtagaa ctccgcgagg    1620
tcgtccagcc tcaggcagca gctgaaccaa ctcgcgaggg gatcgagccc ctgctgagcc    1680
tcgacatgtt gtcgcaaaat tcgccctgga cccgcccaac gatttgtcgt cactgtcaag    1740
gtttgacctg cacttcattt ggggcccaca tacaccaaaa aaatgctgca taattctcgg    1800
ggcagcaagt cggttacccg gccgccgtgc tggaccgggt tgaatggtgc ccgtaacttt    1860
cggtagagcg gacggccaat actcaacttc aaggaatctc acccatgcgc gccggcgggg    1920
aaccggagtt cccttcagtg aacgttatta gttcgccgct cggtgtgtcg tagatactag    1980
cccctggggc cttttgaaat ttgaataaga tttatgtaat cagtctttta ggtttgaccg    2040
gttctgccgc ttttttaaa attggatttg taataataaa acgcaattgt tgttattgt     2100
ggcgctctat catagatgtc gctataaacc tattcagcac aatatattgt tttcatttta   2160
atattgtaca tataagtagt agggtacaat cagtaaattg aacggagaat attattcata    2220
aaaatacgat agtaacgggt gatatattca ttagaatgaa ccgaaaccgg cggtaaggat    2280
ctgagctaca catgctcagg ttttttacaa cgtgcacaac agaattgaaa gcaaatatca    2340
tgcgatcata ggcgtctcgc atatctcatt aaagcagggg gtgggcgaag aactccagca    2400
tgagatcccc gcgctggagg atcatccagc cggcgtcccg gaaaacgatt ccgaagccca    2460
acctttcata gaaggcggcg gtggaatcga atctcgtga tggcaggttg ggcgtcgctt     2520
ggtcggtcat ttcgaacccc agagtccgc tcagaagaac tcgtcaagaa ggcgatagaa     2580
ggcgatgcgc tgcgaatcgg gagcggcgat accgtaaagc acgaggaagc ggtcagccca    2640
ttcgccgcca agctcttcag caatatcacg ggtagccaac gctatgtcct gatagcggtc    2700
cgccacaccc agccggccac agtcgatgaa tccagaaaag cggccatttt ccaccatgat    2760
attcggcaag caggcatcgc catgggtcac gacgagatcc tcgccgtcgg gcatgccccc    2820
caattcactg gccgtcgttt tacaacgtcg tgactgggaa aaccctggcg ttacccaact    2880
taatcgcctt gcagcacatc ccccttcgc cagctggcgt aatagcgaag aggcccgcac     2940
cgatcgccct tcccaacagt tgcgcagcct gaatggcgaa tggcgcctga tgcggtattt    3000
tctccttacg catctgtgcg gtatttcaca ccgcatatgg tgcactctca gtacaatctg    3060
ctctgatgcc gcatagttaa gccagccccg acacccgcca cacccgctg acgcgccctg     3120
acgggcttgt ctgctcccgg catccgctta cagacaagct gtgaccgtct ccgggagctg    3180
catgtgtcag aggttttcac cgtcatcacc gaaacgcgcg agacgaaagg gcctcgtgat    3240
acgcctattt ttataggtta atgtcatgat aataatggtt tcttagacgt caggtggcac    3300
ttttcgggga aatgtgcgcg gaacccctat ttgtttattt ttctaaatac attcaaatat    3360
gtatccgctc atgagacaat aaccctgata aatgcttcaa taatattgaa aaggaagag    3420
tatgagtatt caacatttcc gtgtcgccct tattccctt tttgcggcat tttgccttcc    3480
tgttttttgct cacccagaaa cgctggtgaa agtaaaagat gctgaagatc agttgggtgc   3540
acgagtgggt tacatcgaac tggatctcaa cagcggtaag atccttgaga gttttcgccc    3600
cgaagaacgt tttccaatga tgagcacttt taaagttctg ctatgtggcg cggtattatc    3660
ccgtattgac gccgggcaag agcaactcgg tcgccgcata cactattctc agaatgactt    3720
```

```
ggttgagtac tcaccagtca cagaaaagca tcttacggat ggcatgacag taagagaatt    3780
atgcagtgct gccataacca tgagtgataa cactgcggcc aacttacttc tgacaacgat    3840
cggaggaccg aaggagctaa ccgctttttt gcacaacatg ggggatcatg taactcgcct    3900
tgatcgttgg gaaccggagc tgaatgaagc cataccaaac gacgagcgtg acaccacgat    3960
gcctgtagca atggcaacaa cgttgcgcaa actattaact ggcgaactac ttactctagc    4020
ttcccggcaa caattaatag actggatgga ggcggataaa gttgcaggac cacttctgcg    4080
ctcggccctt ccggctggct ggtttattgc tgataaatct ggagccggtg agcgtgggtc    4140
tcgcggtatc attgcagcac tggggccaga tggtaagccc tcccgtatcg tagttatcta    4200
cacgacgggg agtcaggcaa ctatggatga acgaaataga cagatcgctg agataggtgc    4260
ctcactgatt aagcattggt aactgtcaga ccaagtttac tcatatatac tttagattga    4320
tttaaaactt catttttaat ttaaaaggat ctaggtgaag atcctttttg ataatctcat    4380
gaccaaaatc ccttaacgtg agttttcgtt ccactgagcg tcagacccccg tagaaaagat    4440 caaaggatct cttgagatcc ttttttttct gcgcgtaatc tgctgcttgc aaacaaaaaa    4500
accaccgcta ccagcggtgg tttgtttgcc ggatcaagag ctaccaactc tttttccgaa    4560
ggtaactggc ttcagcagag cgcagatacc aaatactgtc cttctagtgt agccgtagtt    4620
aggccaccac ttcaagaact ctgtagcacc gcctacatac ctcgctctgc taatcctgtt    4680
accagtggct gctgccagtg gcgataagtc gtgtcttacc gggttggact caagacgata    4740
gttaccggat aaggcgcagc ggtcgggctg aacggggggt tcgtgcacac agcccagctt    4800
ggagcgaacg acctacaccg aactgagata cctacagcgt gagcattgag aaagcgccac    4860
gcttcccgaa gggagaaagg cggacaggta tccggtaagc ggcagggtcg gaacaggaga    4920
gcgcacgagg gagcttccag gggaaacgc ctggtatctt tatagtcctg tcgggtttcg    4980
ccacctctga cttgagcgtc gatttttgtg atgctcgtca ggggggcgga gcctatggaa    5040
aaacgccagc aacgcggcct ttttacggtt cctggccttt tgctggcctt ttgctcacat    5100
gttctttcct gcgttatccc ctgattctgt ggataaccgt attaccgcct ttgagtgagc    5160
tgataccgct cgccgcagcc gaacgaccga gcgcagcgag tcagtgagcg aggaagcgga    5220
agagcgccca atacgcaaac cgcctctccc cgcgcgttgg ccgattcatt aatgcagctg    5280
gcacgacagg tttcccgact ggaaagcggg cagtgagcgc aacgcaatta atgtgagtta    5340
gctcactcat taggcacccc aggctttaca ctttatgctt ccggctcgta tgttgtgtgg    5400
aattgtgagc ggataacaat ttcacacagg aaacagctat gaccatgatt acgccaagct    5460
ttctaggggg ggggtaccga tctgagatcg gtaacgaaaa cgaacgggta gggatgaaaa    5520
cggtcggtaa cggtcggtaa aataccctca ccgttttcat tttcatattt aacttgcggg    5580
acggaaacga aaacgggata taccggtaac gaaaacgaac gggataaata cggtaatcga    5640
aaaccgatac gatccggtcg ggttaaagtc gaaatcggac gggaaccggt attttttgttc    5700 ggtaaaatca cacatgaaaa catatattca aaacttaaaa acaaatataa aaaattgtaa    5760
acacaagtct taattaaaca tagataaaat ccatataaat ctggagcaca catagtttaa    5820
tgtagcacat aagtgataag tcttgggctc ttggctaaca taagaagcca tataagtcta    5880
ctagcacaca tgacacaata taaagtttaa aacacatatt cataatcact tgctcacatc    5940
tggatcactt agcatgctac agctagtgca atattagaca cttccaata tttctcaaac    6000 ttttcactca ttgcaacggc cattctccta atgacaaatt tttcatgaac acaccattgg    6060
tcaatcaaat cctttatctc acagaaacct ttgtaaaata aatttgcagt ggaatattga    6120
```

```
gtaccagata ggagttcagt gagatcaaaa aacttcttca aacacttaaa aagagttaat    6180
gccatcttcc actcctcggc tttaggacaa attgcatcgt acctacaata attgacattt    6240
gattaattga gaatttataa tgatgacatg tacaacaatt gagacaaaca tacctgcgag    6300
gatcacttgt tttaagccgt gttagtgcag gcttataata taaggcatcc ctcaacatca    6360
aataggttga attccatcta gttgagacat catatgagat ccctttagat ttatccaagt    6420
cacattcact agcacacttc attagttctt cccactgcaa aggagaagat tttacagcaa    6480
gaacaatcgc tttgattttc tcaattgttc ctgcaattac agccaagcca tcctttgcaa    6540
ccaagttcag tatgtgacaa gcacacctca catgaaagaa agcaccatca caaactagat    6600
ttgaatcagt gtcctgcaaa tcctcaatta tatcgtgcac agctacttca tttgcactag    6660
cattatccaa agacaaggca aacaattttt tctcaatgtt ccacttaacc atgattgcag    6720
tgaaggtttg tgataaccct tggccagtgt ggcgcccttc aacatgaaaa agccaacaa     6780 ttcttttttg gagacaccaa tcatcatcaa tccaatggat ggtgacacac atgtatgact    6840
tattttgaca agatgtccac atatccatag ttgtactgaa gcgagactga acatctttta    6900
gttttccata caacttttct ttttcttcca aatacaaatc catgatatat tttctagcag    6960
tgacacggga ctttattgga aagtgagggc gcagagactt aacaaactca acaaagtact    7020
catgttctac aatattgaaa ggatattcat gcatgattat tgccaaatga agcttcttta    7080
ggctaaccac ttcatcgtac ttataaggct caatgagatt tatgtctttg ccatgatcct    7140
tttcactttt tagacacaac tgacctttaa ctaaactatg tgatgttctc aagtgatttc    7200
gaaatccgct tgttccatga tgaccctcag ccctatactt agccttgcaa ttaggaaagt    7260
tgcaatgtcc ccatacctga acgtatttct ttccatcgac ctccacttca atttccttct    7320
tggtgaaatg ctgccataca tccgatgtgc acttcttgc cctcttctgt ggtgcttctt     7380
cttcgggttc aggttgtggc tgtggttgtg gttctggttg tggttgtggt tgtggttgtg    7440
gttcatgaac aatagccata tcatcttgac tcggatctgt agctgtacca tttgcattac    7500
tactgcttac actctgaata aaatgcctct cggcctcagc tgttgatgat gatggtgatg    7560
tgcggccaca tccatgccca cgcgcacgtg cacgtacatt ctgaatccga ctagaagagg    7620
cttcagcttt tcttttcaac cctgttataa acagattttt cgtattattc tacagtcaat    7680
atgatgcttc ccaatctaca accaattagt aatgctaatg ctattgctac tgtttttcta    7740
atatatacct tgagcatatg cagagaatac ggaatttgtt ttgcgagtag aaggcgctct    7800
tgtggtagac atcaacttgg ccaatcttat ggctgagcct gagggaggat tatttccaac    7860
cggaggcgtc atctgaggaa tggagtcgta gccggctagc cgaagtggag agcagagccc    7920
tggacagcag gtgttcagca atcagcttgg tgctgtactg ctgtgacttg tgagcacctg    7980
gacggctgga cagcaatcag caggtgttgc agagcccctg acagcacac aaatgacaca     8040 acagcttggt gcaatggtgc tgacgtgctg tactgctaag tgctgtgagc ctgtgagcag    8100
ccgtggagac agggagaccg cggatggccg gatgggcgag cgccgagcag tggaggtctg    8160
gaggaccgct gaccgcagat ggcggatggc ggatgggcgg accgcggatg ggcgagcagt    8220
ggagtggagg tctgggcgga tgggcggacc gcggcgcgga tgggcgagtc gcgagcagtg    8280
gagtggaggg cggaccgtgg atggcggcgt ctgcgtccgg cgtgccgcgt cacggccgtc    8340
accgcgtgtg gtgcctggtg cagcccagcg gccggccggc tggagacag ggagagtcgg     8400 agagagcagg cgagagcgag acgcgtcgcc ggcgtcggcg tgcggctggc ggcgtccgga    8460
```

```
ctccggcgtg ggcgcgtggc ggcgtgtgaa tgtgtgatgc tgttactcgt gtggtgcctg    8520
gccgcctggg agagaggcag agcagcgttc gctaggtatt tcttacatgg gctgggcctc    8580
agtggttatg gatgggagtt ggagctggcc atattgcagt catcccgaat tagaaaatac    8640
ggtaacgaaa cgggatcatc ccgattaaaa acgggatccc ggtgaaacgg tcgggaaact    8700
agctctaccg tttccgtttc cgtttaccgt tttgtatatc ccgtttccgt tccgttttcg    8760 tttttttacct cgggttcgaa atcgatcggg ataaaactaa caaaatcggt tatacgataa    8820
cggtcggtac gggattttcc catcctactt tcatccctga gattattgtc gtttctttcg    8880
cagatcggta cccccccct agagtcgaca tcgatctagt aacatagatg acaccgcgcg    8940
cgataattta tcctagtttg cgcgctatat tttgttttct atcgcgtatt aaatgtataa    9000
ttgcgggact ctaatcataa aaacccatct cataaataac gtcatgcatt acatgttaat    9060
tattacatgc ttaacgtaat tcaacagaaa ttatatgata atcatcgcaa gaccggcaac    9120
aggattcaat cttaagaaac tttattgcca aatgtttgaa cgatctgctt cgacgcactc    9180
cttctttagg tacggactag atctcggtga cgggcaggac cggacggggc ggtaccggca    9240
ggctgaagtc cagctgccag aaacccacgt catgccagtt cccgtgcttg aagccggccg    9300
cccgcagcat gccgcggggg gcatatccga gcgcctcgtg catgcgcacg ctcgggtcgt    9360
tgggcagccc gatgacagcg accacgctct tgaagccctg tgcctccagg gacttcagca    9420
ggtgggtgta gagcgtggag cccagtcccg tccgctggtg gcggggggag acgtacacgg    9480
tcgactcggc cgtccagtcg taggcgttgc gtgccttcca ggggcccgcg taggcgatgc    9540
cggcgacctc gccgtccacc tcggcgacga gccagggata gcgctcccgc agacggacga    9600
ggtcgtccgt ccactcctgc ggttcctgcg gctcggtacg gaagttgacc gtgcttgtct    9660
cgatgtagtg gttgacgatg gtgcagaccg ccggcatgtc cgcctcggtg gcacggcgga    9720
tgtcggccgg gcgtcgttct gggctcatgg atctggattg agagtgaata tgagactcta    9780
attggatacc gagggggaatt tatggaacgt cagtggagca ttttttgacaa gaaatatttg    9840 ctagctgata gtgaccttag gcgacttttg aacgcgcaat aatggtttct gacgtatgtg    9900
cttagctcat taaactccag aaacccgcgc ctgagtggct ccttcaatcg ttgcggttct    9960
gtcagttcca aacgtaaaac ggcttgtccc gcgtcatcgg cggggtcat aacgtgactc    10020 ccttaattct ccgctcatga tccccgggta ccgagctcga attgcggctg agtggctcct    10080
tcaatcgttg cggttctgtc agttccaaac gtaaacggc ttgtcccgcg tcatcggcgg    10140
gggtcataac gtgactccct taattctccg ctcatgatct tgatccctg cgccatcaga    10200 tccttggcgg caagaaagcc atccagttta ctttgcaggg cttcccaacc ttaccagagg    10260 gcgcccagc tggcaattcc ggttcgcttg ctgtatcgat atggtggatt tatcacaaat    10320
gggacccgcc gccgacagag gtgtgatgtt aggccaggac tttgaaaatt tgcgcaacta    10380
tcgtatagtg gccgacaaat tgacgccgag ttgacagact gcctagcatt tgagtgaatt    10440
atgtgaggta atgggctaca ctgaattggt agctcaaact gtcagtattt atgtatatga    10500
gtgtatattt tcgcataatc tcagaccaat ctgaagatga aatgggtatc tgggaatggc    10560
gaaatcaagg catcgatcgt gaagtttctc atctaagccc ccatttggac gtgaatgtag    10620
acacgtcgaa ataaagattt ccgaattaga ataatttgtt tattgctttc gcctataaat    10680
acgacggatc gtaatttgtc gttttatcaa aatgtacttt catttataa taacgctgcg    10740 gacatctaca ttttgaatt gaaaaaaaat tggtaattac tctttctttt tctccatatt    10800
gaccatcata ctcattgctg atccatgtag atttcccgga catgaagcca tttacaattg    10860
```

```
aatatatcct gccgccgctg ccgctttgca cccggtggag cttgcatgtt ggtttctacg    10920
cagaactgag ccggttaggc agataatttc cattgagaac tgagccatgt gcaccttccc    10980
cccaacacgg tgagcgacgg ggcaacggag tgatccacat gggactttta aacatcatcc    11040
gtcggatggc gttgcgagag aagcagtcga tccgtgagat cagccgacgc accgggcagg    11100
cgcgcaacac gatcgcaaag tatttgaacg caggtacaat cgagccgacg ttcaccgtca    11160
ccctggatgc tgtaggcata ggcttggtta tgccggtact gccgggcctc ttgcgggata    11220
tcgtccattc cgacagcatc gccagtcact atggcgtgct gctagcgcta tatgcgttga    11280
tgcaatttct atgcgcaccc gttctcggag cactgtccga ccgctttggc cgccgcccag    11340
tcctgctcgc ttcgctactt ggagccacta tcgactacgc gatcatggcg accacacccg    11400
tcctgtggtc caacccctcc gctgctatag tgcagtcggc ttctgacgtt cagtgcagcc    11460
gtcttctgaa aacgacatgt cgcacaagtc ctaagttacg cgacaggctg ccgccctgcc    11520
cttttcctgg cgtttt cttg tcgcgtgttt tagtcgcata aagtagaata cttgcgacta    11580
gaaccggaga cattacgcca tgaacaagag cgccgccgct ggcctgctgg gctatgcccg    11640
cgtcagcacc gacgaccagg acttgaccaa ccaacgggcc gaactgcacg cggccggctg    11700
caccaagctg tttccgaga agatcaccgg caccaggcgc gaccgcccgg agctggccag    11760
gatgcttgac cacctacgcc ctggcgacgt tgtgacagtg accaggctag accgcctggc    11820
ccgcagcacc cgcgacctac tggacattgc cgagcgcatc caggaggccg gcgcgggcct    11880
gcgtagcctg gcagagccgt gggccgacac caccacgccg gccggccgca tggtgttgac    11940
cgtgttcgcc ggcattgccg agttcgagcg ttccctaatc atcgaccgca cccggagcgg    12000
gcgcgaggcc gccaaggccc gaggcgtgaa gtttggcccc cgccctaccc tcaccccggc    12060
acagatcgcg cacgcccgcg agctgatcga ccaggaaggc cgcaccgtga agaggcggc    12120 tgcactgctt ggcgtgcatc gctcgaccct gtaccgcgca cttgagcgca gcgaggaagt    12180
gacgcccacc gaggccaggc ggcgcggtgc cttccgtgag gacgcattga ccgaggccga    12240
cgccctggcg gccgccgaga atgaacgcca agaggaacaa gcatgaaacc gcaccaggac    12300
ggccaggacg aaccgttttt cattaccgaa gagatcgagg cggagatgat cgcggccggg    12360
tacgtgttcg agccgcccgc gcacgtctca accgtgcggc tgcatgaaat cctggccggt    12420
ttgtctgatg ccaagctggc ggcctggccg gccagcttgg ccgctgaaga aaccgagcgc    12480
cgccgtctaa aaaggtgatg tgtatttgag taaaacagct tgcgtcatgc ggtcgctgcg    12540
tatatgatgc gatgagtaaa taacaaata cgcaagggaa cgcatgaagt tatcgctgta    12600
cttaaccaga aaggcgggtc aggcaagacg accatcgcaa cccatctagc ccgcgccctg    12660
caactcgccg gggccgatgt tctgttagtc gattccgatc cccagggcag tgcccgcgat    12720
tgggcggccg tgcgggaaga tcaaccgcta accgttgtcg gcatcgaccg cccgacgatt    12780
gaccgcgacg tgaaggccat cggcggcgc gacttcgtag tgatcgacgg agcgcccag    12840 gcggcggact tggctgtgtc cgcgatcaag gcagccgact tcgtgctgat tccggtgcag    12900
ccaagccctt acgacatatg gccaccgccg gacctggtgg agctggttaa gcagcgcatt    12960
gaggtcacgg atggaaggct acaagcggcc tttgtcgtgt cgcgggcgat caaaggcacg    13020
cgcatcggcg gtgaggttgc cgaggcgctg gccgggtacg agctgcccat tcttgagtcc    13080
cgtatcacgc agcgcgtgag ctacccaggc actgccgccg ccggcacaac cgttcttgaa    13140
tcagaacccg agggcgacgc tgcccgcgag gtccaggcgc tggccgctga aattaaatca    13200
```

```
aaactcattt gagttaatga ggtaaagaga aaatgagcaa agcacaaac acgctaagtg   13260
ccggccgtcc gagcgcacgc agcagcaagg ctgcaacgtt ggccagcctg cagacacgc   13320
cagccatgaa gcgggtcaac tttcagttgc cggcggagga tcacaccaag ctgaagatgt   13380
acgcggtacg ccaaggcaag accattaccg agctgctatc tgaatacatc gcgcagctac   13440
cagagtaaat gagcaaatga ataaatgagt agatgaattt tagcggctaa aggaggcggc   13500
atggaaaatc aagaacaacc aggcaccgac gccgtggaat gccccatgtg tggaggaacg   13560
ggcggttggc caggcgtaag cggctgggtt gtctgccggc cctgcaatgg cactggaacc   13620
cccaagcccg aggaatcggc gtgagcgtc gcaaaccatc cggcccggta caaatcggcg   13680
cggcgctggg tgatgacctg gtggagaagt tgaaggccgc gcaggccgcc cagcggcaac   13740
gcatcgaggc agaagcacgc cccggtgaat cgtggcaagc ggccgctgat cgaatccgca   13800
aagaatcccg gcaaccgccg gcagccggtg cgccgtcgat taggaagccg cccaagggcg   13860
acgagcaacc agattttttc gttccgatgc tctatgacgt gggcaccgc gatagtcgca   13920
gcatcatgga cgtggccgtt ttccgtctgt cgaagcgtga ccgacgagct ggcgaggtga   13980
tccgctacga gcttccagac gggcacgtag aggtttccgc agggccggcc ggcatggcca   14040
gtgtgtggga ttacgacctg gtactgatgg cggtttccca tctaaccgaa tccatgaacc   14100
gataccggga agggaaggga gacaagcccg gccgcgtgtt ccgtccacac gttgcggacg   14160
tactcaagtt ctgccggcga gccgatggcg gaaagcagaa agacgacctg gtagaaacct   14220
gcattcggtt aaacaccacg cacgttgcca tgcagcgtac gaagaaggcc aagaacggcc   14280
gcctggtgac ggtatccgag ggtgaagcct tgattagccg ctacaagatc gtaaagagcg   14340
aaaccgggcg gccggagtac atcgagatcg agctagctga ttggatgtac cgcgagatca   14400
cagaaggcaa gaaccggac gtgctgacgg ttcaccccga ttacttttg atcgatcccg   14460
gcatcggccg ttttctctac cgcctggcac gccgcgccgc aggcaaggca gaagccagat   14520
ggttgttcaa gacgatctac gaacgcagtg gcagcgccgg agagttcaag aagttctgtt   14580
tcaccgtgcg caagctgatc gggtcaaatg acctgccgga gtacgatttg aaggaggagg   14640
cggggcaggc tggcccgatc ctagtcatgc gctaccgcaa cctgatcgag ggcgaagcat   14700
ccgccggttc ctaatgtacg gagcagatgc tagggcaaat tgccctagca ggggaaaaag   14760
gtcgaaaagg tctctttcct gtggatagca cgtacattgg gaacccaaag ccgtacattg   14820
ggaaccggaa cccgtacatt gggaacccaa agccgtacat tgggaaccgg tcacacatgt   14880
aagtgactga tataaaagag aaaaaaggcg attttttccgc ctaaaactct ttaaaactta   14940
ttaaaactct taaacccgc ctggcctgtg cataactgtc tggccagcgc acagccgaag   15000
agctgcaaaa agcgcctacc cttcggtcgc tgcgctccct acgccccgcc gcttcgcgtc   15060
ggcctatcgc ggccgctggc cgctcaaaaa tggctggcct acggcaggc aatctaccag   15120
ggcgcggaca agccgcgccg tcgccactcg accgccggcg cccacatcaa ggcaccctgc   15180
ctcgcgcgtt tcggtgatga cggtgaaaac tctgacaca tgcagctccc ggagacggtc   15240
acagcttgtc tgtaagcgga tgccgggagc agacaagccc gtcagggcgc gtcagcgggt   15300
gttggcgggt gtcggggcgc agccatgacc cagtcacgta gcgatagcgg agtgtatact   15360
ggcttaacta tgcggcatca gagcagattg tactgagagt gcaccatatg cggtgtgaaa   15420
taccgcacag atgcgtaagg agaaaatacc gcatcaggcg ctcttccgct tcctcgctca   15480
ctgactcgct gcgctcggtc gttcggctgc ggcgagcggt atcagctcac tcaaaggcgg   15540
taatacggtt atccacagaa tcaggggata acgcaggaaa gaacatgtga gcaaaaggcc   15600
```

```
agcaaaaggc caggaaccgt aaaaaggccg cgttgctggc gttttccat aggctccgcc    15660 cccctgacga gcatcacaaa aatcgacgct caagtcagag gtggcgaaac ccgacaggac    15720
tataaagata ccaggcgttt ccccctggaa gctccctcgt gcgctctcct gttccgaccc    15780
tgccgcttac cggatacctg tccgcctttc tcccttcggg aagcgtggcg ctttctcata    15840
gctcacgctg taggtatctc agttcggtgt aggtcgttcg ctccaagctg gctgtgtgc    15900 acgaaccccc cgttcagccc gaccgctgcg ccttatccgg taactatcgt cttgagtcca    15960
acccggtaag acacgactta tcgccactgg cagcagccac tggtaacagg attagcagag    16020
cgaggtatgt aggcggtgct acagagttct gaagtggtg gcctaactac ggctacacta    16080
gaaggacagt atttggtatc tgcgctctgc tgaagccagt taccttcgga aaagagttg    16140 gtagctcttg atccggcaaa caaccaccg ctggtagcgg tggttttttt gtttgcaagc    16200
agcagattac gcgcagaaaa aaaggatctc aagaagatcc tttgatcttt tctacggggt    16260
ctgacgctca gtggaacgaa aactcacgtt aagggatttt ggtcatgaga ttatcaaaaa    16320
ggatcttcac ctagatcctt ttaaattaaa aatgaagttt taaatcaatc taaagtatat    16380
atgagtaaac ttggtctgac agttaccaat gcttaatcag tgaggcacct atctcagcga    16440
tctgtctatt tcgttcatcc atagttgcct gactccccgt cgtgtagata actacgatac    16500
gggagggctt accatctggc cccagtgctg caatgatacc gcgagaccca cgctcaccgg    16560
ctccagattt atcagcaata aaccagccag ccggaagggc cgagcgcaga gtggtcctg    16620 caactttatc cgcctccatc cagtctatta attgttgccg gaagctaga gtaagtagtt    16680 cgccagttaa tagtttgcgc aacgttgttg ccattgctac aggcatcgtg gtgtcacgct    16740
cgtcgtttgg tatggcttca ttcagctccg gttcccaacg atcaaggcga gttacatgat    16800 ccccccatgtt gtgcaaaaaa gcggttagct ccttcggtcc tccgatcgtt gtcagaagta    16860
agttggccgc agtgttatca ctcatggtta tggcagcact gcataattct cttactgtca    16920
tgccatccgt aagatgcttt tctgtgactg gtgagtactc aaccaagtca ttctgagaat    16980
agtgtatgcg gcgaccgagt tgctcttgcc cggcgtcaac acgggataat accgcgccac    17040
atagcagaac tttaaaagtg ctcatcattg gaaaagacct gcaggggggg ggggaaagc    17100 cacgttgtgt ctcaaaatct ctgatgttac attgcacaag ataaaaatat atcatcatga    17160
acaataaaac tgtctgctta cataaacagt aatacaaggg gtgttatgag ccatattcaa    17220
cgggaaacgt cttgctcgag gccgcgatta aattccaaca tggatgctga tttatatggg    17280
tataaatggg ctcgcgataa tgtcgggcaa tcaggtgcga caatctatcg attgtatggg    17340
aagcccgatg cgccagagtt gtttctgaaa catggcaaag gtagcgttgc caatgatgtt    17400
acagatgaga tggtcagact aaactggctg acggaattta tgcctcttcc gaccatcaag    17460
cattttatcc gtactcctga tgatgcatgg ttactcacca ctgcgatccc cgggaaaaca    17520
gcattccagg tattagaaga atatcctgat tcaggtgaaa atattgttga tgcgctggca    17580
gtgttcctgc gccggttgca ttcgattcct gtttgtaatt gtcctttaa cagcgatcgc    17640 gtatttcgtc tcgctcaggc gcaatcacga atgaataacg gtttggttga tgcgagtgat    17700
tttgatgacg agcgtaatgg ctggcctgtt gaacaagtct ggaaagaaat gcataagctt    17760
ttgccattct caccggattc agtcgtcact catggtgatt tctcacttga taaccttatt    17820
tttgacgagg ggaaattaat aggttgtatt gatgttggac gagtcggaat cgcagaccga    17880
taccaggatc ttgccatcct atggaactgc ctcggtgagt tttctccttc attacagaaa    17940
```

| | |
|---|---|
| cggctttttc aaaaatatgg tattgataat cctgatatga ataaattgca gtttcatttg | 18000 |
| atgctcgatg agttttttcta atcagaattg gttaattggt tgtaacactg gcagagcatt | 18060 |
| acgctgactt gacgggacgg cggctttgtt gaataaatcg aacttttgct gagttgaagg | 18120 |
| atcagatcac gcatcttccc gacaacgcag accgttccgt ggcaaagcaa aagttcaaaa | 18180 |
| tcaccaactg gtccacctac aacaaagctc tcatcaaccg tggctccctc actttctggc | 18240 |
| tggatgatgg ggcgattcag gcctggtatg agtcagcaac accttcttca cgaggcagac | 18300 |
| ctcagcgccc cccccccct gcaggtcaat tcggtcgata tggctattac gaagaaggct | 18360 |
| cgtgcgcgga gtcccgtgaa ctttcccacg caacaagtga accgcaccgg gtttgccgga | 18420 |
| ggccatttcg ttaaaatgcg cagc | 18444 |

<210> SEQ ID NO 2
<211> LENGTH: 4291
<212> TYPE: DNA
<213> ORGANISM: artificial sequence
<220> FEATURE:
<223> OTHER INFORMATION: vector

<400> SEQUENCE: 2

| | |
|---|---|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt tcccagtcac gacgttgtaa | 540 |
| aacgacggcc agtcttaagc tcgggcccca ataatgatt ttattttgac tgatagtgac | 600 |
| ctgttcgttg caacacattg atgagcaatg ctttttttata atgccaactt tgtacaaaaa | 660 |
| agctgaacga gaaacgtaaa atgatataaa tatcaatata ttaaattaga ttttgcataa | 720 |
| aaaacagact acataatact gtaaaacaca acatatccag tcactatgaa tcaactactt | 780 |
| agatggtatt agtgacctgt agtcgaccga cagccttcca aatgttcttc gggtgatgct | 840 |
| gccaacttag tcgaccgaca gccttccaaa tgttcttctc aaacggaatc gtcgtatcca | 900 |
| gcctactcgc tattgtcctc aatgccgtat taaatcataa aagaaataa gaaaaagagg | 960 |
| tgcgagcctc tttttttgtgt gacaaaataa aaacatctac ctattcatat acgctagtgt | 1020 |
| catagtcctg aaaatcatct gcatcaagaa caatttcaca actcttatac ttttctctta | 1080 |
| caagtcgttc ggcttcatct ggattttcag cctctatact tactaaacgt gataagttt | 1140 |
| ctgtaatttc tactgtatcg acctgcagac tggctgtgta agggagcc tgacatttat | 1200 |
| attccccaga acatcaggtt aatggcgttt ttgatgtcat tttcgcggtg gctgagatca | 1260 |
| gccacttctt ccccgataac ggagaccggc acactggcca tatcggtggt catcatgcgc | 1320 |
| cagctttcat ccccgatatg caccaccggg taaagttcac gggagacttt atctgacagc | 1380 |
| agacgtgcac tggccagggg gatcaccatc cgtcgcccgg gcgtgtcaat aatatcactc | 1440 |
| tgtacatcca caaacagacg ataacggctc tctcttttat aggtgtaaac cttaaactgc | 1500 |
| atttcaccag cccctgttct cgtcagcaaa agagccgttc atttcaataa accgggcgac | 1560 |

```
ctcagccatc ccttcctgat tttccgcttt ccagcgttcg gcacgcagac gacgggcttc    1620
attctgcatg gttgtgctta ccagaccgga gatattgaca tcatatatgc cttgagcaac    1680
tgatagctgt cgctgtcaac tgtcactgta atacgctgct tcatagcata cctcttttg     1740 acatacttcg ggtatacata tcagtatata ttcttatacc gcaaaaatca gcgcgcaaat    1800
acgcatactg ttatctggct tttagtaagc cggatccacg cggcgtttac gccccgccct    1860
gccactcatc gcagtactgt tgtaattcat taagcattct gccgacatgg aagccatcac    1920
agacggcatg atgaacctga atcgccagcg gcatcagcac cttgtcgcct gcgtataat     1980 atttgcccat ggtgaaaacg ggggcgaaga agttgtccat attggccacg tttaaatcaa    2040
aactggtgaa actcacccag ggattggctg agacgaaaaa catattctca ataaacccctt   2100 tagggaaata ggccaggttt tcaccgtaac acgccacatc ttgcgaatat atgtgtagaa    2160
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttattttc tttacggtct ttaaaaaggc cgtaatatcc agctgaacgg     2400
tctggttata ggtacattga gcaactgact gaaatgcctc aaaatgttct ttacgatgcc    2460
attgggatat atcaacggtg gtatatccag tgattttttt ctccatttta gcttccttag    2520
ctcctgaaaa tctcgataac tcaaaaaata cgcccggtag tgatcttatt tcattatggt    2580
gaaagttgga acctcttacg tgccgatcaa cgtctcattt tcgccaaaag ttgggcccagg  2640 gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg ttttttatgc aaaatctaat ttaatatatt gatatttata tcattttacg    2880
tttctcgttc agctttcttg tacaaagttg gcattataag aaagcattgc ttatcaattt    2940
gttgcaacga acaggtcact atcagtcaaa ataaaatcat tatttgccat ccagctgata    3000
tcccctatag tgagtcgtat tacatggtca tagctgtttc ctggcagctc tggcccgtgt    3060
ctcaaaatct ctgatgttac attgcacaag ataaataat atcatcatga tcagtcctgc    3120
tcctcggcca cgaagtgcac gcagttgccg gccgggtcgc gcagggcgaa ctcccgcccc   3180
cacggctgct cgccgatctc ggtcatggcc ggcccggagg cgtcccggaa gttcgtggac    3240
acgacctccg accactcggc gtacagctcg tccaggccgc gcacccacac ccaggccagg    3300
gtgttgtccg gcaccacctg gtcctggacc gcgctgatga acagggtcac gtcgtcccgg    3360
accacaccgg cgaagtcgtc ctccacgaag tcccgggaga acccgagccg gtcggtccag    3420
aactcgaccg ctccggcgac gtcgcgcgcg gtgagcaccg gaacggcact ggtcaacttg    3480
gccatggttt agttcctcac cttgtcgtat tatactatgc cgatatacta tgccgatgat    3540
taattgtcaa cacgtgctga tcatgaccaa aatcccttaa cgtgagttac gcgtcgttcc    3600
actgagcgtc agacccgta gaaaagatca aaggatcttc ttgagatcct ttttttctgc     3660
gcgtaatctg ctgcttgcaa acaaaaaaac caccgctacc agcggtggtt tgtttgccgg    3720
atcaagagct accaactctt tttccgaagg taactggctt cagcagagcg cagataccaa    3780
atactgttct tctagtgtag ccgtagttag gccaccactt caagaactct gtagcaccgc    3840
ctacatacct cgctctgcta atcctgttac cagtggctgc tgccagtggc gataagtcgt    3900
```

| | |
|---|---:|
| gtcttaccgg gttggactca agacgatagt taccggataa ggcgcagcgg tcgggctgaa | 3960 |
| cgggggggttc gtgcacacag cccagcttgg agcgaacgac ctacaccgaa ctgagatacc | 4020 |
| tacagcgtga gctatgagaa agcgccacgc ttcccgaagg gagaaaggcg gacaggtatc | 4080 |
| cggtaagcgg cagggtcgga acaggagagc gcacgaggga gcttccaggg ggaaacgcct | 4140 |
| ggtatcttta tagtcctgtc gggtttcgcc acctctgact tgagcgtcga ttttttgtgat | 4200 |
| gctcgtcagg gggcggagc ctatggaaaa acgccagcaa cgcggccttt ttacggttcc | 4260 |
| tggccttttg ctggcctttt gctcacatgt t | 4291 |

<210> SEQ ID NO 3
<211> LENGTH: 4762
<212> TYPE: DNA
<213> ORGANISM: artificial sequence
<220> FEATURE:
<223> OTHER INFORMATION: vector

<400> SEQUENCE: 3

| | |
|---|---:|
| ctttcctgcg ttatcccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca aatccgctcc cggcggattt gtcctactca ggagagcgtt caccgacaaa | 420 |
| caacagataa aacgaaaggc ccagtcttcc gactgagcct ttcgttttat ttgatgcctg | 480 |
| gcagttccct actctcgcgt taacgctagc atggatgttt tcccagtcac gacgttgtaa | 540 |
| aacgacggcc agtcttaagc tcgggcccca ataatgatt ttattttgac tgatagtgac | 600 |
| ctgttcgttg caacacattg atgagcaatg cttttttata atgccaactt tgtacaaaaa | 660 |
| agctgaacga gaaacgtaaa atgatataaa tatcaatata ttaaattaga ttttgcataa | 720 |
| aaaacagact acataatact gtaaaacaca acatatccag tcactatgaa tcaactactt | 780 |
| agatggtatt agtgacctgt agtcgaccga cagccttcca aatgttcttc gggtgatgct | 840 |
| gccaacttag tcgaccgaca gccttccaaa tgttcttctc aaacggaatc gtcgtatcca | 900 |
| gcctactcgc tattgtcctc aatgccgtat taaatcataa aagaaataa gaaaagagg | 960 |
| tgcgagcctc ttttttgtgt gacaaaataa aaacatctac ctattcatat acgctagtgt | 1020 |
| catagtcctg aaaatcatct gcatcaagaa caatttcaca actcttatac ttttctctta | 1080 |
| caagtcgttc ggcttcatct ggattttcag cctctatact tactaaacgt gataaagttt | 1140 |
| ctgtaatttc tactgtatcg acctgcagac tggctgtgta taagggagcc tgacatttat | 1200 |
| attccccaga acatcaggtt aatggcgttt ttgatgtcat tttcgcggtg ctgagatca | 1260 |
| gccacttctt ccccgataac ggagaccggc acactggcca tatcggtggt catcatgcgc | 1320 |
| cagctttcat ccccgatatg caccaccggg taaagttcac gggagacttt atctgacagc | 1380 |
| agacgtgcac tggccagggg gatcaccatc cgtcgcccgg gcgtgtcaat aatatcactc | 1440 |
| tgtacatcca caaacagacg ataacggctc tctcttttat aggtgtaaac cttaaactgc | 1500 |
| atttcaccag cccctgttct cgtcagcaaa agagccgttc atttcaataa accgggcgac | 1560 |
| ctcagccatc ccttcctgat tttcgctttt ccagcgttcg gcacgcagac gacgggcttc | 1620 |
| attctgcatg gttgtgctta ccagaccgga gatattgaca tcatatatgc cttgagcaac | 1680 |

```
tgatagctgt cgctgtcaac tgtcactgta atacgctgct tcatagcata cctcttttg    1740 acatacttcg ggtatacata tcagtatata ttcttatacc gcaaaaatca gcgcgcaaat    1800
acgcatactg ttatctggct tttagtaagc cggatccacg cggcgtttac gccccgccct    1860
gccactcatc gcagtactgt tgtaattcat taagcattct gccgacatgg aagccatcac    1920
agacggcatg atgaacctga atcgccagcg gcatcagcac cttgtcgcct tgcgtataat    1980
atttgcccat ggtgaaaacg ggggcgaaga agttgtccat attggccacg tttaaatcaa    2040
aactggtgaa actcacccag ggattggctg agacgaaaaa catattctca ataaacccct    2100
tagggaaata ggccaggttt tcaccgtaac acgccacatc ttgcgaatat atgtgtagaa    2160
actgccggaa atcgtcgtgg tattcactcc agagcgatga aaacgtttca gtttgctcat    2220
ggaaaacggt gtaacaaggg tgaacactat cccatatcac cagctcaccg tctttcattg    2280
ccatacggaa ttccggatga gcattcatca ggcgggcaag aatgtgaata aaggccggat    2340
aaaacttgtg cttattttc tttacggtct ttaaaaaggc cgtaatatcc agctgaacgg    2400
tctggttata ggtacattga gcaactgact gaaatgcctc aaaatgttct ttacgatgcc    2460
attgggatat atcaacggtg gtatatccag tgatttttt ctccatttta gcttccttag    2520
ctcctgaaaa tctcgataac tcaaaaaata cgcccggtag tgatcttatt tcattatggt    2580
gaaagttgga acctcttacg tgccgatcaa cgtctcattt cgccaaaag ttggcccagg    2640 gcttcccggt atcaacaggg acaccaggat ttatttattc tgcgaagtga tcttccgtca    2700
caggtattta ttcggcgcaa agtgcgtcgg gtgatgctgc caacttagtc gactacaggt    2760
cactaatacc atctaagtag ttgattcata gtgactggat atgttgtgtt ttacagtatt    2820
atgtagtctg ttttttatgc aaaatctaat ttaatatatt gatatttata tcattttacg    2880
tttctcgttc agctttcttg tacaaagttg gcattataag aaagcattgc ttatcaattt    2940
gttgcaacga acaggtcact atcagtcaaa ataaaatcat tatttgccat ccagctgata    3000
tcccctatag tgagtcgtat tacatggtca tagctgtttc ctggcagctc tggcccgtgt    3060
ctcaaaatct ctgatgttac attgcacaag ataaaataat atcatcatga acaataaaac    3120
tgtctgctta cataaacagt aatacaaggg gtgttatgag ccatattcaa cgggaaacgt    3180
cgaggccgcg attaaattcc aacatggatg ctgatttata tgggtataaa tgggctcgcg    3240
ataatgtcgg gcaatcaggt gcgacaatct atcgcttgta tgggaagccc gatgcgccag    3300
agttgtttct gaaacatggc aaaggtagcg ttgccaatga tgttacagat gagatggtca    3360
gactaaactg gctgacggaa tttatgcctc ttccgaccat caagcatttt atccgtactc    3420
ctgatgatgc atggttactc accactgcga tccccggaaa aacagcattc caggtattag    3480
aagaatatcc tgattcaggt gaaaatattg ttgatgcgct ggcagtgttc ctgcgccggt    3540
tgcattcgat tcctgtttgt aattgtcctt ttaacagcga tcgcgtattt cgtctcgctc    3600
aggcgcaatc acgaatgaat aacggtttgg ttgatgcgag tgattttgat gacgagcgta    3660
atggctggcc tgttgaacaa gtctggaaag aaatgcataa acttttgcca ttctcaccgg    3720
attcagtcgt cactcatggt gatttctcac ttgataacct tattttgac gaggggaaat    3780 taataggttg tattgatgtt ggacgagtcg gaatcgcaga ccgataccag gatcttgcca    3840
tcctatggaa ctgcctcggt gagttttctc cttcattaca gaaacggctt tttcaaaaat    3900
atggtattga taatcctgat atgaataaat tgcagtttca tttgatgctc gatgagtttt    3960
tctaatcaga attggttaat tggttgtaac actggcagag cattacgctg acttgacggg    4020
```

```
acggcgcaag ctcatgacca aaatccctta acgtgagtta cgcgtcgttc cactgagcgt    4080
cagaccccgt agaaaagatc aaaggatctt cttgagatcc ttttttttctg cgcgtaatct    4140 gctgcttgca acaaaaaaa ccaccgctac cagcggtggt ttgtttgccg gatcaagagc     4200
taccaactct ttttccgaag gtaactggct tcagcagagc gcagatacca aatactgttc     4260
ttctagtgta gccgtagtta ggccaccact tcaagaactc tgtagcaccg cctacatacc    4320
tcgctctgct aatcctgtta ccagtggctg ctgccagtgg cgataagtcg tgtcttaccg    4380
ggttggactc aagacgatag ttaccggata aggcgcagcg gtcgggctga acggggggtt    4440
cgtgcacaca gcccagcttg gagcgaacga cctacaccga actgagatac ctacagcgtg    4500
agctatgaga aagcgccacg cttcccgaag ggagaaaggc ggacaggtat ccggtaagcg    4560
gcagggtcgg aacaggagag cgcacgaggg agcttccagg gggaaacgcc tggtatcttt    4620
atagtcctgt cgggtttcgc cacctctgac ttgagcgtcg attttttgtga tgctcgtcag    4680 ggggggcggag cctatggaaa aacgccagca acgcggcctt tttacggttc ctggccttttt  4740 gctggccttt tgctcacatg tt                                             4762

<210> SEQ ID NO 4
<211> LENGTH: 16843
<212> TYPE: DNA
<213> ORGANISM: artificial sequence
<220> FEATURE:
<223> OTHER INFORMATION: vector

<400> SEQUENCE: 4
ccgggctggt tgccctcgcc gctgggctgg cggccgtcta tggccctgca aacgcgccag      60
aaacgccgtc gaagccgtgt gcgagacacc gcggccgccg gcgttgtgga tacctcgcgg    120
aaaacttggc cctcactgac agatgagggg cggacgttga cacttgaggg gccgactcac    180
ccggcgcggc gttgacagat gaggggcagg ctcgatttcg gccggcgacg tggagctggc    240
cagcctcgca aatcggcgaa aacgcctgat tttacgcgag tttcccacag atgatgtgga    300
caagcctggg gataagtgcc ctgcggtatt gacacttgag gggcgcgact actgacagat    360
gaggggcgcg atccttgaca cttgaggggc agagtgctga cagatgaggg gcgcacccta    420
tgacatttga ggggctgtcc acaggcagaa atccagcat ttgcaagggt tccgcccgt     480 ttttcggcca ccgctaacct gtcttttaac ctgcttttaa accaatattt ataaaccttg    540
tttttaacca gggctgcgcc ctgtgcgcgt gaccgcgcac gccgaagggg ggtgcccccc    600
cttctcgaac cctcccggcc cgctaacgcg ggcctcccat ccccccaggg gctgcgcccc    660
tcggccgcga acggcctcac cccaaaaatg gcagcgctgg cagtccttgc cattgccggg   720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa    1020
acgagaattg gacctttaca gaattactct atgaagcgcc atatttaaaa agctaccaag    1080
acgaagagga tgaagaggat gaggaggcag attgccttga atatattgac aatactgata    1140
agataatata tcttttatat agaagatatc gccgtatgta aggatttcag ggggcaaggc    1200
ataggcagcg cgcttatcaa tatatctata gaatgggcaa agcataaaaa cttgcatgga    1260
ctaatgcttg aaacccagga caataacctt atagcttgta aattctatca taattgggta    1320
```

```
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgcccagc gtcgccatag tgcgttcacc gaatacgtgc    1620
gcaacaaccg tcttccggag actgtcatac gcgtaaaaca gccagcgctg gcgcgattta   1680
gccccgacat agccccactg ttcgtccatt ccgcgcaga cgatgacgtc actgcccggc    1740
tgtatgcgcg aggttaccga ctgcggcctg agttttttaa gtgacgtaaa atcgtgttga   1800
ggccaacgcc cataatgcgg gctgttgccc ggcatccaac gccattcatg gccatatcaa   1860
tgattttctg gtgcgtaccg ggttgagaag cggtgtaagt gaactgcagt tgccatgttt   1920
tacggcagtg agagcagaga tagcgctgat gtccggcggt gcttttgccg ttacgcacca   1980
ccccgtcagt agctgaacag gagggacagc tgatagacac agaagccact ggagcacctc   2040
aaaaacacca tcatacacta atcagtaag ttggcagcat cacccataat tgtggtttca    2100
aaatcggctc cgtcgatact atgttatacg ccaactttga aaacaacttt gaaaaagctg   2160
ttttctggta tttaaggttt tagaatgcaa ggaacagtga attggagttc gtcttgttat   2220
aattagcttc ttggggtatc tttaaatact gtagaaaaga ggaaggaaat aataaatggc   2280
taaaatgaga atatcaccgg aattgaaaaa actgatcgaa aaataccgct gcgtaaaaga   2340 tacgaagga atgtctcctg ctaaggtata taagctggtg ggagaaaatg aaaacctata    2400
tttaaaaatg acgacagcc ggtataaagg gaccacctat gatgtggaac gggaaaagga    2460
catgatgcta tggctggaag gaaagctgcc tgttccaaag gtcctgcact ttgaacggca   2520
tgatggctgg agcaatctgc tcatgagtga ggccgatggc gtcctttgct cggaagagta   2580
tgaagatgaa caaagccctg aaaagattat cgagctgtat gcggagtgca tcaggctctt   2640
tcactccatc gacatatcgg attgtcccta tacgaatagc ttagacagcc gcttagccga   2700
attggattac ttactgaata acgatctggc cgatgtggat tgcgaaaact gggaagaaga   2760
cactccattt aaagatccgc gcgagctgta tgattttta aagacggaaa agcccgaaga    2820
ggaacttgtc ttttcccacg cgacctggg agacagcaac atctttgtga aagatggcaa    2880
agtaagtggc tttattgatc ttgggagaag cggcagggcg acaagtggt atgacattgc    2940 cttctgcgtc cggtcgatca gggaggatat cggggaagaa cagtatgtcg agctattttt   3000
tgacttactg gggatcaagc ctgattggga gaaaataaaa tattatattt tactggatga   3060
attgttttag tacctagatg tggcgcaacg atgccggcga caagcaggag cgcaccgact   3120
tcttccgcat caagtgtttt ggctctcagg ccgaggccca cggcaagtat ttgggcaagg   3180
ggtcgctggt attcgtgcag ggcaagattc ggaataccaa gtacgagaag gacggccaga   3240
cggtctacgg gaccgacttc attgccgata aggtggatta tctggacacc aaggcaccag   3300
gcgggtcaaa tcaggaataa gggcacattg ccccggcgtg agtcggggca atcccgcaag   3360
gagggtgaat gaatcggacg tttgaccgga aggcatacag gcaagaactg atcgacgcgg   3420
ggttttccgc cgaggatgcc gaaaccatcg caagccgcac cgtcatgcgt gcgccccgcg   3480
aaaccttcca gtccgtcggc tcgatggtcc agcaagctac ggccaagatc gagcgcgaca   3540
gcgtgcaact ggctcccccT gccctgcccg cgccatcggc cgccgtggag cgttcgcgtc   3600
gtctcgaaca ggaggcggca ggtttggcga agtcgatgac catcgacacg cgaggaacta   3660
```

```
tgacgaccaa gaagcgaaaa accgccggcg aggacctggc aaaacaggtc agcgaggcca    3720
agcaggccgc gttgctgaaa cacacgaagc agcagatcaa ggaaatgcag ctttccttgt    3780
tcgatattgc gccgtggccg gacacgatgc gagcgatgcc aaacgacacg gcccgctctg    3840
ccctgttcac cacgcgcaac aagaaaatcc cgcgcgaggc gctgcaaaac aaggtcattt    3900
tccacgtcaa caaggacgtg aagatcacct acaccggcgt cgagctgcgg gccgacgatg    3960
acgaactggt gtggcagcag gtgttggagt acgcgaagcg caccccgatc ggcgagccga    4020
tcaccttcac gttctacgag cttttgccagg acctgggctg gtcgatcaat ggccggtatt    4080
acacgaaggc cgaggaatgc ctgtcgcgcc tacaggcgac ggcgatgggc ttcacgtccg    4140
accgcgttgg gcacctggaa tcggtgtcgc tgctgcaccg cttccgcgtc ctggaccgtg    4200
gcaagaaaac gtcccgttgc caggtcctga tcgacgagga atcgtcgtg ctgtttgctg    4260
gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
gcctcatgtg cggatcggat tccacccgcg tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtggggt cagttccggc tgggggttca gcagccagcg    4560
cttttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat    4740
ccgattgtcg gccctgaaga aagctccaga gatgttcggg tccgtttacg agcacgagga    4800
gaaaaagccc atggaggcgt tcgctgaacg gttgcgagat gccgtggcat tcggcgccta    4860
catcgacggc gagatcattg gctgtcggt cttcaaacag gaggacggcc ccaaggacgc    4920
tcacaaggcg catctgtccg gcgttttcgt ggagcccgaa cagcgaggcc gaggggtcgc    4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggctttctca gccccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
cgagaaatga ataagaaggc tgataattcg gatctctgcg agggagatga tatttgatca    5880
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
```

```
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaatccc ttataaatca aagaatagc     6360 ccgagatagg gttgagtgtt gttccagttt ggaacaagag tccactatta agaacgtgg    6420 actccaacgt caaagggcga aaaaccgtct atcagggcga tggcccacta cctgtatggc    6480
cgcattcgca aaacacacct agactagatt tgttttgcta acccaattga tattaattat    6540
atatgattaa tatttatatg tatatggatt tggttaatga aatgcatctg gttcatcaaa    6600
gaattataaa gacacgtgac attcatttag gataagaaat atggatgatc tctttctctt    6660
ttattcagat aactagtaat tacacataac acacaacttt gatgcccaca ttatagtgat    6720
tagcatgtca ctatgtgtgc atcctttat ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcggt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg gcaccggtac cggccgccgt    7020
ccttcagcag caggtacatg ctcacgtcgc ccttcaggat gccctgctta ggcacgggca    7080
tgatcttctc gcagctggcc tcccagttgg tggtcatctt cttcatcacg gggccgtcgg    7140
cggggaagtt cacgccgttg aagatgctct tgtggtagat gcagttctcc ttcacgctca    7200
cggtgatgtc cacgttacag atgcacacgg cgccgtcctc gaacaggaag ctccggcccc    7260
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atctttttt ttgcttttg gaactcatgt    7740 cggtagtata tcttttattt attttttctt tttttccctt tctttcaaa ctgatgtcgg    7800 tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatcttta    7980 ttttatacgt aaaattaaaa ttgaatgatg tcaagaacga aaattaattt gtatttacaa    8040
aggagctaaa tattgtttat tcctctactg gtagaagata aagaagtag atgaaataat    8100 gatcttacta gagaatattc ctcatttaca ctagtcaaat ggaaatcttg taaacttta    8160 caataattta tcctgaaaat atgaaaaat agaagaaaat gtttacctcc tctctcctct    8220
taattcacct acgatcggtg cgggcctctt cgctattacg ccagctggcg aaggggggat    8280
gtgctgcaag gcgattaagt tgggtaacgc caggggtttc ccagtcacga cgttgtaaaa    8340
cgacggccag tgaattcgag ctcggtaccc ggggatcctc tagagtcgac ctgcaggcat    8400
```

```
gcaagcttgt tgaaacatcc ctgaagtgtc tcattttatt ttatttattc tttgctgata      8460
aaaaaataaa ataaaagaag ctaagcacac ggtcaaccat tgctctactg ctaaaagggt      8520
tatgtgtagt gttttactgc ataaattatg cagcaaacaa gacaactcaa attaaaaaat      8580
ttcctttgct tgtttttttg ttgtctctga cttgactttc ttgtggaagt tggttgtata      8640
aggattggga cacaccattg tccttcttaa tttaattta tttctttgct gataaaaaaa       8700
aaaaatttca tatagtgtta aataataatt tgttaaataa ccaaaaagtc aaatatgttt      8760
actctcgttt aaataattga gagtcgtcca gcaaggctaa acgattgtat agatttatga      8820
caatatttac ttttttatag ataaatgtta tattataata aatttatata catatattat      8880
atgttattta ttatttatta ttatttaaa tccttcaata ttttatcaaa ccaactcata       8940
attttttttt tatctgtaag aagcaataaa attaaataga cccactttaa ggatgatcca      9000
acctttatac agagtaagag agttcaaata gtacccttc atatacatat caactaaaat       9060
attagaaata tcatggatca aaccttataa agacattaaa taagtggata agtataatat      9120
ataaatgggt agtatataat atataaatgg atacaaactt ctctctttat aattgttatg      9180
tctccttaac atcctaatat aatacataag tgggtaatat ataatatata aatggagaca      9240
aacttcttcc attataattg ttatgtcttc ttaacactta tgtctcgttc acaatgctaa      9300
agttagaatt gtttagaaag tcttatagta cacatttgtt tttgtactat ttgaagcatt      9360
ccataagccg tcacgattca gatgatttat aataataaga ggaaatttat catagaacaa      9420
taaggtgcat agatagagtg ttaatatatc ataacatcct tgttttattc atagaagaag      9480
tgagatggag ctcagttatt atactgttac atggtcggat acaatattcc atgctctcca      9540
tgagctctta cacctacatg cattttagtt catacttcat gcacgtggcc atcacagcta      9600
gctgcagcta catatttaca ttttacaaca ccaggagaac tgccctgtta gtgcataaca      9660
atcagaagat ggccgtggct actcgagtta tcgaaccact ttgtacaaga aagctgaacg      9720
agaaacgtaa aatgatataa atatcaatat attaaattag attttgcata aaaaacagac      9780
tacataatac tgtaaaacac aacatatcca gtcactatgg tcgacctgca gactggctgt      9840
gtataaggga gcctgacatt tatattcccc agaacatcag gttaatggcg ttttgatgt       9900 cattttcgcg gtggctgaga tcagccactt cttccccgat aacggagacc ggcacactgg      9960
ccatatcggt ggtcatcatg cgccagcttt catccccgat atgcaccacc gggtaaagtt      10020
cacgggagac tttatctgac agcagacgtg cactggccag ggggatcacc atccgtcgcc      10080
cgggcgtgtc aataatatca ctctgtacat ccacaaacag acgataacgg ctctctcttt      10140
tataggtgta aaccttaaac tgcatttcac cagtccctgt tctcgtcagc aaaagagccg      10200
ttcatttcaa taaccgggc gacctcagcc atccccttcct gattttccgc tttccagcgt      10260
tcggcacgca gacgacgggc ttcattctgc atggttgtgc ttaccagacc ggagatattg      10320
acatcatata tgccttgagc aactgatagc tgtcgctgtc aactgtcact gtaatacgct      10380
gcttcatagc acacctcttt ttgacatact tcgggtatac atatcagtat atattcttat      10440
accgcaaaaa tcagcgcgca aatacgcata ctgttatctg gcttttagta agccggatcc      10500
tctagattac gccccgccct gccactcatc gcagtactgt tgtaattcat taagcattct      10560
gccgacatgg aagccatcac agacggcatg atgaacctga atcgccagcg gcatcagcac      10620
cttgtcgcct tgcgtataat atttgcccat ggtgaaaacg ggggcgaaga agttgtccat      10680
attggccacg tttaaatcaa aactggtgaa actcacccag ggattggctg agacgaaaaa      10740
catattctca ataaacccctt tagggaaata ggccaggttt tcaccgtaac acgccacatc      10800
```

```
ttgcgaatat atgtgtagaa actgccggaa atcgtcgtgg tattcactcc agagcgatga   10860
aaacgtttca gtttgctcat ggaaaacggt gtaacaaggg tgaacactat cccatatcac   10920
cagctcaccg tctttcattg ccatacgaaa ttccggatga gcattcatca ggcgggcaag   10980
aatgtgaata aaggccggat aaaacttgtg cttattttc tttacggtct ttaaaaaggc    11040
cgtaatatcc agctgaacgg tctggttata ggtacattga gcaactgact gaaatgcctc   11100
aaaatgttct ttacgatgcc attgggatat atcaacggtg gtatatccag tgattttttt   11160
ctccatttta gcttccttag ctcctgaaaa tctcgccgga tcctaactca aaatccacac   11220
attatacgag ccggaagcat aaagtgtaaa gcctggggtg cctaatgcgg ccgccatagt   11280
gactggatat gttgtgtttt acagtattat gtagtctgtt ttttatgcaa aatctaattt   11340
aatatattga tatttatatc attttacgtt tctcgttcag ctttttttgta caaacttgtt   11400
tgataaccgg tactagtgtg cacgtcgagc gtgtcctctc caaatgaaat gaacttcctt   11460
atatagagga agggtcttgc gaaggatagt gggattgtgc gtcatccctt acgtcagtgg   11520
agatgtcaca tcaatccact tgctttgaag acgtggttgg aacgtcttct ttttccacga   11580
tgctcctcgt gggtggggt ccatctttgg gaccactgtc ggcagaggca tcttgaatga    11640
tagcctttcc tttatcgcaa tgatggcatt tgtaggagcc accttccttt tctactgtcc   11700
tttcgatgaa gtgacagata gctgggcaat ggaatccgag gaggtttccc gaaattatcc   11760
tttgttgaaa agtctcaata gcccctttggt cttctgagac tgtatctttg acatttttgg   11820
agtagaccag agtgtcgtgc tccaccatgt tgacgaagat tttcttcttg tcattgagtc   11880
gtaaaagact ctgtatgaac tgttcgccag tcttcacggc gagttctgtt agatcctcga   11940
tttgaatctt agactccatg catggcctta gattcagtag gaactacctt tttagagact   12000
ccaatctcta ttacttgcct tggtttatga agcaagcctt gaatcgtcca tactggaata   12060
gtacttctga tcttgagaaa tatgtctttc tctgtgttct tgatgcaatt agtcctgaat   12120
cttttgactg catctttaac cttcttggga aggtatttga tctcctggag attgttactc   12180
gggtagatcg tcttgatgag acctgctgcg taggcctctc taaccatctg tgggtcagca   12240
ttctttctga aattgaagag gctaaccttc tcattatcag tggtgaacat agtgtcgtca   12300
ccttcacctt cgaacttcct tcctagatcg taaagataga ggaaatcgtc cattgtaatc   12360
tccggggcaa aggagatctc tttttgggct ggatcactgc tgggcctttt ggttcctagc   12420
gtgagccagt gggcttttg ctttggtggg cttgttaggg ccttagcaaa gctcttgggc    12480
ttgagttgag cttctccttt ggggatgaag ttcaacctgt ctgtttgctg acttgttgtg   12540
tacgcgtcag ctgctgctct tgcctctgta atagtggcaa atttcttgtg tgcaactccg   12600
ggaacgccgt ttgttgccgc ctttgtacaa ccccagtcat cgtatatacc ggcatgtgga   12660
ccgttataca caacgtagta gttgatatga gggtgttgaa tacccgattc tgctctgaga   12720
ggagcaactg tgctgttaag ctcagatttt tgtgggattg gaattggatc ctctagagca   12780
aagcttggcg taatcatggt catagctgtt tcctgtgtga aattgttatc cgctcacaat   12840
tccacacaac atacgagccg gaagcataaa gtgtaaagcc tggggtgcct aatgagtgag   12900
ctaactcaca ttaattgcgt tgcgctcact gcccgctttc cagtcgggaa acctgtcgtg   12960
ccagctgcat taatgaatcg gccaacgcgc ggggagaggc ggtttgcgta ttgggccaaa   13020
gacaaaaggg cgacattcaa ccgattgagg gagggaaggt aaatattgac ggaaattatt   13080
cattaaaggt gaattatcac cgtcaccgac ttgagccatt tgggaattag agccagcaaa   13140
```

```
atcaccagta gcaccattac cattagcaag gccggaaacg tcaccaatga aaccatcatc   13200
tagtaacata gatgacaccg cgcgcgataa tttatcctag tttgcgcgct atattttgtt   13260
ttctatcgcg tattaaatgt ataattgcgg gactctaatc ataaaaaccc atctcataaa   13320
taacgtcatg cattacatgt taattattac atgcttaacg taattcaaca gaaattatat   13380
gataatcatc gcaagaccgg caacaggatt caatcttaag aaactttatt gccaaatgtt   13440
tgaacgatct gcttcgacgc actccttctt taggtacgga ctagatctcg gtgacgggca   13500
ggaccggacg gggcggtacc ggcaggctga agtccagctg ccagaaaccc acgtcatgcc   13560
agttcccgtg cttgaagccg ccgcccgca gcatgccgcg gggggcatat ccagcgcct    13620 cgtgcatgcg cacgctcggg tcgttgggca gcccgatgac agcgaccacg ctcttgaagc   13680
cctgtgcctc cagggacttc agcaggtggg tgtagagcgt ggagcccagt cccgtccgct   13740
ggtggcgggg ggagacgtac acggtcgact cggccgtcca gtcgtaggcg ttgcgtgcct   13800
tccaggggcc cgcgtaggcg atgccggcga cctcgccgtc cacctcggcg acgagccagg   13860
gatagcgctc ccgcagacgg acgaggtcgt ccgtccactc ctgcggttcc tgcggctcgg   13920
tacggaagtt gaccgtgctt gtctcgatgt agtggttgac gatggtgcag accgccggca   13980
tgtccgcctc ggtggcacgg cggatgtcgg ccgggcgtcg ttctgggctc atggatctgg   14040
attgagagtg aatatgagac tctaattgga taccgagggg aatttatgga acgtcagtgg   14100
agcatttttg acaagaaata tttgctagct gatagtgacc ttaggcgact tttgaacgcg   14160
caataatggt ttctgacgta tgtgcttagc tcattaaact ccagaaaccc gcggctgagt   14220
ggctccttca acgttgcggt tctgtcagtt ccaaacgtaa aacggcttgt cccgcgtcat   14280 cggcggggt cataacgtga ctcccttaat tctccgctca tgatcagatt gtcgtttccc    14340
gccttcagtt taaactatca gtgtttgaca ggatatattg gcgggtaaac ctaagagaaa   14400
agagcgttta ttagaataat cggatattta aagggcgtg aaaaggttta tccgttcgtc    14460
catttgtatg tgcatgccaa ccacagggtt ccccagatct ggcgccggcc agcgagacga   14520
gcaagattgg ccgccgcccg aaacgatccg acagcgcgcc cagcacaggt gcgcaggcaa   14580
attgcaccaa cgcatacagc gccagcagaa tgccatagtg ggcggtgacg tcgttcgagt   14640
gaaccagatc gcgcaggagg cccggcagca ccggcataat caggccgatg ccgacagcgt   14700
cgagcgcgac agtgctcaga attacgatca ggggtatgtt gggtttcacg tctggcctcc   14760
ggaccagcct ccgctggtcc gattgaacgc gcggattctt tatcactgat aagttggtgg   14820
acatattatg tttatcagtg ataaagtgtc aagcatgaca aagttgcagc cgaatacagt   14880
gatccgtgcc gccctggacc tgttgaacga ggtcggcgta gacggtctga cgacacgcaa   14940
actggcggaa cggttggggg ttcagcagcc ggcgctttac tggcacttca ggaacaagcg   15000
ggcgctgctc gacgcactgg ccgaagccat gctggcggag aatcatacgc attcggtgcc   15060
gagagccgac gacgactggc gctcatttct gatcgggaat gcccgcagct tcaggcaggc   15120
gctgctcgcc taccgcgatg gcgcgcgcat ccatgccggc acgcgaccgg gcgcaccgca   15180
gatggaaacg gccgacgcgc agcttcgctt cctctgcgag gcgggttttt cggccgggga   15240
cgccgtcaat gcgctgatga caatcagcta cttcactgtt ggggccgtgc ttgaggagca   15300
ggccggcgac agcgatgccg gcgagcgcgg cggcaccgtt gaacaggctc cgctctcgcc   15360
gctgttgcgg gccgcgatag acgccttcga cgaagccggt ccggacgcag cgttcgagca   15420
gggactcgcg gtgattgtcg atggattggc gaaaaggagg ctcgttgtca ggaacgttga   15480
aggaccgaga aagggtgacg attgatcagg accgctgccg gagcgcaacc cactcactac   15540
```

```
agcagagcca tgtagacaac atccctccc cctttccacc gcgtcagacg cccgtagcag    15600
cccgctacgg gcttttcat gccctgccct agcgtccaag cctcacggcc gcgctcggcc    15660
tctctggcgg ccttctggcg ctcttccgct tcctcgctca ctgactcgct gcgctcggtc    15720
gttcggctgc ggcgagcggt atcagctcac tcaaaggcgg taatacggtt atccacagaa    15780 tcagggata acgcaggaaa gaacatgtga gcaaaaggcc agcaaaaggc caggaaccgt    15840
aaaaaggccg cgttgctggc gtttttccat aggctccgcc cccctgacga gcatcacaaa    15900
aatcgacgct caagtcagag gtggcgaaac ccgacaggac tataaagata ccaggcgttt    15960
ccccctggaa gctccctcgt gcgctctcct gttccgaccc tgccgcttac cggatacctg    16020
tccgcctttc tcccttcggg aagcgtggcg cttttccgct gcataaccct gcttcggggt    16080
cattatagcg attttttcgg tatatccatc ctttttcgca cgatatacag gattttgcca    16140
aagggttcgt gtagactttc cttggtgtat ccaacggcgt cagccgggca ggataggtga    16200
agtaggccca cccgcgagcg ggtgttcctt cttcactgtc ccttattcgc acctggcggt    16260
gctcaacggg aatcctgctc tgcgaggctg gccggctacc gccggcgtaa cagatgaggg    16320
caagcggatg gctgatgaaa ccaagccaac caggaagggc agcccaccta tcaaggtgta    16380
ctgccttcca gacgaacgaa gagcgattga ggaaaaggcg cggcggccg gcatgagcct    16440 gtcggcctac tgctggccg tcggccaggg ctacaaaatc acgggcgtcg tggactatga    16500
gcacgtccgc gagctggccc gcatcaatgg cgacctgggc cgcctgggcg gcctgctgaa    16560
actctggctc accgacgacc gcgcacggc gcggttcggt gatgccacga tcctcgccct    16620
gctggcgaag atcgaagaga agcaggacga gcttggcaag gtcatgatgg gcgtggtccg    16680
cccgagggca gagccatgac ttttttagcc gctaaaacgg ccggggggtg cgcgtgattg    16740
ccaagcacgt cccatgcgc tccatcaaga agagcgactt cgcggagctg gtgaagtaca    16800
tcaccgacga gcaaggcaag accgagcgcc tttgcgacgc tca                      16843
```

<210> SEQ ID NO 5
<211> LENGTH: 9142
<212> TYPE: DNA
<213> ORGANISM: artificial sequence
<220> FEATURE:
<223> OTHER INFORMATION: vector

<400> SEQUENCE: 5

```
ctagttatct gaataaaaga gaaagagatc atccatattt cttatcctaa atgaatgtca      60
cgtgtcttta taattctttg atgaaccaga tgcatttcat taaccaaatc catatacata     120
taaatattaa tcatatataa ttaatatcaa ttgggttagc aaaacaaatc tagtctaggt     180
gtgttttgcg aattcgatat caagcttgat gggtaccggc gcgccgatc atccggatat     240 agttcctcct ttcagcaaaa aacccctcaa gacccgttta gaggccccaa ggggttatgc     300
tagttattgc tcagcggtgg cagcagccaa ctcagcttcc tttcgggctt tgttagcagc     360
cggatcgatc caagctgtac ctcactattc ctttgccctc ggacgagtgc tggggcgtcg     420
gtttccacta tcggcgagta cttctacaca gccatcggtc cagacggccg cgcttctgcg     480
ggcgatttgt gtacgcccga cagtcccggc tccggatcgg acgattgcgt cgcatcgacc     540
ctgcgcccaa gctgcatcat cgaaattgcc gtcaaccaag ctctgataga gttggtcaag     600
accaatgcgg agcatatacg cccggagccg cggcgatcct gcaagctccg gatgcctccg     660
ctcgaagtag cgcgtctgct gctccataca agccaaccac ggcctccaga agaagatgtt     720
```

```
ggcgacctcg tattgggaat ccccgaacat cgcctcgctc cagtcaatga ccgctgttat    780
gcggccattg tccgtcagga cattgttgga gccgaaatcc gcgtgcacga ggtgccggac    840
ttcggggcag tcctcggccc aaagcatcag ctcatcgaga gcctgcgcga cggacgcact    900
gacggtgtcg tccatcacag tttgccagtg atacacatgg ggatcagcaa tcgcgcatat    960
gaaatcacgc catgtagtgt attgaccgat tccttgcggt ccgaatgggc cgaacccgct   1020
cgtctggcta agatcggccg cagcgatcgc atccatagcc tccgcgaccg gctgcagaac   1080
agcgggcagt tcggtttcag gcaggtcttg caacgtgaca ccctgtgcac ggcgggagat   1140
gcaataggtc aggctctcgc tgaattcccc aatgtcaagc acttccggaa tcgggagcgc   1200
ggccgatgca aagtgccgat aaacataacg atctttgtag aaaccatcgg cgcagctatt   1260
tacccgcagg acatatccac gccctcctac atcgaagctg aaagcacgag attcttcgcc   1320
ctccgagagc tgcatcaggt cggagacgct gtcgaacttt tcgatcagaa acttctcgac   1380
agacgtcgcg gtgagttcag gcttttccat gggtatatct ccttcttaaa gttaaacaaa   1440
attatttcta gagggaaacc gttgtggtct ccctatagtg agtcgtatta atttcgcggg   1500
atcgagatct gatcaacctg cattaatgaa tcggccaacg cgcggggaga ggcggtttgc   1560
gtattgggcg ctcttccgct tcctcgctca ctgactcgct gcgctcggtc gttcggctgc   1620
ggcgagcggt atcagctcac tcaaaggcgg taatacggtt atccacagaa tcaggggata   1680
acgcaggaaa gaacatgtga gcaaaaggcc agcaaaaggc caggaaccgt aaaaaggccg   1740
cgttgctggc gtttttccat aggctccgcc cccctgacga gcatcacaaa aatcgacgct   1800
caagtcagag gtggcgaaac ccgacaggac tataaagata ccaggcgttt ccccctggaa   1860
gctccctcgt gcgctctcct gttccgaccc tgccgcttac cggatacctg tccgcctttc   1920
tcccttcggg aagcgtggcg ctttctcaat gctcacgctg taggtatctc agttcggtgt   1980
aggtcgttcg ctccaagctg ggctgtgtgc acgaaccccc cgttcagccc gaccgctgcg   2040
ccttatccgg taactatcgt cttgagtcca acccggtaag acacgactta tcgccactgg   2100
cagcagccac tggtaacagg attagcagag cgaggtatgt aggcggtgct acagagttct   2160
tgaagtggtg gcctaactac ggctacacta aggacagt atttggtatc tgcgctctgc   2220
tgaagccagt taccttcgga aaaagagttg gtagctcttg atccggcaaa caaaccaccg   2280
ctggtagcgg tggttttttt gtttgcaagc agcagattac gcgcagaaaa aaaggatctc   2340
aagaagatcc tttgatcttt tctacggggt ctgacgctca gtggaacgaa aactcacgtt   2400
aagggatttt ggtcatgaca ttaacctata aaaataggcg tatcacgagg cccttttgtc   2460
tcgcgcgttt cggtgatgac ggtgaaaacc tctgacacat gcagctcccg gagacggtca   2520
cagcttgtct gtaagcggat gccgggagca gacaagcccg tcagggcgcg tcagcgggtg   2580
ttggcgggtg tcggggctgg cttaactatg cggcatcaga gcagattgta ctgagagtgc   2640
accatatgga catattgtcg ttagaacgcg gctacaatta atacataacc ttatgtatca   2700
tacacatacg atttaggtga cactatagaa cggcgcgcca agctgggtct agaactagaa   2760
acgtgatgcc acttgttatt gaagtcgatt acagcatcta ttctgtttta ctatttataa   2820
ctttgccatt tctgactttt gaaaactatc tctggatttc ggtatcgctt tgtgaagatc   2880
gagcaaaaga gacgttttgt ggacgcaatg gtccaaatcc gttctacatg aacaaattgg   2940
tcacaatttc cactaaaagt aaataaatgg caagttaaaa aaggaatatg catttactg   3000 attgcctagg tgagctccaa gagaagttga atctacacgt ctaccaaccg ctaaaaaaag   3060
aaaaacattg aatatgtaac ctgattccat tagcttttga cttcttcaac agattctcta   3120
```

-continued

```
cttagatttc taacagaaat attattacta gcacatcatt ttcagtctca ctacagcaaa    3180
aaatccaacg gcacaataca gacaacagga gatatcagac tacagagata gatagatgct    3240
actgcatgta gtaagttaaa taaaaggaaa ataaaatgtc ttgctaccaa aactactaca    3300
gactatgatg ctcaccacag gccaaatcct gcaactagga cagcattatc ttatatatat    3360
tgtacaaaac aagcatcaag gaacatttgg tctaggcaat cagtacctcg ttctaccatc    3420
accctcagtt atcacatcct tgaaggatcc attactggga atcatcggca acacatgctc    3480
ctgatggggc acaatgacat caagaaggta ggggccaggg gtgtccaaca ttctctgaat    3540
tgccgctcta agctcttcct tcttcgtcac tcgcgctgcc ggtatcccac aagcatcagc    3600
aaacttgagc atgtttggga atatctcgct ctcgctagac ggatctccaa gataggtgtg    3660
agctctattg gacttgtaga acctatcctc caactgaacc accatacccca aatgctgatt    3720
gttcaacaac aatatcttaa ctgggagatt ctccactctt atagtggcca actcctgaac    3780
attcatgatg aaactaccat ccccatcaat gtcaaccaca acagcccag ggttagcaac     3840
agcagcacca atagccgcag gcaatccaaa acccatggct ccaagacccc ctgaggtcaa    3900
ccactgcctc ggtctcttgt acttgtaaaa ctgcgcagcc cacatttgat gctgcccaac    3960
cccagtacta acaatagcat ctccattagt caactcatca agaacctcga tagcatgctg    4020
cggagaaatc gcgtcctgga atgtcttgta acccaatgga aacttgtgtt tctgcacatt    4080
aatctcttct ctccaacctc caagatcaaa cttaccctcc actcctttct cctccaaaat    4140
catattaatt cccttcaagg ccaacttcaa atccgcgcaa accgacacgt gcgcctgctt    4200
gttcttccca atctcggcag aatcaatatc aatgtgaaca atcttagccc tactagcaaa    4260
agcctcaagc ttcccagtaa cacggtcatc aaaccttacc ccaaaggcaa gcaacaaatc    4320
actattgtca acagcatagt tagcataaac agtaccatgc atacccagca tctgaaggga    4380
atattcatca ccaataggaa aagttccaag acccattaaa gtgctagcaa cgggaatacc    4440
agtgagttca acaaagcgcc tcaattcagc actggaattc aaactgccac cgccgacgta    4500
gagaacgggc ttttgggcct ccatgatgag tctgacaatg tgttccaatt gggcctcggc    4560
gggggggcctg gcagcctgg cgaggtaacc ggggaggtta acgggctcgt cccaattagg    4620
cacggcgagt tgctgctgaa cgtctttggg aatgtcgatg aggaccggac cggggcggcc    4680
ggaggtggcg acgaagaaag cctcggcgac gacgcggggg atgtcgtcga cgtcgaggat    4740
gaggtagttg tgcttcgtga tggatctgct cacctccacg atcggggttt cttggaaggc    4800
gtcggtgccg atcatccggc gggcgacctg gccggtgatg gcgacgactg ggacgctgtc    4860
cattaaagcg tcggcgaggc cgctcacgag gttggtggcg ccggggccgg aggtggcaat    4920
gcagacgccg gggaggccgg aggaacgcgc gtagccttcg gcggcgaaga cgccgccctg    4980
ctcgtggcgc gggagcacgt tgcggatggc ggcggagcgc gtgagcgcct ggtggatctc    5040
catcgacgca ccgccggggt acgcgaacac cgtcgtcacg ccctgcctct ccagcgcctc    5100
cacaaggatg tccgcgccct tgcgaggttc gccggaggcg aaccgtgaca cgaagggctc    5160
cgtggtcggc gcttccttgg tgaagggcgc cgccgtgggg ggtttggaga tggaacattt    5220
gattttgaga gcgtggttgg gtttggtgag ggtttgatga gagagaggga gggtggatct    5280
agtaatgcgt ttggggaagg tggggtgtga agaggaagaa gagaatcggg tggttctgga    5340
agcggtggcc gccattgtgt tgtgtggcat ggttatactt caaaaactgc acaacaagcc    5400
tagagttagt acctaaacag taaatttaca acagagagca aagacacatg caaaaatttc    5460
```

```
agccataaaa aaagttataa tagaatttaa agcaaaagtt tcattttttta aacatatata  5520 caaacaaact ggatttgaag gaagggatta attcccctgc tcaaagtttg aattcctatt  5580
gtgacctata ctcgaataaa attgaagcct aaggaatgta tgagaaacaa gaaaacaaaa  5640
caaaactaca gacaaacaag tacaattaca aaattcgcta aaattctgta atcaccaaac  5700
cccatctcag tcagcacaag gcccaaggtt tattttgaaa taaaaaaaaa gtgattttat  5760
ttctcataag ctaaaagaaa gaaaggcaat tatgaaatga tttcgactag atctgaaagt  5820
caaacgcgta ttccgcagat attaaagaaa gagtagagtt tcacatggat cctagatgga  5880
cccagttgag gaaaaagcaa ggcaaagcaa accagaagtg caagatccga aattgaacca  5940
cggaatctag gatttggtag agggagaaga aaagtacctt gagaggtaga agagaagaga  6000
agagcagaga gatatatgaa cgagtgtgtc ttggtctcaa ctctgaagcg atacgagttt  6060 agagggagc attgagttcc aatttatagg gaaaccgggt ggcaggggtg agttaatgac  6120
ggaaaagccc ctaagtaacg agattggatt gtgggttaga ttcaaccgtt tgcatccgcg  6180
gcttagattg gggaagtcag agtgaatctc aaccgttgac tgagttgaaa attgaatgta  6240
gcaaccaatt gagccaaccc cagcctttgc cctttgattt tgatttgttt gttgcatact  6300
ttttatttgt cttctggttc tgactctctt tctctcgttt caatgccagg ttgcctactc  6360
ccacaccact cacaagaaga ttctactgtt agtattaaat atttttaat gtattaaatg  6420 atgaatgctt ttgtaaacag aacaagacta tgtctaataa gtgtcttgca acatttttta  6480
agaaattaaa aaaatatat ttattatcaa aatcaaatgt atgaaaaatc atgaataata  6540
taattttata cattttttta aaaatctttt taatttctta attaatatct taaaaataat  6600
gattaatatt taacccaaaa taattagtat gattggtaag gaagatatcc atgttatgtt  6660
tggatgtgag tttgatctag agcaaagctt actagagtcg acctgcagcc cctccaccgc  6720
ggtggcggcc gctctagaga tccgtcaaca tggtggagca cgacactctc gtctactcca  6780
agaatatcaa agatacagtc tcagaagacc aaagggctat tgagactttt caacaaaggg  6840
taatatcggg aaacctcctc ggattccatt gcccagctat ctgtcacttc atcaaaagga  6900
cagtagaaaa ggaaggtggc acctacaaat gccatcattg cgataaagga aaggctatcg  6960
ttcaagatgc ctctgccgac agtggtccca agatggaccc cccacccacg aggagcatcg  7020
tggaaaaaga agacgttcca accacgtctc caaagcaagt ggattgatgt gatgatccta  7080
tgcgtatggt atgacgtgtg ttcaagatga tgacttcaaa cctacctatg acgtatggta  7140
tgacgtgtgt cgactgatga cttagatcca ctcgagcggc tataaatacg tacctacgca  7200
ccctgcgcta ccatccctag agctgcagct tatttttaca acaattacca acaacaacaa  7260
acaacaaaca acattacaat tactatttac aattacagtc gacccatcaa caagtttgta  7320
caaaaaagct gaacgagaaa cgtaaaatga tataaatatc aatatattaa attagatttt  7380
gcataaaaaa cagactacat aatactgtaa aacacaacat atccagtcat attggcggcc  7440
gcattaggca ccccaggctt tacactttat gcttccggct cgtataatgt gtggattttg  7500
agttaggatc cgtcgagatt ttcaggagct aaggaagcta aaatggagaa aaaaatcact  7560
ggatatacca ccgttgatat atcccaatgg catcgtaaag aacattttga ggcatttcag  7620
tcagttgctc aatgtaccta taaccagacc gttcagctgg atattacggc cttttttaaag  7680 accgtaaaga aaaataagca caagttttat ccggccttta ttcacattct tgcccgcctg  7740
atgaatgctc atccggaatt ccgtatggca atgaaagacg gtgagctggt gatatgggat  7800
agtgttcacc cttgttacac cgttttccat gagcaaactg aaacgttttc atcgctctgg  7860
```

| | | | |
|---|---|---|---|
| agtgaatacc | acgacgattt | ccggcagttt | ctacacatat | attcgcaaga tgtggcgtgt | 7920 |
| tacggtgaaa | acctggccta | tttccctaaa | gggtttattg | agaatatgtt tttcgtctca | 7980 |
| gccaatccct | gggtgagttt | caccagtttt | gatttaaacg | tggccaatat ggacaacttc | 8040 |
| ttcgccccg | ttttcaccat | gggcaaatat | tatacgcaag | cgacaaggt gctgatgccg | 8100 |
| ctggcgattc | aggttcatca | tgccgtttgt | gatggcttcc | atgtcggcag aatgcttaat | 8160 |
| gaattacaac | agtactgcga | tgagtggcag | ggcggggcgt | aaagatctgg atccggctta | 8220 |
| ctaaaagcca | gataacagta | tgcgtatttg | cgcgctgatt | tttgcggtat aagaatatat | 8280 |
| actgatatgt | atacccgaag | tatgtcaaaa | agaggtatgc | tatgaagcag cgtattacag | 8340 |
| tgacagttga | cagcgacagc | tatcagttgc | tcaaggcata | tatgatgtca atatctccgg | 8400 |
| tctggtaagc | acaaccatgc | agaatgaagc | ccgtcgtctg | cgtgccgaac gctgaaaagc | 8460 |
| ggaaaatcag | gaagggatgg | ctgaggtcgc | ccggtttatt | gaaatgaacg gctcttttgc | 8520 |
| tgacgagaac | aggggctggt | gaaatgcagt | ttaaggttta | cacctataaa agagagagcc | 8580 |
| gttatcgtct | gtttgtggat | gtacagagtg | atattattga | cacgcccggg cgacggatgg | 8640 |
| tgatccccct | ggccagtgca | cgtctgctgt | cagataaagt | ctcccgtgaa ctttacccgg | 8700 |
| tggtgcatat | cggggatgaa | agctggcgca | tgatgaccac | cgatatggcc agtgtgccgg | 8760 |
| tctccgttat | cggggaagaa | gtggctgatc | tcagccaccg | cgaaaatgac atcaaaaacg | 8820 |
| ccattaacct | gatgttctgg | ggaatataaa | tgtcaggctc | ccttatacac agccagtctg | 8880 |
| caggtcgacc | atagtgactg | gatatgttgt | gttttacagt | attatgtagt ctgtttttta | 8940 |
| tgcaaaatct | aatttaatat | attgatattt | atatcatttt | acgtttctcg ttcagctttc | 9000 |
| ttgtacaaag | tggttgataa | cctagacttg | tccatcttct | ggattggcca acttaattaa | 9060 |
| tgtatgaaat | aaaaggatgc | acacatagtg | acatgctaat | cactataatg tgggcatcaa | 9120 |
| agttgtgtgt | tatgtgtaat | ta | | | 9142 |

<210> SEQ ID NO 6
<211> LENGTH: 49911
<212> TYPE: DNA
<213> ORGANISM: artificial sequence
<220> FEATURE:
<223> OTHER INFORMATION: vector

<400> SEQUENCE: 6

| | | | | | |
|---|---|---|---|---|---|
| gtgcagcgtg | acccggtcgt | gcccctctct | agagataatg | agcattgcat gtctaagtta | 60 |
| taaaaaatta | ccacatattt | tttttgtcac | acttgtttga | agtgcagttt atctatcttt | 120 |
| atacatatat | ttaaacttta | ctctacgaat | aatataatct | atagtactac aataatatca | 180 |
| gtgttttaga | gaatcatata | aatgaacagt | tagacatggt | ctaaaggaca attgagtatt | 240 |
| ttgacaacag | gactctacag | ttttatcttt | ttagtgtgca | tgtgttctcc tttttttttg | 300 |
| caaatagctt | cacctatata | atacttcatc | catttttatta | gtacatccat ttagggttta | 360 |
| gggttaatgg | ttttttataga | ctaattttttt | tagtacatct | attttattct atttttagcct | 420 |
| ctaaattaag | aaaactaaaa | ctctatttta | gttttttttat | ttaataattt agatataaaa | 480 |
| tagaataaaa | taaagtgact | aaaaattaaa | caaatacccct | ttaagaaatt aaaaaaacta | 540 |
| aggaaacatt | tttcttgttt | cgagtagata | atgccagcct | gttaaacgcc gtcgacgagt | 600 |
| ctaacggaca | ccaaccagcg | aaccagcagc | gtcgcgtcgg | ccaagcgaa gcagacggca | 660 |
| cggcatctct | gtcgctgcct | ctggacccct | ctcgagagtt | ccgctccacc gttggacttg | 720 |

```
ctccgctgtc ggcatccaga aattgcgtgg cggagcggca gacgtgagcc ggcacggcag    780
gcggcctcct cctcctctca cggcacggca gctacggggg attcctttcc caccgctcct    840
tcgctttccc ttcctcgccc gccgtaataa atagacaccc cctccacacc ctctttcccc    900
aacctcgtgt tgttcggagc gcacacacac acaaccagat ctcccccaaa tccacccgtc    960
ggcacctccg cttcaaggta cgccgctcgt cctccccccc cccccctctc taccttctct   1020
agatcggcgt tccggtccat ggttagggcc cggtagttct acttctgttc atgtttgtgt   1080
tagatccgtg tttgtgttag atccgtgctg ctagcgttcg tacacggatg cgacctgtac   1140
gtcagacacg ttctgattgc taacttgcca gtgtttctct ttggggaatc ctggatggc    1200
tctagccgtt ccgcagacgg gatcgatttc atgatttttt ttgtttcgtt gcatagggtt   1260
tggtttgccc ttttccttta tttcaatata tgccgtgcac ttgtttgtcg ggtcatcttt   1320
tcatgctttt ttttgtcttg gttgtgatga tgtggtctgg ttgggcggtc gttctagatc   1380
ggagtagaat tctgtttcaa actacctggt ggatttatta attttggatc tgtatgtgtg   1440
tgccatacat attcatagtt acgaattgaa gatgatggat ggaaatatcg atctaggata   1500
ggtatacatg ttgatgcggg ttttactgat gcatatacag agatgctttt tgttcgcttg   1560
gttgtgatga tgtggtgtgg ttgggcggtc gttcattcgt tctagatcgg agtagaatac   1620
tgtttcaaac tacctggtgt atttattaat tttggaactg tatgtgtgtg tcatacatct   1680
tcatagttac gagtttaaga tggatggaaa tatcgatcta ggataggtat acatgttgat   1740
gtgggtttta ctgatgcata tacatgatgg catatgcagc atctattcat atgctctaac   1800
cttgagtacc tatctattat aataaacaag tatgttttat aattattttg atcttgatat   1860
acttggatga tggcatatgc agcagctata tgtggatttt tttagccctg ccttcatacg   1920
ctatttattt gcttggtact gtttcttttg tcgatgctca ccctgttgtt tggtgttact   1980
tctgcaggtc gactctagag gatccacaag tttgtacaaa aaagctgaac gagaaacgta   2040
aaatgatata aatatcaata tattaaatta gattttgcat aaaaaacaga ctacataata   2100
ctgtaaaaca caacatatcc agtcactatg gcggccgcat taggcacccc aggctttaca   2160
ctttatgctt ccggctcgta taatgtgtgg attttgagtt aggatttaaa tacgcgttga   2220
tccggcttac taaaagccag ataacagtat gcgtatttgc gcgctgattt tgcggtata   2280
agaatatata ctgatatgta tacccgaagt atgtcaaaaa gaggtatgct atgaagcagc   2340
gtattacagt gacagttgac agcgacagct atcagttgct caaggcatat atgatgtcaa   2400
tatctccggt ctggtaagca caaccatgca gaatgaagcc cgtcgtctgc gtgccgaacg   2460
ctggaaagcg gaaaatcagg aagggatggc tgaggtcgcc cggtttattg aaatgaacgg   2520
ctcttttgct gacgagaaca ggggctggtg aaatgcagtt taaggtttac acctataaaa   2580
gagagagccg ttatcgtctg tttgtggatg tacagagtga tatcattgac acgcccggtc   2640
gacggatggt gatcccctg gccagtgcac gtctgctgtc agataaagtc tcccgtgaac   2700
tttacccggt ggtgcatatc ggggatgaaa gctggcgcat gatgaccacc gatatggcca   2760
gtgtgccggt ctccgttatc ggggaagaag tggctgatct cagccaccgc gaaaatgaca   2820
tcaaaaacgc cattaacctg atgttctggg aatataaat gtcaggctcc cttatacaca   2880
gccagtctgc aggtcgacca tagtgactgg atatgttgtg ttttacagta ttatgtagtc   2940
tgttttttat gcaaaatcta atttaatata ttgatattta tatcatttta cgtttctcgt   3000
tcagctttct tgtacaaagt ggtgttaacc tagacttgtc catcttctgg attggccaac   3060
ttaattaatg tatgaaataa aaggatgcac acatagtgac atgctaatca ctataatgtg   3120
```

```
ggcatcaaag ttgtgtgtta tgtgtaatta ctagttatct gaataaaaga gaaagagatc    3180
atccatattt cttatcctaa atgaatgtca cgtgtcttta taattctttg atgaaccaga    3240
tgcatttcat taaccaaatc catatacata taaatattaa tcatatataa ttaatatcaa    3300
ttgggttagc aaaacaaatc tagtctaggt gtgttttgcg aattgcggcc gccaccgcgg    3360
tggagctcga attccggtcc gggtcacctt tgtccaccaa gatggaactg cggccgctca    3420
ttaattaagt caggcgcgcc tctagttgaa gacacgttca tgtcttcatc gtaagaagac    3480
actcagtagt cttcggccag aatggccatc tggattcagc aggcctagaa ggccatttaa    3540
atcctgagga tctggtcttc ctaaggaccc gggatatcgg accgattaaa ctttaattcg    3600
gtccgaagct tgcatgcctg cagtgcagcg tgacccggtc gtgcccctct ctagagataa    3660
tgagcattgc atgtctaagt tataaaaaat taccacatat ttttttttgtc acacttgttt    3720 gaagtgcagt ttatctatct ttatacatat atttaaactt tactctacga ataatataat    3780
ctatagtact acaataatat cagtgtttta gagaatcata taaatgaaca gttagacatg    3840
gtctaaagga caattgagta ttttgacaac aggactctac agttttatct ttttagtgtg    3900
catgtgttct ccttttttttt tgcaaatagc ttcacctata taatacttca tccattttat    3960
tagtacatcc atttagggtt tagggttaat ggttttttata gactaatttt tttagtacat    4020
ctattttatt ctatttttagc ctctaaatta agaaaactaa aactctatttt tagttttttt    4080 atttaataat ttagatataa aatagaataa aataaagtga ctaaaaatta aacaaatacc    4140
ctttaagaaa ttaaaaaaac taaggaaaca ttttttcttgt ttcgagtaga taatgccagc    4200
ctgttaaacg ccgtcgacga gtctaacgga caccaaccag cgaaccagca gcgtcgcgtc    4260
gggccaagcg aagcagacgg cacggcatct ctgtcgctgc ctctggaccc ctctcgagag    4320
ttccgctcca ccgttggact tgctccgctg tcggcatcca gaaattgcgt ggcggagcgg    4380
cagacgtgag ccggcacggc aggcggcctc ctcctcctct cacggcaccg gcagctacgg    4440
gggattcctt tcccaccgct ccttcgcttt cccttcctcg cccgccgtaa taaatagaca    4500
ccccctccac accctctttc cccaacctcg tgttgttcgg agcgcacaca cacacaacca    4560
gatctccccc aaatccaccc gtcggcacct ccgcttcaag gtacgccgct cgtcctcccc    4620 ccccccccctc tctaccttct ctagatcggc gttccggtcc atgcatggtt agggcccggt    4680
agttctactt ctgttcatgt ttgtgttaga tccgtgtttg tgttagatcc gtgctgctag    4740
cgttcgtaca cggatgcgac ctgtacgtca gacacgttct gattgctaac ttgccagtgt    4800 ttctcttttgg ggaatcctgg gatggctcta gccgttccgc agacgggatc gatttcatga    4860
ttttttttgt ttcgttgcat agggtttggt ttgccctttt cctttatttc aatatatgcc    4920
gtgcacttgt ttgtcgggtc atctttttcat gcttttttttt gtcttggttg tgatgatgtg    4980
gtctggttgg gcggtcgttc tagatcggag tagaattctg tttcaaacta cctggtggat    5040
ttattaattt tggatctgta tgtgtgtgcc atacatattc atagttacga attgaagatg    5100
atggatggaa atatcgatct aggataggta tacatgttga tgcgggtttt actgatgcat    5160
atacagagat gcttttttgtt cgcttggttg tgatgatgtg gtgtggttgg gcggtcgttc    5220
attcgttcta gatcggagta gaatactgtt tcaaactacc tggtgtattt attaattttg    5280
gaactgtatg tgtgtgtcat acatcttcat agttacgagt ttaagatgga tggaaatatc    5340
gatctaggat aggtatacat gttgatgtgg gttttactga tgcatataca tgatggcata    5400
tgcagcatct attcatatgc tctaaccttg agtacctatc tattataata aacaagtatg    5460
```

```
tttataatt attttgatct tgatatactt ggatgatggc atatgcagca gctatatgtg    5520
gattttttta gccctgcctt catacgctat ttatttgctt ggtactgttt cttttgtcga    5580
tgctcaccct gttgtttggt gttacttctg caggtcgact ttaacttagc ctaggatcca    5640
cacgacacca tgtcccccga gcgccgcccc gtcgagatcc gcccgccac cgccgccgac    5700
atggccgccg tgtgcgacat cgtgaaccac tacatcgaga cctccaccgt gaacttccgc    5760
accgagccgc agaccccgca ggagtggatc gacgacctgg agcgcctcca ggaccgctac    5820
ccgtggctcg tggccgaggt ggagggcgtg gtggccggca tcgcctacgc cggcccgtgg    5880
aaggcccgca acgcctacga ctggaccgtg gagtccaccg tgtacgtgtc ccaccgccac    5940
cagcgcctcg gcctcggctc caccctctac acccacctcc tcaagagcat ggaggcccag    6000
ggcttcaagt ccgtggtggc cgtgatcggc ctcccgaacg acccgtccgt gcgcctccac    6060
gaggccctcg gctacaccgc ccgcggcacc ctccgcgccg ccggctacaa gcacggcggc    6120
tggcacgacg tcggcttctg gcagcgcgac ttcgagctgc cggccccgcc gcgcccggtg    6180
cgcccggtga cgcagatctg agtcgaaacc tagacttgtc catcttctgg attggccaac    6240
ttaattaatg tatgaaataa aaggatgcac acatagtgac atgctaatca ctataatgtg    6300
ggcatcaaag ttgtgtgtta tgtgtaatta ctagttatct gaataaaaga gaagagatc    6360
atccatattt cttatcctaa atgaatgtca cgtgtcttta taattctttg atgaaccaga    6420
tgcatttcat taaccaaatc catatacata taaatattaa tcatatataa ttaatatcaa    6480
ttgggttagc aaaacaaatc tagtctaggt gtgttttgcg aattgcggcc gccaccgcgg    6540
tggagctcga attcattccg attaatcgtg gcctcttgct cttcaggatg aagagctatg    6600
tttaaacgtg caagcgctac tagacaattc agtacattaa aaacgtccgc aatgtgttat    6660
taagttgtct aagcgtcaat ttggtttaca ccacaatata tcctgccacc agccagccaa    6720
cagctccccg accggcagct cggcacaaaa tcaccactcg atacaggcag cccatcagtc    6780
cgggacggc tcagcgggag agccgttgta aggcggcaga cttgtgctcat gttaccgatg    6840
ctattcggaa gaacggcaac taagctgccg ggtttgaaac acggatgatc tcgcggaggg    6900
tagcatgttg attgtaacga tgacagagcg ttgctgcctg tgatcaaata tcatctccct    6960
cgcagagatc cgaattatca gccttcttat tcatttctcg cttaaccgtg acaggctgtc    7020
gatcttgaga actatgccga cataatagga aatcgctgga taaagccgct gaggaagctg    7080
agtggcgcta tttctttaga agtgaacgtt gacgatcgtc gaccgtaccc cgatgaatta    7140
attcggacgt acgttctgaa cacagctgga tacttacttg ggcgattgtc atacatgaca    7200
tcaacaatgt acccgtttgt gtaaccgtct cttggaggtt cgtatgacac tagtggttcc    7260
cctcagcttg cgactagatg ttgaggccta acattttatt agagagcagg ctagttgctt    7320
agatacatga tcttcaggcc gttatctgtc agggcaagcg aaaattggcc atttatgacg    7380
accaatgccc cgcagaagct cccatctttg ccgccataga cgccgcgccc ccttttggg    7440
gtgtagaaca tccttttgcc agatgtggaa aagaagttcg ttgtcccatt gttggcaatg    7500
acgtagtagc cggcgaaagt gcgagaccca tttgcgctat atataagcct acgatttccg    7560
ttgcgactat tgtcgtaatt ggatgaacta ttatcgtagt tgctctcaga gttgtcgtaa    7620
tttgatggac tattgtcgta attgcttatg gagttgtcgt agttgcttgg agaaatgtcg    7680
tagttggatg gggagtagtc atagggaaga cgagcttcat ccactaaaac aattggcagg    7740
tcagcaagtg cctgccccga tgccatcgca agtacgaggc ttagaaccac cttcaacaga    7800
tcgcgcatag tcttccccag ctctctaacg cttgagttaa gccgcgccgc gaagcggcgt    7860
```

```
cggcttgaac gaattgttag acattatttg ccgactacct tggtgatctc gcctttcacg   7920
tagtgaacaa attcttccaa ctgatctgcg cgcgaggcca agcgatcttc ttgtccaaga   7980
taagcctgcc tagcttcaag tatgacgggc tgatactggg ccggcaggcg ctccattgcc   8040
cagtcggcag cgacatcctt cggcgcgatt ttgccggtta ctgcgctgta ccaaatgcgg   8100
gacaacgtaa gcactacatt tcgctcatcg ccagcccagt cgggcggcga gttccatagc   8160
gttaaggttt catttagcgc ctcaaataga tcctgttcag gaaccggatc aaagagttcc   8220
tccgccgctg gacctaccaa ggcaacgcta tgttctcttg cttttgtcag caagatagcc   8280
agatcaatgt cgatcgtggc tggctcgaag atacctgcaa gaatgtcatt gcgctgccat   8340
tctccaaatt gcagttcgcg cttagctgga taacgccacg gaatgatgtc gtcgtgcaca   8400
acaatggtga cttctacagc gcggagaatc tcgctctctc caggggaagc cgaagtttcc   8460
aaaaggtcgt tgatcaaagc tcgccgcgtt gtttcatcaa gccttacagt caccgtaacc   8520
agcaaatcaa tatcactgtg tggcttcagg ccgccatcca ctgcggagcc gtacaaatgt   8580
acggccagca acgtcggttc gagatggcgc tcgatgacgc caactacctc tgatagttga   8640
gtcgatactt cggcgatcac cgcttccctc atgatgttta actcctgaat taagccgcgc   8700
cgcgaagcgg tgtcggcttg aatgaattgt taggcgtcat cctgtgctcc cgagaaccag   8760
taccagtaca tcgctgtttc gttcgagact tgaggtctag ttttatacgt gaacaggtca   8820
atgccgccga gagtaaagcc acattttgcg tacaaattgc aggcaggtac attgttcgtt   8880
tgtgtctcta atcgtatgcc aaggagctgt ctgcttagtg cccactttttt cgcaaattcg   8940 atgagactgt gcgcgactcc tttgcctcgg tgcgtgtgcg acacaacaat gtgttcgata   9000
gaggctagat cgttccatgt tgagttgagt tcaatcttcc cgacaagctc ttggtcgatg   9060
aatgcgccat agcaagcaga gtcttcatca gagtcatcat ccgagatgta atccttccgg   9120 tagggctca cacttctggt agatagttca aagccttggt cggataggtg cacatcgaac   9180
acttcacgaa caatgaaatg gttctcagca tccaatgttt ccgccacctg ctcagggatc   9240
accgaaatct tcatatgacg cctaacgcct ggcacagcgg atcgcaaacc tggcgcggct   9300
tttggcacaa aaggcgtgac aggtttgcga atccgttgct gccacttgtt aacccttttg   9360
ccagatttgg taactataat ttatgttaga ggcgaagtct tgggtaaaaa ctggcctaaa   9420
attgctgggg atttcaggaa agtaaacatc accttccggc tcgatgtcta ttgtagatat   9480
atgtagtgta tctacttgat cgggggatct gctgcctcgc gcgtttcggt gatgacggtg   9540
aaaacctctg acacatgcag ctcccggaga cggtcacagc ttgtctgtaa gcggatgccg   9600
ggagcagaca agcccgtcag ggcgcgtcag cgggtgttgg cgggtgtcgg ggcgcagcca   9660
tgacccagtc acgtagcgat agcggagtgt atactggctt aactatgcgg catcagcaga   9720
gattgtactg agagtgcacc atatgcggtg tgaaataccg cacagatgcg taaggagaaa   9780
ataccgcatc aggcgctctt ccgcttcctc gctcactgac tcgctgcgct cggtcgttcg   9840
gctgcggcga gcggtatcag ctcactcaaa ggcggtaata cggttatcca cagaatcagg   9900
ggataacgca ggaaagaaca tgtgagcaaa aggccagcaa aaggccagga accgtaaaaa   9960
ggccgcgttg ctggcgtttt tccataggct ccgcccccct gacgagcatc acaaaaatcg  10020
acgctcaagt cagaggtggc gaaacccgac aggactataa agataccagg cgtttccccc  10080
tggaagctcc ctcgtgcgct ctcctgttcc gaccctgccg cttaccggat acctgtccgc  10140
ctttctccct tcgggaagcg tggcgctttc tcatagctca cgctgtaggt atctcagttc  10200
```

-continued

```
ggtgtaggtc gttcgctcca agctgggctg tgtgcacgaa ccccccgttc agcccgaccg   10260
ctgcgcctta tccggtaact atcgtcttga gtccaacccg gtaagacacg acttatcgcc   10320
actggcagca gccactggta acaggattag cagagcgagg tatgtaggcg gtgctacaga   10380
gttcttgaag tggtggccta actacggcta cactagaagg acagtatttg gtatctgcgc   10440
tctgctgaag ccagttacct tcggaaaaag agttggtagc tcttgatccg gcaaacaaac   10500
caccgctggt agcggtggtt ttttgtttg caagcagcag attacgcgca gaaaaaaagg   10560
atctcaagaa gatcctttga tcttttctac ggggtctgac gctcagtgga acgaaaactc   10620
acgttaaggg attttggtca tgagattatc aaaaaggatc ttcacctaga tccttttaaa   10680
ttaaaaatga agttttaaat caatctaaag tatatatgag taaacttggt ctgacagtta   10740
ccaatgctta atcagtgagg cacctatctc agcgatctgt ctatttcgtt catccatagt   10800
tgcctgactc cccgtcgtgt agataactac gatacgggag ggcttaccat ctggccccag   10860
tgctgcaatg ataccgcgag acccacgctc accggctcca gatttatcag caataaacca   10920
gccagccgga agggccgagc gcagaagtgg tcctgcaact ttatccgcct ccatccagtc   10980
tattaattgt tgccgggaag ctagagtaag tagttcgcca gttaatagtt tgcgcaacgt   11040
tgttgccatt gctgcagggg gggggggggg ggggacttc cattgttcat tccacggaca   11100
aaaacagaga aaggaaacga cagaggccaa aaagcctcgc tttcagcacc tgtcgtttcc   11160
tttcttttca gagggtattt taaataaaaa cattaagtta tgacgaagaa gaacggaaac   11220
gccttaaacc ggaaaatttt cataaatagc gaaaacccgc gaggtcgccg ccccgtaacc   11280
tacctgtcgg atcaccggaa aggacccgta aagtgataat gattatcatc tacatatcac   11340
aacgtgcgtg gaggccatca aaccacgtca aataatcaat tatgacgcag gtatcgtatt   11400
aattgatctg catcaactta acgtaaaaac aacttcagac aatacaaatc agcgacactg   11460
aatacggggc aacctcatgt cccccccccc cccccccctg caggcatcgt ggtgtcacgc   11520
tcgtcgtttg gtatggcttc attcagctcc ggttcccaac gatcaaggcg agttacatga   11580
tcccccatgt tgtgcaaaaa agcggttagc tccttcggtc ctccgatcgt tgtcagaagt   11640
aagttggccg cagtgttatc actcatggtt atggcagcac tgcataattc tcttactgtc   11700
atgccatccg taagatgctt ttctgtgact ggtgagtact caaccaagtc attctgagaa   11760
tagtgtatgc ggcgaccgag ttgctcttgc ccggcgtcaa cacgggataa taccgcgcca   11820
catagcagaa ctttaaaagt gctcatcatt ggaaaacgtt cttcggggcg aaaactctca   11880
aggatcttac cgctgttgag atccagttcg atgtaaccca ctcgtgcacc caactgatct   11940
tcagcatctt ttactttcac cagcgtttct gggtgagcaa aaacaggaag gcaaaatgcc   12000
gcaaaaaagg gaataaggc gacacggaaa tgttgaatac tcatactctt cctttttcaa   12060
tattattgaa gcatttatca gggttattgt ctcatgagcg gatacatatt tgaatgtatt   12120
tagaaaaata aacaaatagg ggttccgcgc acatttcccc gaaaagtgcc acctgacgtc   12180
taagaaacca ttattatcat gacattaacc tataaaaata ggcgtatcac gaggcccttt   12240
cgtcttcaag aattcggagc ttttgccatt ctcaccggat tcagtcgtca ctcatggtga   12300
tttctcactt gataacctta tttttgacga ggggaaatta ataggttgta ttgatgttgg   12360
acgagtcgga atcgcagacc gataccagga tcttgccatc ctatggaact gcctcggtga   12420
gttttctcct tcattacaga aacggctttt tcaaaaatat ggtattgata atcctgatat   12480
gaataaattg cagtttcatt tgatgctcga tgagttttc taatcagaat tggttaattg   12540
gttgtaacac tggcagagca ttacgctgac ttgacgggac ggcggctttg ttgaataaat   12600
```

```
cgaactttig ctgagttgaa ggatcagatc acgcatcttc ccgacaacgc agaccgttcc   12660
gtggcaaagc aaaagttcaa aatcaccaac tggtccacct acaacaaagc tctcatcaac   12720
cgtggctccc tcactttctg gctggatgat ggggcgattc aggcctggta tgagtcagca   12780
acaccttctt cacgaggcag acctcagcgc cagaaggccg ccagagaggc cgagcgcggc   12840
cgtgaggctt ggacgctagg gcagggcatg aaaaagcccg tagcgggctg ctacgggcgt   12900
ctgacgcggt ggaaagggg agggatgtt gtctacatgg ctctgctgta gtgagtgggt    12960
tgcgctccgg cagcggtcct gatcaatcgt caccctttct cggtccttca acgttcctga   13020
caacgagcct cctttcgcc aatccatcga caatcaccgc gagtccctgc tcgaacgctg    13080
cgtccggacc ggcttcgtcg aaggcgtcta tcgcggcccg caacagcggc gagagcggag   13140
cctgttcaac ggtgccgccg cgctcgccgg catcgctgtc gccggcctgc tcctcaagca   13200
cggccccaac agtgaagtag ctgattgtca tcagcgcatt gacggcgtcc ccggccgaaa   13260
aacccgcctc gcagaggaag cgaagctgcg cgtcggccgt ttccatctgc ggtgcgcccg   13320
gtcgcgtgcc ggcatggatg cgcgcgccat cgcggtaggc gagcagcgcc tgcctgaagc   13380
tgcgggcatt cccgatcaga aatgagcgcc agtcgtcgtc ggctctcggc accgaatgcg   13440
tatgattctc cgccagcatg gcttcggcca gtgcgtcgag cagcgcccgc ttgttcctga   13500
agtgccagta aagcgccggc tgctgaaccc ccaaccgttc cgccagtttg cgtgcgtca    13560 gaccgtctac gccgacctcg ttcaacaggt ccagggcggc acggatcact gtattcggct   13620
gcaactttgt catgcttgac actttatcac tgataaacat aatatgtcca ccaacttatc   13680
agtgataaag aatccgcgcg ttcaatcgga ccagcggagg ctggtccgga ggccagacgt   13740
gaaacccaac ataccctga tcgtaattct gagcactgtc gcgctcgacg ctgtcggcat    13800
cggcctgatt atgccggtgc tgccgggcct cctgcgcgat ctggttcact cgaacgacgt   13860
caccgcccac tatggcattc tgctggcgct gtatgcgttg gtgcaatttg cctgcgcacc   13920
tgtgctgggc gcgctgtcgg atcgtttcgg gcggcggcca atcttgctcg tctcgctggc   13980
cggcgccact gtcgactacg ccatcatggc gacagcgcct ttcctttggg ttctctatat   14040
cgggcggatc gtggccggca tcaccggggc gactggggcg gtagccggcg cttatattgc   14100
cgatatcact gatggcgatg agcgcgcgcg gcacttcggc ttcatgagcg cctgtttcgg   14160
gttcgggatg gtcgcgggac ctgtgctcgg tgggctgatg ggcggtttct ccccccacgc   14220
tccgttcttc gccgcggcag ccttgaacgg cctcaatttc ctgacgggct gtttcctttt   14280
gccggagtcg cacaaaggcg aacgccggcc gttacgccgg gaggctctca acccgctcgc   14340
ttcgttccgg tgggcccggg gcatgaccgt cgtcgccgcc ctgatggcgg tcttcttcat   14400
catgcaactt gtcggacagg tgccggccgc gcttgggtc attttcggcg aggatcgctt    14460
tcactgggac gcgaccacga tcggcatttc gcttgccgca tttggcattc tgcattcact   14520
cgcccaggca atgatcaccg gccctgtagc cgcccggctc ggcgaaaggc gggcactcat   14580
gctcggaatg attgccgacg gcacaggcta catcctgctt gccttcgcga cacggggatg   14640
gatggcgttc ccgatcatgg tcctgcttgc ttcgggtggc atcggaatgc cggcgctgca   14700
agcaatgttg tccaggcagg tggatgagga acgtcagggg cagctgcaag gctcactggc   14760
ggcgctcacc agcctgacct cgatcgtcgg acccctcctc ttcacggcga tctatgcggc   14820
ttctataaca acgtggaacg ggtgggcatg gattgcaggc gctgccctct acttgctctg   14880
cctgccggcg ctgcgtcgcg ggctttggag cggcgcaggg caacgagccg atcgctgatc   14940
```

```
gtggaaacga taggcctatg ccatgcgggt caaggcgact tccggcaagc tatacgcgcc   15000
ctaggagtgc ggttggaacg ttggcccagc cagatactcc cgatcacgag caggacgccg   15060
atgatttgaa gcgcactcag cgtctgatcc aagaacaacc atcctagcaa cacggcggtc   15120
cccgggctga aaagcccag taaggaaaca actgtaggtt cgagtcgcga gatccccgg    15180 aaccaaagga agtaggttaa acccgctccg atcaggccga gccacgccag gccgagaaca   15240
ttggttcctg taggcatcgg gattggcgga tcaaacacta aagctactgg aacgagcaga   15300
agtcctccgg ccgccagttg ccaggcggta aaggtgagca gaggcacggg aggttgccac   15360
ttgcgggtca gcacggttcc gaacgccatg gaaaccgccc ccgccaggcc cgctgcgacg   15420
ccgacaggat ctagcgctgc gtttggtgtc aacaccaaca gcgccacgcc cgcagttccg   15480
caaatagccc ccaggaccgc catcaatcgt atcgggctac ctagcagagc ggcagagatg   15540
aacacgacca tcagcggctg cacagcgcct accgtcgccg cgaccccgcc cggcaggcgg   15600
tagaccgaaa taaacaacaa gctccagaat agcgaaatat taagtgcgcc gaggatgaag   15660
atgcgcatcc accagattcc cgttggaatc tgtcggacga tcatcacgag caataaaccc   15720
gccggcaacg cccgcagcag cataccggcg acccctcggc ctcgctgttc gggctccacg   15780
aaaacgccgg acagatgcgc cttgtgagcg tccttgggc cgtcctcctg tttgaagacc    15840
gacagcccaa tgatctcgcc gtcgatgtag gcgccgaatg ccacggcatc tcgcaaccgt   15900
tcagcgaacg cctccatggg cttttttctcc tcgtgctcgt aaacggaccc gaacatctct   15960
ggagctttct tcagggccga caatcggatc tcgcggaaat cctgcacgtc ggccgctcca   16020
agccgtcgaa tctgagcctt aatcacaatt gtcaatttta atcctctgtt tatcggcagt   16080
tcgtagagcg cgccgtgcgt cccgagcgat actgagcgaa gcaagtgcgt cgagcagtgc   16140
ccgcttgttc ctgaaatgcc agtaaagcgc tggctgctga accccagcc ggaactgacc    16200 ccacaaggcc ctagcgtttg caatgcacca ggtcatcatt gacccaggcg tgttccacca   16260
ggccgctgcc tcgcaactct tcgcaggctt cgccgacctg ctcgcgccac ttcttcacgc   16320
gggtggaatc cgatccgcac atgaggcgga aggtttccag cttgagcggg tacggctccc   16380
ggtgcgagct gaaatagtcg aacatccgtc gggccgtcgg cgacagcttg cggtacttct   16440
cccatatgaa tttcgtgtag tggtcgccag caaacagcac gacgatttcc tcgtcgatca   16500
ggacctggca acgggacgtt ttcttgccac ggtccaggac gcggaagcgg tgcagcagcg   16560
acaccgattc caggtgccca acgcggtcgg acgtgaagcc catcgccgtc gcctgtaggc   16620
gcgacaggca ttcctcggcc ttcgtgtaat accggccatt gatcgaccag cccaggtcct   16680
ggcaaagctc gtagaacgtg aaggtgatcg gctcgccgat aggggtgcgc ttcgcgtact   16740
ccaacacctg ctgccacacc agttcgtcat cgtcggcccg cagctcgacg ccggtgtagg   16800
tgatcttcac gtccttgttg acgtggaaaa tgaccttgtt ttgcagcgcc tcgcgcggga   16860
ttttcttgtt gcgcgtggtg aacagggcag agcgggccgt gtcgtttggc atcgctcgca   16920
tcgtgtccgg ccacggcgca atatcgaaca aggaaagctg catttccttg atctgctgct   16980
tcgtgtgttt cagcaacgcg gcctgcttgg cctcgctgac ctgttttgcc aggtcctcgc   17040
cggcggtttt tcgcttcttg gtcgtcatag ttcctcgcgt gtcgatggtc atcgacttcg   17100
ccaaacctgc cgcctcctgt tcgagacgac gcgaacgctc cacggcggcc gatggcgcgg   17160
gcagggcagg gggagccagt tgcacgctgt cgcgctcgat cttggccgta gcttgctgga   17220
ccatcgagcc gacggactgg aaggtttcgc ggggcgcacg catgacggtg cggcttgcga   17280
tggtttcggc atcctcggcg gaaaacccccg cgtcgatcag ttcttgcctg tatgccttcc   17340
```

```
ggtcaaacgt ccgattcatt caccctcctt gcgggattgc cccgactcac gccggggcaa    17400
tgtgccctta ttcctgattt gacccgcctg gtgccttggt gtccagataa tccaccttat    17460
cggcaatgaa gtcggtcccg tagaccgtct ggccgtcctt ctcgtacttg gtattccgaa    17520
tcttgccctg cacgaatacc agcgacccct gcccaaata cttgccgtgg gcctcggcct    17580
gagagccaaa acacttgatg cggaagaagt cggtgcgctc ctgcttgtcg ccggcatcgt    17640
tgcgccactc ttcattaacc gctatatcga aaattgcttg cggcttgtta gaattgccat    17700
gacgtacctc ggtgtcacgg gtaagattac cgataaactg gaactgatta tggctcatat    17760
cgaaagtctc cttgagaaag gagactctag tttagctaaa cattggttcc gctgtcaaga    17820
actttagcgg ctaaaatttt gcgggccgcg accaaggtg cgaggggcgg cttccgctgt    17880
gtacaaccag atatttttca ccaacatcct tcgtctgctc gatgagcggg gcatgacgaa    17940
acatgagctg tcggagaggg caggggtttc aatttcgttt ttatcagact taaccaacgg    18000
taaggccaac ccctcgttga aggtgatgga ggcattgcc gacgccctgg aaactcccct    18060
acctcttctc ctggagtcca ccgaccttga ccgcgaggca ctcgcggaga ttgcgggtca    18120
tcctttcaag agcagcgtgc cgcccggata cgaacgcatc agtgtggttt tgccgtcaca    18180
taaggcgttt atcgtaaaga aatggggcga cgacacccga aaaagctgc gtggaaggct    18240 ctgacgccaa gggttagggc ttgcacttcc ttctttagcc gctaaaacgg ccccttctct    18300
gcgggccgtc ggctcgcgca tcatatcgac atcctcaacg gaagccgtgc gcgaatggc    18360 atcgggcggg tgcgctttga cagttgtttt ctatcagaac ccctacgtcg tgcggttcga    18420
ttagctgttt gtcttgcagg ctaaacactt tcggtatatc gtttgcctgt gcgataatgt    18480
tgctaatgat ttgttgcgta ggggttactg aaaagtgagc gggaagaag agtttcagac    18540 catcaaggag cgggccaagc gcaagctgga acgcgacatg ggtgcggacc tgttggccgc    18600
gctcaacgac ccgaaaaccg ttgaagtcat gctcaacgcg gacggcaagg tgtggcacga    18660
acgccttggc gagccgatgc ggtacatctg cgacatgcgg cccagccagt cgcaggcgat    18720
tatagaaacg gtggccggat ccacggcaa agaggtcacg cggcattcgc ccatcctgga    18780
aggcgagttc cccttggatg gcagccgctt tgccggccaa ttgccgccgg tcgtggccgc    18840
gccaaccttt gcgatccgca agcgcgcggt cgccatcttc acgctggaac agtacgtcga    18900
ggcgggcatc atgacccgcg agcaaatacga ggtcattaaa agcgccgtcg cggcgcatcg    18960
aaacatcctc gtcattggcg gtactggctc gggcaagacc acgctcgtca acgcgatcat    19020
caatgaaatg gtcgccttca acccgtctga gcgcgtcgtc atcatcgagg acaccggcga    19080
aatccagtgc gccgcagaga acgccgtcca ataccacacc agcatcgacg tctcgatgac    19140
gctgctgctc aagacaacgc tgcgtatgcg ccccgaccgc atcctggtcg gtgaggtacg    19200
tggccccgaa gcccttgatc tgttgatggc ctggaacacc gggcatgaag gaggtgccgc    19260
caccctgcac gcaaacaacc ccaaagcggg cctgagccgg ctcgccatgc ttatcagcat    19320
gcacccggat tcaccgaaac ccattgagcc gctgattggc gaggcggttc atgtggtcgt    19380
ccatatcgcc aggaccccta gcggccgtcg agtgcaagaa attctcgaag ttcttggtta    19440
cgagaacggc cagtacatca ccaaaaccct gtaaggagta tttccaatga caacggctgt    19500
tccgttccgt ctgaccatga atcgcggcat tttgttctac cttgccgtgt tcttcgttct    19560
cgctctcgcg ttatccgcgc atccggcgat ggcctcggaa ggcaccggcg gcagcttgcc    19620
atatgagagc tggctgacga acctgcgcaa ctccgtaacc ggcccggtgg ccttcgcgct    19680
```

```
gtccatcatc ggcatcgtcg tcgccggcgg cgtgctgatc ttcggcggcg aactcaacgc   19740
cttcttccga accctgatct tcctggttct ggtgatggcg ctgctggtcg gcgcgcagaa   19800
cgtgatgagc accttcttcg gtcgtggtgc cgaaatcgcg gccctcggca acggggcgct   19860
gcaccaggtg caagtcgcgg cggcggatgc cgtgcgtgcg gtagcggctg acggctcgc    19920 ctaatcatgg ctctgcgcac gatccccatc cgtcgcgcag gcaaccgaga aacctgttc    19980 atgggtggtg atcgtgaact ggtgatgttc tcgggcctga tggcgtttgc gctgattttc   20040
agcgcccaag agctgcgggc caccgtggtc ggtctgatcc tgtggttcgg ggcgctctat   20100
gcgttccgaa tcatggcgaa ggccgatccg aagatgcggt tcgtgtacct gcgtcaccgc   20160
cggtacaagc cgtattaccc ggcccgctcg accccgttcc gcgagaacac caatagccaa   20220
gggaagcaat accgatgatc caagcaattg cgattgcaat cgcgggcctc ggcgcgcttc   20280
tgttgttcat cctctttgcc cgcatccgcg cggtcgatgc cgaactgaaa ctgaaaaagc   20340
atcgttccaa ggacgccggc ctggccgatc tgctcaacta cgccgctgtc gtcgatgacg   20400
gcgtaatcgt gggcaagaac ggcagcttta tggctgcctg gctgtacaag ggcgatgaca   20460
acgcaagcag caccgaccag cagcgcgaag tagtgtccgc ccgcatcaac caggccctcg   20520
cgggcctggg aagtgggtgg atgatccatg tggacgccgt gcggcgtcct gctccgaact   20580
acgcggagcg gggcctgtcg gcgttccctg accgtctgac ggcagcgatt gaagaagagc   20640
gctcggtctt gccttgctcg tcggtgatgt acttcaccag ctccgcgaag tcgctcttct   20700
tgatggagcg catggggacg tgcttggcaa tcacgcgcac cccccggccg ttttagcggc   20760 taaaaagtc atggctctgc cctcgggcgg accacgccca tcatgacctt gccaagctcg    20820
tcctgcttct cttcgatctt cgccagcagg gcgaggatcg tggcatcacc gaaccgcgcc   20880
gtgcgcgggt cgtcggtgag ccagagtttc agcaggccgc ccaggcggcc caggtcgcca   20940
ttgatgcggg ccagctcgcg gacgtgctca tagtccacga cgcccgtgat tttgtagccc   21000
tggccgacgg ccagcaggta ggccgacagg ctcatgccgg ccgccgccgc cttttcctca   21060
atcgctcttc gttcgtctgg aaggcagtac accttgatag gtgggctgcc cttcctggtt   21120
ggcttggttt catcagccat ccgcttgccc tcatctgtta cgccggcggt agccggccag   21180
cctcgcagag caggattccc gttgagcacc gccaggtgcg aataagggac agtgaagaag   21240
gaacacccgc tcgcgggtgg gcctacttca cctatcctgc ccggctgacg ccgttggata   21300
caccaaggaa agtctacacg aacccttggg caaaatcctg tatatcgtgc gaaaaaggat   21360
ggatataccg aaaaaatcgc tataatgacc ccgaagcagg gttatgcagc ggaaaagcgc   21420
tgcttccctg ctgttttgtg gaatatctac cgactggaaa caggcaaatg caggaaatta   21480
ctgaactgag gggacaggcg agagacgatg ccaaagagct acaccgacga gctggccgag   21540
tgggttgaat cccgcgcggc caagaagcgc cggcgtgatg aggctgcggt tgcgttcctg   21600
gcggtgaggg cggatgtcga ggcggcgtta gcgtccggct atgcgctcgt caccatttgg   21660
gagcacatgc gggaaacggg gaaggtcaag ttctcctacg agacgttccg ctcgcacgcc   21720
aggcggcaca tcaaggccaa gcccgccgat gtgcccgcac cgcaggccaa ggctgcggaa   21780
cccgcgccgg cacccaagac gccggagcca cggcggccga agcagggggg caaggctgaa   21840
aagccggccc ccgctgcggc cccgaccggc ttcaccttca acccaacacc ggacaaaaag   21900
gatctactgt aatggcgaaa attcacatgg ttttgcaggg caagggcggg tcggcaagt    21960 cggccatcgc cgcgatcatt gcgcagtaca agatggacaa ggggcagaca ccttgtgca    22020 tcgacaccga cccggtgaac gcgacgttcg agggctacaa ggccctgaac gtccgccggc   22080
```

```
tgaacatcat ggccggcgac gaaattaact cgcgcaactt cgacaccctg gtcgagctga    22140
ttgcgccgac caaggatgac gtggtgatcg acaacggtgc cagctcgttc gtgcctctgt    22200
cgcattacct catcagcaac caggtgccgg ctctgctgca agaaatgggg catgagctgg    22260
tcatccatac cgtcgtcacc ggcggccagg ctctcctgga cacggtgagc ggcttcgccc    22320
agctcgccag ccagttcccg gccgaagcgc ttttcgtggt ctggctgaac ccgtattggg    22380
ggcctatcga gcatgagggc aagagctttg agcagatgaa ggcgtacacg ccaacaaggg    22440
cccgcgtgtc gtccatcatc cagattccgg ccctcaagga agaaacctac ggccgcgatt    22500
tcagcgacat gctgcaagag cggctgacgt tcgaccaggc gctggccgat gaatcgctca    22560
cgatcatgac gcggcaacgc ctcaagatcg tgcggcgcgg cctgtttgaa cagctcgacg    22620
cggcggccgt gctatgagcg accagattga agagctgatc cgggagattg cggccaagca    22680
cggcatcgcc gtcggccgcg acgacccggt gctgatcctg cataccatca acgcccggct    22740
catgccgac agtgcggcca agcaagagga aatccttgcc gcgttcaagg aagagctgga    22800
agggatcgcc catcgttggg gcgaggacgc caaggccaaa gcggagcgga tgctgaacgc    22860
ggccctggcg gccagcaagg acgcaatggc gaaggtaatg aaggacagcg ccgcgcaggc    22920
ggccgaagcg atccgcaggg aaatcgacga cggccttggc cgccagctcg cggccaaggt    22980
cgcggacgcg cggcgcgtgg cgatgatgaa catgatcgcc ggcggcatgg tgttgttcgc    23040
ggccgccctg gtggtgtggg cctcgttatg aatcgcagag gcgcagatga aaaagcccgg    23100
cgttgccggg ctttgttttt gcgttagctg ggcttgtttg acaggcccaa gctctgactg    23160
cgcccgcgct cgcgctcctg ggcctgtttc ttctcctgct cctgcttgcg catcagggcc    23220
tggtgccgtc gggctgcttc acgcatcgaa tcccagtcgc cggccagctc gggatgctcc    23280
gcgcgcatct tgcgcgtcgc cagttcctcg atcttgggcg cgtgaatgcc catgccttcc    23340
ttgatttcgc gcaccatgtc cagccgcgtg tgcagggtct gcaagcgggc ttgctgttgg    23400
gcctgctgct gctgccaggc ggccttttgta cgcggcaggg acagcaagcc gggggcattg    23460
gactgtagct gctgcaaacg cgcctgctga cggtctacga gctgttctag gcggtcctcg    23520
atgcgctcca cctggtcatg ctttgcctgc acgtagagcg caagggtctg ctggtaggtc    23580
tgctcgatgg gcgcggattc taagagggcc tgctgttccg tctcggcctc ctgggccgcc    23640
tgtagcaaat cctcgccgct gttgccgctg gactgctttta ctgccgggga ctgctgttgc    23700
cctgctcgcg ccgtcgtcgc agttcggctt gcccccactc gattgactgc ttcatttcga    23760
gccgcagcga tgcgatctcg gattgcgtca acggacgggg cagcgcggag gtgtccggct    23820
tctccttggg tgagtcggtc gatgccatag ccaaaggttt ccttccaaaa tgcgtccatt    23880
gctggaccgt gtttctcatt gatgcccgca agcatcttcg gcttgaccgc caggtcaagc    23940
gcgccttcat gggcggtcat gacggacgcc gccatgacct tgccgccgtt gttctcgatg    24000
tagccgcgta atgaggcaat ggtgccgccc atcgtcagcg tgtcatcgac aacgatgtac    24060
ttctggccgg ggatcacctc ccctcgaaa gtcgggttga acgccaggcg atgatctgaa    24120
ccggctccgg ttcgggcgac cttctcccgc tgcacaatgt ccgtttcgac ctcaaggcca    24180
aggcggtcgc ccagaacgac cgccatcatg gccggaatct tgttgttccc cgccgcctcg    24240
acggcgagga ctggaacgat gcggggcttg tcgtcgccga tcagcgtctt gagctgggca    24300
acagtgtcgt ccgaaatcag gcgctcgacc aaattaagcg ccgcttccgc gtcgccctgc    24360
ttcgcagcct ggtattcagg ctcgttggtc aaagaaccaa ggtcgccgtt gcgaaccacc    24420
```

```
ttcgggaagt ctccccacgg tgcgcgctcg gctctgctgt agctgctcaa gacgcctccc   24480
tttttagccg ctaaaactct aacgagtgcg cccgcgactc aacttgacgc tttcggcact   24540
tacctgtgcc ttgccacttg cgtcataggt gatgcttttc gcactcccga tttcaggtac   24600
tttatcgaaa tctgaccggg cgtgcattac aaagttcttc cccacctgtt ggtaaatgct   24660
gccgctatct gcgtggacga tgctgccgtc gtggcgctgc gacttatcgg ccttttgggc   24720
catatagatt ttgtaaatgc caggtttcag ggccccggct ttatctacct tctggttcgt   24780
ccatgcgcct tggttctcgg tctggacaat tctttgccca ttcatgacca ggaggcggtg   24840
tttcattggg tgactcctga cggttgcctc tggtgttaaa cgtgtcctgg tcgcttgccg   24900
gctaaaaaaa agccgacctc ggcagttcga ggccggcttt ccctagagcc gggcgcgtca   24960
aggttgttcc atctatttta gtgaactgcg ttcgatttat cagttacttt cctcccgctt   25020
tgtgtttcct cccactcgtt tccgcgtcta gccgacccct caacatagcg gcctcttctt   25080
gggctgcctt tgcctcttgc cgcgcttcgt cacgctcggc ttgcaccgtc gtaaagcgct   25140
cggcctgcct ggccgcctct tgcgccgcca acttcctttg ctcctggtgg gcctcggcgt   25200
cggcctgcgc cttcgctttc accgctgcca actccgtgcg caaactctcc gcttcgcgcc   25260
tggtggcgtc gcgctcgccg cgaagcgcct gcatttcctg gttggccgcg tccagggtct   25320
tgcggctctc ttctttgaat gcgcgggcgt cctggtgagc gtagtccagc tcggcgcgca   25380
gctcctgcgc tcgacgctcc acctcgtcgg cccgctgcgt cgccagcgcg gccgctgct   25440 cggctcctgc cagggcggtg cgtgcttcgg ccagggcttg ccgctggcgt gcggccagct   25500
cggccgcctc ggcggcctgc tgctctagca atgtaacgcg cgcctgggct tcttccagct   25560
cgcgggcctg cgcctcgaag gcgtcggcca gctcccgcg cacggcttcc aactcgttgc   25620
gctcacgatc ccagccggct tgcgctgcct gcaacgattc attggcaagg gcctgggcgg   25680
cttgccagag ggcggccacg gcctggttgc cggcctgctg caccgcgtcc ggcacctgga   25740
ctgccagcgg ggcggcctgc gccgtgcgct ggcgtcgcca ttcgcgcatg ccggcgctgg   25800
cgtcgttcat gttgacgcgg gcggccttac gcactgcatc cacggtcggg aagttctccc   25860
ggtcgccttg ctcgaacagc tcgtccgcag ccgcaaaaat gcggtcgcgc gtctctttgt   25920
tcagttccat gttggctccg gtaattggta agaataataa tactcttacc taccttatca   25980
gcgcaagagt ttagctgaac agttctcgac ttaacggcag gttttttagc ggctgaaggg   26040
caggcaaaaa aagccccgca cggtcggcgg gggcaaaggg tcagcgggaa ggggattagc   26100
gggcgtcggg cttcttcatg cgtcggggcc gcgcttcttg ggatggagca cgacgaagcg   26160
cgcacgcgca tcgtcctcgg ccctatcggc ccgcgtcgcg gtcaggaact tgtcgcgcgc   26220
taggtcctcc ctggtgggca ccaggggcat gaactcggcc tgctcgatgt aggtccactc   26280
catgaccgca tcgcagtcga ggccgcgttc cttcaccgtc tcttgcaggt cgcggtacgc   26340
ccgctcgttg agcggctggt aacgggccaa ttggtcgtaa atggctgtcg gccatgagcg   26400 gccttttcctg ttgagccagc agccgacgac gaagccggca atgcaggccc ctggcacaac   26460
caggccgacg ccggggggcag gggatggcag cagctcgcca accaggaacc ccgccgcgat   26520
gatgccgatg ccggtcaacc agcccttgaa actatccggc cccgaaacac ccctgcgcat   26580
tgcctggatg ctgcgccgga tagcttgcaa catcaggagc cgtttctttt gttcgtcagt   26640
catggtccgc cctcaccagt tgttcgtatc ggtgtcggac gaactgaaat cgcaagagct   26700
gccggtatcg gtccagccgc tgtccgtgtc gctgctgccg aagcacggcg aggggtccgc   26760
gaacgccgca gacggcgtat ccggccgcag cgcatcgccc agcatggccc cggtcagcga   26820
```

```
gccgccggcc aggtagccca gcatggtgct gttggtcgcc ccggccacca gggccgacgt   26880
gacgaaatcg ccgtcattcc ctctggattg ttcgctgctc ggcggggcag tgcgccgcgc   26940
cggcggcgtc gtggatggct cgggttggct ggcctgcgac ggccggcgaa aggtgcgcag   27000
cagctcgtta tcgaccggct gcggcgtcgg ggccgccgcc ttgcgctgcg gtcggtgttc   27060
cttcttcggc tcgcgcagct tgaacagcat gatcgcggaa accagcagca acgccgcgcc   27120
tacgcctccc gcgatgtaga acagcatcgg attcattctt cggtcctcct tgtagcggaa   27180
ccgttgtctg tgcggcgcgg gtggcccgcg ccgctgtctt tggggatcag ccctcgatga   27240
gcgcgaccag tttcacgtcg gcaaggttcg cctcgaactc ctggccgtcg tcctcgtact   27300
tcaaccaggc atagccttcc gccggcggcc gacggttgag gataaggcgg gcagggcgct   27360
cgtcgtgctc gacctggacg atggcctttt tcagcttgtc cgggtccggc tccttcgcgc   27420
cctttccctt ggcgtcctta ccgtcctggt cgccgtcctc gccgtcctgg ccgtcgccgg   27480
cctccgcgtc acgctcggca tcagtctggc cgttgaaggc atcgacggtg ttgggatcgc   27540
ggcccttctc gtccaggaac tcgcgcagca gcttgaccgt gccgcgcgtg atttcctggg   27600
tgtcgtcgtc aagccacgcc tcgacttcct ccgggcgctt cttgaaggcc gtcaccagct   27660
cgttcaccac ggtcacgtcg cgcacgcggc cggtgttgaa cgcatcggcg atcttctccg   27720
gcaggtccag cagcgtgacg tgctgggtga tgaacgccgg cgacttgccg atttccttgg   27780
cgatatcgcc tttcttcttg cccttcgcca gctcgcggcc aatgaagtcg gcaatttcgc   27840
gcggggtcag ctcgttgcgt tgcaggttct cgataacctg gtcggcttcg ttgtagtcgt   27900
tgtcgatgaa cgccgggatg gacttcttgc cggcccactt cgagccacgg tagcggcggg   27960
cgccgtgatt gatgatatag cggcccggct gctcctggtt ctcgcgcacc gaaatgggtg   28020
acttcacccc gcgctctttg atcgtggcac cgatttccgc gatgctctcc ggggaaaagc   28080
cggggttgtc ggccgtccgc ggctgatgcg gatcttcgtc gatcaggtcc aggtccagct   28140
cgatagggcc ggaaccgccc tgagacgccg caggagcgtc caggaggctc gacaggtcgc   28200
cgatgctatc caaccccagg ccggacggct gcgccgcgcc tgcggcttcc tgagcggccg   28260
cagcggtgtt tttcttggtg gtcttggctt gagccgcagt cattgggaaa tctccatctt   28320
cgtgaacacg taatcagcca gggcgcgaac ctctttcgat gccttgcgcg cggccgtttt   28380
cttgatcttc cagaccggca caccggatgc gagggcatcg gcgatgctgc tgcgcaggcc   28440
aacggtggcc ggaatcatca tcttggggta cgcgccagc agctcggctt ggtggcgcgc   28500
gtggcgcgga ttccgcgcat cgaccttgct gggcaccatg ccaaggaatt gcagcttggc   28560
gttcttctgg cgcacgttcg caatggtcgt gaccatcttc ttgatgccct ggatgctgta   28620
cgcctcaagc tcgatggggg acagcacata gtcggccgcg aagagggcgg ccgccaggcc   28680
gacgccaagg gtcggggccg tgtcgatcag gcacacgtcg aagccttggt tcgccagggc   28740
cttgatgttc gccccgaaca gctcgcgggc gtcgtccagc gacagccgtt cggcgttcgc   28800
cagtaccggg ttggactcga tgagggcgag gcgcgcggcc tggccgtcgc cggctgcggg   28860
tgcggtttcg gtccagccgc cggcaggcac agcgccgaac agcttgcttg catgcaggcc   28920
ggtagcaaag tccttgagcg tgtaggacgc attgccctgg gggtccaggt cgatcacggc   28980
aacccgcaag ccgcgctcga aaagtcgaa ggcaagatgc acaagggtcg aagtcttgcc   29040
gacgccgcct ttctgttgg ccgtgaccaa agttttcatc gtttggtttc ctgttttttc   29100
ttggcgtccg cttcccactt ccggacgatg tacgcctgat gttccggcag aaccgccgtt   29160
```

-continued

```
acccgcgcgt accccctcggg caagttcttg tcctcgaacg cggcccacac gcgatgcacc    29220
gcttgcgaca ctgcgcccct ggtcagtccc agcgacgttg cgaacgtcgc ctgtggcttc    29280
ccatcgacta agacgccccg cgctatctcg atggtctgct gccccacttc cagcccctgg    29340
atcgcctcct ggaactggct ttcggtaagc cgtttcttca tggataacac ccataatttg    29400
ctccgcgcct tggttgaaca tagcggtgac agccgccagc acatgagaga agtttagcta    29460
aacatttctc gcacgtcaac acctttagcc gctaaaactc gtccttggcg taacaaaaca    29520
aaagcccgga aaccgggctt tcgtctcttg ccgcttatgg ctctgcaccc ggctccatca    29580
ccaacaggtc gcgcacgcgc ttcactcggt tgcggatcga cactgccagc caacaaagc     29640
cggttgccgc cgccgccagg atcgcgccga tgatgccggc cacaccggcc atcgcccacc    29700
aggtcgccgc cttccggttc cattcctgct ggtactgctt cgcaatgctg gacctcggct    29760
caccataggc tgaccgctcg atggcgtatg ccgcttctcc ccttggcgta aaacccagcg    29820
ccgcaggcgg cattgccatg ctgcccgccg ctttcccgac cacgacgcgc gcaccaggct    29880
tgcggtccag accttcggcc acggcgagct gcgcaaggac ataatcagcc gccgacttgg    29940
ctccacgcgc ctcgatcagc tcttgcactc gcgcgaaatc cttggcctcc acggccgcca    30000
tgaatcgcgc acgcggcgaa ggctccgcag ggccggcgtc gtgatcgccg ccgagaatgc    30060
ccttcaccaa gttcgacgac acgaaaatca tgctgacggc tatcaccatc atgcagacgg    30120
atcgcacgaa cccgctgaat tgaacacgag cacggcaccc gcgaccacta tgccaagaat    30180
gcccaaggta aaaattgccg gccccgccat gaagtccgtg aatgccccga cggccgaagt    30240
gaagggcagg ccgccaccca ggccgccgcc ctcactgccc ggcacctggt cgctgaatgt    30300
cgatgccagc acctgcggca cgtcaatgct tccgggcgtc gcgctcgggc tgatcgccca    30360
tcccgttact gccccgatcc cggcaatggc aaggactgcc agcgctgcca ttttgggt     30420
gaggccgttc gcggccgagg ggcgcagccc ctgggggat gggaggcccg cgttagcggg     30480
ccgggagggt tcgagaaggg ggggcacccc ccttcggcgt gcgcggtcac gcgcacaggg    30540
cgcagccctg gttaaaaaca aggtttataa atattggttt aaaagcaggt taaaagacag    30600
gttagcggtg gccgaaaaac gggcggaaac ccttgcaaat gctggatttt ctgcctgtgg    30660
acagcccctc aaatgtcaat aggtgcgccc ctcatctgtc agcactctgc ccctcaagtg    30720
tcaaggatcg cgcccctcat ctgtcagtag tcgcgcccct caagtgtcaa taccgcaggg    30780
cacttatccc caggcttgtc cacatcatct gtgggaaact cgcgtaaaat caggcgtttt    30840
cgccgatttg cgaggctggc cagctccacg tcgccggccg aaatcgagcc tgcccctcat    30900
ctgtcaacgc cgcgccgggt gagtcggccc ctcaagtgtc aacgtccgcc cctcatctgt    30960
cagtgagggc caagttttcc gcgaggtatc cacaacgccg cggccgcgg tgtctcgcac     31020
acggcttcga cggcgtttct ggcgcgtttg cagggccata gacggccgcc agcccagcgg    31080
cgagggcaac cagcccggtg agcgtcggaa aggcgctgga agcccccgtag cgacgcggag    31140
aggggcgaga caagccaagg gcgcaggctc gatgcgcagc acgacatagc cggttctcgc    31200
aaggacgaga atttccctgc ggtgcccctc aagtgtcaat gaaagtttcc aacgcgagcc    31260
attcgcgaga gccttgagtc cacgctagat gagagctttt tgtaggtgg accagttggt     31320
gattttgaac ttttgctttg ccacggaacg gtctgcgttg tcgggaagat gcgtgatctg    31380
atccttcaac tcagcaaaag ttcgatttat tcaacaaagc cacgttgtgt ctcaaaatct    31440
ctgatgttac attgcacaag ataaaaatat atcatcatga acaataaaac tgtctgctta    31500
cataaacagt aatacaaggg gtgttatgag ccatattcaa cgggaaacgt cttgctcgac    31560
```

```
tctagagctc gttcctcgag gaacggtacc tgcggggaag cttacaataa tgtgtgttgt    31620
taagtcttgt tgcctgtcat cgtctgactg actttcgtca taaatcccgg cctccgtaac    31680
ccagctttgg gcaagctcac ggatttgatc cggcggaacg ggaatatcga gatgccgggc    31740
tgaacgctgc agttccagct ttcccttcg ggacaggtac tccagctgat tgattatctg     31800
ctgaagggtc ttggttccac ctcctggcac aatgcgaatg attacttgag cgcgatcggg    31860
catccaattt tctcccgtca ggtgcgtggt caagtgctac aaggcacctt tcagtaacga    31920
gcgaccgtcg atccgtcgcc gggatacgga caaaatggag cgcagtagtc catcgagggc    31980
ggcgaaagcc tcgccaaaag caatacgttc atctcgcaca gcctccagat ccgatcgagg    32040
gtcttcggcg taggcagata gaagcatgga tacattgctt gagagtattc cgatggactg    32100
aagtatggct tccatctttt ctcgtgtgtc tgcatctatt tcgagaaagc ccccgatgcg    32160
gcgcaccgca acgcgaattg ccatactatc cgaaagtccc agcaggcgcg cttgatagga    32220
aaaggtttca tactcggccg atcgcagacg ggcactcacg accttgaacc cttcaacttt    32280
cagggatcga tgctggttga tggtagtctc actcgacgtg gctctggtgt gttttgacat    32340
agcttcctcc aaagaaagcg gaaggtctgg atactccagc acgaaatgtg cccggggtaga   32400 cggatggaag tctagccctg ctcaatatga aatcaacagt acatttacag tcaatactga    32460
atatacttgc tacatttgca attgtcttat aacgaatgtg aaataaaaat agtgtaacaa    32520
cgcttttact catcgataat cacaaaaaca tttatacgaa caaaaataca aatgcactcc    32580
ggtttcacag gataggcggg atcagaatat gcaactttg acgttttgtt ctttcaaagg     32640
gggtgctggc aaaaccaccg cactcatggg cctttgcgct gctttggcaa atgacggtaa    32700
acgagtggcc ctctttgatg ccgacgaaaa ccggcctctg acgcgatgga gagaaaacgc    32760
cttacaaagc agtactggga tcctcgctgt gaagtctatt ccgccgacga aatgccccctt   32820 cttgaagcag cctatgaaaa tgccgagctc gaaggatttg attatgcgtt ggccgatacg    32880
cgtggcggct cgagcgagct caacaacaca atcatcgcta gctcaaacct gcttctgatc    32940
cccaccatgc taacgccgct cgacatcgat gaggcactat ctacctaccg ctacgtcatc    33000
gagctgctgt tgagtgaaaa tttggcaatt cctacagctg ttttgcgcca acgcgtcccg    33060
gtcggccgat tgacaacatc gcaacgcagg atgtcagaga cgctagagag ccttccagtt    33120
gtaccgtctc ccatgcatga aagagatgca tttgccgcga tgaaagaacg cggcatgttg    33180
catcttacat tactaaacac gggaactgat ccgacgatgc gcctcataga gaggaatctt    33240
cggattgcga tggaggaagt cgtggtcatt tcgaaactga tcagcaaaat cttggaggct    33300
tgaagatggc aattcgcaag cccgcattgt cggtcggcga agcacggcgg cttgctggtg    33360
ctcgacccga gatccaccat cccaacccga cacttgttcc ccagaagctg gacctccagc    33420
acttgcctga aaaagccgac gagaaagacc agcaacgtga gcctctcgtc gccgatcaca    33480
tttacagtcc cgatcgacaa cttaagctaa ctgtggatgc ccttagtcca cctccgtccc    33540
cgaaaaagct ccaggttttt cttcagcgc gaccgcccgc gcctcaagtg tcgaaaacat     33600
atgacaacct cgttcggcaa tacagtccct cgaagtcgct acaaatgatt ttaaggcgcg    33660
cgttggacga tttcgaaagc atgctggcag atggatcatt tcgcgtggcc ccgaaaagtt    33720
atccgatccc ttcaactaca gaaaaatccg ttctcgttca gacctcacgc atgttcccgg    33780
ttgcgttgct cgaggtcgct cgaagtcatt ttgatccgtt ggggttggag accgctcgag    33840
cttcggccca caagctggct accgccgcgc tcgcgtcatt ctttgctgga gagaagccat    33900
```

```
cgagcaattg gtgaagaggg acctatcgga accccteace aaatattgag tgtaggtttg   33960
aggccgctgg ccgcgtcctc agtcacettt tgagccagat aattaagagc caaatgcaat   34020
tggctcaggc tgccatcgtc cccccgtgcg aaacctgcac gtccgcgtca agaaataac    34080
cggcacctct tgctgttttt atcagttgag ggcttgacgg atccgcctca agtttgcggc   34140
gcagccgcaa aatgagaaca tctatactcc tgtcgtaaac ctcctcgtcg cgtactcgac   34200
tggcaatgag aagttgctcg cgcgatagaa cgtcgcgggg tttctctaaa acgcgagga    34260
gaagattgaa ctcacctgcc gtaagtttca cctcaccgcc agcttcggac atcaagcgac   34320
gttgcctgag attaagtgtc cagtcagtaa aacaaaaaga ccgtcggtct ttggagcgga   34380
caacgttggg gcgcacgcgc aaggcaaccc gaatgcgtgc aagaaactct ctcgtactaa   34440
acggcttagc gataaaatca cttgctccta gctcgagtgc aacaacttta tccgtctcct   34500
caaggcggtc gccactgata attatgattg gaatatcaga cttttgccgcc agatttcgaa   34560
cgatctcaag cccatcttca cgacctaaat ttagatcaac aaccacgaca tcgaccgtcg   34620
cggaagagag tactctagtg aactgggtgc tgtcggctac cgcggtcact ttgaaggcgt   34680
ggatcgtaag gtattcgata ataagatgcc gcatagcgac atcgtcatcg ataagaagaa   34740
cgtgtttcaa cggctcacct ttcaatctaa aatctgaacc cttgttcaca gcgcttgaga   34800
aattttcacg tgaaggatgt acaatcatct ccagctaaat gggcagttcg tcagaattgc   34860
ggctgaccgc ggatgacgaa aatgcgaacc aagtatttca attttatgac aaaagttctc   34920
aatcgttgtt acaagtgaaa cgcttcgagg ttacagctac tattgattaa ggagatcgcc   34980
tatggtctcg ccccggcgtc gtgcgtccgc cgcgagccag atctcgccta cttcataaac   35040
gtcctcatag gcacggaatg gaatgatgac atcgatcgcc gtagagagca tgtcaatcag   35100
tgtgcgatct tccaagctag caccttgggc gctactttg acaagggaaa acagtttctt    35160
gaatccttgg attggattcg cgccgtgtat tgttgaaatc gatcccggat gtcccgagac   35220
gacttcactc agataagccc atgctgcatc gtcgcgcatc tcgccaagca atatccggtc   35280
cggccgcata cgcagacttg cttggagcaa gtgctcggcg ctcacagcac ccagcccagc   35340
accgttcttg gagtagagta gtctaacatg attatcgtgt ggaatgacga gttcgagcgt   35400
atcttctatg gtgattagcc ttcctgggg ggggatggcg ctgatcaagg tcttgctcat    35460
tgttgtcttg ccgcttccgg tagggccaca tagcaacatc gtcagtcggc tgacgacgca   35520
tgcgtgcaga aacgcttcca aatccccgtt gtcaaaatgc tgaaggatag cttcatcatc   35580
ctgattttgg cgtttccttc gtgtctgcca ctggttccac ctcgaagcat cataacggga   35640
ggagacttct ttaagaccag aaacacgcga gcttggccgt cgaatggtca agctgacggt   35700
gcccgaggga acggtcggcg gcagacagat ttgtagtcgt tcaccaccag gaagttcagt   35760
ggcgcagagg gggttacgtg gtccgacatc ctgctttctc agcgcgcccg ctaaaatagc   35820
gatatcttca agatcatcat aagagacggg caaaggcatc ttggtaaaaa tgccggcttg   35880
gcgcacaaat gcctctccag gtcgattgat cgcaatttct tcagtcttcg ggtcatcgag   35940
ccattccaaa atcggcttca gaagaaagcg tagttgcgga tccacttcca tttacaatgt   36000
atcctatctc taagcggaaa tttgaattca ttaagagcgg cggttcctcc ccgcgtggc    36060
gccgccagtc aggcggagct ggtaaacacc aaagaaatcg aggtcccgtg ctacgaaaat   36120
ggaaacggtg tcaccctgat tcttcttcag ggttggcggt atgttgatgg ttgccttaag   36180
ggctgtctca gttgtctgct caccgttatt ttgaaagctg ttgaagctca tcccgccacc   36240
cgagctgccg gcgtaggtgc tagctgcctg gaaggcgcct tgaacaacac tcaagagcat   36300
```

```
agctccgcta aaacgctgcc agaagtggct gtcgaccgag cccggcaatc ctgagcgacc   36360
gagttcgtcc gcgcttggcg atgttaacga gatcatcgca tggtcaggtg tctcggcgcg   36420
atcccacaac acaaaaacgc gcccatctcc ctgttgcaag ccacgctgta tttcgccaac   36480
aacggtggtg ccacgatcaa gaagcacgat attgttcgtt gttccacgaa tatcctgagg   36540
caagacacac tttacatagc ctgccaaatt tgtgtcgatt gcggtttgca agatgcacgg   36600
aattattgtc ccttgcgtta ccataaaatc ggggtgcggc aagagcgtgg cgctgctggg   36660
ctgcagctcg gtgggtttca tacgtatcga caaatcgttc tcgccggaca cttcgccatt   36720
cggcaaggag ttgtcgtcac gcttgccttc ttgtcttcgg cccgtgtcgc cctgaatggc   36780
gcgtttgctg accccttgat cgccgctgct atatgcaaaa atcggtgttt cttccggccg   36840
tggctcatgc cgctccggtt cgcccctcgg cggtagagga gcagcaggct gaacagcctc   36900
ttgaaccgct ggaggatccg gcggcacctc aatcggagct ggatgaaatg gcttggtgtt   36960
tgttgcgatc aaagttgacg gcgatgcgtt ctcattcacc ttcttttggc gcccacctag   37020
ccaaatgagg cttaatgata acgcgagaac gacacctccg acgatcaatt tctgagaccc   37080
cgaaagacgc cggcgatgtt tgtcggagac cagggatcca gatgcatcaa cctcatgtgc   37140
cgcttgctga ctatcgttat tcatcccttc gcccccttca ggacgcgttt cacatcgggc   37200 ctaccgtgc ccgtttgcgg cctttggcca acgggatcgt aagcggtgtt ccagatacat   37260
agtactgtgt ggccatccct cagacgccaa cctcgggaaa ccgaagaaat ctcgacatcg   37320
ctccctttaa ctgaatagtt ggcaacagct tccttgccat caggattgat ggtgtagatg   37380
gagggtatgc gtacattgcc cggaaagtgg aataccgtcg taaatccatt gtcgaagact   37440
tcgagtggca acagcgaacg atcgccttgg gcgacgtagt gccaattact gtccgccgca   37500
ccaagggctg tgacaggctg atccaataaa ttctcagctt tccgttgata ttgtgcttcc   37560
gcgtgtagtc tgtccacaac agccttctgt tgtgcctccc ttcgccgagc cgccgcatcg   37620 tcggcgggt aggcgaattg gacgctgtaa tagagatcgg gctgctcttt atcgaggtgg   37680
gacagagtct tggaacttat actgaaaaca taacggcgca tcccggagtc gcttgcggtt   37740
agcacgatta ctggctgagg cgtgaggacc tggcttgcct tgaaaaatag ataatttccc   37800
cgcggtaggg ctgctagatc tttgctattt gaaacggcaa ccgctgtcac cgtttcgttc   37860
gtggcgaatg ttacgaccaa agtagctcca accgccgtcg agaggcgcac cacttgatcg   37920
ggattgtaag ccaaataacg catgcgcgga tctagcttgc ccgccattgg agtgtcttca   37980
gcctccgcac cagtcgcagc ggcaaataaa catgctaaaa tgaaaagtgc ttttctgatc   38040
atggttcgct gtggcctacg tttgaaacgg tatcttccga tgtctgatag gaggtgacaa   38100
ccagacctgc cgggttggtt agtctcaatc tgccgggcaa gctggtcacc tttcgtagc   38160 gaactgtcgc ggtccacgta ctcaccacag gcatttgcc gtcaacgacg agggtccttt   38220
tatagcgaat tgctgcgtg cttggagtta catcatttga agcgatgtgc tcgacctcca   38280
ccctgccgcg tttgccaaga atgacttgag gcgaactggg attgggatag ttgaagaatt   38340
gctggtaatc ctggcgcact gttggggcac tgaagttcga taccaggtcg taggcgtact   38400
gagcggtgtc ggcatcataa ctctcgcgca ggcgaacgta ctcccacaat gaggcgttaa   38460
cgacggcctc ctcttgagtt gcaggcaatc gcgagacaga cacctcgctg tcaacggtgc   38520
cgtccggccg tatccataga tatacgggca caagcctgct caacggcacc attgtggcta   38580
tagcgaacgc ttgagcaaca tttcccaaaa tcgcgatagc tgcgacagct gcaatgagtt   38640
```

```
tggagagacg tcgcgccgat ttcgctcgcg cggtttgaaa ggcttctact tccttatagt    38700
gctcggcaag gctttcgcgc gccactagca tggcatattc aggccccgtc atagcgtcca    38760
cccgaattgc cgagctgaag atctgacgga gtaggctgcc atcgcccac  attcagcggg    38820 aagatcgggc ctttgcagct cgctaatgtg tcgtttgtct ggcagccgct caaagcgaca    38880
actaggcaca gcaggcaata cttcatagaa ttctccattg aggcgaattt ttgcgcgacc    38940
tagcctcgct caacctgagc gaagcgacgg tacaagctgc tggcagattg ggttgcgccg    39000
ctccagtaac tgcctccaat gttgccggcg atcgccggca aagcgacaat gagcgcatcc    39060
cctgtcagaa aaacatatc  gagttcgtaa agaccaatga tcttggccgc ggtcgtaccg    39120
gcgaaggtga ttacaccaag cataagggtg agcgcagtcg cttcggttag gatgacgatc    39180
gttgccacga ggtttaagag gagaagcaag agaccgtagg tgataagttg cccgatccac    39240
ttagctgcga tgtcccgcgt gcgatcaaaa atatatccga cgaggatcag aggcccgatc    39300
gcgagaagca ctttcgtgag aattccaacg gcgtcgtaaa ctccgaaggc agaccagagc    39360
gtgccgtaaa ggacccactg tgccccttgg aaagcaagga tgtcctggtc gttcatcgga    39420
ccgatttcgg atgcgatttt ctgaaaaacg gcctgggtca cggcgaacat tgtatccaac    39480
tgtgccggaa cagtctgcag aggcaagccg gttacactaa actgctgaac aaagtttggg    39540
accgtctttt cgaagatgga aaccacatag tcttggtagt tagcctgccc aacaattaga    39600
gcaacaacga tggtgaccgt gatcacccga gtgataccgc tacgggtatc gacttcgccg    39660
cgtatgacta aaatacccctg aacaataatc caaagagtga cacaggcgat caatggcgca    39720
ctcaccgcct cctggatagt ctcaagcatc gagtccaagc ctgtcgtgaa ggctacatcg    39780
aagatcgtat gaatggccgt aaacggcgcc ggaatcgtga aattcatcga ttggacctga    39840
acttgactgg tttgtcgcat aatgttggat aaaatgagct cgcattcggc gaggatgcgg    39900
gcggatgaac aaatcgccca gccttagggg agggcaccaa agatgacagc ggtcttttga    39960
tgctccttgc gttgagcggc cgcctcttcc gcctcgtgaa ggccggcctg cgcggtagtc    40020
atcgttaata ggcttgtcgc ctgtacattt tgaatcattg cgtcatggat ctgcttgaga    40080
agcaaaccat tggtcacggt tgcctgcatg atattgcgag atcgggaaag ctgagcagac    40140
gtatcagcat tcgccgtcaa gcgtttgtcc atcgtttcca gattgtcagc cgcaatgcca    40200
gcgctgtttg cggaaccggt gatctgcgat cgcaacaggt ccgcttcagc atcactaccc    40260
acgactgcac gatctgtatc gctggtgatc gcacgtgccg tggtcgacat tggcattcgc    40320
ggcgaaaaca tttcattgtc taggtccttc gtcgaaggat actgattttt ctggttgagc    40380
gaagtcagta gtccagtaac gccgtaggcc gacgtcaaca tcgtaaccat cgctatagtc    40440
tgagtgagat tctccgcagt cgcgagcgca gtcgcgagcg tctcagcctc cgttgccggg    40500
tcgctaacaa caaactgcgc ccgcgcgggc tgaatatata gaaagctgca ggtcaaaact    40560
gttgcaataa gttgcgtcgt cttcatcgtt tcctaccttaa tcaatcttct gcctcgtggt    40620
gacgggccat gaattcgctg agccagccag atgagttgcc ttcttgtgcc tcgcgtagtc    40680
gagttgcaaa gcgcaccgtg ttggcacgcc ccgaaagcac ggcgacatat tcacgcatat    40740
cccgcagatc aaattcgcag atgacgcttc cactttctcg tttaagaaga aacttacggc    40800
tgccgaccgt catgtcttca cggatcgcct gaaattcctt ttcggtacat ttcagtccat    40860
cgacataagc cgatcgatct gcggttggtg atggatagaa aatcttcgtc atacattgcg    40920
caaccaagct ggctcctagc ggcgattcca gaacatgctc tggttgctgc gttgccagta    40980
ttagcatccc gttgtttttt cgaacggtca ggaggaattt gtcgacgaca gtcgaaaatt    41040
```

```
tagggtttaa caaataggcg cgaaactcat cgcagctcat cacaaaacgg cggccgtcga   41100
tcatggctcc aatccgatgc aggagatatg ctgcagcggg agcgcatact tcctcgtatt   41160
cgagaagatg cgtcatgtcg aagccggtaa tcgacggatc taactttact tcgtcaactt   41220
cgccgtcaaa tgcccagcca agcgcatggc cccggcacca gcgttggagc gcgctcctg    41280 cgccttcggc gggcccatgc aacaaaaatt cacgtaaccc cgcgattgaa cgcatttgtg   41340
gatcaaacga gagctgacga tggataccac ggaccagacg gcggttctct tccggagaaa   41400
tcccaccccg accatcactc tcgatgagag ccacgatcca ttcgcgcaga aaatcgtgtg   41460
aggctgctgt gttttctagg ccacgcaacg gcgccaaccc gctgggtgtg cctctgtgaa   41520
gtgccaaata tgttcctcct gtggcgcgaa ccagcaattc gccaccccgg tccttgtcaa   41580
agaacacgac cgtacctgca cggtcgacca tgctctgttc gagcatggct agaacaaaca   41640
tcatgagcgt cgtcttaccc ctcccgatag gcccgaatat tgccgtcatg ccaacatcgt   41700
gctcatgcgg gatatagtcg aaaggcgttc cgccattggt acgaaatcgg gcaatcgcgt   41760
tgccccagtg gcctgagctg gcgccctctg gaaagttttc gaaagagaca aaccctgcga   41820
aattgcgtga agtgattgcg ccagggcgtg tgcgccactt aaaattcccc ggcaattggg   41880
accaataggc cgcttccata ccaataccct cttggacaac cacggcacct gcatccgcca   41940
ttcgtgtccg agcccgcgcg cccctgtccc caagactatt gagatcgtct gcatagacgc   42000
aaaggctcaa atgatgtgag cccataacga attcgttgct cgcaagtgcg tcctcagcct   42060
cggataattt gccgatttga gtcacggctt tatcgccgga actcagcatc tggctcgatt   42120
tgaggctaag tttcgcgtgc gcttgcgggc gagtcaggaa cgaaaaactc tgcgtgagaa   42180
caagtggaaa atcgagggat agcagcgcgt tgagcatgcc cggccgtgtt tttgcagggt   42240
attcgcgaaa cgaatagatg gatccaacgt aactgtcttt tggcgttctg atctcgagtc   42300
ctcgcttgcc gcaaatgact ctgtcggtat aaatcgaagc gccgagtgag ccgctgacga   42360
ccggaaccgg tgtgaaccga ccagtcatga tcaaccgtag cgcttcgcca atttcggtga   42420
agagcacacc ctgcttctcg cggatgccaa gacgatgcag gccatacgct ttaagagagc   42480
cagcgacaac atgccaaaga tcttccatgt tcctgatctg gcccgtgaga tcgttttccc   42540
tttttccgct tagcttggtg aacctcctct ttaccttccc taaagccgcc tgtgggtaga   42600
caatcaacgt aaggaagtgt tcattgcgga ggagttggcc ggagagcacg cgctgttcaa   42660
aagcttcgtt caggctagcg gcgaaaacac tacggaagtg tcgcggcgcc gatgatggca   42720
cgtcggcatg acgtacgagg tgagcatata ttgacacatg atcatcagcg atattgcgca   42780
acagcgtgtt gaacgcacga caacgcgcat tgcgcatttc agtttcctca agctcgaatg   42840
caacgccatc aattctcgca atggtcatga tcgatccgtc ttcaagaagg acgatatggt   42900
cgctgaggtg gccaatataa gggagataga tctcaccgga tctttcggtc gttccactcg   42960
cgccgagcat cacaccattc ctctccctcg tggggaacc  ctaattggat ttgggctaac   43020
agtagcgccc cccaaactg  cactatcaat gcttcttccc gcggtccgca aaaatagcag   43080
gacgacgctc gccgcattgt agtctcgctc cacgatgagc cgggctgcaa accataacgg   43140
cacgagaacg acttcgtaga gcgggttctg aacgataacg atgacaaagc cggcgaacat   43200
catgaataac cctgccaatg tcagtggcac cccaagaaac aatgcgggcc gtgtggctgc   43260
gaggtaaagg gtcgattctt ccaaacgatc agccatcaac taccgccagt gagcgtttgg   43320
ccgaggaagc tcgccccaaa catgataaca atgccgccga cgacgccggc aaccagccca   43380
```

```
agcgaagccc gcccgaacat ccaggagatc ccgatagcga caatgccgag aacagcgagt    43440
gactggccga acggaccaag gataaacgtg catatattgt taaccattgt ggcggggtca    43500
gtgccgccac ccgcagattg cgctgcggcg ggtccggatg aggaaatgct ccatgcaatt    43560
gcaccgcaca agcttggggc gcagctcgat atcacgcgca tcatcgcatt cgagagcgag    43620
aggcgattta gatgtaaacg gtatctctca aagcatcgca tcaatgcgca cctccttagt    43680
ataagtcgaa taagacttga ttgtcgtctg cggatttgcc gttgtcctgg tgtggcggtg    43740
gcggagcgat taaaccgcca gcgccatcct cctgcgagcg gcgctgatat gaccccccaaa   43800 catcccacgt ctcttcggat tttagcgcct cgtgatcgtc ttttggaggc tcgattaacg    43860
cgggcaccag cgattgagca gctgtttcaa cttttcgcac gtagccgttt gcaaaaccgc    43920
cgatgaaatt accggtgttg taagcggaga tcgcccgacg aagcgcaaat tgcttctcgt    43980
caatcgtttc gccgcctgca taacgacttt tcagcatgtt tgcagcggca gataatgatg    44040
tgcacgcctg gagcgcaccg tcaggtgtca gaccgagcat agaaaaattt cgagagttta    44100
tttgcatgag gccaacatcc agcgaatgcc gtgcatcgag acggtgcctg acgacttggg    44160
ttgcttggct gtgatcttgc cagtgaagcg tttcgccggt cgtgttgtca tgaatcgcta    44220
aaggatcaaa gcgactctcc accttagcta tcgccgcaag cgtagatgtc gcaactgatg    44280
gggcacactt gcgagcaaca tggtcaaact cagcagatga gagtggcgtg caaggctcg    44340 acgaacagaa ggagaccatc aaggcaagag aaagcgaccc cgatctctta agcatacctt    44400
atctccttag ctcgcaacta acaccgcctc tcccgttgga agaagtgcgt tgttttatgt    44460
tgaagattat cgggagggtc ggttactcga aaattttcaa ttgcttcttt atgatttcaa    44520
ttgaagcgag aaacctcgcc cggcgtcttg gaacgcaaca tggaccgaga accgcgcatc    44580
catgactaag caaccggatc gacctattca ggccgcagtt ggtcaggtca ggctcagaac    44640
gaaaatgctc ggcgaggtta cgctgtctgt aaacccattc gatgaacggg aagcttcctt    44700
ccgattgctc ttggcaggaa tattggccca tgcctgcttg cgctttgcaa atgctcttat    44760
cgcgttggta tcatatgcct tgtccgccag cagaaacgca ctctaagcga ttatttgtaa    44820 aaatgttttcg gtcatgcggc ggtcatgggc ttgacccgct gtcagcgcaa gacggatcgg    44880
tcaaccgtcg gcatcgacaa cagcgtgaat cttggtggtc aaaccgccac gggaacgtcc    44940
catacagcca tcgtcttgat cccgctgttt ccgtcgccg catgttggtg gacgcggaca    45000
caggaactgt caatcatgac gacattctat cgaaagcctt ggaaatcaca ctcagaatat    45060
gatcccagac gtctgcctca cgccatcgta caaagcgatt gtagcaggtt gtacaggaac    45120
cgtatcgatc aggaacgtct gcccagggcg ggcccgtccg gaagcgccac aagatgacat    45180
tgatcacccg cgtcaacgcg cggcacgcga cgcggcttat ttgggaacaa aggactgaac    45240
aacagtccat tcgaaatcgg tgacatcaaa gcggggacgg gttatcagtg gcctccaagt    45300
caagcctcaa tgaatcaaaa tcagaccgat ttgcaaacct gatttatgag tgtgcggcct    45360
aaatgatgaa atcgtccttc tagatcgcct ccgtggtgta gcaacacctc gcagtatcgc    45420
cgtgctgacc ttggccaggg aattgactgg caagggtgct ttcacatgac cgctcttttg    45480
gccgcgatag atgatttcgt tgctgctttg ggcacgtaga aggagagaag tcatatcgga    45540
gaaattcctc ctggcgcgag agcctgctct atcgcgacgg catcccactg tcgggaacag    45600
accggatcat tcacgaggcg aaagtcgtca acacatgcgt tataggcatc ttcccttgaa    45660
ggatgatctt gttgctgcca atctggaggt gcggcagccg caggcagatg cgatctcagc    45720
gcaacttgcg gcaaaacatc tcactcacct gaaaaccact agcgagtctc gcgatcagac    45780
```

```
gaaggccttt tacttaacga cacaatatcc gatgtctgca tcacaggcgt cgctatccca   45840
gtcaatacta aagcggtgca ggaactaaag attactgatg acttaggcgt gccacgaggc   45900
ctgagacgac gcgcgtagac agttttttga aatcattatc aaagtgatgg cctccgctga   45960
agcctatcac ctctgcgccg gtctgtcgga gagatgggca agcattatta cggtcttcgc   46020
gcccgtacat gcattggacg attgcagggt caatggatct gagatcatcc agaggattgc   46080
cgcccttacc ttccgtttcg agttggagcc agcccctaaa tgagacgaca tagtcgactt   46140
gatgtgacaa tgccaagaga gagatttgct taacccgatt tttttgctca agcgtaagcc   46200
tattgaagct tgccggcatg acgtccgcgc cgaaagaata tcctacaagt aaaacattct   46260
gcacaccgaa atgcttggtg tagacatcga ttatgtgacc aagatcctta gcagtttcgc   46320
ttggggaccg ctccgaccag aaataccgaa gtgaactgac gccaatgaca ggaatccctt   46380
ccgtctgcag ataggtacca tcgatagatc tgctgcctcg cgcgtttcgg tgatgacggt   46440
gaaaacctct gacacatgca gctcccggag acggtcacag cttgtctgta agcggatgcc   46500
gggagcagac aagcccgtca gggcgcgtca gcgggtgttg gcgggtgtcg ggcgcagcc   46560 atgacccagt cacgtagcga tagcggagtg tatactggct taactatgcg gcatcagagc   46620
agattgtact gagagtgcac catatgcggt gtgaaatacc gcacagatgc gtaaggagaa   46680
aataccgcat caggcgctct tccgcttcct cgctcactga ctcgctgcgc tcggtcgttc   46740
ggctgcggcg agcggtatca gctcactcaa aggcggtaat acggttatcc acagaatcag   46800
gggataacgc aggaaagaac atgtgagcaa aaggccagca aaaggccagg aaccgtaaaa   46860
aggccgcgtt gctggcgttt ttccataggc tccgcccccc tgacgagcat cacaaaaatc   46920
gacgctcaag tcagaggtgg cgaaacccga caggactata agataccagg cgtttcccc   46980 ctggaagctc cctcgtgcgc tctcctgttc cgaccctgcc gcttaccgga tacctgtccg   47040
cctttctccc ttcgggaagc gtggcgcttt ctcatagctc acgctgtagg tatctcagtt   47100
cggtgtaggt cgttcgctcc aagctgggct gtgtgcacga accccccgtt cagcccgacc   47160
gctgcgcctt atccggtaac tatcgtcttg agtccaaccc ggtaagacac gacttatcgc   47220
cactggcagc agccactggt aacaggatta gcagagcgag gtatgtaggc ggtgctacag   47280
agttcttgaa gtggtggcct aactacggct acactagaag gacagtattt ggtatctgcg   47340
ctctgctgaa gccagttacc ttcggaaaaa gagttggtag ctcttgatcc ggcaaacaaa   47400
ccaccgctgg tagcggtggt ttttttgttt gcaagcagca gattacgcgc agaaaaaaag   47460
gatctcaaga agatcctttg atcttttcta cggggtctga cgctcagtgg aacgaaaact   47520
cacgttaagg gattttggtc atgagattat caaaaaggat cttcacctag atcctttaa   47580 attaaaaatg aagttttaaa tcaatctaaa gtatatatga gtaaacttgg tctgacagtt   47640
accaatgctt aatcagtgag gcacctatct cagcgatctg tctatttcgt tcatccatag   47700
ttgcctgact ccccgtcgtg tagataacta cgatacggga gggcttacca tctggcccca   47760
gtgctgcaat gataccgcga gacccacgct caccggctcc agatttatca gcaataaacc   47820
agccagccgg aagggccgag cgcagaagtg gtcctgcaac tttatccgcc tccatccagt   47880
ctattaattg ttgccgggaa gctagagtaa gtagttcgcc agttaatagt ttgcgcaacg   47940
ttgttgccat tgctgcaggg gggggggggg gggggactt ccattgttca ttccacggac   48000
aaaaacagag aaaggaaacg acagaggcca aaaagcctcg ctttcagcac ctgtcgtttc   48060
cttctttttc agagggtatt ttaaataaaa acattaagtt atgacgaaga agaacggaaa   48120
```

-continued

```
cgccttaaac cggaaaattt tcataaatag cgaaaacccg cgaggtcgcc gccccgtagt    48180
cggatcaccg gaaaggaccc gtaaagtgat aatgattatc atctacatat cacaacgtgc    48240
gtggaggcca tcaaaccacg tcaaataatc aattatgacg caggtatcgt attaattgat    48300
ctgcatcaac ttaacgtaaa aacaacttca gacaatacaa atcagcgaca ctgaatacgg    48360
ggcaacctca tgtccccccc ccccccccc  ctgcaggcat cgtggtgtca cgctcgtcgt    48420
ttggtatggc ttcattcagc tccggttccc aacgatcaag gcgagttaca tgatccccca    48480
tgttgtgcaa aaaagcggtt agctccttcg gtcctccgat cgttgtcaga agtaagttgg    48540
ccgcagtgtt atcactcatg gttatggcag cactgcataa ttctcttact gtcatgccat    48600
ccgtaagatg cttttctgtg actggtgagt actcaaccaa gtcattctga aatagtgta    48660 tgcggcgacc gagttgctct tgcccggcgt caacacggga taataccgcg ccacatagca    48720
gaactttaaa agtgctcatc attggaaaac gttcttcggg gcgaaaactc tcaaggatct    48780
taccgctgtt gagatccagt tcgatgtaac ccactcgtgc acccaactga tcttcagcat    48840
cttttacttt caccagcgtt tctgggtgag caaaaacagg aaggcaaaat gccgcaaaaa    48900
agggaataag ggcgacacgg aaatgttgaa tactcatact cttccttttt caatattatt    48960
gaagcattta tcagggttat tgtctcatga gcggatacat atttgaatgt atttagaaaa    49020
ataaacaaat aggggttccg cgcacatttc cccgaaaagt gccacctgac gtctaagaaa    49080
ccattattat catgacatta acctataaaa ataggcgtat cacgaggccc tttcgtcttc    49140
aagaattggt cgacgatctt gctgcgttcg gatattttcg tggagttccc gccacagacc    49200
cggattgaag cgagatcca gcaactcgcg ccagatcatc ctgtgacgga actttggcgc    49260
gtgatgactg gccaggacgt cggccgaaag agcgacaagc agatcacgct tttcgacagc    49320
gtcggatttg cgatcgagga ttttttcggcg ctgcgctacg tccgcgaccg cgttgaggga    49380
tcaagccaca gcagcccact cgaccttcta gccgacccag acgagccaag ggatcttttt    49440
ggaatgctgc tccgtcgtca ggcttttccga cgtttgggtg gttgaacaga agtcattatc    49500
gtacggaatg ccaagcactc ccgaggggaa ccctgtggtt ggcatgcaca tacaaatgga    49560
cgaacggata aaccttttca cgcccttttta aatatccgtt attctaataa acgctctttt    49620
ctcttaggtt tacccgccaa tatatcctgt caaacactga tagtttaaac tgaaggcggg    49680
aaacgacaat ctgatcatga gcggagaatt aagggagtca cgttatgacc cccgccgatg    49740
acgcgggaca agccgtttta cgtttggaac tgacagaacc gcaacgttga aggagccact    49800
cagcaagctg gtacgattgt aatacgactc actataggc  gaattgagcg ctgtttaaac    49860
gctcttcaac tggaagagcg gttacccgga ccgaagcttg catgcctgca g            49911
```

<210> SEQ ID NO 7
<211> LENGTH: 36909
<212> TYPE: DNA
<213> ORGANISM: artificial sequence
<220> FEATURE:
<223> OTHER INFORMATION: vector

<400> SEQUENCE: 7

```
tctagagctc gttcctcgag gcctcgaggc ctcgaggaac ggtacctgcg gggaagctta      60
caataatgtg tgttgttaag tcttgttgcc tgtcatcgtc tgactgactt tcgtcataaa     120
tcccggcctc cgtaacccag ctttgggcaa gctcacggat ttgatccggc ggaacgggaa     180
tatcgagatg ccgggctgaa cgctgcagtt ccagctttcc ctttcgggac aggtactcca     240
gctgattgat tatctgctga agggtcttgg ttccacctcc tggcacaatg cgaatgatta     300
```

-continued

```
cttgagcgcg atcgggcatc caattttctc ccgtcaggtg cgtggtcaag tgctacaagg    360
cacctttcag taacgagcga ccgtcgatcc gtcgccggga tacggacaaa atggagcgca    420
gtagtccatc gagggcggcg aaagcctcgc caaaagcaat acgttcatct cgcacagcct    480
ccagatccga tcgagggtct tcggcgtagg cagatagaag catggataca ttgcttgaga    540
gtattccgat ggactgaagt atggcttcca tcttttctcg tgtgtctgca tctatttcga    600
gaaagccccc gatgcggcgc accgcaacgc gaattgccat actatccgaa agtcccagca    660
ggcgcgcttg ataggaaaag gtttcatact cggccgatcg cagacgggca ctcacgacct    720
tgaaccctt c aactttcagg gatcgatgct ggttgatggt agtctcactc gacgtggctc    780
tggtgtgttt tgacatagct tcctccaaag aaagcggaag gtctggatac tccagcacga    840
aatgtgcccg ggtagacgga tggaagtcta gccctgctca atatgaaatc aacagtacat    900
ttacagtcaa tactgaatat acttgctaca tttgcaattg tcttataacg aatgtgaaat    960
aaaaatagtg taacaacgct tttactcatc gataatcaca aaaacattta tacgaacaaa    1020
aatacaaatg cactccggtt tcacaggata ggcgggatca gaatatgcaa cttttgacgt    1080
tttgttcttt caaggggggt gctggcaaaa ccaccgcact catgggcctt tgcgctgctt    1140
tggcaaatga cggtaaacga gtggccctct ttgatgccga cgaaaccgg cctctgacgc     1200
gatggagaga aaacgcctta caaagcagta ctgggatcct cgctgtgaag tctattccgc    1260
cgacgaaatg ccccttcttg aagcagccta tgaaaatgcc gagctcgaag gatttgatta    1320
tgcgttggcc gatacgcgtg gcggctcgag cgagctcaac aacacaatca tcgctagctc    1380
aaacctgctt ctgatcccca ccatgctaac gccgctcgac atcgatgagg cactatctac    1440
ctaccgctac gtcatcgagc tgctgttgag tgaaaatttg gcaattccta cagctgtttt    1500
gcgccaacgc gtcccggtcg gccgattgac aacatcgcaa cgcaggatgt cagagacgct    1560
agagagcctt ccagttgtac cgtctcccat gcatgaaaga gatgcatttg ccgcgatgaa    1620
agaacgcggc atgttgcatc ttacattact aaacacggga actgatccga cgatgcgcct    1680
catagagagg aatcttcgga ttgcgatgga ggaagtcgtg gtcatttcga aactgatcag    1740
caaaatcttg gaggcttgaa gatggcaatt cgcaagcccg cattgtcggt cggcgaagca    1800
cggcggcttg ctggtgctcg acccgagatc caccatccca acccgacact tgttccccag    1860
aagctggacc tccagcactt gcctgaaaaa gccgacgaga aagaccagca acgtgagcct    1920
ctcgtcgccg atcacattta cagtcccgat cgacaactta agctaactgt ggatgccctt    1980
agtccacctc cgtccccgaa aaagctccag gttttctttt cagcgcgacc gcccgcgcct    2040
caagtgtcga aaacatatga caacctcgtt cggcaataca gtccctcgaa gtcgctacaa    2100
atgatttta a ggcgcgcgtt ggacgatttc gaaagcatgc tggcagatgg atcatttcgc    2160
gtggccccga aaagttatcc gatcccttca actacagaaa aatccgttct cgttcagacc    2220
tcacgcatgt tcccggttgc gttgctcgag gtcgctcgaa gtcatttga tccgttgggg     2280
ttggagaccg ctcgagcttt cggccacaag ctggctaccg ccgcgctcgc gtcattcttt    2340
gctggagaga agccatcgag caattggtga agagggacct atcggaaccc ctcaccaaat    2400
attgagtgta ggtttgaggc cgctggccgc gtcctcagtc acctttgag ccagataatt     2460
aagagccaaa tgcaattggc tcaggctgcc atcgtccccc cgtgcgaaac ctgcacgtcc    2520
gcgtcaaaga aataaccggc acctcttgct gttttatca gttgagggct tgacggatcc     2580
gcctcaagtt tgcggcgcag ccgcaaaatg agaacatcta tactcctgtc gtaaacctcc    2640
```

```
tcgtcgcgta ctcgactggc aatgagaagt tgctcgcgcg atagaacgtc gcggggtttc    2700
tctaaaaacg cgaggagaag attgaactca cctgccgtaa gtttcacctc accgccagct    2760
tcggacatca agcgacgttg cctgagatta agtgtccagt cagtaaaaca aaaagaccgt    2820
cggtctttgg agcggacaac gttggggcgc acgcgcaagg caacccgaat gcgtgcaaga    2880
aactctctcg tactaaacgg cttagcgata aaatcacttg ctcctagctc gagtgcaaca    2940
actttatccg tctcctcaag gcggtcgcca ctgataatta tgattggaat atcagacttt    3000
gccgccagat ttcgaacgat ctcaagccca tcttcacgac ctaaatttag atcaacaacc    3060
acgacatcga ccgtcgcgga agagagtact ctagtgaact gggtgctgtc ggctaccgcg    3120
gtcactttga aggcgtggat cgtaaggtat tcgataataa gatgccgcat agcgacatcg    3180
tcatcgataa aagaacgtg tttcaacggc tcacctttca atctaaaatc tgaacccttg    3240
ttcacagcgc ttgagaaatt ttcacgtgaa ggatgtacaa tcatctccag ctaaatgggc    3300
agttcgtcag aattgcggct gaccgcggat gacgaaaatg cgaaccaagt atttcaattt    3360
tatgacaaaa gttctcaatc gttgttacaa gtgaaacgct tcgaggttac agctactatt    3420
gattaaggag atcgcctatg gtctcgcccc ggcgtcgtgc gtccgccgcg agccagatct    3480
cgcctacttc ataaacgtcc tcataggcac ggaatggaat gatgacatcg atcgccgtag    3540
agagcatgtc aatcagtgtg cgatcttcca agctagcacc ttgggcgcta cttttgacaa    3600
gggaaaacag tttcttgaat ccttggattg gattcgcgcc gtgtattgtt gaaatcgatc    3660
ccggatgtcc cgagacgact tcactcagat aagcccatgc tgcatcgtcg cgcatctcgc    3720
caagcaatat ccggtccggc cgcatacgca gacttgcttg gagcaagtgc tcggcgctca    3780
cagcacccag cccagcaccg ttcttggagt agagtagtct aacatgatta tcgtgtggaa    3840
tgacgagttc gagcgtatct tctatggtga ttagcctttc ctgggggggg atggcgctga    3900
tcaaggtctt gctcattgtt gtcttgccgc ttccggtagg gccacatagc aacatcgtca    3960
gtcggctgac gacgcatgcg tgcagaaacg cttccaaatc cccgttgtca aaatgctgaa    4020
ggatagcttc atcatcctga ttttggcgtt tccttcgtgt ctgccactgg ttccacctcg    4080
aagcatcata acgggaggag acttctttaa gaccagaaac acgcgagctt ggccgtcgaa    4140
tggtcaagct gacggtgccc gagggaacgg tcggcggcag acagatttgt agtcgttcac    4200
caccaggaag ttcagtggcg cagagggggt tacgtggtcc gacatcctgc tttctcagcg    4260
cgcccgctaa aatagcgata tcttcaagat catcataaga gacgggcaaa ggcatcttgg    4320
taaaaatgcc ggcttggcgc acaaatgcct ctccaggtcg attgatcgca atttcttcag    4380
tcttcgggtc atcgagccat tccaaaatcg gcttcagaag aaagcgtagt tgcggatcca    4440 cttccatttta caatgtatcc tatctctaag cggaaatttg aattcattaa gagcggcggt    4500
tcctcccccg cgtggcgccg ccagtcaggc ggagctggta acaccaaag aaatcgaggt    4560 cccgtgctac gaaaatggaa acggtgtcac cctgattctt cttcagggtt ggcggtatgt    4620
tgatggttgc cttaagggct gtctcagttg tctgctcacc gttatttga aagctgttga    4680 agctcatccc gccacccgag ctgccggcgt aggtgctagc tgcctggaag gcgccttgaa    4740
caacactcaa gagcatagct ccgctaaaac gctgccagaa gtggctgtcg accgagcccg    4800
gcaatcctga gcgaccgagt tcgtccgcgc ttggcgatgt taacgagatc atcgcatggt    4860
caggtgtctc ggcgcgatcc cacaaacacaa aaacgcgccc atctccctgt tgcaagccac    4920
gctgtatttc gccaacaacg gtggtgccac gatcaagaag cacgatattg ttcgttgttc    4980
cacgaatatc ctgaggcaag acacacttta catagcctgc caaatttgtg tcgattgcgg    5040
```

```
tttgcaagat gcacggaatt attgtccctt gcgttaccat aaaatcgggg tgcggcaaga    5100
gcgtggcgct gctgggctgc agctcggtgg gtttcatacg tatcgacaaa tcgttctcgc    5160
cggacacttc gccattcggc aaggagttgt cgtcacgctt gccttcttgt cttcggcccg    5220
tgtcgccctg aatggcgcgt ttgctgaccc cttgatcgcc gctgctatat gcaaaaatcg    5280
gtgtttcttc cggccgtggc tcatgccgct ccggttcgcc cctcggcggt agaggagcag    5340
caggctgaac agcctcttga accgctggag gatccggcgg cacctcaatc ggagctggat    5400
gaaatggctt ggtgtttgtt gcgatcaaag ttgacggcga tgcgttctca ttcaccttct    5460
tttggcgccc acctagccaa atgaggctta atgataacgc gagaacgaca cctccgacga    5520
tcaatttctg agaccccgaa agacgccggc gatgtttgtc ggagaccagg gatccagatg    5580
catcaacctc atgtgccgct tgctgactat cgttattcat cccttcgccc ccttcaggac    5640
gcgtttcaca tcgggcctca ccgtgcccgt ttgcggcctt tggccaacgg gatcgtaagc    5700
ggtgttccag atacatagta ctgtgtggcc atccctcaga cgccaacctc gggaaaccga    5760
agaaatctcg acatcgctcc ctttaactga atagttggca acagcttcct tgccatcagg    5820
attgatggta tagatggagg gtatgcgtac attgcccgga aagtggaata ccgtcgtaaa    5880
tccattgtcg aagacttcga gtggcaacag cgaacgatcg ccttgggcga cgtagtgcca    5940
attactgtcc gccgcaccaa gggctgtgac aggctgatcc aataaattct cagctttccg    6000
ttgatattgt gcttccgcgt gtagtctgtc cacaacagcc ttctgttgtg cctcccttcg    6060
ccgagccgcc gcatcgtcgg cggggtaggc gaattggacg ctgtaataga gatcgggctg    6120
ctctttatcg aggtgggaca gagtcttgga acttatactg aaaacataac ggcgcatccc    6180
ggagtcgctt gcggttagca cgattactgg ctgaggcgtg aggacctggc ttgccttgaa    6240
aaatagataa tttccccgcg gtagggctgc tagatctttg ctatttgaaa cggcaaccgc    6300
tgtcaccgtt tcgttcgtgg cgaatgttac gaccaaagta gctccaaccg ccgtcgagag    6360
gcgcaccact tgatcgggat tgtaagccaa ataacgcatg cgcggatcta gcttgcccgc    6420
cattggagtg tcttcagcct ccgcaccagt cgcagcggca aataaacatg ctaaaatgaa    6480
aagtgctttt ctgatcatgg ttcgctgtgg cctacgtttg aaacggtatc ttccgatgtc    6540
tgataggagg tgacaaccag acctgccggg ttggttagtc tcaatctgcc gggcaagctg    6600 gtcaccttt cgtagcgaac tgtcgcggtc cacgtactca ccacaggcat tttgccgtca    6660
acgacgaggg tccttttata gcgaatttgc tgcgtgcttg gagttacatc atttgaagcg    6720
atgtgctcga cctccaccct gccgcgtttg ccaagaatga cttgaggcga actgggattg    6780
ggatagttga agaattgctg gtaatcctgg cgcactgttg gggcactgaa gttcgatacc    6840
aggtcgtagg cgtactgagc ggtgtcggca tcataactct cgcgcaggcg aacgtactcc    6900
cacaatgagg cgttaacgac ggcctcctct tgagttgcag gcaatcgcga gacagacacc    6960
tcgctgtcaa cggtgccgtc cggccgtatc catagatata cggcacaag cctgctcaac    7020 ggcaccattg tggctatagc gaacgcttga gcaacatttc ccaaaatcgc gatagctgcg    7080
acagctgcaa tgagtttgga gagacgtcgc gccgatttcg ctcgcgcggt ttgaaaggct    7140
tctacttcct tatagtgctc ggcaaggctt tcgcgcgcca ctagcatggc atattcaggc    7200 ccgtcatag cgtccacccg aattgccgag ctgaagatct gacggagtag ctgccatcg    7260 ccccacattc agcgggaaga tcgggccttt gcagctcgct aatgtgtcgt ttgtctggca    7320
gccgctcaaa gcgacaacta ggcacagcag gcaatacttc atagaattct ccattgaggc    7380
```

```
gaatttttgc gcgacctagc ctcgctcaac ctgagcgaag cgacggtaca agctgctggc    7440
agattgggtt gcgccgctcc agtaactgcc tccaatgttg ccggcgatcg ccggcaaagc    7500
gacaatgagc gcatcccctg tcagaaaaaa catatcgagt tcgtaaagac caatgatctt    7560
ggccgcggtc gtaccggcga aggtgattac accaagcata agggtgagcg cagtcgcttc    7620
ggttaggatg acgatcgttg ccacgaggtt aagaggaga agcaagagac cgtaggtgat    7680
aagttgcccg atccacttag ctgcgatgtc ccgcgtgcga tcaaaaatat atccgacgag    7740
gatcagaggc ccgatcgcga aagcactttt cgtgagaatt ccaacggcgt cgtaaactcc    7800
gaaggcagac cagagcgtgc cgtaaaggac ccactgtgcc ccttggaaag caaggatgtc    7860
ctggtcgttc atcggaccga tttcggatgc gattttctga aaaacggcct gggtcacggc    7920
gaacattgta tccaactgtg ccggaacagt ctgcagaggc aagccggtta cactaaactg    7980
ctgaacaaag tttgggaccg tcttttcgaa gatggaaacc acatagtctt ggtagttagc    8040
ctgcccaaca attagagcaa caacgatggt gaccgtgatc acccgagtga taccgctacg    8100
ggtatcgact tcgccgcgta tgactaaaat accctgaaca ataatccaaa gagtgacaca    8160
ggcgatcaat ggcgcactca ccgcctcctg gatagtctca agcatcgagt ccaagcctgt    8220
cgtgaaggct acatcgaaga tcgtatgaat ggccgtaaac ggcgccggaa tcgtgaaatt    8280
catcgattgg acctgaactt gactggtttg tcgcataatg ttggataaaa tgagctcgca    8340
ttcggcgagg atgcgggcgg atgaacaaat cgcccagcct tagggagggg caccaaagat    8400
gacagcggtc tttttgatgct ccttgcgttg agcggccgcc tcttccgcct cgtgaaggcc    8460
ggcctgcgcg gtagtcatcg ttaataggct tgtcgcctgt acattttgaa tcattgcgtc    8520
atggatctgc ttgagaagca aaccattggt cacggttgcc tgcatgatat tgcgagatcg    8580
ggaaagctga gcagacgtat cagcattcgc cgtcaagcgt ttgtccatcg tttccagatt    8640
gtcagccgca atgccagcgc tgtttgcgga accggtgatc tgcgatcgca acaggtccgc    8700
ttcagcatca ctacccacga ctgcacgatc tgtatcgctg gtgatcgcac gtgccgtggt    8760
cgacattggc attcgcggcg aaaacatttc attgtctagg tccttcgtcg aaggatactg    8820 attttttctgg ttgagcgaag tcagtagtcc agtaacgccg taggccgacg tcaacatcgt    8880
aaccatcgct atagtctgag tgagattctc cgcagtcgcg agcgcagtcg cgagcgtctc    8940
agcctccgtt gccgggtcgc taacaacaaa ctgcgcccgc gcgggctgaa tatatagaaa    9000
gctgcaggtc aaaactgttg caataagttg cgtcgtcttc atcgtttcct accttatcaa    9060
tcttctgcct cgtggtgacg ggccatgaat tcgctgagcc agccagatga gttgccttct    9120
tgtgcctcgc gtagtcgagt tgcaaagcgc accgtgttgg cacgccccga aagcacggcg    9180
acatattcac gcatatcccg cagatcaaat tcgcagatga cgcttccact ttctcgttta    9240
agaagaaact tacggctgcc gaccgtcatg tcttcacgga tcgcctgaaa ttccttttcg    9300
gtacatttca gtccatcgac ataagccgat cgatctgcgg ttggtgatgg atagaaaatc    9360
ttcgtcatac attgcgcaac caagctggct cctagcggcg attccagaac atgctctggt    9420
tgctgcgttg ccagtattag catcccgttg ttttttcgaa cggtcaggag gaatttgtcg    9480
acgacagtcg aaaatttagg gtttaacaaa taggcgcgaa actcatcgca gctcatcaca    9540
aaacggcggc cgtcgatcat ggctccaatc cgatgcagga gatatgctgc agcgggagcg    9600
catacttcct cgtattcgag aagatgcgtc atgtcgaagc cggtaatcga cggatctaac    9660
tttacttcgt caacttcgcc gtcaaatgcc cagccaagcg catggccccg gcaccagcgt    9720
tggagccgcg ctcctgcgcc ttcggcgggc ccatgcaaca aaaattcacg taaccccgcg    9780
```

```
attgaacgca tttgtggatc aaacgagagc tgacgatgga taccacggac cagacggcgg   9840
ttctcttccg gagaaatccc accccgacca tcactctcga tgagagccac gatccattcg   9900
cgcagaaaat cgtgtgaggc tgctgtgttt tctaggccac gcaacggcgc caacccgctg   9960
ggtgtgcctc tgtgaagtgc caaatatgtt cctcctgtgg cgcgaaccag caattcgcca  10020
ccccggtcct tgtcaaagaa cacgaccgta cctgcacggt cgaccatgct ctgttcgagc  10080
atggctagaa caaacatcat gagcgtcgtc ttacccctcc cgataggccc gaatattgcc  10140
gtcatgccaa catcgtgctc atgcgggata tagtcgaaag gcgttccgcc attggtacga  10200
aatcgggcaa tcgcgttgcc ccagtggcct gagctggcgc cctctggaaa gttttcgaaa  10260
gagacaaacc ctgcgaaatt gcgtgaagtg attgcgccag ggcgtgtgcg ccacttaaaa  10320
ttccccggca attgggacca ataggccgct tccataccaa taccttcttg gacaaccacg  10380
gcacctgcat ccgccattcg tgtccgagcc cgcgcgcccc tgtccccaag actattgaga  10440
tcgtctgcat agacgcaaag gctcaaatga tgtgagccca taacgaattc gttgctcgca  10500
agtgcgtcct cagcctcgga taatttgccg atttgagtca cggctttatc gccggaactc  10560
agcatctggc tcgatttgag gctaagtttc gcgtgcgctt gcgggcgagt caggaacgaa  10620
aaactctgcg tgagaacaag tggaaaatcg agggatagca gcgcgttgag catgcccggc  10680 cgtgttttg cagggtattc gcgaaacgaa tagatggatc caacgtaact gtcttttggc  10740
gttctgatct cgagtcctcg cttgccgcaa atgactctgt cggtataaat cgaagcgccg  10800
agtgagccgc tgacgaccgg aaccggtgtg aaccgaccag tcatgatcaa ccgtagcgct  10860
tcgccaattt cggtgaagag cacaccctgc ttctcgcgga tgccaagacg atgcaggcca  10920
tacgctttaa gagagccagc gacaacatgc caaagatctt ccatgttcct gatctggccc  10980
gtgagatcgt tttcccttt tccgcttagc ttggtgaacc tcctctttac cttccctaaa  11040
gccgcctgtg ggtagacaat caacgtaagg aagtgttcat tgcggaggag ttggccggag  11100
agcacgcgct gttcaaaagc ttcgttcagg ctagcggcga aaacactacg gaagtgtcgc  11160
ggcgccgatg atggcacgtc ggcatgacgt acgaggtgag catatattga cacatgatca  11220
tcagcgatat tgcgcaacag cgtgttgaac gcacgacaac gcgcattgcg catttcagtt  11280
tcctcaagct cgaatgcaac gccatcaatt ctcgcaatgg tcatgatcga tccgtcttca  11340
agaaggacga tatggtcgct gaggtggcca atataaggga gatagatctc accggatctt  11400
tcggtcgttc cactcgcgcc gagcatcaca ccattcctct ccctcgtggg ggaaccctaa  11460
ttggatttgg gctaacagta gcgccccccc aaactgcact atcaatgctt cttccgcgcg  11520
tccgcaaaaa tagcaggacg acgctcgccg cattgtagtc tcgctccacg atgagccggg  11580
ctgcaaacca taacggcacg agaacgactt cgtagagcgg ttctgaacg ataacgatga   11640 caaagccggc gaacatcatg aataaccctg ccaatgtcag tggcaccca agaaacaatg   11700 cgggccgtgt ggctgcgagg taagggtcg attcttccaa acgatcagcc atcaactacc   11760
gccagtgagc gtttggccga ggaagctcgc cccaaacatg ataacaatgc cgccgacgac   11820
gccggcaacc agcccaagcg aagcccgccc gaacatccag gagatcccga tagcgacaat   11880
gccgagaaca gcgagtgact ggccgaacgg accaaggata aacgtgcata tattgttaac   11940
cattgtggcg gggtcagtgc cgccacccgc agattgcgct gcggcgggtc cggatgagga  12000
aatgctccat gcaattgcac cgcacaagct tggggcgcag ctcgatatca cgcgcatcat  12060
cgcattcgag agcgagaggc gatttagatg taaacggtat ctctcaaagc atcgcatcaa  12120
```

```
tgcgcacctc cttagtataa gtcgaataag acttgattgt cgtctgcgga tttgccgttg   12180
tcctggtgtg gcggtggcgg agcgattaaa ccgccagcgc catcctcctg cgagcggcgc   12240
tgatatgacc cccaaacatc ccacgtctct tcggatttta gcgcctcgtg atcgtctttt   12300
ggaggctcga ttaacgcggg caccagcgat tgagcagctg tttcaacttt tcgcacgtag   12360
ccgtttgcaa aaccgccgat gaaattaccg gtgttgtaag cggagatcgc ccgacgaagc   12420
gcaaattgct tctcgtcaat cgtttcgccg cctgcataac gacttttcag catgtttgca   12480
gcggcagata atgatgtgca cgcctggagc gcaccgtcag gtgtcagacc gagcatagaa   12540
aaatttcgag agtttatttg catgaggcca acatccagcg aatgccgtgc atcgagacgg   12600
tgcctgacga cttgggttgc ttggctgtga tcttgccagt gaagcgtttc gccggtcgtg   12660
ttgtcatgaa tcgctaaagg atcaaagcga ctctccacct tagctatcgc cgcaagcgta   12720
gatgtcgcaa ctgatggggc acacttgcga gcaacatggt caaactcagc agatgagagt   12780
ggcgtggcaa ggctcgacga acagaaggag accatcaagg caagagaaag cgaccccgat   12840
ctcttaagca taccttatct ccttagctcg caactaacac cgcctctccc gttggaagaa   12900
gtgcgttgtt ttatgttgaa gattatcggg agggtcggtt actcgaaaat tttcaattgc   12960
ttctttatga tttcaattga agcgagaaac ctcgcccggc gtcttggaac gcaacatgga   13020
ccgagaaccg cgcatccatg actaagcaac cggatcgacc tattcaggcc gcagttggtc   13080
aggtcaggct cagaacgaaa atgctcggcg aggttacgct gtctgtaaac ccattcgatg   13140
aacgggaagc ttccttccga ttgctcttgg caggaatatt ggcccatgcc tgcttgcgct   13200
ttgcaaatgc tcttatcgcg ttggtatcat atgccttgtc cgccagcaga aacgcactct   13260
aagcgattat ttgtaaaaat gtttcggtca tgcggcggtc atgggcttga cccgctgtca   13320
gcgcaagacg gatcggtcaa ccgtcggcat cgacaacagc gtgaatcttg gtggtcaaac   13380
cgccacggga acgtcccata cagccatcgt cttgatcccg ctgtttcccg tcgccgcatg   13440
ttggtggacg cggacacagg aactgtcaat catgacgaca ttctatcgaa gccttggaa   13500 atcacactca gaatatgatc ccagacgtct gcctcacgcc atcgtacaaa gcgattgtag   13560
caggttgtac aggaaccgta tcgatcagga acgtctgccc agggcgggcc cgtccggaag   13620
cgccacaaga tgacattgat cacccgcgtc aacgcgcggc acgcgacgcg cttatttgg    13680 gaacaaagga ctgaacaaca gtccattcga aatcggtgac atcaaagcgg ggacgggtta   13740
tcagtggcct ccaagtcaag cctcaatgaa tcaaaatcag accgatttgc aaacctgatt   13800
tatgagtgtg cggcctaaat gatgaaatcg tccttctaga tcgcctccgt ggtgtagcaa   13860
cacctcgcag tatcgccgtg ctgaccttgg ccagggaatt gactggcaag ggtgctttca   13920
catgaccgct cttttggccg cgatagatga tttcgttgct gctttgggca cgtagaagga   13980
gagaagtcat atcggagaaa ttcctcctgg cgcgagagcc tgctctatcg cgacggcatc   14040
ccactgtcgg gaacagaccg gatcattcac gaggcgaaag tcgtcaacac atgcgttata   14100
ggcatcttcc cttgaaggat gatcttgttg ctgccaatct ggaggtgcgg cagccgcagg   14160
cagatgcgat ctcagcgcaa cttgcggcaa acatctcac tcacctgaaa accactagcg    14220
agtctcgcga tcagacgaag gccttttact taacgacaca atatccgatg tctgcatcac   14280
aggcgtcgct atcccagtca atactaaagc ggtgcaggaa ctaaagatta ctgatgactt   14340
aggcgtgcca cgaggcctga gacgacgcgc gtagacagtt ttttgaaatc attatcaaag   14400
tgatggcctc cgctgaagcc tatcacctct gcgccggtct gtcggagaga tgggcaagca   14460
ttattacggt cttcgcgccc gtacatgcat tggacgattg cagggtcaat ggatctgaga   14520
```

```
tcatccagag gattgccgcc cttaccttcc gtttcgagtt ggagccagcc cctaaatgag    14580
acgacatagt cgacttgatg tgacaatgcc aagagagaga tttgcttaac ccgatttttt    14640
tgctcaagcg taagcctatt gaagcttgcc ggcatgacgt ccgcgccgaa agaatatcct    14700
acaagtaaaa cattctgcac accgaaatgc ttggtgtaga catcgattat gtgaccaaga    14760
tccttagcag tttcgcttgg ggaccgctcc gaccagaaat accgaagtga actgacgcca    14820
atgacaggaa tcccttccgt ctgcagatag gtaccatcga tagatctgct gcctcgcgcg    14880
tttcggtgat gacggtgaaa acctctgaca catgcagctc ccggagacgg tcacagcttg    14940
tctgtaagcg gatgccggga gcagacaagc ccgtcagggc gcgtcagcgg gtgttggcgg    15000 gtgtcgggc gcagccatga cccagtcacg tagcgatagc ggagtgtata ctggcttaac    15060
tatgcggcat cagagcagat tgtactgaga gtgcaccata tgcggtgtga ataccgcac    15120 agatgcgtaa ggagaaaata ccgcatcagg cgctcttccg cttcctcgct cactgactcg    15180
ctgcgctcgg tcgttcggct gcggcgagcg gtatcagctc actcaaaggc ggtaatacgg    15240
ttatccacag aatcagggga taacgcagga aagaacatgt gagcaaaagg ccagcaaaag    15300
gccaggaacc gtaaaaaggc cgcgttgctg gcgtttttcc ataggctccg ccccctgac    15360 gagcatcaca aaaatcgacg ctcaagtcag aggtggcgaa acccgacagg actataaaga    15420
taccaggcgt ttccccctgg aagctccctc gtgcgctctc ctgttccgac cctgccgctt    15480
accggatacc tgtccgcctt tctcccttcg ggaagcgtgg cgctttctca tagctcacgc    15540
tgtaggtatc tcagttcggt gtaggtcgtt cgctccaagc tgggctgtgt gcacgaaccc    15600
cccgttcagc ccgaccgctg cgccttatcc ggtaactatc gtcttgagtc caacccggta    15660
agacacgact tatcgccact ggcagcagcc actggtaaca ggattagcag agcgaggtat    15720
gtaggcggtg ctacagagtt cttgaagtgg tggcctaact acggctacac tagaaggaca    15780
gtatttggta tctgcgctct gctgaagcca gttaccttcg gaaaaagagt tggtagctct    15840
tgatccggca acaaaccac cgctggtagc ggtggttttt ttgtttgcaa gcagcagatt    15900
acgcgcagaa aaaaggatc tcaagaagat cctttgatct tttctacggg gtctgacgct    15960
cagtggaacg aaaactcacg ttaagggatt ttggtcatga gattatcaaa aaggatcttc    16020
acctagatcc ttttaaatta aaaatgaagt tttaaatcaa tctaaagtat atatgagtaa    16080
acttggtctg acagttacca atgcttaatc agtgaggcac ctatctcagc gatctgtcta    16140
tttcgttcat ccatagttgc ctgactcccc gtcgtgtaga taactacgat acgggagggc    16200
ttaccatctg gccccagtgc tgcaatgata ccgcgagacc cacgctcacc ggctccagat    16260
ttatcagcaa taaaccagcc agccggaagg gccgagcgca gaagtggtcc tgcaacttta    16320
tccgcctcca tccagtctat taattgttgc cgggaagcta gagtaagtag ttcgccagtt    16380
aatagtttgc gcaacgttgt tgccattgct gcagggggg ggggggggg gttccattgt    16440 tcattccacg gacaaaaaca gagaaaggaa acgacagagg ccaaaaagct cgctttcagc    16500
acctgtcgtt tcctttcttt tcagagggta ttttaaataa aaacattaag ttatgacgaa    16560
gaagaacgga aacgccttaa accggaaaat tttcataaat agcgaaaacc cgcgaggtcg    16620
ccgccccgta acctgtcgga tcaccggaaa ggacccgtaa agtgataatg attatcatct    16680
acatatcaca acgtgcgtgg aggccatcaa accacgtcaa ataatcaatt atgacgcagg    16740
tatcgtatta attgatctgc atcaacttaa cgtaaaaaca acttcagaca atacaaatca    16800
gcgacactga atacggggca acctcatgtc ccccccccc cccccctgc aggcatcgtg    16860
```

```
gtgtcacgct cgtcgtttgg tatggcttca ttcagctccg gttcccaacg atcaaggcga   16920
gttacatgat cccccatgtt gtgcaaaaaa gcggttagct ccttcggtcc tccgatcgtt   16980
gtcagaagta agttggccgc agtgttatca ctcatggtta tggcagcact gcataattct   17040
cttactgtca tgccatccgt aagatgcttt tctgtgactg gtgagtactc aaccaagtca   17100
ttctgagaat agtgtatgcg gcgaccgagt tgctcttgcc cggcgtcaac acgggataat   17160
accgcgccac atagcagaac tttaaaagtg ctcatcattg gaaaacgttc ttcggggcga   17220
aaactctcaa ggatcttacc gctgttgaga tccagttcga tgtaacccac tcgtgcaccc   17280
aactgatctt cagcatcttt tactttcacc agcgtttctg ggtgagcaaa acaggaagg   17340 caaaatgccg caaaaagggg aataagggcg acacggaaat gttgaatact catactcttc   17400
ctttttcaat attattgaag catttatcag ggttattgtc tcatgagcgg atacatattt   17460
gaatgtattt agaaaaataa acaaataggg gttccgcgca catttccccg aaaagtgcca   17520
cctgacgtct aagaaaccat tattatcatg acattaacct ataaaaatag gcgtatcacg   17580
aggccctttc gtcttcaaga attcggagct tttgccattc tcaccggatt cagtcgtcac   17640
tcatggtgat ttctcacttg ataaccttat ttttgacgag gggaaattaa taggttgtat   17700
tgatgttgga cgagtcggaa tcgcagaccg ataccaggat cttgccatcc tatggaactg   17760
cctcggtgag ttttctcctt cattacagaa acggcttttt caaaaatatg gtattgataa   17820
tcctgatatg aataaattgc agtttcattt gatgctcgat gagttttttct aatcagaatt   17880 ggttaattgg ttgtaacact ggcagagcat tacgctgact tgacgggacg gcggctttgt   17940
tgaataaatc gaacttttgc tgagttgaag gatcagatca cgcatcttcc cgacaacgca   18000
gaccgttccg tggcaaagca aaagttcaaa atcaccaact ggtccaccta caacaaagct   18060
ctcatcaacc gtggctccct cactttctgg ctggatgatg gggcgattca ggcctggtat   18120
gagtcagcaa caccttcttc acgaggcaga cctcagcgcc agaaggccgc cagagaggcc   18180
gagcgcggcc gtgaggcttg gacgctaggg cagggcatga aaaagcccgt agcgggctgc   18240
tacgggcgtc tgacgcggtg gaaaggggga ggggatgttg tctacatggc tctgctgtag   18300
tgagtgggtt gcgctccggc agcggtcctg atcaatcgtc accctttctc ggtccttcaa   18360
cgttcctgac aacgagcctc ttttcgcca atccatcgac aatcaccgcg agtccctgct   18420
cgaacgctgc gtccggaccg gcttcgtcga aggcgtctat cgcggcccgc aacagcggcg   18480
agagcggagc ctgttcaacg gtgccgccgc gctcgccggc atcgctgtcg ccggcctgct   18540
cctcaagcac ggccccaaca gtgaagtagc tgattgtcat cagcgcattg acggcgtccc   18600
cggccgaaaa accgcctcg cagaggaagc gaagctgcgc gtcggccgtt ccatctgcg   18660 gtgcgcccgg tcgcgtgccg gcatggatgc gcgcgccatc gcggtaggcg agcagcgcct   18720
gcctgaagct gcgggcattc ccgatcagaa atgagcgcca gtcgtcgtcg gctctcggca   18780
ccgaatgcgt atgattctcc gccagcatgg cttcggccag tcgtcgagc agcgcccgct   18840 tgttcctgaa gtgccagtaa agcgccggct gctgaacccc caaccgttcc gccagtttgc   18900
gtgtcgtcag accgtctacg ccgacctcgt tcaacaggtc cagggcggca cggatcactg   18960
tattcggctg caactttgtc atgcttgaca ctttatcact gataaacata atatgtccac   19020
caacttatca gtgataaaga atccgcgcgt tcaatcggac cagcggaggc tggtccggag   19080
gccagacgtg aaacccaaca taccccctgat cgtaattctg agcactgtcg cgctcgacgc   19140
tgtcggcatc ggcctgatta tgccggtgct gccgggcctc ctgcgcgatc tggttcactc   19200
gaacgacgtc accgcccact atggcattct gctggcgctg tatgcgttgg tgcaatttgc   19260
```

```
ctgcgcacct gtgctgggcg cgctgtcgga tcgtttcggg cggcggccaa tcttgctcgt   19320
ctcgctggcc ggcgccactg tcgactacgc catcatggcg acagcgcctt cctttgggt    19380 tctctatatc gggcggatcg tggccggcat caccggggcg actggggcgg tagccggcgc   19440
ttatattgcc gatatcactg atggcgatga gcgcgcgcgg cacttcggct tcatgagcgc   19500
ctgtttcggg ttcgggatgg tcgcgggacc tgtgctcggt gggctgatgg gcggtttctc   19560
cccccacgct ccgttcttcg ccgcggcagc cttgaacggc ctcaatttcc tgacgggctg   19620
tttccttttg ccggagtcgc acaaaggcga acgccggccg ttacgccggg aggctctcaa   19680
cccgctcgct tcgttccggt gggcccgggg catgaccgtc gtcgccgccc tgatggcggt   19740
cttcttcatc atgcaacttg tcggacaggt gccggccgcg ctttgggtca ttttcggcga   19800
ggatcgcttt cactgggacg cgaccacgat cggcatttcg cttgccgcat ttggcattct   19860
gcattcactc gcccaggcaa tgatcaccgg ccctgtagcc gcccggctcg gcgaaaggcg   19920
ggcactcatg ctcggaatga ttgccgacgg cacaggctac atcctgcttg ccttcgcgac   19980
acggggatgg atggcgttcc cgatcatggt cctgcttgct tcgggtggca tcggaatgcc   20040
ggcgctgcaa gcaatgttgt ccaggcaggt ggatgaggaa cgtcaggggc agctgcaagg   20100
ctcactggcg gcgctcacca gcctgacctc gatcgtcgga cccctcctct tcacggcgat   20160
ctatgcggct tctataacaa cgtggaacgg gtgggcatgg attgcaggcg ctgccctcta   20220
cttgctctgc ctgccggcgc tgcgtcgcgg gctttggagc ggcgcagggc aacgagccga   20280
tcgctgatcg tggaaacgat aggcctatgc catgcgggtc aaggcgactt ccggcaagct   20340
atacgcgccc taggagtgcg gttggaacgt tggcccagcc agatactccc gatcacgagc   20400
aggacgccga tgatttgaag cgcactcagc gtctgatcca agaacaacca tcctagcaac   20460
acggcggtcc ccgggctgag aaagcccagt aaggaaacaa ctgtaggttc gagtcgcgag   20520
atccccggga accaaaggaa gtaggttaaa cccgctccga tcaggccgag ccacgccagg   20580
ccgagaacat tggttcctgt aggcatcggg attggcggat caaacactaa agctactgga   20640
acgagcagaa gtcctccggc cgccagttgc caggcggtaa aggtgagcag aggcacggga   20700
ggttgccact tgcgggtcag cacggttccg aacgccatgg aaaccgcccc cgccaggccc   20760
gctgcgacgc cgacaggatc tagcgctgcg tttggtgtca acaccaacag cgccacgccc   20820
gcagttccgc aaatagcccc caggaccgcc atcaatcgta tcgggctacc tagcagagcg   20880
gcagagatga acacgaccat cagcggctgc acagcgccta ccgtcgccgc gaccccgccc   20940
ggcaggcggt agaccgaaat aaacaacaag ctccagaata gcgaaatatt aagtgcgccg   21000
aggatgaaga tgcgcatcca ccagattccc gttggaatct gtcggacgat catcacgagc   21060
aataaacccg ccggcaacgc ccgcagcagc ataccggcga cccctcggcc tcgctgttcg   21120
ggctccacga aaacgccgga cagatgcgcc ttgtgagcgt ccttggggcc gtcctcctgt   21180
ttgaagaccg acagcccaat gatctcgccg tcgatgtagg cgccgaatgc cacggcatct   21240
cgcaaccgtt cagcgaacgc ctccatgggc tttttctcct cgtgctcgta acggacccg    21300 aacatctctg gagctttctt cagggccgac aatcggatct cgcggaaatc ctgcacgtcg   21360
gccgctccaa gccgtcgaat ctgagcctta atcacaattg tcaattttaa tcctctgttt   21420
atcggcagtt cgtagagcgc gccgtgcgtc ccgagcgata ctgagcgaag caagtgcgtc   21480
gagcagtgcc cgcttgttcc tgaaatgcca gtaaagcgct ggctgctgaa cccccagccg   21540
gaactgaccc cacaaggccc tagcgtttgc aatgcaccag gtcatcattg acccaggcgt   21600
```

```
gttccaccag gccgctgcct cgcaactctt cgcaggcttc gccgacctgc tcgcgccact   21660
tcttcacgcg gtggaatcc gatccgcaca tgaggcggaa ggtttccagc ttgagcgggt    21720
acggctcccg gtgcgagctg aaatagtcga acatccgtcg ggccgtcggc gacagcttgc   21780
ggtacttctc ccatatgaat ttcgtgtagt ggtcgccagc aaacagcacg acgatttcct   21840
cgtcgatcag gacctggcaa cgggacgttt tcttgccacg gtccaggacg cggaagcggt   21900
gcagcagcga caccgattcc aggtgcccaa cgcggtcgga cgtgaagccc atcgccgtcg   21960
cctgtaggcg cgacaggcat tcctcggcct tcgtgtaata ccggccattg atcgaccagc   22020
ccaggtcctg gcaaagctcg tagaacgtga aggtgatcgg ctcgccgata ggggtgcgct   22080
tcgcgtactc caacacctgc tgccacacca gttcgtcatc gtcggcccgc agctcgacgc   22140
cggtgtaggt gatcttcacg tccttgttga cgtggaaaat gaccttgttt tgcagcgcct   22200
cgcgcgggat tttcttgttg cgcgtggtga acagggcaga gcgggccgtg tcgtttggca   22260
tcgctcgcat cgtgtccggc cacgcgcaa tatcgaacaa ggaaagctgc atttccttga    22320
tctgctgctt cgtgtgtttc agcaacgcgg cctgcttggc ctcgctgacc tgttttgcca   22380
ggtcctcgcc ggcggttttt cgcttcttgg tcgtcatagt tcctcgcgtg tcgatggtca   22440
tcgacttcgc caaacctgcc gcctcctgtt cgagacgacg cgaacgctcc acggcggcg    22500 atggcgcggg cagggcaggg ggagccagtt gcacgctgtc gcgctcgatc ttggccgtag   22560
cttgctggac catcgagccg acggactgga aggtttcgcg gggcgcacgc atgacggtgc   22620
ggcttgcgat ggtttcggca tcctcggcgg aaaaccccgc gtcgatcagt tcttgcctgt   22680
atgccttccg gtcaaacgtc cgattcattc accctccttg cgggattgcc ccgactcacg   22740
ccggggcaat gtgcccttat tcctgatttg acccgcctgg tgccttggtg tccagataat   22800
ccaccttatc ggcaatgaag tcggtcccgt agaccgtctg gccgtccttc tcgtacttgg   22860
tattccgaat cttgccctgc acgaatacca gcgacccctt gcccaaatac ttgccgtggg   22920
cctcggcctg agagccaaaa cacttgatgc ggaagaagtc ggtgcgctcc tgcttgtcgc   22980
cggcatcgtt gcgccactct tcattaaccg ctatatcgaa aattgcttgc ggcttgttag   23040
aattgccatg acgtacctcg gtgtcacggg taagattacc gataaactgg aactgattat   23100
ggctcatatc gaaagtctcc ttgagaaagg agactctagt ttagctaaac attggttccg   23160
ctgtcaagaa ctttagcggc taaaattttg cgggccgcga ccaaaggtgc gaggggcggc   23220
ttccgctgtg tacaaccaga tattttcac caacatcctt cgtctgctcg atgagcgggg    23280
catgacgaaa catgagctgt cggagagggc aggggtttca atttcgtttt tatcagactt    23340
aaccaacggt aaggccaacc cctcgttgaa ggtgatggag gccattgccg acgccctgga   23400
aactccccta cctcttctcc tggagtccac cgaccttgac cgcgaggcac tcgcggagat   23460
tgcgggtcat cctttcaaga gcagcgtgcc gcccggatac gaacgcatca gtgtggtttt   23520
gccgtcacat aaggcgttta tcgtaaagaa atggggcgac gacacccgaa aaaagctgcg   23580
tggaaggctc tgacgccaag ggttagggct tgcacttcct tctttagccg ctaaaacggc   23640
cccttctctg cgggccgtcg gctcgcgcat catatcgaca tcctcaacgg aagccgtgcc   23700
gcgaatggca tcgggcgggt gcgctttgac agttgttttc tatcagaacc cctacgtcgt   23760
gcggttcgat tagctgtttg tcttgcaggc taaacacttt cggtatatcg tttgcctgtg   23820
cgataatgtt gctaatgatt tgttgcgtag gggttactga aaagtgagcg ggaaagaaga   23880
gtttcagacc atcaaggagc gggccaagcg caagctggaa cgcgacatgg gtgcggacct   23940
gttggccgcg ctcaacgacc cgaaaaccgt tgaagtcatg ctcaacgcgg acggcaaggt   24000
```

```
gtggcacgaa cgccttggcg agccgatgcg gtacatctgc gacatgcggc ccagccagtc   24060
gcaggcgatt atagaaacgg tggccggatt ccacggcaaa gaggtcacgc ggcattcgcc   24120
catcctggaa ggcgagttcc ccttggatgg cagccgcttt gccggccaat tgccgccggt   24180
cgtggccgcg ccaacctttg cgatccgcaa gcgcgcggtc gccatcttca cgctggaaca   24240
gtacgtcgag gcgggcatca tgacccgcga gcaatacgag gtcattaaaa gcgccgtcgc   24300
ggcgcatcga aacatcctcg tcattggcgg tactggctcg ggcaagacca cgctcgtcaa   24360
cgcgatcatc aatgaaatgg tcgccttcaa cccgtctgag cgcgtcgtca tcatcgagga   24420
caccggcgaa atccagtgcg ccgcagagaa cgccgtccaa taccacacca gcatcgacgt   24480
ctcgatgacg ctgctgctca agacaacgct gcgtatgcgc cccgaccgca tcctggtcgg   24540
tgaggtacgt ggccccgaag cccttgatct gttgatggcc tggaacaccg gcatgaagg    24600
aggtgccgcc accctgcacg caaacaaccc caaagcgggc ctgagccggc tcgccatgct   24660
tatcagcatg cacccggatt caccgaaacc cattgagccg ctgattggcg aggcggttca   24720
tgtggtcgtc catatcgcca ggaccccctag cggccgtcga gtgcaagaaa ttctcgaagt   24780
tcttggttac gagaacggcc agtacatcac caaaaccctg taaggagtat ttccaatgac   24840
aacggctgtt ccgttccgtc tgaccatgaa tcgcggcatt ttgttctacc ttgccgtgtt   24900
cttcgttctc gctctcgcgt tatccgcgca tccggcgatg gcctcggaag gcaccggcgg   24960
cagcttgcca tatgagagct ggctgacgaa cctgcgcaac tccgtaaccg gcccggtggc   25020
cttcgcgctg tccatcatcg gcatcgtcgt cgccggcggc gtgctgatct tcggcggcga   25080
actcaacgcc ttcttccgaa ccctgatctt cctggttctg gtgatggcgc tgctggtcgg   25140
cgcgcagaac gtgatgagca ccttcttcgg tcgtggtgcc gaaatcgcgg ccctcggcaa   25200
cggggcgctg caccaggtgc aagtcgcggc ggcggatgcc gtgcgtgcgg tagcggctgg   25260
acggctcgcc taatcatggc tctgcgcacg atccccatcc gtcgcgcagg caaccgagaa   25320
aacctgttca tgggtggtga tcgtgaactg gtgatgttct cgggcctgat ggcgtttgcg   25380
ctgattttca gcgcccaaga gctgcgggcc accgtggtcg gtctgatcct gtggttcggg   25440
gcgctctatg cgttccgaat catggcgaag gccgatccga agatgcggtt cgtgtacctg   25500
cgtcaccgcc ggtacaagcc gtattacccg gcccgctcga ccccgttccg cgagaacacc   25560
aatagccaag ggaagcaata ccgatgatcc aagcaattgc gattgcaatc gcgggcctcg   25620
gcgcgcttct gttgttcatc ctctttgccc gcatccgcgc ggtcgatgcc gaactgaaac   25680
tgaaaaagca tcgttccaag gacgccggcc tggccgatct gctcaactac gccgctgtcg   25740
tcgatgacgg cgtaatcgtg ggcaagaacg gcagctttat ggctgcctgg ctgtacaagg   25800
gcgatgacaa cgcaagcagc accgaccagc agcgcgaagt agtgtccgcc cgcatcaacc   25860
aggccctcgc gggcctggga agtgggtgga tgatccatgt ggacgccgtg cggcgtcctg   25920
ctccgaacta cgcggagcgg ggcctgtcgg cgttccctga ccgtctgacg gcagcgattg   25980
aagaagagcg ctcggtcttg ccttgctcgt cggtgatgta cttcaccagc tccgcgaagt   26040
cgctcttctt gatggagcgc atggggacgt gcttggcaat cacgcgcacc ccccggccgt   26100
tttagcggct aaaaaagtca tggctctgcc ctcgggcgga ccacgccat catgaccttg    26160
ccaagctcgt cctgcttctc ttcgatcttc gccagcaggg cgaggatcgt ggcatcaccg   26220
aaccgcgccg tgcgcgggtc gtcggtgagc cagagtttca gcaggccgcc caggcggccc   26280
aggtcgccat tgatgcgggc cagctcgcgg acgtgctcat agtccacgac gcccgtgatt   26340
```

```
ttgtagccct ggccgacggc cagcaggtag gccgacaggc tcatgccggc cgccgccgcc    26400
ttttcctcaa tcgctcttcg ttcgtctgga aggcagtaca ccttgatagg tgggctgccc    26460
ttcctggttg gcttggtttc atcagccatc cgcttgccct catctgttac gccggcggta    26520
gccggccagc ctcgcagagc aggattcccg ttgagcaccg ccaggtgcga ataagggaca    26580
gtgaagaagg aacacccgct cgcgggtggg cctacttcac ctatcctgcc cggctgacgc    26640
cgttggatac accaaggaaa gtctacacga accctttggc aaaatcctgt atatcgtgcg    26700
aaaaaggatg atataccga aaaaatcgct ataatgaccc cgaagcaggg ttatgcagcg    26760
gaaaagcgct gcttccctgc tgttttgtgg aatatctacc gactggaaac aggcaaatgc    26820
aggaaattac tgaactgagg ggacaggcga gagacgatgc caaagagcta caccgacgag    26880
ctggccgagt gggttgaatc ccgcgcggcc aagaagcgcc ggcgtgatga ggctgcggtt    26940
gcgttcctgg cggtgagggc ggatgtcgag gcggcgttag cgtccggcta tgcgctcgtc    27000
accatttggg agcacatgcg ggaaacgggg aaggtcaagt tctcctacga gacgttccgc    27060
tcgcacgcca ggcggcacat caaggccaag cccgccgatg tgcccgcacc gcaggccaag    27120
gctgcggaac ccgcgccggc acccaagacg ccggagccac ggcggccgaa gcagggggc    27180 aaggctgaaa agccggcccc cgctgcggcc ccgaccggct tcaccttcaa cccaacaccg    27240
gacaaaaagg atctactgta atggcgaaaa ttcacatggt tttgcagggc aagggcgggg    27300
tcggcaagtc ggccatcgcc gcgatcattg cgcagtacaa gatggacaag gggcagacac    27360
ccttgtgcat cgacaccgac ccggtgaacg cgacgttcga gggctacaag gccctgaacg    27420
tccgccggct gaacatcatg gccggcgacg aaattaactc gcgcaacttc gacaccctgg    27480
tcgagctgat tgcgccgacc aaggatgacg tggtgatcga caacggtgcc agctcgttcg    27540
tgcctctgtc gcattacctc atcagcaacc aggtgccggc tctgctgcaa gaaatggggc    27600
atgagctggt catccatacc gtcgtcaccg gcggccaggc tctcctggac acggtgagcg    27660
gcttcgccca gctcgccagc cagttcccgg ccgaagcgct tttcgtggtc tggctgaacc    27720
cgtattgggg gcctatcgag catgagggca agagctttga gcagatgaag gcgtacacgg    27780
ccaacaaggc ccgcgtgtcg tccatcatcc agattccggc cctcaaggaa gaaacctacg    27840
gccgcgattt cagcgacatg ctgcaagagc ggctgacgtt cgaccaggcg ctggccgatg    27900
aatcgctcac gatcatgacg cggcaacgcc tcaagatcgt gcggcgcggc ctgtttgaac    27960
agctcgacgc ggcggccgtg ctatgagcga ccagattgaa gagctgatcc gggagattgc    28020
ggccaagcac ggcatcgccg tcggccgcga cgacccggtg ctgatcctgc ataccatcaa    28080
cgccccggct catggccgaca gtgcggccaa gcaagaggaa tccttgccgc cgttcaagga    28140
agagctggaa gggatcgccc atcgttgggg cgaggacgcc aaggccaaag cggagcggat    28200
gctgaacgcg ccctggcgg ccagcaagga cgcaatggcg aaggtaatga aggacagcgc    28260
cgcgcaggcg gccgaagcga tccgcaggga aatcgacgac ggccttggcc gccagctcgc    28320
ggccaaggtc gcggacgcgc ggcgcgtggc gatgatgaac atgatcgccg gcggcatggt    28380
gttgttcgcg gccgccctgg tggtgtgggc ctcgttatga atcgcagagg cgcagatgaa    28440
aaagcccggc gttgccgggc tttgttttg cgttagctgg gcttgtttga caggcccaag    28500
ctctgactgc gcccgcgctc gcgctcctgg gcctgtttct tctcctgctc ctgcttgcgc    28560
atcagggcct ggtgccgtcg ggctgcttca cgcatcgaat cccagtcgcc ggccagctcg    28620
ggatgctccg cgcgcatctt gcgcgtcgcc agttcctcga tcttgggcgc gtgaatgccc    28680
atgccttcct tgatttcgcg caccatgtcc agccgcgtgt gcagggtctg caagcgggct    28740
```

```
tgctgttggg cctgctgctg ctgccaggcg gcctttgtac gcggcaggga cagcaagccg   28800
ggggcattgg actgtagctg ctgcaaacgc gcctgctgac ggtctacgag ctgttctagg   28860
cggtcctcga tgcgctccac ctggtcatgc tttgcctgca cgtagagcgc aagggtctgc   28920
tggtaggtct gctcgatggg cgcggattct aagagggcct gctgttccgt ctcggcctcc   28980
tgggccgcct gtagcaaatc ctcgccgctg ttgccgctgg actgctttac tgccggggac   29040
tgctgttgcc ctgctcgcgc cgtcgtcgca gttcggcttg cccccactcg attgactgct   29100
tcatttcgag ccgcagcgat gcgatctcgg attgcgtcaa cggacggggc agcgcggagg   29160
tgtccggctt ctccttgggt gagtcggtcg atgccatagc caaaggtttc cttccaaaat   29220
gcgtccattg ctggaccgtg tttctcattg atgcccgcaa gcatcttcgg cttgaccgcc   29280
aggtcaagcg cgccttcatg ggcggtcatg acggacgccg ccatgacctt gccgccgttg   29340
ttctcgatgt agccgcgtaa tgaggcaatg gtgccgccca tcgtcagcgt gtcatcgaca   29400
acgatgtact tctggccggg gatcacctcc ccctcgaaag tcgggttgaa cgccaggcga   29460
tgatctgaac cggctccggt tcgggcgacc ttctcccgct gcacaatgtc cgtttcgacc   29520
tcaaggccaa ggcggtcggc cagaacgacc gccatcatgg ccggaatctt gttgttcccc   29580
gccgcctcga cggcgaggac tggaacgatg cggggcttgt cgtcgccgat cagcgtcttg   29640
agctgggcaa cagtgtcgtc cgaaatcagg cgctcgacca aattaagcgc gcttccgcg   29700 tcgccctgct tcgcagcctg gtattcaggc tcgttggtca agaaccaag gtcgccgttg   29760 cgaaccacct tcgggaagtc tccccacggt gcgcgctcgg ctctgctgta gctgctcaag   29820
acgcctccct ttttagccgc taaaactcta acgagtcgc ccgcgactca acttgacgct   29880
ttcggcactt acctgtgcct tgccacttgc gtcataggtg atgcttttcg cactcccgat   29940
ttcaggtact ttatcgaaat ctgaccgggc gtgcattaca aagttcttcc ccacctgttg   30000
gtaaatgctg ccgctatctg cgtggacgat gctgccgtcg tggcgctgcg acttatcggc   30060
cttttgggcc atatagatgt tgtaaatgcc aggtttcagg gccccggctt tatctacctt   30120
ctggttcgtc catgcgcctt ggttctcggt ctggacaatt ctttgcccat tcatgaccag   30180
gaggcggtgt tcattgggt gactcctgac ggttgcctct ggtgttaaac gtgtcctggt   30240
cgcttgccgg ctaaaaaaaa gccgacctcg gcagttcgag gccggctttc cctagagccg   30300
ggcgcgtcaa ggttgttcca tctattttag tgaactgcgt tcgatttatc agttactttc   30360
ctcccgcttt gtgtttcctc ccactcgttt ccgcgtctag ccgacccctc aacatagcgg   30420
cctcttcttg ggctgccttt gcctcttgcc gcgcttcgtc acgctcggct tgcaccgtcg   30480
taaagcgctc ggcctgcctg gccgcctctt gcgccgccaa cttcctttgc tcctggtggg   30540
cctcggcgtc ggcctgcgcc ttcgctttca ccgctgccaa ctccgtgcgc aaactctccg   30600
cttcgcgcct ggtggcgtcg cgctcgccgc gaagcgcctg catttcctgg ttggccgcgt   30660
ccagggtctt gcggctctct tctttgaatg cgcgggcgtc ctggtgagcg tagtccagct   30720
cggcgcgcag ctcctgcgct cgacgctcca cctcgtcggc ccgctgcgtc gccagcgcgg   30780
cccgctgctc ggctcctgcc agggcggtgc gtgcttcggc cagggcttgc cgctggcgtg   30840
cggccagctc ggccgcctcg gcggcctgct gctctagcaa tgtaacgcgc gcctgggctt   30900
cttccagctc gcgggcctgc gcctcgaagg cgtcggccag ctccccgcgc acggcttcca   30960
actcgttgcg ctcacgatcc cagccggctt gcgctgcctg caacgattca ttggcaaggg   31020
cctgggcggc ttgccagagg gcggccacgg cctggttgcc ggcctgctgc accgcgtccg   31080
```

-continued

```
gcacctggac tgccagcggg gcggcctgcg ccgtgcgctg gcgtcgccat tcgcgcatgc    31140
cggcgctggc gtcgttcatg ttgacgcggg cggccttacg cactgcatcc acggtcggga    31200
agttctcccg gtcgccttgc tcgaacagct cgtccgcagc cgcaaaaatg cggtcgcgcg    31260
tctctttgtt cagttccatg ttggctccgg taattggtaa gaataataat actcttacct    31320
accttatcag cgcaagagtt tagctgaaca gttctcgact taacggcagg ttttttagcg    31380
gctgaagggc aggcaaaaaa agccccgcac ggtcggcggg ggcaaagggt cagcgggaag    31440
gggattagcg ggcgtcgggc ttcttcatgc gtcggggccg cgcttcttgg gatggagcac    31500
gacgaagcgc gcacgcgcat cgtcctcggc cctatcggcc cgcgtcgcgg tcaggaactt    31560
gtcgcgcgct aggtcctccc tggtgggcac caggggcatg aactcggcct gctcgatgta    31620
ggtccactcc atgaccgcat cgcagtcgag gccgcgttcc ttcaccgtct cttgcaggtc    31680
gcggtacgcc cgctcgttga gcggctggta acgggccaat tggtcgtaaa tggctgtcgg    31740
ccatgagcgg cctttcctgt tgagccagca gccgacgacg aagccggcaa tgcaggcccc    31800
tggcacaacc aggccgacgc cggggcaggg gatggcagc agctcgccaa ccaggaaccc    31860
cgccgcgatg atgccgatgc cggtcaacca gcccttgaaa ctatccggcc ccgaaacacc    31920
cctgcgcatt gcctggatgc tgccgccgat agcttgcaac atcaggagcc gtttcttttg    31980
ttcgtcagtc atggtccgcc ctcaccagtt gttcgtatcg gtgtcggacg aactgaaatc    32040
gcaagagctg ccggtatcgg tccagccgct gtccgtgtcg ctgctgccga agcacggcga    32100
ggggtccgcg aacgccgcag acggcgtatc cggccgcagc gcatcgccca gcatggcccc    32160
ggtcagcgag ccgccggcca ggtagcccag catggtgctg ttggtcgccc cggccaccag    32220
ggccgacgtg acgaaatcgc cgtcattccc tctggattgt tcgctgctcg gcggggcagt    32280
gcgccgcgcc ggcggcgtcg tggatggctc gggttggctg gcctgcgacg gccggcgaaa    32340
ggtgcgcagc agctcgttat cgaccggctg cggcgtcggg gccgccgcct tgcgctgcgg    32400
tcggtgttcc ttcttcggct cgcgcagctt gaacagcatg atcgcggaaa ccagcagcaa    32460
cgccgcgcct acgcctcccg cgatgtagaa cagcatcgga ttcattcttc ggtcctcctt    32520
gtagcggaac cgttgtctgt gcggcgcggg tggcccgcgc cgctgtcttt ggggatcagc    32580
cctcgatgag cgcgaccagt ttcacgtcgg caaggttcgc ctcgaactcc tggccgtcgt    32640
cctcgtactt caaccaggca tagccttccg ccggcggccg acggttgagg ataaggcggg    32700
cagggcgctc gtcgtgctcg acctggacga tggccttttt cagcttgtcc gggtccggct    32760
ccttcgcgcc cttttccttg gcgtccttac cgtcctggtc gccgtcctcg ccgtcctggc    32820
cgtcgccggc ctccgcgtca cgctcggcat cagtctggcc gttgaaggca tcgacggtgt    32880
tgggatcgcg gcccttctcg tccaggaact cgcgcagcag cttgaccgtg ccgcgcgtga    32940
tttcctgggt gtcgtcgtca agccacgcct cgacttcctc cgggcgcttc ttgaaggccg    33000
tcaccagctc gttcaccacg gtcacgtcgc gcacgcggcc ggtgttgaac gcatcggcga    33060
tcttctccgg caggtccagc agcgtgacgt gctgggtgat gaacgccggc gacttgccga    33120
tttccttggc gatatcgcct ttcttcttgc ccttcgccag ctcgcggcca atgaagtcgg    33180
caatttcgcg cggggtcagc tcgttgcgtt gcaggttctc gataacctgg tcggcttcgt    33240
tgtagtcgtt gtcgatgaac gccgggatgg acttcttgcc ggcccacttc gagccacggt    33300
agcggcgggc gccgtgattg atgatatagc ggcccggctg ctcctggttc tcgcgcaccg    33360
aaatgggtga cttcaccccg cgctctttga tcgtggcacc gatttccgcg atgctctccg    33420
gggaaaagcc ggggttgtcg gccgtccgcg gctgatgcgg atcttcgtcg atcaggtcca    33480
```

```
ggtccagctc gatagggccg gaaccgccct gagacgccgc aggagcgtcc aggaggctcg   33540
acaggtcgcc gatgctatcc aacccaggc cggacggctg cgccgcgcct gcggcttcct    33600
gagcggccgc agcggtgttt ttcttggtgg tcttggcttg agccgcagtc attgggaaat   33660
ctccatcttg gtgaacacgt aatcagccag ggcgcgaacc tctttcgatg ccttgcgcgc   33720
ggccgttttc ttgatcttcc agaccggcac accggatgcg agggcatcgg cgatgctgct   33780
gcgcaggcca acggtggccg gaatcatcat cttggggtac gcggccagca gctcggcttg   33840
gtggcgcgcg tggcgcggat tccgcgcatc gaccttgctg gcaccatgc caaggaattg    33900
cagcttggcg ttcttctggc gcacgttcgc aatggtcgtg accatcttct tgatgccctg   33960
gatgctgtac gcctcaagct cgatggggga cagcacatag tcggccgcga agagggcggc   34020
cgccaggccg acgccaaggg tcggggccgt gtcgatcagg cacacgtcga agccttggtt   34080
cgccagggcc ttgatgttcg ccccgaacag ctcgcgggcg tcgtccagcg acagccgttc   34140
ggcgttcgcc agtaccgggt tggactcgat gagggcgagg cgcgcggcct ggccgtcgcc   34200
ggctgcgggt gcggtttcgg tccagccgcc ggcagggaca cgccgaaca gcttgcttgc    34260
atgcaggccg gtagcaaagt ccttgagcgt gtaggacgca ttgccctggg ggtccaggtc   34320
gatcacggca acccgcaagc cgcgctcgaa aaagtcgaag gcaagatgca caagggtcga   34380
agtcttgccg acgccgcctt tctggttggc cgtgaccaaa gttttcatcg tttggtttcc   34440
tgttttttct tggcgtccgc ttcccacttc cggacgatgt acgcctgatg ttccggcaga   34500
accgccgtta cccgcgcgta cccctcgggc aagttcttgt cctcgaacgc ggcccacacg   34560
cgatgcaccg cttgcgacac tgcgccctg gtcagtccca gcgacgttgc gaacgtcgcc    34620
tgtggcttcc catcgactaa gacgcccgc gctatctcga tggtctgctg ccccacttcc    34680
agcccctgga tcgcctcctg gaactggctt tcggtaagcc gtttcttcat ggataacacc   34740
cataattgc tccgcgcctt ggttgaacat agcggtgaca gccgccagca catgagagaa    34800
gtttagctaa acatttctcg cacgtcaaca cctttagccg ctaaaactcg tccttggcgt   34860
aacaaaacaa aagcccggaa accgggcttt cgtctcttgc cgcttatggc tctgcacccg   34920
gctccatcac caacaggtcg cgcacgcgct tcactcggtt gcggatcgac actgccagcc   34980
caacaaagcc ggttgccgcc gccgccagga tcgcgccgat gatgccggcc acaccggcca   35040
tcgcccacca ggtcgccgcc ttccggttcc attcctgctg gtactgcttc gcaatgctgg   35100
acctcggctc accataggct gaccgctcga tggcgtatgc cgcttctccc cttggcgtaa   35160
aacccagcgc cgcaggcggc attgccatgc tgcccgccgc tttcccgacc acgacgcgcg   35220
caccaggctt gcggtccaga ccttcggcca cggcgagctg cgcaaggaca taatcagccg   35280
ccgacttggc tccacgcgcc tcgatcagct cttgcactcg cgcgaaatcc ttggcctcca   35340
cggccgccat gaatcgcgca cgcggcgaag ctccgcagg gccggcgtcg tgatcgccgc    35400
cgagaatgcc cttcaccaag ttcgacgaca cgaaaatcat gctgacggct atcaccatca   35460
tgcagacgga tcgcacgaac ccgctgaatt gaacacgagc acggcacccg cgaccactat   35520
gccaagaatg cccaaggtaa aaattgccgg ccccgccatg aagtccgtga atgccccgac   35580
ggccgaagtg aagggcaggc cgccaccag gccgccgccc tcactgcccg gcacctggtc    35640
gctgaatgtc gatgccagca cctgcggcac gtcaatgctt ccgggcgtcg cgctcgggct   35700
gatcgcccat cccgttactg cccgatccc ggcaatggca aggactgcca gcgctgccat    35760
ttttggggtg aggccgttcg cggccgaggg gcgcagcccc tgggggatg ggaggccgc     35820
```

```
gttagcgggc cgggagggtt cgagaagggg gggcacccccc cttcggcgtg cgcggtcacg    35880
cgcacagggc gcagccctgg ttaaaaacaa ggtttataaa tattggttta aaagcaggtt    35940
aaaagacagg ttagcggtgg ccgaaaaacg ggcggaaacc cttgcaaatg ctggattttc    36000
tgcctgtgga cagcccctca aatgtcaata ggtgcgcccc tcatctgtca gcactctgcc    36060
cctcaagtgt caaggatcgc gcccctcatc tgtcagtagt cgcgcccctc aagtgtcaat    36120
accgcagggc acttatcccc aggcttgtcc acatcatctg tgggaaactc gcgtaaaatc    36180
aggcgttttc gccgatttgc gaggctggcc agctccacgt cgccggccga aatcgagcct    36240
gcccctcatc tgtcaacgcc gcgcggtgt  agtcggcccc tcaagtgtca acgtccgccc    36300
ctcatctgtc agtgagggcc aagttttccg cgaggtatcc acaacgccgg cggccgcggt    36360
gtctcgcaca cggcttcgac ggcgtttctg gcgcgtttgc agggccatag acggccgcca    36420
gcccagcggc gagggcaacc agcccggtga gcgtcggaaa ggcgctggaa gccccgtagc    36480
gacgcggaga ggggcgagac aagccaaggg cgcaggctcg atgcgcagca cgacatagcc    36540
ggttctcgca aggacgagaa tttccctgcg gtgcccctca agtgtcaatg aaagtttcca    36600
acgcgagcca ttcgcgagag ccttgagtcc acgctagatg agagctttgt tgtaggtgga    36660
ccagttggtg attttgaact tttgcttttgc cacggaacgg tctgcgttgt cgggaagatg    36720
cgtgatctga tccttcaact cagcaaaagt tcgatttatt caacaaagcc acgttgtgtc    36780
tcaaaatctc tgatgttaca ttgcacaaga taaaaatata tcatcatgaa caataaaact    36840
gtctgcttac ataaacagta ataacaagggg tgttatgagc catattcaac gggaaacgtc    36900
ttgctcgac                                                            36909

<210> SEQ ID NO 8
<211> LENGTH: 13019
<212> TYPE: DNA
<213> ORGANISM: artificial sequence
<220> FEATURE:
<223> OTHER INFORMATION: vector

<400> SEQUENCE: 8
gttacccgga ccgaagctta gcccgggcat gcctgcagtg cagcgtgacc cggtcgtgcc      60
cctctctaga gataatgagc attgcatgtc taagttataa aaaattacca catatttttt     120
ttgtcacact tgtttgaagt gcagtttatc tatctttata catatattta aactttactc     180
tacgaataat ataatctata gtactacaat aatatcagtg ttttagagaa tcatataaat     240
gaacagttag acatggtcta aaggacaatt gagtattttg acaacaggac tctacagttt     300
tatcttttta gtgtgcatgt gttctccttt ttttttgcaa atagcttcac ctatataata     360
cttcatccat tttattagta catccattta gggtttaggg ttaatggttt ttatagacta     420 attttttttag tacatctatt ttattctatt ttagcctcta aattaagaaa actaaaactc     480 tatttttagtt ttttttattta ataatttaga tataaaatag aataaaataa agtgactaaa     540
aattaaacaa ataccctta agaaattaaa aaaactaagg aaacatttttt cttgtttcga     600 gtagataatg ccagcctgtt aaacgccgtc gacgagtcta acggacacca accagcgaac     660
cagcagcgtc gcgtcgggcc aagcgaagca gacggcacgg catctctgtc gctgcctctg     720 gaccccctctc gagagttccg ctccaccgtt ggacttgctc cgctgtcggc atccagaaat     780
tgcgtggcgg agcggcagac gtgagccggc acgcaggcg gcctcctcct cctctcacgg     840
cacggcagct acgggggatt cctttcccac cgctccttcg ctttcccttc ctcgcccgcc     900
gtaataaata gacaccccct ccacacccctc tttcccccaac ctcgtgttgt tcggagcgca     960
```

```
cacacacaca accagatctc ccccaaatcc acccgtcggc acctccgctt caaggtacgc    1020
cgctcgtcct cccccccccc ccctctctac cttctctaga tcggcgttcc ggtccatggt    1080
tagggcccgg tagttctact tctgttcatg tttgtgttag atccgtgttt gtgttagatc    1140
cgtgctgcta gcgttcgtac acggatgcga cctgtacgtc agacacgttc tgattgctaa    1200
cttgccagtg tttctctttg gggaatcctg ggatggctct agccgttccg cagacgggat    1260
cgatttcatg attttttttg tttcgttgca tagggtttgg tttgcccttt tcctttattt    1320
caatatatgc cgtgcacttg tttgtcgggt catcttttca tgctttttt tgtcttggtt     1380 gtgatgatgt ggtctggttg ggcggtcgtt ctagatcgga gtagaattct gtttcaaact    1440
acctggtgga tttattaatt ttggatctgt atgtgtgtgc catacatatt catagttacg    1500
aattgaagat gatggatgga aatatcgatc taggataggt atacatgttg atgcgggttt    1560
tactgatgca tatacagaga tgctttttgt tcgcttggtt gtgatgatgt ggtgtggttg    1620
ggcggtcgtt cattcgttct agatcggagt agaatactgt ttcaaactac ctggtgtatt    1680
tattaatttt ggaactgtat gtgtgtgtca tacatcttca tagttacgag tttaagatgg    1740
atggaaatat cgatctagga taggtataca tgttgatgtg ggttttactg atgcatatac    1800
atgatggcat atgcagcatc tattcatatg ctctaacctt gagtacctat ctattataat    1860
aaacaagtat gttttataat tattttgatc ttgatatact tggatgatgg catatgcagc    1920
agctatatgt ggattttttt agccctgcct tcatacgcta tttatttgct tggtactgtt    1980
tcttttgtcg atgctcaccc tgttgtttgg tgttacttct gcaggtcgac tctagaggat    2040
ccacaagttt gtacaaaaaa gctgaacgag aaacgtaaaa tgatataaat atcaatatat    2100
taaattagat tttgcataaa aaacagacta cataatactg taaaacacaa catatccagt    2160
cactatggcg gccgcattag gcaccccagg ctttacactt tatgcttccg gctcgtataa    2220
tgtgtggatt ttgagttagg atttaaatac gcgttgatcc ggcttactaa agccagata    2280 acagtatgcg tatttgcgcg ctgattttg cggtataaga atatatactg atatgtatac    2340
ccgaagtatg tcaaaaagag gtatgctatg aagcagcgta ttacagtgac agttgacagc    2400
gacagctatc agttgctcaa ggcatatatg atgtcaatat ctccggtctg gtaagcacaa    2460
ccatgcagaa tgaagcccgt cgtctgcgtg ccgaacgctg gaaagcggaa atcaggaag    2520 ggatggctga ggtcgcccgg tttattgaaa tgaacggctc ttttgctgac gagaacaggg    2580
gctggtgaaa tgcagtttaa ggtttacacc tataaaagag agagccgtta tcgtctgttt    2640
gtggatgtac agagtgatat cattgacacg cccggtcgac ggatggtgat cccctggcc    2700 agtgcacgtc tgctgtcaga taaagtctcc cgtgaacttt acccggtggt gcatatcggg    2760
gatgaaagct ggcgcatgat gaccaccgat atggccagtg tgccggtctc cgttatcggg    2820
gaagaagtgg ctgatctcag ccaccgcgaa aatgacatca aaaacgccat taacctgatg    2880
ttctggggaa tataaatgtc aggctcccct atacacagcc agtctgcagg tcgaccatag    2940
tgactggata tgttgtgttt tacagtatta tgtagtctgt ttttatgcaa aaatctaatt    3000
taatatattg atatttatat cattttacgt ttctcgttca gctttcttgt acaaagtggt    3060
gttaacctag acttgtccat cttctggatt ggccaactta attaatgtat gaaataaaag    3120
gatgcacaca tagtgacatg ctaatcacta taatgtgggc atcaaagttg tgtgttatgt    3180
gtaattacta gttatctgaa taaaagagaa agagatcatc catatttctt atcctaaatg    3240
aatgtcacgt gtctttataa ttctttgatg aaccagatgc atttcattaa ccaaatccat    3300
```

| | | | | | |
|---|---|---|---|---|---|
| atacatataa | atattaatca | tatataatta | atatcaattg | ggttagcaaa | acaaatctag | 3360 |
| tctaggtgtg | ttttgcgaat | tgcggccgcc | accgcggtgg | agctcgaatt | ccggtccggg | 3420 |
| tcacctttgt | ccaccaagat | ggaactgcgg | ccgctcatta | attaagtcag | gcgcgcctct | 3480 |
| agttgaagac | acgttcatgt | cttcatcgta | agaagacact | cagtagtctt | cggccagaat | 3540 |
| ggccatctgg | attcagcagg | cctagaaggc | catttaaatc | ctgaggatct | ggtcttccta | 3600 |
| aggacccggg | atatcggacc | gattaaactt | taattcggtc | cgaagcttgc | atgcctgcag | 3660 |
| tgcagcgtga | cccggtcgtg | cccctctcta | gagataatga | gcattgcatg | tctaagttat | 3720 |
| aaaaaattac | cacatatttt | ttttgtcaca | cttgtttgaa | gtgcagttta | tctatcttta | 3780 |
| tacatatatt | taaactttac | tctacgaata | atataatcta | tagtactaca | ataatatcag | 3840 |
| tgttttagag | aatcatataa | atgaacagtt | agacatggtc | taaaggacaa | ttgagtattt | 3900 |
| tgacaacagg | actctacagt | tttatctttt | tagtgtgcat | gtgttctcct | ttttttttgc | 3960 |
| aaatagcttc | acctatataa | tacttcatcc | attttattag | tacatccatt | tagggtttag | 4020 |
| ggttaatggt | ttttatagac | taatttttttt | agtcacatcta | ttttattcta | ttttagcctc | 4080 |
| taaattaaga | aaactaaaac | tctattttag | ttttttttatt | taataattta | gatataaaat | 4140 |
| agaataaaat | aaagtgacta | aaaattaaac | aaatacccttt | taagaaatta | aaaaaactaa | 4200 |
| ggaaacattt | ttcttgtttc | gagtagataa | tgccagcctg | ttaaacgccg | tcgacgagtc | 4260 |
| taacggacac | caaccagcga | accagcagcg | tcgcgtcggg | ccaagcgaag | cagacggcac | 4320 |
| ggcatctctg | tcgctgcctc | tggaccccctc | tcgagagttc | cgctccaccg | ttggacttgc | 4380 |
| tccgctgtcg | gcatccagaa | attgcgtggc | ggagcggcag | acgtgagccg | gcacggcagg | 4440 |
| cggcctcctc | ctcctctcac | ggcaccggca | gctacggggg | attcctttcc | caccgctcct | 4500 |
| tcgctttccc | ttcctcgccc | gccgtaataa | atagacaccc | cctccacacc | ctctttcccc | 4560 |
| aacctcgtgt | tgttcggagc | gcacacacac | acaaccagat | ctcccccaaa | tccacccgtc | 4620 |
| ggcacctccg | cttcaaggta | cgccgctcgt | cctccccccc | ccccctctct | accttctcta | 4680 |
| gatcggcgtt | ccggtccatg | catggttagg | gcccggtagt | tctacttctg | ttcatgtttg | 4740 |
| tgttagatcc | gtgtttgtgt | tagatccgtg | ctgctagcgt | tcgtacacgg | atgcgacctg | 4800 |
| tacgtcagac | acgttctgat | tgctaacttg | ccagtgtttc | tctttgggga | atcctgggat | 4860 |
| ggctctagcc | gttccgcaga | cgggatcgat | ttcatgattt | tttttgtttc | gttgcatagg | 4920 |
| gtttggtttg | cccttttcct | ttatttcaat | atatgccgtg | cacttgtttg | tcgggtcatc | 4980 |
| ttttcatgct | ttttttttgtc | ttggttgtga | tgatgtggtc | tggttgggcg | tcgttctag | 5040 |
| atcggagtag | aattctgttt | caaactacct | ggtggattta | ttaattttgg | atctgtatgt | 5100 |
| gtgtgccata | catattcata | gttacgaatt | gaagatgatg | gatggaaata | tcgatctagg | 5160 |
| ataggtatac | atgttgatgc | gggttttact | gatgcatata | cagagatgct | ttttgttcgc | 5220 |
| ttggttgtga | tgatgtggtg | tggttgggcg | gtcgttcatt | cgttctagat | cggagtagaa | 5280 |
| tactgtttca | aactacctgg | tgtatttatt | aattttggaa | ctgtatgtgt | gtgtcataca | 5340 |
| tcttcatagt | tacgagttta | agatggatgg | aaatatcgat | ctaggatagg | tatacatgtt | 5400 |
| gatgtgggtt | ttactgatgc | atatacatga | tggcatatgc | agcatctatt | catatgctct | 5460 |
| aaccttgagt | acctatctat | tataataaac | aagtatgttt | tataattatt | ttgatcttga | 5520 |
| tatacttgga | tgatggcata | tgcagcagct | atatgtggat | ttttttagcc | ctgccttcat | 5580 |
| acgctatttta | tttgcttggt | actgtttctt | ttgtcgatgc | tcaccctgtt | gtttggtgtt | 5640 |
| acttctgcag | gtcgacttta | acttagccta | ggatccacac | gacaccatgt | cccccgagcg | 5700 |

-continued

```
ccgccccgtc gagatccgcc cggccaccgc cgccgacatg gccgccgtgt gcgacatcgt    5760
gaaccactac atcgagacct ccaccgtgaa cttccgcacc gagccgcaga ccccgcagga    5820
gtggatcgac gacctggagc gcctccagga ccgctacccg tggctcgtgg ccgaggtgga    5880
gggcgtggtg gccggcatcg cctacgccgg cccgtggaag gccgcaacg cctacgactg     5940 gaccgtggag tccaccgtgt acgtgtccca ccgccaccag cgcctcggcc tcggctccac    6000
cctctacacc cacctcctca agagcatgga ggcccagggc ttcaagtccg tggtggccgt    6060
gatcggcctc ccgaacgacc cgtccgtgcg cctccacgag gccctcggct acaccgcccg    6120 cggcacccic cgcgccgccg gctacaagca cggcggctgg cacgacgtcg gcttctggca    6180
gcgcgacttc gagctgccgg ccccgccgcg cccggtgcgc ccggtgacgc agatctgagt    6240
cgaaacctag acttgtccat cttctggatt ggccaactta attaatgtat gaaataaaag    6300
gatgcacaca tagtgacatg ctaatcacta taatgtgggc atcaaagttg tgtgttatgt    6360
gtaattacta gttatctgaa taaaagagaa agagatcatc catatttctt atcctaaatg    6420
aatgtcacgt gtcttfataa ttcttfgatg aaccagatgc atttcattaa ccaaatccat    6480
atacatataa atattaatca tatataatta atatcaattg ggttagcaaa acaaatctag    6540
tctaggtgtg ttttgcgaat tgcggccgcc accgcggtgg agctcgaatt cattccgatt    6600
aatcgtggcc tcttgctctt caggatgaag agctatgttt aaacgtgcaa gcgctactag    6660
acaattcagt acattaaaaa cgtccgcaat gtgttattaa gttgtctaag cgtcaatttg    6720
tttacaccac aatatatcct gccaccagcc agcaacagc tccccgaccg gcagctcggc     6780
acaaaatcac cactcgatac aggcagccca tcagtccggg acggcgtcag cgggagagcc    6840
gttgtaaggc ggcagacttt gctcatgtta ccgatgctat tcggaagaac ggcaactaag    6900
ctgccgggtt tgaaacacgg atgatctcgc ggagggtagc atgttgattg taacgatgac    6960
agagcgttgc tgcctgtgat caaatatcat ctccctcgca gagatccgaa ttatcagcct    7020
tcttattcat ttctcgctta accgtgacag gctgtcgatc ttgagaacta tgccgacata    7080
ataggaaatc gctggataaa gccgctgagg aagctgagtg gcgctatttc tttagaagtg    7140
aacgttgacg atcgtcgacc gtaccccgat gaattaattc ggacgtacgt tctgaacaca    7200
gctggatact tacttgggcg attgtcatac atgacatcaa caatgtaccc gtttgtgtaa    7260
ccgtctcttg gaggttcgta tgacactagt ggttcccctc agcttgcgac tagatgttga    7320
ggcctaacat tttattagag agcaggctag ttgcttagat acatgatctt caggccgtta    7380
tctgtcaggc caagcgaaaa ttggccattt atgacgacca atgccccgca gaagctccca    7440
tctttgccgc catagacgcc gcgcccccct tttgggggtgt agaacatcct tttgccagat    7500
gtggaaaaga agttcgttgt cccattgttg gcaatgacgt agtagccggc gaaagtgcga    7560
gacccatttg cgctatatat aagcctacga tttccgttgc gactattgtc gtaattggat    7620
gaactattat cgtagttgct ctcagagttg tcgtaatttg atggactatt gtcgtaattg    7680
cttatggagt tgtcgtagtt gcttggagaa atgtcgtagt tggatgggga gtagtcatag    7740
ggaagacgag cttcatccac taaaacaatt ggcaggtcag caagtgcctg ccccgatgcc    7800
atcgcaagta cgaggcttag aaccaccttc aacagatcgc gcatagtctt ccccagctct    7860
ctaacgcttg agttaagccg cgccgcgaag cggcgtcggc ttgaacgaat tgttagacat    7920
tatttgccga ctaccttggt gatctcgcct ttcacgtagt gaacaaattc ttccaactga    7980
tctgcgcgcg aggccaagcg atcttcttgt ccaagataag cctgcctagc ttcaagtatg    8040
```

```
acgggctgat actgggccgg caggcgctcc attgcccagt cggcagcgac atccttcggc    8100
gcgattttgc cggttactgc gctgtaccaa atgcgggaca acgtaagcac tacatttcgc    8160
tcatcgccag cccagtcggg cggcgagttc catagcgtta aggtttcatt tagcgcctca    8220
aatagatcct gttcaggaac cggatcaaag agttcctccg ccgctggacc taccaaggca    8280
acgctatgtt ctcttgcttt tgtcagcaag atagccagat caatgtcgat cgtggctggc    8340
tcgaagatac ctgcaagaat gtcattgcgc tgccattctc caaattgcag ttcgcgctta    8400
gctggataac gccacggaat gatgtcgtcg tgcacaacaa tggtgacttc tacagcgcgg    8460
agaatctcgc tctctccagg ggaagccgaa gtttccaaaa ggtcgttgat caaagctcgc    8520
cgcgttgttt catcaagcct tacagtcacc gtaaccagca aatcaatatc actgtgtggc    8580
ttcaggccgc catccactgc ggagccgtac aaatgtacgg ccagcaacgt cggttcgaga    8640
tggcgctcga tgacgccaac tacctctgat agttgagtcg atacttcggc gatcaccgct    8700
tccctcatga tgtttaactc ctgaattaag ccgcgccgcg aagcggtgtc ggcttgaatg    8760
aattgttagg cgtcatcctg tgctcccgag aaccagtacc agtacatcgc tgtttcgttc    8820
gagacttgag gtctagtttt atacgtgaac aggtcaatgc cgccgagagt aaagccacat    8880
tttgcgtaca aattgcaggc aggtacattg ttcgtttgtg tctctaatcg tatgccaagg    8940
agctgtctgc ttagtgccca cttttttcgca aattcgatga gactgtgcgc gactcctttg    9000
cctcggtgcg tgtgcgacac aacaatgtgt tcgatagagg ctagatcgtt ccatgttgag    9060
ttgagttcaa tcttcccgac aagctcttgg tcgatgaatg cgccatagca agcagagtct    9120
tcatcagagt catcatccga gatgtaatcc ttccggtagg ggctcacact tctggtagat    9180
agttcaaagc cttggtcgga taggtgcaca tcgaacactt cacgaacaat gaaatggttc    9240
tcagcatcca atgtttccgc cacctgctca gggatcaccg aaatcttcat atgacgccta    9300
acgcctggca cagcggatcg caaacctggc gcggcttttg gcacaaaagg cgtgacaggt    9360
ttgcgaatcc gttgctgcca cttgttaacc cttttgccag atttggtaac tataatttat    9420
gttagaggcg aagtcttggg taaaaactgg cctaaaattg ctggggattt caggaaagta    9480
aacatcacct tccggctcga tgtctattgt agatatatgt agtgtatcta cttgatcggg    9540
ggatctgctg cctcgcgcgt ttcggtgatg acggtgaaaa cctctgacac atgcagctcc    9600
cggagacggt cacagcttgt ctgtaagcgg atgccgggag cagacaagcc cgtcagggcg    9660
cgtcagcggg tgttggcggg tgtcggggcg cagccatgac ccagtcacgt agcgatagcg    9720
gagtgtatac tggcttaact atgcggcatc agagcagatt gtactgagag tgcaccatat    9780
gcggtgtgaa ataccgcaca gatgcgtaag gagaaaatac cgcatcaggc gctcttccgc    9840
ttcctcgctc actgactcgc tgcgctcggt cgttcggctg cggcgagcgg tatcagctca    9900
ctcaaaggcg gtaatacggt tatccacaga atcagggat aacgcaggaa agaacatgtg    9960
agcaaaaggc cagcaaaagg ccaggaaccg taaaaaggcc gcgttgctgg cgttttccca    10020
taggctccgc cccctgacg agcatcacaa aaatcgacgc tcaagtcaga ggtggcgaaa    10080
cccgacagga ctataaagat accaggcgtt tccccctgga agctccctcg tgcgctctcc    10140
tgttccgacc ctgccgctta ccggatacct gtccgccttt ctcccttcgg gaagcgtggc    10200
gctttctcat agctcacgct gtaggtatct cagttcggtg taggtcgttc gctccaagct    10260
gggctgtgtg cacgaacccc ccgttcagcc cgaccgctgc gccttatccg gtaactatcg    10320
tcttgagtcc aacccggtaa gacacgactt atcgccactg gcagcagcca ctggtaacag    10380
gattagcaga gcgaggtatg taggcggtgc tacagagttc ttgaagtggt ggcctaacta    10440
```

```
cggctacact agaaggacag tatttggtat ctgcgctctg ctgaagccag ttaccttcgg    10500
aaaaagagtt ggtagctctt gatccggcaa acaaaccacc gctggtagcg gtggtttttt    10560
tgtttgcaag cagcagatta cgcgcagaaa aaaaggatct caagaagatc ctttgatctt    10620
ttctacgggg tctgacgctc agtggaacga aaactcacgt taagggattt tggtcatgag    10680
attatcaaaa aggatcttca cctagatcct tttaaattaa aaatgaagtt ttaaatcaat    10740
ctaaagtata tatgagtaaa cttggtctga cagttaccaa tgcttaatca gtgaggcacc    10800
tatctcagcg atctgtctat ttcgttcatc catagttgcc tgactccccg tcgtgtagat    10860
aactacgata cgggagggct taccatctgg ccccagtgct gcaatgatac cgcgagaccc    10920
acgctcaccg gctccagatt tatcagcaat aaaccagcca gccggaaggg ccgagcgcag    10980
aagtggtcct gcaactttat ccgcctccat ccagtctatt aattgttgcc gggaagctag    11040
agtaagtagt tcgccagtta atagtttgcg caacgttgtt gccattgctg cagggggggg    11100
gggggggggg gacttccatt gttcattcca cggacaaaaa cagagaaagg aaacgacaga    11160
ggccaaaaag cctcgctttc agcacctgtc gtttcctttc ttttcagagg gtattttaaa    11220
taaaaacatt aagttatgac gaagaagaac ggaaacgcct taaaccggaa aattttcata    11280
aatagcgaaa acccgcgagg tcgccgcccc gtaacctgtc ggatcaccgg aaaggacccg    11340
taaagtgata atgattatca tctacatatc acaacgtgcg tggaggccat caaaccacgt    11400
caaataatca attatgacgc aggtatcgta ttaattgatc tgcatcaact aacgtaaaa    11460 acaacttcag acaatacaaa tcagcgacac tgaatacggg gcaacctcat gtccccccc    11520 ccccccccc tgcaggcatc gtggtgtcac gctcgtcgtt tggtatggct tcattcagct    11580
ccggttccca acgatcaagg cgagttacat gatcccccat gttgtgcaaa aaagcggtta    11640
gctccttcgg tcctccgatc gttgtcagaa gtaagttggc cgcagtgtta tcactcatgg    11700
ttatggcagc actgcataat tctcttactg tcatgccatc cgtaagatgc ttttctgtga    11760
ctggtgagta ctcaaccaag tcattctgag aatagtgtat gcggcgaccg agttgctctt    11820
gcccggcgtc aacacgggat aataccgcgc cacatagcag aactttaaaa gtgctcatca    11880
ttggaaaacg ttcttcgggg cgaaaactct caaggatctt accgctgttg agatccagtt    11940
cgatgtaacc cactcgtgca cccaactgat cttcagcatc ttttactttc accagcgttt    12000
ctgggtgagc aaaaacagga aggcaaaatg ccgcaaaaaa gggaataagg gcgacacgga    12060
aatgttgaat actcatactc ttcctttttc aatattattg aagcatttat cagggttatt    12120
gtctcatgag cggatacata tttgaatgta tttagaaaaa taaacaaata ggggttccgc    12180
gcacatttcc ccgaaaagtg ccacctgacg tctaagaaac cattattatc atgacattaa    12240
cctataaaaa taggcgtatc acgaggccct ttcgtcttca agaattggtc gacgatcttg    12300
ctgcgttcgg atattttcgt ggagttcccg ccacagaccc ggattgaagg cgagatccag    12360
caactcgcgc cagatcatcc tgtgacgaa cttggcgcg tgatgactgg ccaggacgtc    12420
ggccgaaaga gcgacaagca gatcacgctt ttcgacagcg tcggatttgc gatcgaggat    12480
ttttcggcgc tgcgctacgt ccgcgaccgc gttgagggat caagccacag cagcccactc    12540
gaccttctag ccgacccaga cgagccaagg gatcttttg gaatgctgct ccgtcgtcag    12600
gctttccgac gtttgggtgg ttgaacagaa gtcattatcg tacggaatgc caagcactcc    12660
cgaggggaac cctgtggttg gcatgcacat acaaatggac gaacggataa acctttcac    12720 gcccttttaa atatccgtta ttctaataaa cgctcttttc tcttaggttt acccgccaat    12780
```

```
atatcctgtc aaacactgat agtttaaact gaaggcggga aacgacaatc tgatcatgag    12840
cggagaatta agggagtcac gttatgaccc ccgccgatga cgcgggacaa gccgttttac    12900
gtttggaact gacagaaccg caacgttgaa ggagccactc agcaagctgg tacgattgta    12960
atacgactca ctatagggcg aattgagcgc tgtttaaacg ctcttcaact ggaagagcg     13019
```

<210> SEQ ID NO 9
<211> LENGTH: 2991
<212> TYPE: DNA
<213> ORGANISM: artificial sequence
<220> FEATURE:
<223> OTHER INFORMATION: vector

<400> SEQUENCE: 9

```
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca aatccgctcc cggcggattt gtcctactca ggagagcgtt caccgacaaa     420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggccctg cagctctaga gctcgaattc tacaggtcac     600
taataccatc taagtagttg gttcatagtg actgcatatg ttgtgtttta cagtattatg     660
tagtctgttt tttatgcaaa atctaattta atatattgat atttatatca ttttacgttt     720
ctcgttcaac tttcttgtac aaagtggccg ttaacggatc cagacttgtc catcttctgg     780
attggccaac ttaattaatg tatgaaataa aaggatgcac acatagtgac atgctaatca     840
ctataatgtg ggcatcaaag ttgtgtgtta tgtgtaatta ctagttatct gaataaaaga     900
gaaagagatc atccatatttt cttatcctaa atgaatgtca cgtgtcttta taattctttg     960
atgaaccaga tgcatttcat taaccaaatc catatacata taaatattaa tcatatataa    1020
ttaatatcaa ttgggttagc aaaacaaatc tagtctaggt gtgttttgcg aattgcggca    1080
agcttgcggc cgccccgggc aactttatta tacaaagttg gcattataaa aaagcattgc    1140
ttatcaattt gttgcaacga acaggtcact atcagtcaaa ataaaatcat tatttggagc    1200
tccatggtag cgttaacgcg gccgcgatat cccctatagt gagtcgtatt acatggtcat    1260 agctgttttcc tggcagctct ggcccgtgtc tcaaaatctc tgatgttaca ttgcacaaga    1320
taaaaatata tcatcatgaa caataaaact gtctgcttac ataaacagta atacaagggg    1380
tgttatgagc catattcaac gggaaacgtc gaggccgcga ttaaattcca acatggatgc    1440
tgatttatat gggtataaat gggctcgcga taatgtcggg caatcaggtg cgacaatcta    1500
tcgcttgtat gggaagcccg atgcgccaga gttgtttctg aaacatggca aaggtagcgt    1560
tgccaatgat gttacagatg agatggtcag actaaactgg ctgacggaat ttatgcctct    1620
tccgaccatc aagcatttta tccgtactcc tgatgatgca tggttactca ccactgcgat    1680
ccccggaaaa acagcattcc aggtattaga agaatatcct gattcaggtg aaaatattgt    1740
tgatgcgctg gcagtgttcc tgcgccggtt gcattcgatt cctgtttgta attgtccttt    1800
taacagcgat cgcgtatttc gtctcgctca ggcgcaatca cgaatgaata cggtttggt     1860
```

```
tgatgcgagt gattttgatg acgagcgtaa tggctggcct gttgaacaag tctggaaaga    1920
aatgcataaa cttttgccat tctcaccgga ttcagtcgtc actcatggtg atttctcact    1980
tgataacctt attttttgacg aggggaaatt aataggttgt attgatgttg acgagtcgg    2040
```



```
tgatgcgagt gattttgatg acgagcgtaa tggctggcct gttgaacaag tctggaaaga    1920
aatgcataaa cttttgccat tctcaccgga ttcagtcgtc actcatggtg atttctcact    1980
tgataacctt attttttgacg aggggaaatt aataggttgt attgatgttg acgagtcgg    2040 aatcgcagac cgataccagg atcttgccat cctatggaac tgcctcggtg agttttctcc    2100
ttcattacag aaacggcttt ttcaaaaata tggtattgat aatcctgata tgaataaatt    2160
gcagtttcat ttgatgctcg atgagttttt ctaatcagaa ttggttaatt ggttgtaaca    2220
ctggcagagc attacgctga cttgacggga cggcgcaagc tcatgaccaa atcccttaa    2280 cgtgagttac gcgtcgttcc actgagcgtc agaccccgta gaaaagatca aaggatcttc    2340
ttgagatcct ttttttctgc gcgtaatctg ctgcttgcaa acaaaaaaac caccgctacc    2400
agcggtggtt tgtttgccgg atcaagagct accaactctt tttccgaagg taactggctt    2460
cagcagagcg cagataccaa atactgtcct tctagtgtag ccgtagttag gccaccactt    2520
caagaactct gtagcaccgc ctacatacct cgctctgcta atcctgttac cagtggctgc    2580
tgccagtggc gataagtcgt gtcttaccgg gttggactca agacgatagt taccggataa    2640
ggcgcagcgg tcgggctgaa cggggggttc gtgcacacag cccagcttgg agcgaacgac    2700
ctacaccgaa ctgagatacc tacagcgtga gcattgagaa agcgccacgc ttcccgaagg    2760
gagaaaggcg gacaggtatc cggtaagcgg cagggtcgga acaggagagc gcacgaggga    2820
gcttccaggg ggaaacgcct ggtatcttta tagtcctgtc gggtttcgcc acctctgact    2880
tgagcgtcga ttttttgtgat gctcgtcagg ggggcggagc ctatggaaaa acgccagcaa    2940
cgcggccttt ttacggttcc tggccttttg ctggcctttt gctcacatgt t    2991
```

<210> SEQ ID NO 10
<211> LENGTH: 13807
<212> TYPE: DNA
<213> ORGANISM: artificial sequence
<220> FEATURE:
<223> OTHER INFORMATION: vector

<400> SEQUENCE: 10

```
aagctggtac gattgtaata cgactcacta tagggcgaat tgagcgctgt ttaaacgctc      60
ttcaactgga agagcggtta ccagagctgg tcacctttgt ccaccaagat ggaactgcgg     120
ccgctcatta attaagtcag cgcgcctct agttgaagac acgttcatgt cttcatcgta     180
agaagacact cagtagtctt cggccagaat ggccgtaggt gaattaagag gagagaggag     240
gtaaacattt tcttctattt tttcatattt tcaggataaa ttattgtaaa agtttacaag     300
atttccattt gactagtgta aatgaggaat attctctagt aagatcatta tttcatctac     360
ttcttttatc ttctaccagt agaggaataa acaatattta gctcctttgt aaatacaaat     420
taattttcgt tcttgacatc attcaattt aattttacgt ataaaataaa agatcatacc     480
tattagaacg attaaggaga aatacaattc gaatgagaag gatgtgccgt ttgttataat     540
aaacagccac acgacgtaaa cgtaaaatga ccacatgatg ggccaataga catggaccga     600
ctactaataa tagtaagtta catttttagga tggaataaat atcataccga catcagtttg     660
aaagaaaagg gaaaaaaga aaaataaat aaaagatata ctaccgacat gagttccaaa     720
agcaaaaaaa aaagatcaag ccgacacaga cacgcgtaga gagcaaaatg actttgacgt     780
cacaccacga aaacagacgc ttcatacgtg tcccttttatc tctctcagtc tctctataaa     840
cttagtgaga ccctcctctg ttttactcag gatccccggg taccgagctc gaattcaccg     900
```

-continued

```
gtcgccacca tggcccacag caagcacggc ctgaaggagg agatgaccat gaagtaccac    960
atggagggct gcgtgaacgg ccacaagttc gtgatcaccg cgagggcat cggctacccc    1020
ttcaagggca agcagaccat caacctgtgc gtgatcgagg cggccccct gcccttcagc    1080
gaggacatcc tgagcgccgg cttcaagtac ggcgaccgga tcttcaccga gtacccccag    1140
gacatcgtgg actacttcaa gaacagctgc cccgccggct acacctgggg ccggagcttc    1200
ctgttcgagg acgcgccgt gtgcatctgt aacgtggaca tcaccgtgag cgtgaaggag    1260
aactgcatct accacaagag catcttcaac ggcgtgaact ccccgccga cggccccgtg    1320
atgaagaaga tgaccaccaa ctgggaggcc agctgcgaga gatcatgcc cgtgcctaag    1380
cagggcatcc tgaagggcga cgtgagcatg tacctgctgc tgaaggacgg cggccggtac    1440
cggtgccagt tcgacaccgt gtacaaggcc aagagcgtgc ccagcaagat gcccgagtgg    1500
cacttcatcc agcacaagct gctgcgggag gaccggagcg acgccaagaa ccagaagtgg    1560
cagctgaccg agcacgccat cgccttcccc agcgccctgg cctgaagcgg cccatggata    1620
ttcgaacgcg taggtaccac atggttaacc tagacttgtc catcttctgg attggccaac    1680
ttaattaatg tatgaaataa aaggatgcac acatagtgac atgctaatca ctataatgtg    1740
ggcatcaaag ttgtgtgtta tgtgtaatta ctagttatct gaataaaaga gaaagagatc    1800
atccatattt cttatcctaa atgaatgtca cgtgtcttta taattctttg atgaaccaga    1860
tgcatttcat taaccaaatc catatacata taaatattaa tcatatataa ttaatatcaa    1920
ttggggttagc aaaacaaatc tagtctaggt gtgttttgcg aatgcggcca ttggcctaga    1980
aggccattta atcctgagg atctggtctt cctaaggacc cgggatatcg ctatcaactt    2040
tgtatagaaa agttgaacga gaaacgtaaa atgatataaa tatcaatata ttaaattaga    2100
ttttgcataa aaaacagact acataatact gtaaaacaca acatatccag tcactatggt    2160
cgacctgcag actggctgtg tataagggag cctgacattt atattcccca gaacatcagg    2220
ttaatggcgt ttttgatgtc attttcgcgg tggctgagat cagccacttc ttccccgata    2280
acggagaccg gcacactggc catatcggtg gtcatcatgc ccagctttc atccccgata    2340
tgcaccaccg ggtaaagttc acgggggact ttatctgaca gcagacgtgc actggccagg    2400
gggatcacca tccgtcgccc gggcgtgtca ataatatcac tctgtacatc cacaaacaga    2460
cgataacggc tctctctttt ataggtgtaa accttaaact gcatttcacc agcccctgtt    2520
ctcgtcggca aaagagccgt tcatttcaat aaaccgggcg acctcagcca tcccttcctg    2580
attttccgct ttccagcgtt cggcacgcag acgacgggc tcattctgca tggttgtgct    2640
taccgaaccg gagatattga catcatatat gccttgagca actgatagct gtcgctgtca    2700
actgtcactg taatacgctg cttcatagca tacctctttt tgacatactt cgggtataca    2760
tatcagtata tattcttata ccgcaaaaat cagcgcgcaa atacgcatac tgttatctgg    2820
cttttagtaa gccggatcct ctagattacg ccccgcctgc cactcatcgc agtactgttg    2880
taattcatta agcattctgc cgacatggaa gccatcacaa acggcatgat gaacctgaat    2940
cgccagcggc atcagcacct tgtcgccttg cgtataatat ttgcccatgg tgaaaacggg    3000
ggcgaagaag ttgtccatat tggccacgtt taaatcaaaa ctggtgaaac tcacccaggg    3060
attggctgag acgaaaaaca tattctcaat aaacccttta gggaaatagg ccaggttttc    3120
accgtaacac gccacatctt gcgaatatat gtgtagaaac tgccggaaat cgtcgtggta    3180
ttcactccag agcgatgaaa acgtttcagt ttgctcatgg aaaacggtgt aacaagggtg    3240
aacactatcc catatcacca gctcaccgtc tttcattgcc atacggaatt ccggatgagc    3300
```

```
attcatcagg cgggcaagaa tgtgaataaa ggccggataa aacttgtgct tattttctt      3360 tacggtcttt aaaaaggccg taatatccag ctgaacggtc tggttatagg tacattgagc     3420
aactgactga aatgcctcaa aatgttcttt acgatgccat tgggatatat caacggtggt    3480
atatccagtg attttttctt ccattttagc ttccttagct cctgaaaatc tcgacggatc    3540
ctaactcaaa atccacacat tatacgagcc ggaagcataa agtgtaaagc ctggggtgcc    3600
ctaatgcggc cgccatagtg actggatatg ttgtgtttta cagtattatg tagtctgttt   3660
tttatgcaaa atctaattta atatattgat atttatatca ttttacgttt ctcgttcaac    3720
tttattatac aaagttgata gatatcggac cgattaaact ttaattcggt ccgaagcttg    3780
catgcctgca gtgcagcgtg acccggtcgt gcccctctct agagataatg agcattgcat    3840
gtctaagtta taaaaaatta ccacatattt tttttgtcac acttgtttga agtgcagttt    3900
atctatcttt atacatatat ttaaacttta ctctacgaat aatataatct atagtactac    3960
aataatatca gtgttttaga gaatcatata aatgaacagt tagacatggt ctaaaggaca    4020
attgagtatt ttgacaacag gactctacag ttttatcttt ttagtgtgca tgtgttctcc    4080 ttttttttg caaatagctt cacctatata atacttcatc catttttatta gtacatccat    4140 ttagggttta gggttaatgg tttttataga ctaattttt tagtacatct atttttattct   4200 attttagcct ctaaattaag aaaactaaaa ctctatttta gttttttat ttaataattt      4260 agatataaaa tagaataaaa taaagtgact aaaaattaaa caaatacctt ttaagaaatt    4320
aaaaaaacta aggaaacatt tttcttgttt cgagtagata atgccagcct gttaaacgcc     4380
gtcgacgagt ctaacggaca ccaaccagcg aaccagcagc gtcgcgtcgg gccaagcgaa    4440
gcagacggca cggcatctct gtcgctgcct ctggacccct ctcgagagtt ccgctccacc    4500
gttggacttg ctccgctgtc ggcatccaga aattgcgtgg cggagcggca gacgtgagcc    4560
ggcacggcag gcggcctcct cctcctctca cggcaccggc agctacgggg gattcctttc    4620
ccaccgctcc ttcgctttcc cttcctcgcc cgccgtaata aatagacacc ccctccacac    4680
cctctttccc caacctcgtg ttgttcggag cgcacacaca acaaccaga tctcccccaa     4740 atccacccgt cggcacctcc gcttcaaggt acgccgctcg tcctccccc ccccctctc      4800 taccttctct agatcggcgt tccggtccat gcatggttag ggcccggtag ttctacttct    4860
gttcatgttt gtgttagatc cgtgtttgtg ttagatccgt gctgctagcg ttcgtacacg    4920
gatgcgacct gtacgtcaga cacgttctga ttgctaactt gccagtgttt ctctttgggg    4980
aatcctggga tggctctagc cgttccgcag acgggatcga tttcatgatt tttttgtttt    5040
cgttgcatag ggtttggttt gccctttcc tttatttcaa tatatgccgt gcacttgttt     5100
gtcgggtcat cttttcatgc ttttttttgt cttggttgtg atgatgtggt ctggttgggc    5160
ggtcgttcta gatcggagta gaattctgtt tcaaactacc tggtggattt attaattttg    5220
gatctgtatg tgtgtgccat acatattcat agttacgaat tgaagatgat ggatggaaat    5280
atcgatctag gataggtata catgttgatg cgggttttac tgatgcatat acagagatgc    5340
tttttgttcg cttggttgtg atgatgtggt gtggttgggc ggtcgttcat tcgttctaga    5400
tcggagtaga atactgtttc aaactacctg gtgtatttat taattttgga actgtatgtg    5460
tgtgtcatac atcttcatag ttacgagttt aagatggatg gaaatatcga tctaggatag    5520
gtatacatgt tgatgtgggt tttactgatg catatacatg atggcatatg cagcatctat    5580
tcatatgctc taaccttgag tacctatcta ttataataaa caagtatgtt ttataattat    5640
```

```
tttgatcttg atatacttgg atgatggcat atgcagcagc tatatgtgga ttttttttagc    5700
cctgccttca tacgctattt atttgcttgg tactgtttct tttgtcgatg ctcaccctgt    5760
tgtttggtgt tacttctgca ggtcgacttt aacttagcct aggatccaca cgacaccatg    5820
tcccccgagc gccgccccgt cgagatccgc ccggccaccg ccgccgacat ggccgccgtg    5880
tgcgacatcg tgaaccacta catcgagacc tccaccgtga acttccgcac cgagccgcag    5940
accccgcagg agtggatcga cgacctggag cgcctccagg accgctaccc gtggctcgtg    6000
gccgaggtgg agggcgtggt ggccggcatc gcctacgccg gcccgtggaa ggcccgcaac    6060
gcctacgact ggaccgtgga gtccaccgtg tacgtgtccc accgccacca cgcctcggc    6120
ctcggctcca ccctctacac ccacctcctc aagagcatgg aggcccaggg cttcaagtcc    6180
gtggtggccg tgatcggcct cccgaacgac ccgtccgtgc gcctcacga ggccctcggc    6240
tacaccgccc gcggcaccct ccgcgccgcc ggctacaagc acggcggctg gcacgacgtc    6300
ggcttctggc agcgcgactt cgagctgccg gccccgccgc gccggtgcg cccggtgacg    6360
cagatctccg gtggaggcgg cagcggtggc ggaggctccg gaggcggtgg ctccatggcc    6420
tcctccgagg acgtcatcaa ggagttcatg cgcttcaagg tgcgcatgga gggctccgtg    6480
aacggccacg agttcgagat cgagggcgag ggcgagggcc gcccctacga gggcacccag    6540
accgccaagc tgaaggtgac caagggcggc cccctgccct tcgcctggga catcctgtcc    6600
cccccagttcc agtacggctc caaggtgtac gtgaagcacc ccgccgacat ccccgactac    6660
aagaagctgt ccttccccga gggcttcaag tgggagcgcg tgatgaactt cgaggacggc    6720
ggcgtggtga ccgtgaccca ggactcctcc ctgcaggacg gctccttcat ctacaaggtg    6780
aagttcatcg gcgtgaactt cccctccgac ggccccgtaa tgcagaagaa gactatgggc    6840
tgggaggcct ccaccgagcg cctgtacccc cgcgacggcg tgctgaaggg cgagatccac    6900
aaggccctga gctgaagga cggcggccac tacctggtgg agttcaagtc catctacatg    6960
gccaagaagc ccgtgcagct gcccggctac tactacgtgg actccaagct ggacatcacc    7020
tcccacaacg aggactacac catcgtggag cagtacgagc gcgccgaggg ccgccaccac    7080
ctgttcctgt agtcaggatc tgagtcgaaa cctagacttg tccatcttct ggattggcca    7140
acttaattaa tgtatgaaat aaaaggatgc acacatagtg acatgctaat cactataatg    7200
tgggcatcaa agttgtgtgt tatgtgtaat tactagttat ctgaataaaa gagaaagaga    7260
tcatccatat ttcttatcct aaatgaatgt cacgtgtctt tataattctt tgatgaacca    7320
gatgcatttc attaaccaaa tccatataca tataaatatt aatcatatat aattaatatc    7380
aattgggtta gcaaaacaaa tctagtctag gtgtgttttg cgaatgcggc cgccaccgcg    7440
gtggagctcg aattcattcc gattaatcgt ggcctcttgc tcttcaggat gaagagctat    7500
gtttaaacgt gcaagcgcta ctagacaatt cagtacatta aaaacgtccg caatgtgtta    7560
ttaagttgtc taagcgtcaa tttgtttaca ccacaatata tcctgccacc agccagccaa    7620
cagctccccg accggcagct cggcacaaaa tcaccactcg atacaggcag cccatcagtc    7680
cgggacggcg tcagcgggag agccgttgta aggcggcaga cttttgctcat gttaccgatg    7740
ctattcggaa gaacggcaac taagctgccg ggtttgaaac acggatgatc tcgcggaggg    7800
tagcatgttg attgtaacga tgcacagagcg ttgctgcctg tgatcaaata tcatctccct    7860
cgcagagatc cgaattatca gccttcttat tcatttctcg cttaaccgtg acaggctgtc    7920
gatcttgaga actatgccga cataatagga aatcgctgga taaagccgct gaggaagctg    7980
agtggcgcta tttctttaga agtgaacgtt gacgatcgtc gaccgtaccc cgatgaatta    8040
```

```
attcggacgt acgttctgaa cacagctgga tacttacttg ggcgattgtc atacatgaca   8100
tcaacaatgt acccgtttgt gtaaccgtct cttggaggtt cgtatgacac tagtggttcc   8160
cctcagcttg cgactagatg ttgaggccta acattttatt agagagcagg ctagttgctt   8220
agatacatga tcttcaggcc gttatctgtc agggcaagcg aaaattggcc atttatgacg   8280
accaatgccc cgcagaagct cccatctttg ccgccataga cgccgcgccc cccttttggg   8340
gtgtagaaca tccttttgcc agatgtggaa aagaagttcg ttgtcccatt gttggcaatg   8400
acgtagtagc cggcgaaagt gcgagaccca tttgcgctat atataagcct acgatttccg   8460
ttgcgactat tgtcgtaatt ggatgaacta ttatcgtagt tgctctcaga gttgtcgtaa   8520
tttgatggac tattgtcgta attgcttatg gagttgtcgt agttgcttgg agaaatgtcg   8580
tagttggatg gggagtagtc atagggaaga cgagcttcat ccactaaaac aattggcagg   8640
tcagcaagtg cctgccccga tgccatcgca agtacgaggc ttagaaccac cttcaacaga   8700
tcgcgcatag tcttccccag ctctctaacg cttgagttaa gccgcgccgc gaagcggcgt   8760
cggcttgaac gaattgttag acattatttg ccgactacct tggtgatctc gcctttcacg   8820
tagtgaacaa attcttccaa ctgatctgcg cgcgaggcca agcgatcttc ttgtccaaga   8880
taagcctgcc tagcttcaag tatgacgggc tgatactggg ccggcaggcg ctccattgcc   8940
cagtcggcag cgacatcctt cggcgcgatt ttgccggtta ctgcgctgta ccaaatgcgg   9000
gacaacgtaa gcactacatt tcgctcatcg ccagcccagt cgggcggcga gttccatagc   9060
gttaaggttt catttagcgc ctcaaataga tcctgttcag gaaccggatc aaagagttcc   9120
tccgccgctg gacctaccaa ggcaacgcta tgttctcttg cttttgtcag caagatagcc   9180
agatcaatgt cgatcgtggc tggctcgaag atacctgcaa gaatgtcatt gcgctgccat   9240
tctccaaatt gcagttcgcg cttagctgga taacgccacg gaatgatgtc gtcgtgcaca   9300
acaatggtga cttctacagc gcggagaatc tcgctctctc caggggaagc cgaagtttcc   9360
aaaaggtcgt tgatcaaagc tcgccgcgtt gtttcatcaa gccttacagt caccgtaacc   9420
agcaaatcaa tatcactgtg tggcttcagg ccgccatcca ctgcggagcc gtacaaatgt   9480
acggccagca acgtcggttc gagatggcgc tcgatgacgc caactacctc tgatagttga   9540
gtcgatactt cggcgatcac cgcttccctc atgatgttta actcctgaat taagccgcgc   9600
cgcgaagcgg tgtcggcttg aatgaattgt taggcgtcat cctgtgctcc cgagaaccag   9660
taccagtaca tcgctgtttc gttcgagact tgaggtctag ttttatacgt gaacaggtca   9720
atgccgccga gagtaaagcc acattttgcg tacaaattgc aggcaggtac attgttcgtt   9780
tgtgtctcta atcgtatgcc aaggagctgt ctgcttagtg cccactttt cgcaaattcg   9840
atgagactgt gcgcgactcc tttgcctcgg tgcgtgtgcg acacaacaat gtgttcgata   9900
gaggctagat cgttccatgt tgagttgagt tcaatcttcc cgacaagctc ttggtcgatg   9960
aatgcgccat agcaagcaga gtcttcatca gagtcatcat ccgagatgta atccttccgg   10020
tagggctca cacttctggt agatagttca aagccttggt cggataggtg cacatcgaac   10080
acttcacgaa caatgaaatg gttctcagca tccaatgttt ccgccacctg ctcagggatc   10140
accgaaatct tcatatgacg cctaacgcct ggcacagcgg atcgcaaacc tggcgcggct   10200
tttggcacaa aaggcgtgac aggtttgcga atccgttgct gccacttgtt aacccttttg   10260
ccagatttgg taactataat ttatgttaga ggcgaagtct tgggtaaaaa ctggcctaaa   10320
attgctgggg atttcaggaa agtaaacatc accttccggc tcgatgtcta ttgtagatat   10380
```

```
atgtagtgta tctacttgat cgggggatct gctgcctcgc gcgtttcggt gatgacggtg   10440
aaaacctctg acacatgcag ctcccggaga cggtcacagc ttgtctgtaa gcggatgccg   10500
ggagcagaca agcccgtcag ggcgcgtcag cgggtgttgg cgggtgtcgg ggcgcagcca   10560
tgacccagtc acgtagcgat agcggagtgt atactggctt aactatgcgg catcagagca   10620
gattgtactg agagtgcacc atatgcggtg tgaaataccg cacagatgcg taaggagaaa   10680
ataccgcatc aggcgctctt ccgcttcctc gctcactgac tcgctgcgct cggtcgttcg   10740
gctgcggcga gcggtatcag ctcactcaaa ggcggtaata cggttatcca cagaatcagg   10800
ggataacgca ggaaagaaca tgtgagcaaa aggccagcaa aaggccagga accgtaaaaa   10860
ggccgcgttg ctggcgtttt tccataggct ccgcccccct gacgagcatc acaaaaatcg   10920
acgctcaagt cagaggtggc gaaacccgac aggactataa agataccagg cgtttccccc   10980
tggaagctcc ctcgtgcgct ctcctgttcc gaccctgccg cttaccggat acctgtccgc   11040
ctttctccct tcgggaagcg tggcgctttc tcatagctca cgctgtaggt atctcagttc   11100
ggtgtaggtc gttcgctcca agctgggctg tgtgcacgaa ccccccgttc agcccgaccg   11160
ctgcgcctta tccggtaact atcgtcttga gtccaacccg gtaagacacg acttatcgcc   11220
actggcagca gccactggta acaggattag cagagcgagg tatgtaggcg gtgctacaga   11280
gttcttgaag tggtggccta actacggcta cactagaagg acagtatttg gtatctgcgc   11340
tctgctgaag ccagttacct tcggaaaaag agttggtagc tcttgatccg gcaaacaaac   11400
caccgctggt agcggtggtt tttttgtttg caagcagcag attacgcgca gaaaaaaagg   11460
atctcaagaa gatcctttga tcttttctac ggggtctgac gctcagtgga acgaaaactc   11520
acgttaaggg attttggtca tgagattatc aaaaaggatc ttcacctaga tccttttaaa   11580
ttaaaaatga agttttaaat caatctaaag tatatatgag taaacttggt ctgacagtta   11640
ccaatgctta atcagtgagg cacctatctc agcgatctgt ctatttcgtt catccatagt   11700
tgcctgactc cccgtcgtgt agataactac gatacgggag ggcttaccat ctggccccag   11760
tgctgcaatg ataccgcgag acccacgctc accggctcca gatttatcag caataaacca   11820
gccagccgga agggccgagc gcagaagtgg tcctgcaact ttatccgcct ccatccagtc   11880
tattaattgt tgccgggaag ctagagtaag tagttcgcca gttaatagtt tgcgcaacgt   11940
tgttgccatt gctgcagggg gggggggggg ggggacttc cattgttcat tccacgggaca   12000 aaaacagaga aggaaacga cagaggccaa aaagcctcgc tttcagcacc tgtcgtttcc   12060
tttcttttca gagggtattt taaataaaaa cattaagtta tgacgaagaa gaacggaaac   12120
gccttaaacc ggaaaatttt cataaatagc gaaaacccgc gaggtcgccg ccccgtaacc   12180
tgtcggatca ccggaaagga cccgtaaagt gataatgatt atcatctaca tatcacaacg   12240
tgcgtggagg ccatcaaacc acgtcaaata atcaattatg acgcaggtat cgtattaatt   12300
gatctgcatc aacttaacgt aaaaacaact tcagacaata caaatcagcg acactgaata   12360
cggggcaacc tcatgtcccc ccccccccc ccctgcagg catcgtggtg tcacgctcgt   12420
cgtttggtat ggcttcattc agctccggtt cccaacgatc aaggcgagtt acatgatccc   12480
ccatgttgtg caaaaaagcg gttagctcct tcggtcctcc gatcgttgtc agaagtaagt   12540
tggccgcagt gttatcactc atggttatgg cagcactgca taattctctt actgtcatgc   12600
catccgtaag atgcttttct gtgactggtg agtactcaac caagtcattc tgagaatagt   12660
gtatgcggcg accgagttgc tcttgcccgg cgtcaacacg gataatacc gcgccacata   12720 gcagaacttt aaaagtgctc atcattggaa aacgttcttc ggggcgaaaa ctctcaagga   12780
```

```
tcttaccgct gttgagatcc agttcgatgt aacccactcg tgcacccaac tgatcttcag  12840
catcttttac tttcaccagc gtttctgggt gagcaaaaac aggaaggcaa aatgccgcaa  12900
aaaagggaat aagggcgaca cggaaatgtt gaatactcat actcttcctt tttcaatatt  12960
attgaagcat ttatcagggt tattgtctca tgagcggata catatttgaa tgtatttaga  13020
aaaataaaca aataggggtt ccgcgcacat ttccccgaaa agtgccacct gacgtctaag  13080
aaaccattat tatcatgaca ttaacctata aaaataggcg tatcacgagg ccctttcgtc  13140
ttcaagaatt ggtcgacgat cttgctgcgt tcggatattt tcgtggagtt cccgccacag  13200
acccggattg aaggcgagat ccagcaactc gcgccagatc atcctgtgac ggaactttgg  13260
cgcgtgatga ctggccagga cgtcggccga aagagcgaca agcagatcac gcttttcgac  13320
agcgtcggat ttgcgatcga ggatttttcg gcgctgcgct acgtccgcga ccgcgttgag  13380
ggatcaagcc acagcagccc actcgacctt ctagccgacc cagacgagcc aagggatctt  13440
tttggaatgc tgctccgtcg tcaggctttc cgacgtttgg gtggttgaac agaagtcatt  13500
atcgtacgga atgccaagca ctcccgaggg gaaccctgtg gttggcatgc acatacaaat  13560
ggacgaacgg ataaaccttt tcacgccctt ttaaatatcc gttattctaa taaacgctct  13620
tttctcttag gtttacccgc caatatatcc tgtcaaacac tgatagttta aactgaaggc  13680
gggaaacgac aatctgatca tgagcggaga attaagggag tcacgttatg acccccgccg  13740
atgacgcggg acaagccgtt ttacgtttgg aactgacaga accgcaacgt tgaaggagcc  13800
actcagc                                                            13807
```

<210> SEQ ID NO 11
<211> LENGTH: 4678
<212> TYPE: DNA
<213> ORGANISM: artificial sequence
<220> FEATURE:
<223> OTHER INFORMATION: vector

<400> SEQUENCE: 11

```
gaaaggccca gtcttccgac tgagcctttc gttttatttg atgcctggca gttccctact    60
ctcgcgttaa cgctagcatg gatgttttcc cagtcacgac gttgtaaaac gacggccagt   120
cttaagctcg ggcccgcgtt aacgctacca tggagctcca aataatgatt ttattttgac   180
tgatagtgac ctgttcgttg caacaaattg ataagcaatg ctttttttata atgccaactt   240 tgtatagaaa agttgggccg aattcgagct cggtacggcc agaatggccc ggaccgggtt   300
accgaattcg agctcggtac cctgggatcc ctggtaatta ttggctgtag gattctaaac   360
agagcctaaa tagctggaat agctctagcc ctcaatccaa actaatgata tctatactta   420
tgcaactcta aatttttatt ctaaaagtaa tatttcattt ttgtcaacga gattctctac   480
tctattccac aatcttttga agcaatattt accttaaatc tgtactctat accaataatc   540
atatattcta ttatttattt ttatctctct cctaaggagc atccccctat gtctgcatgg   600
cccccgcctc gggtcccaat ctcttgctct gctagtagca cagaagaaaa cactagaaat   660
gacttgcttg acttagagta tcagataaac atcatgttta cttaacttta atttgtatcg   720
gtttctacta tttttataat atttttgtct ctatagatac tacgtgcaac agtataatca   780
acctagttta atccagagcg aaggattttt tactaagtac gtgactccat atgcacagcg   840
ttccttttat ggttcctcac tgggcacagc ataaacgaac cctgtccaat gttttcagcg   900
cgaacaaaca gaaattccat cagcgaacaa acaacataca tgcgagatga aaataaataa   960
```

-continued

```
taaaaaaagc tccgtctcga taggccggca cgaatcgaga gcctccatag ccagtttttt    1020
ccatcggaac ggcggttcgc gcacctaatt atatgcacca cacgcctata aagccaacca    1080
acccgtcgga ggggcgcaag ccagacagaa gacagcccgt cagcccctct cgtttttcat    1140
ccgccttcgc ctccaaccgc gtgcgctcca cgcctcctcc aggaaagcga ggatctcccc    1200
caaatccacc cgtcggcacc tccgcttcaa ggtacgccgc tcgtcctccc ccccccccc    1260
tctctacctt ctctagatcg gcgttccggt ccatggttag ggcccggtag ttctacttct    1320
gttcatgttt gtgttagatc cgtgtttgtg ttagatccgt gctgctagcg ttcgtacacg    1380
gatgcgacct gtacgtcaga cacgttctga ttgctaactt gccagtgttt ctctttgggg    1440
aatcctggga tggctctagc cgttccgcag acgggatcga tttcatgatt ttttttgttt    1500
cgttgcatag ggtttggttt gcccтттттcc tttatttcaa tatatgccgt gcacttgttt    1560
gtcgggtcat cttttcatgc тттттттттgт cttggttgtg atgatgtggt ctggttgggc    1620
ggtcgttcta gatcggagta gaattctgtt caaactacc tggtggattt attaattttg    1680
gatctgtatg tgtgtgccat acatattcat agttacgaat tgaagatgat ggatggaaat    1740
atcgatctag gataggtata catgttgatg cgggttttac tgatgcatat acagagatgc    1800
tttttgttcg cttggttgtg atgatgtggt gtggttgggc ggtcgttcat tcgttctaga    1860
tcggagtaga atactgtttc aaactacctg gtgtatttat таатттттgga actgtatgtg    1920
tgtgtcatac atcttcatag ttacgagttt aagatggatg gaaatatcga tctaggatag    1980
gtatacatgt tgatgtgggt tttactgatg catatacatg atggcatatg cagcatctat    2040
tcatatgctc taaccttgag tacctatcta ttataataaa caagtatgtt tataattat    2100
tttgatcttg ататaстттgg atgatggcat atgcagcagc tatatgtgga ттттттттagc    2160
cctgccttca tacgctatt atttgcttgg tactgtttct tttgtcgatg ctcaccctgt    2220
tgtttggtgt tacttctgca ggtcgactct agaagcttgg tcacccggtc cgggcctaga    2280
aggccagctt caagtttgta caaaaaagtt gaacagaaaa cgtaaaatga tataaatatc    2340
aatatattaa attagatttt gcataaaaaa cagactacat aatactgtaa aacacaacat    2400
atgcagtcac tatgaatcaa ctactagat ggtattagtg acctgtagaa ttcgagctct    2460
agagctgcag ggcggccgcg атаtcсссcтa tagtgagtcg tattacatgg tcatagctgt    2520
ttcctggcag ctctggcccg tgtctcaaaa tctctgatgt tacattgcac aagataaaaa    2580
tatatcatca tgaacaataa aactgtctgc ttacataaac agtaatacaa ggggtgttat    2640
gagccatatt caacgggaaa cgtcgaggcc gcgatttaat tccaacatgg atgctgatt    2700
atatgggtat aaatgggctc gcgataatgt cgggcaatca ggtgcgacaa tctatcgctt    2760
gtatgggaag cccgatgcgc cagagttgtt tctgaaacat ggcaaaggta gcgttgccaa    2820
tgatgttaca gatgagatgg tcagactaaa ctggctgacg gaatttatgc ctcttccgac    2880
catcaagcat tttatccgta ctcctgatga tgcatggtta ctcaccactg cgatccccgg    2940
aaaaacagca ttccaggtat tagaagaata tcctgatca ggtgaaaata tgttgatgc    3000
gctggcagtg ttcctgcgcc ggttgcattc gattcctgtt tgtaattgtc cttttaacag    3060
cgatcgcgta tttcgtctcg ctcaggcgca atcacgaatg aataacggtt tggttgatgc    3120
gagtgatttt gatgacgagc gtaatggctg gcctgttgaa caagtctgga agaaatgca    3180
taaactttt cстаттстсac cggатткагт cgtcactcat ggtgatttct cacttgataa    3240
ccttatttt gacgагggga aattaatagg ttgtattgat gttggacgag tcggaatcgc    3300
agaccgatac caggatcttg ccatcctatg gaactgcctc ggtgagtttt ctccttcatt    3360
```

```
acagaaacgg cttttcaaa aatatggtat tgataatcct gatatgaata aattgcagtt    3420
tcatttgatg ctcgatgagt tttctaatc agaattggtt aattggttgt aacactggca    3480
gagcattacg ctgacttgac gggacggcgc aagctcatga ccaaaatccc ttaacgtgag    3540
ttacgcgtcg ttccactgag cgtcagaccc cgtagaaaag atcaaaggat cttcttgaga    3600 tcctttttt ctgcgcgtaa tctgctgctt gcaaacaaaa aaaccaccgc taccagcggt    3660
ggtttgtttg ccggatcaag agctaccaac tctttttccg aaggtaactg gcttcagcag    3720
agcgcagata ccaaatactg tccttctagt gtagccgtag ttaggccacc acttcaagaa    3780
ctctgtagca ccgcctacat acctcgctct gctaatcctg ttaccagtgg ctgctgccag    3840
tggcgataag tcgtgtctta ccgggttgga ctcaagacga tagttaccgg ataaggcgca    3900
gcggtcgggc tgaacggggg gttcgtgcac acagcccagc ttggagcgaa cgacctacac    3960
cgaactgaga tacctacagc gtgagcattg agaaagcgcc acgcttcccg aagggagaaa    4020
ggcggacagg tatccggtaa gcggcagggt cggaacagga gagcgcacga gggagcttcc    4080
agggggaaac gcctggtatc tttatagtcc tgtcgggttt cgccacctct gacttgagcg    4140
tcgatttttg tgatgctcgt cagggggcg gagcctatgg aaaaacgcca gcaacgcggc    4200 cttttacgg ttcctggcct tttgctggcc ttttgctcac atgttctttc ctgcgttatc    4260
ccctgattct gtggataacc gtattaccgc ctttgagtga gctgataccg ctcgccgcag    4320
ccgaacgacc gagcgcagcg agtcagtgag cgaggaagcg gaagagcgcc caatacgcaa    4380
accgcctctc cccgcgcgtt ggccgattca ttaatgcagc tggcacgaca ggtttcccga    4440
ctggaaagcg ggcagtgagc gcaacgcaat taatacgcgt accgctagcc aggaagagtt    4500
tgtagaaacg caaaaaggcc atccgtcagg atggccttct gcttagtttg atgcctggca    4560
gtttatggcg ggcgtcctgc ccgccaccct ccgggccgtt gcttcacaac gttcaaatcc    4620
gctcccggcg gatttgtcct actcaggaga gcgttcaccg acaaacaaca gataaaac    4678
```

<210> SEQ ID NO 12
<211> LENGTH: 3505
<212> TYPE: DNA
<213> ORGANISM: artificial sequence
<220> FEATURE:
<223> OTHER INFORMATION: vector

<400> SEQUENCE: 12

```
gatccccggg taccgagctc gaattcggcc caagtttgta caaaaaagtt gaacgagaaa      60
cgtaaaatga tataaatatc aatatattaa attagatttt gcataaaaaa cagactacat     120
aatactgtaa aacacaacat atgcagtcac tatgaatcaa ctacttagat ggtattagtg     180
acctgtagaa ttcgagctct agagctgcag gcggccgcg atatcccta tagtgagtcg     240 tattacatgg tcatagctgt ttcctggcag ctctggcccg tgtctcaaaa tctctgatgt     300
tacattgcac aagataaaaa tatatcatca tgaacaataa aactgtctgc ttacataaac     360
agtaatacaa ggggtgttat gagccatatt caacgggaaa cgtcgaggcc gcgattaaat     420
tccaacatgg atgctgattt atatgggtat aaatgggctc gcgataatgt cgggcaatca     480
ggtgcgacaa tctatcgctt gtatgggaag cccgatgcgc cagagttgtt ctgaaacat     540 ggcaaaggta gcgttgccaa tgatgttaca gatgagatgg tcagactaaa ctggctgacg     600
gaatttatgc ctcttccgac catcaagcat tttatccgta ctcctgatga tgcatggtta     660
ctcaccactg cgatccccgg aaaaacagca ttccaggtat tagaagaata tcctgattca     720
```

```
ggtgaaaata ttgttgatgc gctggcagtg ttcctgcgcc ggttgcattc gattcctgtt    780
tgtaattgtc cttttaacag cgatcgcgta tttcgtctcg ctcaggcgca atcacgaatg    840
aataacggtt tggttgatgc gagtgatttt gatgacgagc gtaatggctg gcctgttgaa    900
caagtctgga agaaatgcta taaacttttg ccattctcac cggattcagt cgtcactcat    960
ggtgatttct cacttgataa ccttattttt gacgagggga aattaatagg ttgtattgat   1020
gttggacgag tcggaatcgc agaccgatac caggatcttg ccatcctatg gaactgcctc   1080
ggtgagtttt ctccttcatt acagaaacgg ctttttcaaa aatatggtat tgataatcct   1140
gatatgaata aattgcagtt tcatttgatg ctcgatgagt ttttctaatc agaattggtt   1200
aattggttgt aacactggca gagcattacg ctgacttgac gggacggcgc aagctcatga   1260
ccaaaatccc ttaacgtgag ttacgcgtcg ttccactgag cgtcagaccc cgtagaaaag   1320
atcaaaggat cttcttgaga tcctttttt ctgcgcgtaa tctgctgctt gcaaacaaaa   1380
aaaccaccgc taccagcggt ggtttgtttg ccggatcaag agctaccaac tcttttccg    1440 aaggtaactg gcttcagcag agcgcagata ccaaatactg tccttctagt gtagccgtag   1500
ttaggccacc acttcaagaa ctctgtagca ccgcctacat acctcgctct gctaatcctg   1560
ttaccagtgg ctgctgccag tggcgataag tcgtgtctta ccgggttgga ctcaagacga   1620
tagttaccgg ataaggcgca gcggtcgggc tgaacggggg gttcgtgcac acagcccagc   1680
ttggagcgaa cgacctacac cgaactgaga tacctacagc gtgagcattg agaaagcgcc   1740
acgcttcccg aagggagaaa ggcggacagg tatccggtaa gcggcagggt cggaacagga   1800
gagcgcacga gggagcttcc agggggaaac gcctggtatc tttatagtcc tgtcgggttt   1860
cgccacctct gacttgagcg tcgatttttg tgatgctcgt cagggggggcg agcctatgg    1920 aaaaacgcca gcaacgcggc cttttacgg ttcctggcct tttgctggcc ttttgctcac   1980
atgttctttc ctgcgttatc ccctgattct gtggataacc gtattaccgc ctttgagtga   2040
gctgataccg ctcgccgcag ccgaacgacc gagcgcagcg agtcagtgag cgaggaagcg   2100
gaagagcgcc caatacgcaa accgcctctc cccgcgcgtt ggccgattca ttaatgcagc   2160
tggcacgaca ggtttcccga ctggaaagcg ggcagtgagc gcaacgcaat taatacgcgt   2220
accgctagcc aggaagagtt tgtagaaacg caaaaaggcc atccgtcagg atggccttct   2280
gcttagtttg atgcctggca gtttatggcg ggcgtcctgc ccgccaccct ccgggccgtt   2340
gcttcacaac gttcaaatcc gctcccggcg gatttgtcct actcaggaga gcgttcaccg   2400
acaaacaaca gataaaacga aaggcccagt cttccgactg agcctttcgt tttatttgat   2460
gcctggcagt tccctactct cgcgttaacg ctagcatgga tgttttccca gtcacgacgt   2520
tgtaaaacga cggccagtct taagctcggg cccgcgttaa cgctaccatg agctccaaa    2580 taatgatttt attttgactg atagtgacct gttcgttgca acaaattgat aagcaatgct   2640
tttttataat gccaactttg tatagaaaag ttgaagctta atccttaca gaattgctgt    2700 agtttcatag tgctagatgt ggacagcaaa gcgccgctgt atgcttctgc ttttcttttt   2760
tggtgtgtgt agccacatcc tttgttcctg cccggcgcca tcccacttgg ttgttttttt   2820
ttatgattga aagccttcat gcttcctcgg tcaatcaccg gtgcgcactg ggagcatcgc   2880
cggaaaaaaa attcttcggc taagagtaac ttcttttctcc ttttcttctc tgatctcgcg   2940
agcagtgctg ataacgtgtt gtaatctact tagcggtaac gagattgaga gagacaaaat   3000
gacagaacta ttgtctttat tgcagagtgt catgtattta tacaggggat acaaagtctc   3060
ccaaggggtg tgtcccttgg gagtaactgc cagttgatca caggacaata ttttgtaaca   3120
```

```
aaacgtacac atcgtcaaaa tagcgaggca tgaaactggc cttggccatg acgcgtgaa    3180 gcgcgccatg cgttggatat gtggtcaata agtatataca atacaatgtt taacagagct    3240
gatagtactg ctttggcaca tttttgtcca cgcttcatga gagataaaac acctgcacgt    3300
aaattcacat gctgcactga aggcccgatc actgaggagc gaactgccgt aactcccttc    3360
tatatatacc cccagtccct gtttcagttt tcgtcaagct agcagcacca agttgtcgat    3420
cacttgcctg ctcttgagct cgattaagct atcatcagct acagcatccg atcccaaact    3480
gcaactgtag cagcgacaac tgccg                                          3505
```

<210> SEQ ID NO 13
<211> LENGTH: 49765
<212> TYPE: DNA
<213> ORGANISM: artificial sequence
<220> FEATURE:
<223> OTHER INFORMATION: vector

<400> SEQUENCE: 13

```
gggggggggg ggggggggtt ccattgttca ttccacggac aaaaacagag aaaggaaacg      60
acagaggcca aaaagctcgc tttcagcacc tgtcgtttcc tttcttttca gagggtattt     120
taaataaaaa cattaagtta tgacgaagaa gaacggaaac gccttaaacc ggaaaatttt     180
cataaatagc gaaaacccgc gaggtcgccg ccccgtaacc tgtcggatca ccggaaagga     240
cccgtaaagt gataatgatt atcatctaca tatcacaacg tgcgtggagg ccatcaaacc     300
acgtcaaata atcaattatg acgcaggtat cgtattaatt gatctgcatc aacttaacgt     360
aaaaacaact tcagacaata caaatcagcg acactgaata cggggcaacc tcatgtcccc     420
cccccccccc cccctgcagg catcgtggtg tcacgctcgt cgtttggtat ggcttcattc     480
agctccggtt cccaacgatc aaggcgagtt acatgatccc ccatgttgtg caaaaaagcg     540
gttagctcct tcggtcctcc gatcgttgtc agaagtaagt tggccgcagt gttatcactc     600
atggttatgg cagcactgca taattctctt actgtcatgc catccgtaag atgcttttct     660
gtgactggtg agtactcaac caagtcattc tgagaatagt gtatgcggcg accgagttgc     720
tcttgcccgg cgtcaacacg ggataatacc gcgccacata gcagaacttt aaaagtgctc     780
atcattggaa aacgttcttc ggggcgaaaa ctctcaagga tcttaccgct gttgagatcc     840
agttcgatgt aacccactcg tgcacccaac tgatcttcag catcttttac tttcaccagc     900
gtttctgggt gagcaaaaac aggaaggcaa aatgccgcaa aaagggaat aagggcgaca     960 cggaaatgtt gaatactcat actcttcctt tttcaatatt attgaagcat ttatcagggt    1020
tattgtctca tgagcggata catatttgaa tgtatttaga aaaataaaca aataggggtt    1080
ccgcgcacat ttccccgaaa agtgccacct gacgtctaag aaaccattat tatcatgaca    1140
ttaacctata aaaataggcg tatcacgagg ccctttcgtc ttcaagaatt cggagctttt    1200
gccattctca ccggattcag tcgtcactca tggtgatttc tcacttgata accttatttt    1260
tgacgagggg aaattaatag gttgtattga tgttggacga gtcggaatcg cagaccgata    1320
ccaggatctt gccatcctat ggaactgcct cggtgagttt tctccttcat tacagaaacg    1380
gctttttcaa aaatatggta ttgataatcc tgatatgaat aaattgcagt ttcatttgat    1440
gctcgatgag ttttctaat cagaattggt taattggttg taacactggc agagcattac    1500
gctgacttga cggacggcg gctttgttga ataaatcgaa cttttgctga gttgaaggat    1560
cagatcacgc atcttcccga caacgcagac cgttccgtgg caaagcaaaa gttcaaaatc    1620
```

```
accaactggt ccacctacaa caaagctctc atcaaccgtg gctccctcac tttctggctg    1680
gatgatgggg cgattcaggc ctggtatgag tcagcaacac cttcttcacg aggcagacct    1740
cagcgccaga aggccgccag agaggccgag cgcggccgtg aggcttggac gctagggcag    1800
ggcatgaaaa agcccgtagc gggctgctac gggcgtctga cgcggtggaa aggggaggg     1860
gatgttgtct acatggctct gctgtagtga gtgggttgcg ctccggcagc ggtcctgatc    1920
aatcgtcacc ctttctcggt ccttcaacgt tcctgacaac gagcctcctt ttcgccaatc    1980
catcgacaat caccgcgagt ccctgctcga acgctgcgtc cggaccggct tcgtcgaagg    2040
cgtctatcgc ggcccgcaac agcggcgaga cggagcctg ttcaacggtg ccgccgcgct     2100
cgccggcatc gctgtcgccg gcctgctcct caagcacggc cccaacagtg aagtagctga    2160
ttgtcatcag cgcattgacg gcgtcccgg ccgaaaaacc cgcctcgcag aggaagcgaa      2220
gctgcgcgtc ggccgtttcc atctgcggtg cgcccggtcg cgtgccggca tggatgcgcg    2280
cgccatcgcg gtaggcgagc agcgcctgcc tgaagctgcg ggcattcccg atcagaaatg    2340
agcgccagtc gtcgtcggct ctcggcaccg aatgcgtatg attctccgcc agcatggctt    2400
cggccagtgc gtcgagcagc gcccgcttgt tcctgaagtg ccagtaaagc gccggctgct    2460
gaaccccaa ccgttccgcc agtttgcgtg tcgtcagacc gtctacgccg acctcgttca     2520
acaggtccag ggcggcacgg atcactgtat tcggctgcaa ctttgtcatg cttgacactt    2580
tatcactgat aaacataata tgtccaccaa cttatcagtg ataaagaatc cgcgcgttca    2640
atcggaccag cggaggctgg tccggaggcc agacgtgaaa cccaacatac ccctgatcgt    2700
aattctgagc actgtcgcgc tcgacgctgt cggcatcggc ctgattatgc cggtgctgcc    2760
gggcctcctg cgcgatctgg ttcactcgaa cgacgtcacc gcccactatg gcattctgct    2820
ggcgctgtat gcgttggtgc aatttgcctg cgcacctgtg ctgggcgcgc tgtcggatcg    2880
tttcgggcgg cggccaatct tgctcgtctc gctggccggc gccactgtcg actacgccat    2940
catggcgaca gcgcctttcc tttgggttct ctatatcggg cggatcgtgg ccggcatcac    3000
cggggcgact ggggcggtag ccggcgctta tattgccgat atcactgatg gcgatgagcg    3060
cgcgcggcac ttcggcttca tgagcgcctg tttcgggttc gggatggtcg cgggacctgt    3120
gctcggtggg ctgatgggcg gtttctcccc ccacgctccg ttcttcgccg cggcagcctt    3180
gaacggcctc aatttcctga cgggctgttt ccttttgccg gagtcgcaca aaggcgaacg    3240
ccggccgtta cgccgggagg ctctcaaccc gctcgcttcg ttccggtggg cccggggcat    3300
gaccgtcgtc gccgccctga tggcggtctt cttcatcatg caacttgtcg acaggtgcc     3360
ggccgcgctt tgggtcattt tcggcgagga tcgctttcac tgggacgcga ccacgatcgg    3420
catttcgctt gccgcatttg gcattctgca ttcactcgcc caggcaatga tcaccggccc    3480
tgtagccgcc cggctcggcg aaaggcgggc actcatgctc ggaatgattg ccgacggcac    3540
aggctacatc ctgcttgcct tcgcgacacg gggatggatg gcgttcccga tcatggtcct    3600
gcttgcttcg ggtggcatcg gaatgccggc gctgcaagca atgttgtcca ggcaggtgga    3660
tgaggaacgt caggggcagc tgcaaggctc actggcggcg ctcaccagcc tgacctcgat    3720
cgtcggaccc ctcctcttca cggcgatcta tgccggcttct ataacaacgt ggaacgggtg   3780
ggcatggatt gcaggcgctg ccctctactt gctctgcctg ccggcgctgc gtcgcgggct    3840
ttggagcggg gcagggcaac gagccgatcg ctgatcgtgg aaacgatagg cctatgccat    3900
gcgggtcaag gcgacttccg gcaagctata cgcgccctag gagtgcggtt ggaacgttgg    3960
cccagccaga tactcccgat cacgagcagg acgccgatga tttgaagcgc actcagcgtc    4020
```

```
tgatccaaga acaaccatcc tagcaacacg gcggtcccg ggctgagaaa gcccagtaag    4080
gaaacaactg taggttcgag tcgcgagatc ccccggaacc aaaggaagta ggttaaaccc    4140
gctccgatca ggccgagcca cgccaggccg agaacattgg ttcctgtagg catcgggatt    4200
ggcggatcaa acactaaagc tactggaacg agcagaagtc ctccggccgc cagttgccag    4260
gcggtaaagg tgagcagagg cacgggaggt tgccacttgc gggtcagcac ggttccgaac    4320
gccatggaaa ccgcccccgc caggcccgct gcgacgccga caggatctag cgctgcgttt    4380
ggtgtcaaca ccaacagcgc cacgcccgca gttccgcaaa tagcccccag gaccgccatc    4440
aatcgtatcg ggctacctag cagagcggca gagatgaaca cgaccatcag cggctgcaca    4500
gcgcctaccg tcgccgcgac cccgcccggc aggcggtaga ccgaaataaa caacaagctc    4560
cagaatagcg aaatattaag tgcgccgagg atgaagatgc gcatccacca gattcccgtt    4620
ggaatctgtc ggacgatcat cacgagcaat aaacccgccg gcaacgcccg cagcagcata    4680
ccggcgaccc ctcggcctcg ctgttcgggc tccacgaaaa cgccggacag atgcgccttg    4740
tgagcgtcct tggggccgtc ctcctgtttg aagaccgaca gcccaatgat ctcgccgtcg    4800
atgtaggcgc cgaatgccac ggcatctcgc aaccgttcag cgaacgcctc catgggcttt    4860
ttctcctcgt gctcgtaaac ggacccgaac atctctggag cttcttcag ggccgacaat    4920 cggatctcgc ggaaatcctg cacgtcggcc gctccaagcc gtcgaatctg agccttaatc    4980
acaattgtca attttaatcc tctgtttatc ggcagttcgt agagcgcgcc gtgcgtcccg    5040
agcgatactg agcgaagcaa gtgcgtcgag cagtgcccgc ttgttcctga aatgccagta    5100
aagcgctggc tgctgaaccc ccagccggaa ctgacccac aaggccctag cgtttgcaat    5160
gcaccaggtc atcattgacc caggcgtgtt ccaccaggcc gctgcctcgc aactcttcgc    5220
aggcttcgcc gacctgctcg cgccacttct tcacgcgggt ggaatccgat ccgcacatga    5280
ggcggaaggt ttccagcttg agcgggtacg gctcccggtg cgagctgaaa tagtcgaaca    5340
tccgtcgggc cgtcggcgac agcttgcggt acttctccca tatgaatttc gtgtagtggt    5400
cgccagcaaa cagcacgacg atttcctcgt cgatcaggac ctggcaacgg gacgttttct    5460
tgccacggtc caggacgcgg aagcggtgca gcagcgacac cgattccagg tgcccaacgc    5520
ggtcggacgt gaagcccatc gccgtcgcct gtaggcgcga caggcattcc tcggccttcg    5580
tgtaataccg gccattgatc gaccagccca ggtcctggca aagctcgtag aacgtgaagg    5640
tgatcggctc gccgataggg gtgcgcttcg cgtactccaa cacctgctgc cacaccagtt    5700
cgtcatcgtc ggcccgcagc tcgacgccgg tgtaggtgat cttcacgtcc ttgttgacgt    5760
ggaaaatgac cttgttttgc agcgcctcgc gcgggatttt cttgttgcgc gtggtgaaca    5820
gggcagagcg ggccgtgtcg tttggcatcg ctcgcatcgt gtccgccac ggcgcaatat    5880 cgaacaagga aagctgcatt tccttgatct gctgcttcgt gtgtttcagc aacgcggcct    5940
gcttggcctc gctgacctgt tttgccaggt cctcgccggc ggttttttcgc ttcttggtcg    6000 tcatagttcc tcgcgtgtcg atggtcatcg acttcgccaa acctgccgcc tcctgttcga    6060
gacgacgcga acgctccacg gcggccgatg gcgcgggcag ggcaggggga gccagttgca    6120
cgctgtcgcg ctcgatcttg gccgtagctt gctggaccat cgagccgacg gactggaagg    6180
tttcgcgggg cgcacgcatg acggtgcggc ttgcgatggt ttcggcatcc tcggcggaaa    6240
accccgcgtc gatcagttct tgcctgtatg ccttccggtc aaacgtccga ttcattcacc    6300
ctccttgcgg gattgccccg actcacgccg gggcaatgtg cccttattcc tgatttgacc    6360
```

```
cgcctggtgc cttggtgtcc agataatcca ccttatcggc aatgaagtcg gtcccgtaga   6420
ccgtctggcc gtccttctcg tacttggtat tccgaatctt gccctgcacg aataccagcg   6480
accccttgcc caaatacttg ccgtgggcct cggcctgaga gccaaaacac ttgatgcgga   6540
agaagtcggt gcgctcctgc ttgtcgccgg catcgttgcg ccactcttca ttaaccgcta   6600
tatcgaaaat tgcttgcggc ttgttagaat tgccatgacg tacctcggtg tcacgggtaa   6660
gattaccgat aaactggaac tgattatggc tcatatcgaa agtctccttg agaaaggaga   6720
ctctagttta gctaaacatt ggttccgctg tcaagaactt tagcggctaa aattttgcgg   6780
gccgcgacca aaggtgcgag gggcggcttc cgctgtgtac aaccagatat ttttcaccaa   6840
catccttcgt ctgctcgatg agcggggcat gacgaaacat gagctgtcgg agagggcagg   6900
ggtttcaatt tcgttttat cagacttaac caacggtaag gccaacccct cgttgaaggt   6960
gatggaggcc attgccgacg ccctggaaac tcccctacct cttctcctgg agtccaccga   7020
ccttgaccgc gaggcactcg cggagattgc gggtcatcct ttcaagagca gcgtgccgcc   7080
cggatacgaa cgcatcagtg tggttttgcc gtcacataag gcgtttatcg taaagaaatg   7140
gggcgacgac acccgaaaaa agctgcgtgg aaggctctga cgccaagggt tagggcttgc   7200
acttccttct ttagccgcta aaacggcccc ttctctgcgg gccgtcggct cgcgcatcat   7260
atcgacatcc tcaacggaag ccgtgccgcg aatggcatcg ggcgggtgcg ctttgacagt   7320
tgttttctat cagaacccct acgtcgtgcg gttcgattag ctgtttgtct tgcaggctaa   7380
acactttcgg tatatcgttt gcctgtgcga taatgttgct aatgatttgt tgcgtagggg   7440
ttactgaaaa gtgagcggga aagaagagtt tcagaccatc aaggagcggg ccaagcgcaa   7500
gctggaacgc gacatggggt cggacctgtt ggccgcgctc aacgacccga aaaccgttga   7560
agtcatgctc aacgcggacg gcaaggtgtg gcacgaacgc cttggcgagc cgatgcggta   7620
catctgcgac atgcggccca gccagtcgca ggcgattata gaaacggtgg ccggattcca   7680
cggcaaagag gtcacgcggc attcgcccat cctggaaggc gagttcccct ggatggcag   7740
ccgctttgcc ggccaattgc cgccggtcgt ggccgcgcca accttgcga tccgcaagcg   7800
cgcggtcgcc atcttcacgc tggaacagta cgtcgaggcg ggcatcatga cccgcgagca   7860
atacgaggtc attaaaagcg ccgtcgcggc gcatcgaaac atcctcgtca ttggcggtac   7920
tggctcgggc aagaccacgc tcgtcaacgc gatcatcaat gaaatggtcg ccttcaaccc   7980
gtctgagcgc gtcgtcatca tcgaggacac cggcgaaatc cagtgcgccg cagagaacgc   8040
cgtccaatac cacaccagca tcgacgtctc gatgacgctg ctgctcaaga caacgctgcg   8100
tatgcgcccc gaccgcatcc tggtcggtga ggtacgtggc cccgaagccc ttgatctgtt   8160
gatggcctgg aacaccgggc atgaaggagg tgccgccacc ctgcacgcaa acaaccccaa   8220
agcgggcctg agccggctcg ccatgcttat cagcatgcac ccggattcac cgaaacccat   8280
tgagccgctg attggcgagg cggttcatgt ggtcgtccat atcgccagga cccctagcgg   8340
ccgtcgagtg caagaaattc tcgaagttct tggttacgag aacggccagt acatcaccaa   8400
aaccctgtaa ggagtatttc caatgacaac ggctgttccg ttccgtctga ccatgaatcg   8460
cggcattttg ttctaccttg ccgtgttctt cgttctcgct ctcgcgttat ccgcgcatcc   8520
ggcgatggcc tcggaaggca ccggcggcag cttgccatat gagagctggc tgacgaacct   8580
gcgcaactcc gtaaccggcc cggtggcctt cgcgctgtcc atcatcggca tcgtcgtcgc   8640
cggcggcgtg ctgatcttcg gcggcgaact caacgccttc ttccgaaccc tgatcttcct   8700
ggttctggtg atggcgctgc tggtcggcgc gcagaacgtg atgagcacct tcttcggtcg   8760
```

```
tggtgccgaa atcgcggccc tcggcaacgg ggcgctgcac caggtgcaag tcgcggcggc    8820
ggatgccgtg cgtgcggtag cggctggacg gctcgcctaa tcatggctct gcgcacgatc    8880
cccatccgtc gcgcaggcaa ccgagaaaac ctgttcatgg gtggtgatcg tgaactggtg    8940
atgttctcgg gcctgatggc gtttgcgctg attttcagcg cccaagagct gcgggccacc    9000
gtggtcggtc tgatcctgtg gttcggggcg ctctatgcgt tccgaatcat ggcgaaggcc    9060
gatccgaaga tgcggttcgt gtacctgcgt caccgccggt acaagccgta ttacccggcc    9120
cgctcgaccc cgttccgcga gaacaccaat agccaaggga agcaataccg atgatccaag    9180
caattgcgat tgcaatcgcg ggcctcggcg cgcttctgtt gttcatcctc tttgcccgca    9240
tccgcgcggt cgatgccgaa ctgaaactga aaaagcatcg ttccaaggac gccggcctgg    9300
ccgatctgct caactacgcc gctgtcgtcg atgacgcgct aatcgtgggc aagaacggca    9360
gctttatggc tgcctggctg tacaagggcg atgacaacgc aagcagcacc gaccagcagc    9420
gcgaagtagt gtccgcccgc atcaaccagg ccctcgcggg cctggaagt gggtggatga    9480 tccatgtgga cgccgtgcgg cgtcctgctc cgaactacgc ggagcggggc ctgtcggcgt    9540
tccctgaccg tctgacggca gcgattgaag aagagcgctc ggtcttgcct tgctcgtcgg    9600
tgatgtactt caccagctcc gcgaagtcgc tcttcttgat ggagcgcatg ggacgtgct    9660 tggcaatcac gcgcaccccc cggccgtttt agcggctaaa aaagtcatgg ctctgccctc    9720
gggcggacca cgcccatcat gaccttgcca agctcgtcct gcttctcttc gatcttcgcc    9780
agcagggcga ggatcgtggc atcaccgaac cgcgccgtgc gcgggtcgtc ggtgagccag    9840
agtttcagca ggccgcccag gcggcccagg tcgccattga tgcgggccag ctcgcggacg    9900
tgctcatagt ccacgacgcc cgtgattttg tagccctggc cgacggccag caggtaggcc    9960
gacaggctca tgccggccgc cgccgccttt tcctcaatcg ctcttcgttc gtctggaagg    10020
cagtacacct tgataggtgg gctgcccttc ctggttggct tggtttcatc agccatccgc    10080
ttgccctcat ctgttacgcc ggcggtagcc ggccagcctc gcagagcagg attcccgttg    10140
agcaccgcca ggtgcgaata agggacagtg aagaaggaac accgctcgc gggtgggcct    10200 acttcaccta tcctgcccgg ctgacgccgt tggatacacc aaggaaagtc tacacgaacc    10260 cttttggcaaa atcctgtata tcgtgcgaaa aaggatggat ataccgaaaa aatcgctata    10320 atgacccga agcagggtta tgcagcgaa aagcgctgct tccctgctgt tttgtggaat    10380
atctaccgac tggaaacagg caaatgcagg aaattactga actgagggga caggcgagag    10440
acgatgccaa agagctacac cgacgagctg gccgagtggg ttgaatcccg cgcggccaag    10500
aagcgccggc gtgatgaggc tgcggttgcg ttcctggcgg tgagggcgga tgtcgaggcg    10560
gcgttagcgt ccggctatgc gctcgtcacc atttgggagc acatgcggga aacggggaag    10620
gtcaagttct cctacgagac gttccgctcg cacgccaggc ggcacatcaa ggccaagccc    10680
gccgatgtgc ccgcaccgca ggccaaggct cggaacccg cgccggcacc caagacgccg    10740
gagccacggc ggccgaagca gggggcaag gctgaaaagc cggcccccgc tgcggccccg    10800
accggcttca ccttcaaccc aacaccggac aaaaaggatc tactgtaatg gcgaaaattc    10860
acatggtttt gcagggcaag ggcggggtcg gcaagtcggc catcgccgcg atcattgcgc    10920
agtacaagat ggacaagggg cagacaccct tgtgcatcga caccgacccg gtgaacgcga    10980
cgttcgaggg ctacaaggcc ctgaacgtcc gccggctgaa catcatggcc ggcgacgaaa    11040
ttaactcgcg caacttcgac accctggtcg agctgattgc gccgaccaag gatgacgtgg    11100
```

```
tgatcgacaa cggtgccagc tcgttcgtgc ctctgtcgca ttacctcatc agcaaccagg  11160
tgccggctct gctgcaagaa atggggcatg agctggtcat ccataccgtc gtcaccggcg  11220
gccaggctct cctggacacg gtgagcggct cgcccagct cgccagccag ttcccggccg   11280
aagcgctttt cgtggtctgg ctgaacccgt attgggggcc tatcgagcat gagggcaaga  11340
gctttgagca gatgaaggcg tacacggcca acaaggcccg cgtgtcgtcc atcatccaga  11400
ttccggccct caaggaagaa acctacggcc gcgatttcag cgacatgctg caagagcggc  11460
tgacgttcga ccaggcgctg ccgatgaat cgctcacgat catgacgcgg caacgcctca   11520
agatcgtgcg gcgcggcctg tttgaacagc tcgacgcggc ggccgtgcta tgagcgacca  11580
gattgaagag ctgatccggg agattgcggc caagcacggc atcgccgtcg gccgcgacga  11640
cccggtgctg atcctgcata ccatcaacgc ccggctcatg gccgacagtg cggccaagca  11700
agaggaaatc cttgccgcgt tcaaggaaga gctggaaggg atcgcccatc gttggggcga  11760
ggacgccaag gccaaagcgg agcggatgct gaacgcggcc ctggcggcca gcaaggacgc  11820
aatggcgaag gtaatgaagg acagcgccgc gcaggcggcc gaagcgatcc gcagggaaat  11880
cgacgacggc cttggccgcc agctcgcggc caaggtcgcg gacgcgcggc gcgtggcgat  11940
gatgaacatg atcgccggcg gcatggtgtt gttcgcggcc gccctggtgg tgtgggcctc  12000
gttatgaatc gcagaggcgc agatgaaaaa gcccggcgtt gccgggcttt gttttgcgt   12060
tagctgggct tgtttgacag gcccaagctc tgactgcgcc cgcgctcgcg ctcctgggcc  12120
tgtttcttct cctgctcctg cttgcgcatc agggcctggt gccgtcgggc tgcttcacgc  12180
atcgaatccc agtcgccggc cagctcggga tgctccgcgc gcatcttgcg cgtcgccagt  12240
tcctcgatct tgggcgcgtg aatgcccatg ccttccttga tttcgcgcac catgtccagc  12300
cgcgtgtgca gggtctgcaa gcgggcttgc tgtttgggcct gctgctgctg ccaggcggcc  12360
tttgtacgcg gcagggacag caagccgggg gcattggact gtagctgctg caaacgcgcc  12420
tgctgacggt ctacgagctg ttctaggcgg tcctcgatgc gctccacctg gtcatgcttt  12480
gcctgcacgt agagcgcaag ggtctgctgg taggtctgct cgatgggcgc ggattctaag  12540
agggcctgct gttccgtctc ggcctcctgg gccgcctgta gcaaatcctc gccgctgttg  12600
ccgctggact gctttactgc cggggactgc tgttgccctg ctcgcgccgt cgtcgcagtt  12660
cggcttgccc ccactcgatt gactgcttca tttcgagccg cagcgatgcg atctcggatt  12720
gcgtcaacgg acggggcagc gcggaggtgt ccggcttctc cttgggtgag tcggtcgatg  12780
ccatagccaa aggtttcctt ccaaaatgcg tccattgctg gaccgtgttt ctcattgatg  12840
cccgcaagca tcttcggctt gaccgccagg tcaagcgcgc cttcatgggc ggtcatgacg  12900
gacgccgcca tgaccttgcc gccgttgttc tcgatgtagc cgcgtaatga ggcaatggtg  12960
ccgcccatcg tcagcgtgtc atcgacaacg atgtacttct ggccggggat cacctccccc  13020
tcgaaagtcg ggttgaacgc caggcgatga tctgaaccgg ctccggttcg ggcgaccttc  13080
tcccgctgca caatgtccgt ttcgacctca aggccaaggc ggtcggccag aacgaccgcc  13140
atcatggccg gaatcttgtt gttccccgcc gcctcgacgg cgaggactgg aacgatgcgg  13200
ggcttgtcgt cgccgatcag cgtcttgagc tgggcaacag tgtcgtccga atcaggcgc   13260
tcgaccaaat taagcgccgc ttccgcgtcg ccctgcttcg cagcctggta ttcaggctcg  13320
ttggtcaaag aaccaaggtc gccgttgcga accaccttcg ggaagtctcc ccacggtgcg  13380
cgctcggctc tgctgtagct gctcaagacg cctccctttt tagccgctaa aactctaacg  13440
agtgcgcccg cgactcaact tgacgctttc ggcacttacc tgtgccttgc cacttgcgtc  13500
```

```
ataggtgatg cttttcgcac tcccgatttc aggtacttta tcgaaatctg accgggcgtg   13560
cattacaaag ttcttcccca cctgttggta aatgctgccg ctatctgcgt ggacgatgct   13620
gccgtcgtgg cgctgcgact tatcggcctt ttgggccata tagatgttgt aaatgccagg   13680
tttcagggcc ccggctttat ctaccttctg gttcgtccat gcgccttggt tctcggtctg   13740
gacaattctt tgcccattca tgaccaggag gcggtgtttc attgggtgac tcctgacggt   13800
tgcctctggt gttaaacgtg tcctggtcgc ttgccggcta aaaaaaagcc gacctcggca   13860
gttcgaggcc ggctttccct agagccgggc gcgtcaaggt tgttccatct attttagtga   13920
actgcgttcg atttatcagt tactttcctc ccgctttgtg tttcctccca ctcgtttccg   13980
cgtctagccg acccctcaac atagcggcct cttcttgggc tgcctttgcc tcttgccgcg   14040
cttcgtcacg ctcggcttgc accgtcgtaa agcgctcggc ctgcctggcc gcctcttgcg   14100
ccgccaactt cctttgctcc tggtgggcct cggcgtcggc ctgcgccttc gctttcaccg   14160
ctgccaactc cgtgcgcaaa ctctccgctt cgcgcctggt ggcgtcgcgc tcgccgcgaa   14220
gcgcctgcat ttcctggttg gccgcgtcca gggtcttgcg gctctcttct ttgaatgcgc   14280
gggcgtcctg gtgagcgtag tccagctcgg cgcgcagctc ctgcgctcga cgctccacct   14340
cgtcggcccg ctgcgtcgcc agcgcggccc gctgctcggc tcctgccagg gcggtgcgtg   14400
cttcggccag ggcttgccgc tggcgtgcgg ccagctcggc cgcctcggcg gcctgctgct   14460
ctagcaatgt aacgcgcgcc tgggcttctt ccagctcgcg ggcctgcgcc tcgaaggcgt   14520
cggccagctc cccgcgcacg gcttccaact cgttgcgctc acgatcccag ccggcttgcg   14580
ctgcctgcaa cgattcattg gcaagggcct gggcggcttg ccagagggcg ccacggcct   14640 ggttgccggc ctgctgcacc gcgtccggca cctggactgc cagcggggcg gcctgcgccg   14700
tgcgctggcg tcgccattcg cgcatgccgg cgctggcgtc gttcatgttg acgcgggcgg   14760
ccttacgcac tgcatccacg gtcgggaagt tctcccggtc gccttgctcg aacagctcgt   14820
ccgcagccgc aaaaatgcgg tcgcgcgtct ctttgttcag ttccatgttg gctccggtaa   14880
ttggtaagaa taataatact cttacctacc ttatcagcgc aagagtttag ctgaacagtt   14940
ctcgacttaa cggcaggttt tttagcggct gaagggcagg caaaaaaagc cccgcacggt   15000 cggcggggc aaagggtcag cgggaagggg attagcgggc gtcgggcttc ttcatgcgtc   15060
ggggccgcgc ttcttgggat ggagcacgac gaagcgcgca cgcgcatcgt cctcggccct   15120
atcggcccgc gtcgcggtca ggaacttgtc gcgcgctagg tcctccctgg tgggcaccag   15180
gggcatgaac tcggcctgct cgatgtaggt ccactccatg accgcatcgc agtcgaggcc   15240
gcgttccttc accgtctctt gcaggtcgcg gtacgcccgc tcgttgagcg gctggtaacg   15300
ggccaattgg tcgtaaatgg ctgtcggcca tgagcggcct ttcctgttga gccagcagcc   15360
gacgacgaag ccggcaatgc aggcccctgg cacaaccagg ccgacgccgg gggcagggga   15420
tggcagcagc tcgccaacca ggaacccgc gcgatgatg ccgatgccgg tcaaccagcc   15480
cttgaaacta tccggccccg aaacacccct gcgcattgcc tggatgctgc gccggatagc   15540
ttgcaacatc aggagccgtt tcttttgttc gtcagtcatg gtccgccctc accagttgtt   15600
cgtatcggtg tcggacgaac tgaaatcgca agagctgccg gtatcggtcc agccgctgtc   15660
cgtgtcgctg ctgccgaagc acggcgaggg gtccgcgaac gccgcagacg gcgtatccgg   15720
ccgcagcgca tcgcccagca tggccccggt cagcgagccg ccggcaggt agcccagcat   15780 ggtgctgttg gtcgccccgg ccaccagggc cgacgtgacg aaatcgccgt cattccctct   15840
```

-continued

```
ggattgttcg ctgctcggcg gggcagtgcg ccgcgccggc ggcgtcgtgg atggctcggg    15900
ttggctggcc tgcgacggcc ggcgaaaggt gcgcagcagc tcgttatcga ccggctgcgg    15960
cgtcggggcc gccgccttgc gctgcggtcg gtgttccttc ttcggctcgc gcagcttgaa    16020
cagcatgatc gcggaaacca gcagcaacgc cgcgcctacg cctcccgcga tgtagaacag    16080
catcggattc attcttcggt cctccttgta gcggaaccgt tgtctgtgcg gcgcgggtgg    16140
cccgcgccgc tgtctttggg gatcagccct cgatgagcgc gaccagtttc acgtcggcaa    16200
ggttcgcctc gaactcctgg ccgtcgtcct cgtacttcaa ccaggcatag ccttccgccg    16260
gcggccgacg gttgaggata aggcgggcag ggcgctcgtc gtgctcgacc tggacgatgg    16320
ccttttttcag cttgtccggg tccggctcct tcgcgccctt ttccttggcg tccttaccgt    16380
cctggtcgcc gtcctcgccg tcctggccgt cgccggcctc cgcgtcacgc tcggcatcag    16440
tctggccgtt gaaggcatcg acggtgttgg gatcgcggcc cttctcgtcc aggaactcgc    16500
gcagcagctt gaccgtgccg cgcgtgattt cctgggtgtc gtcgtcaagc cacgcctcga    16560
cttcctccgg gcgcttcttg aaggccgtca ccagctcgtt caccacggtc acgtcgcgca    16620
cgcggccggt gttgaacgca tcggcgatct tctccggcag gtccagcagc gtgacgtgct    16680
gggtgatgaa cgccggcgac ttgccgattt ccttggcgat atcgcctttc ttcttgcccc    16740
tcgccagctc gcggccaatg aagtcggcaa tttcgcgcgg ggtcagctcg ttgcgttgca    16800
ggttctcgat aacctggtcg gcttcgttgt agtcgttgtc gatgaacgcc gggatggact    16860
tcttgccggc ccacttcgag ccacggtagc ggcgggcgcc gtgattgatg atatagcggc    16920
ccggctgctc ctggttctcg cgcaccgaaa tgggtgactt caccccgcgc tctttgatcg    16980
tggcaccgat ttccgcgatg ctctccgggg aaaagccggg gttgtcggcc gtccgcggct    17040
gatgcggatc ttcgtcgatc aggtccaggt ccagctcgat agggccggaa ccgccctgag    17100
acgccgcagg agcgtccagg aggctcgaca ggtcgccgat gctatccaac cccaggccgg    17160
acggctgcgc cgcgcctgcg gcttcctgag cggccgcagc ggtgtttttc ttggtggtct    17220
tggcttgagc cgcagtcatt gggaaatctc catcttcgtg aacacgtaat cagccagggc    17280
gcgaacctct ttcgatgcct tgcgcgcggc cgttttcttg atcttccaga ccggcacacc    17340
ggatgcgagg gcatcggcga tgctgctgcg caggccaacg gtggccggaa tcatcatctt    17400
ggggtacgcg gccagcagct cggcttggtg gcgcgcgtgg cgcggattcc gcgcatcgac    17460
cttgctgggc accatgccaa ggaattgcag cttggcgttc ttctggcgca cgttcgcaat    17520
ggtcgtgacc atcttcttga tgccctggat gctgtacgcc tcaagctcga tggggggacag    17580
cacatagtcg gccgcgaaga gggcggccgc caggccgacg ccaagggtcg gggccgtgtc    17640
gatcaggcac acgtcgaagc cttggttcgc cagggccttg atgttcgccc cgaacagctc    17700
gcgggcgtcg tccagcgaca gccgttcggc gttcgccagt accgggttgg actcgatgag    17760
ggcgaggcgc gcggcctggc cgtcgccggc tgcgggtgcg gtttcggtcc agccgccggc    17820
agggacagcg ccgaacagct tgcttgcatg caggccggta gcaaagtcct tgagcgtgta    17880
ggacgcattg ccctgggggt ccaggtcgat cacggcaacc gcaagccgc gctcgaaaaa    17940
gtcgaaggca agatgcacaa gggtcgaagt cttgccgacg ccgcctttct ggttggccgt    18000
gaccaaagtt ttcatcgttt ggtttcctgt tttttcttgg cgtccgcttc ccacttccgg    18060
acgatgtacg cctgatgttc cggcagaacc gccgttaccc gcgcgtaccc ctcgggcaag    18120
ttcttgtcct cgaacgcggc ccacacgcga tgcaccgctt cgacactgc gccctggtc    18180
agtcccagcg acgttgcgaa cgtcgcctgt ggcttcccat cgactaagac gccccgcgct    18240
```

```
atctcgatgg tctgctgccc cacttccagc ccctggatcg cctcctggaa ctggctttcg   18300
gtaagccgtt tcttcatgga taacacccat aatttgctcc gcgccttggt tgaacatagc   18360
ggtgacagcc gccagcacat gagagaagtt tagctaaaca tttctcgcac gtcaacacct   18420
ttagccgcta aaactcgtcc ttggcgtaac aaaacaaaag cccggaaacc gggctttcgt   18480
ctcttgccgc ttatggctct gcacccggct ccatcaccaa caggtcgcgc acgcgcttca   18540
ctcggttgcg gatcgacact gccagcccaa caaagccggt tgccgccgcc gccaggatcg   18600
cgccgatgat gccggccaca ccggccatcg cccaccaggt cgccgccttc cggttccatt   18660
cctgctggta ctgcttcgca atgctggacc tcggctcacc ataggctgac cgctcgatgg   18720
cgtatgccgc ttctccccct tggcgtaaaac ccagcgccgc aggcggcatt gccatgctgc   18780
ccgccgcttt cccgaccacg acgcgcgcac caggcttgcg gtccagacct tcggccacgg   18840
cgagctgcgc aaggacataa tcagccgccg acttggctcc acgcgcctcg atcagctctt   18900
gcactcgcgc gaaatccttg gcctccacgg ccgccatgaa tcgcgcacgc ggcgaaggct   18960
ccgcagggcc ggcgtcgtga tcgccgccga gaatgcccct caccaagttc gacgacacga   19020
aaatcatgct gacggctatc accatcatgc agacggatcg cacgaacccg ctgaattgaa   19080
cacgagcacg gcaccgcgca ccactatgcc aagaatgccc aaggtaaaaa ttgccggccc   19140
cgccatgaag tccgtgaatg ccccgacggc cgaagtgaag ggcaggccgc cacccaggcc   19200
gccgccctca ctgcccggca cctggtcgct gaatgtcgat gccagcacct gcggcacgtc   19260
aatgcttccg ggcgtcgcgc tcgggctgat cgcccatccc gttactgccc cgatcccggc   19320
aatggcaagg actgccagcg ctgccatttt tggggtgagg ccgttcgcgg ccgaggggcg   19380
cagcccctgg ggggatggga ggcccgcgtt agcgggccgg gagggttcga aaggggggg   19440 cacccccctt cggcgtgcgc ggtcacgcgc acagggcgca gccctggtta aaaacaaggt   19500
ttataaatat tggtttaaaa gcaggttaaa agacaggtta gcggtggccg aaaaacgggc   19560 ggaaacccctt gcaaatgctg gattttctgc ctgtggacag cccctcaaat gtcaataggt   19620
gcgcccctca tctgtcagca ctctgccccct caagtgtcaa ggatcgcgcc cctcatctgt   19680
cagtagtcgc gccccctcaag tgtcaatacc gcagggcact tatccccagg cttgtccaca   19740
tcatctgtgg gaaactcgcg taaaatcagg cgttttcgcc gatttgcgag gctggccagc   19800
tccacgtcgc cggccgaaat cgagcctgcc cctcatctgt caacgccgcg ccgggtgagt   19860
cggcccctca agtgtcaacg tccgcccctc atctgtcagt gagggccaag ttttccgcga   19920
ggtatccaca acgccggcgg ccgcggtgtc tcgcacacgg cttcgacggc gtttctggcg   19980
cgtttgcagg gccatagacg gccgccagcc cagcggcgag ggcaaccagc ccggtgagcg   20040
tcggaaaggc gctggaagcc ccgtagcgac gcggagaggg gcgagacaag ccaagggcgc   20100
aggctcgatg cgcagcacga catagccggt tctcgcaagg acgagaattt ccctgcggtg   20160
cccctcaagt gtcaatgaaa gtttccaacg cgagccattc gcgagagcct tgagtccacg   20220
ctagatgaga gctttgttgt aggtggacca gttggtgatt tgaactttt gctttgccac   20280 ggaacggtct gcgttgtcgg gaagatgcgt gatctgatcc ttcaactcag caaaagttcg   20340
atttattcaa caaagccacg ttgtgtctca aaatctctga tgttacattg cacaagataa   20400
aaatatatca tcatgaacaa taaaactgtc tgcttacata aacagtaata caagggggtgt   20460 tatgagccat attcaacggg aaacgtcttg ctcgactcta gagctcgttc ctcgaggcct   20520
cgaggcctcg aggaacggta cctgcgggga agcttacaat aatgtgtgtt gttaagtctt   20580
```

```
gttgcctgtc atcgtctgac tgactttcgt cataaatccc ggcctccgta acccagcttt   20640
gggcaagctc acggatttga tccggcggaa cgggaatatc gagatgccgg gctgaacgct   20700
gcagttccag ctttcccttt cgggacaggt actccagctg attgattatc tgctgaaggg   20760
tcttggttcc acctcctggc acaatgcgaa tgattacttg agcgcgatcg ggcatccaat   20820
tttctcccgt caggtgcgtg gtcaagtgct acaaggcacc tttcagtaac gagcgaccgt   20880
cgatccgtcg ccgggatacg gacaaaatgg agcgcagtag tccatcgagg gcggcgaaag   20940
cctcgccaaa agcaatacgt tcatctcgca cagcctccag atccgatcga gggtcttcgg   21000
cgtaggcaga tagaagcatg gatacattgc ttgagagtat tccgatggac tgaagtatgg   21060
cttccatctt ttctcgtgtg tctgcatcta tttcgagaaa gcccccgatg cggcgcaccg   21120
caacgcgaat tgccatacta tccgaaagtc ccagcaggcg cgcttgatag gaaaaggttt   21180
catactcggc cgatcgcaga cgggcactca cgaccttgaa cccttcaact ttcagggatc   21240
gatgctggtt gatggtagtc tcactcgacg tggctctggt gtgttttgac atagcttcct   21300
ccaaagaaag cggaaggtct ggatactcca gcacgaaatg tgcccgggta gacggatgga   21360
agtctagccc tgctcaatat gaaatcaaca gtacatttac agtcaatact gaatatactt   21420
gctacatttg caattgtctt ataacgaatg tgaaataaaa atagtgtaac aacgctttta   21480
ctcatcgata atcacaaaaa catttatacg aacaaaaata caaatgcact ccggtttcac   21540
aggataggcg ggatcagaat atgcaacttt tgacgttttg ttctttcaaa ggggtgctg   21600
gcaaaaccac cgcactcatg ggcctttgcg ctgctttggc aaatgacggt aaacgagtgg   21660
ccctctttga tgccgacgaa aaccggcctc tgacgcgatg gagagaaaac gccttacaaa   21720
gcagtactgg gatcctcgct gtgaagtcta ttccgccgac gaaatgcccc ttcttgaagc   21780
agcctatgaa aatgccgagc tgaaggatt tgattatgcg ttggccgata cgcgtggcgg   21840
ctcgagcgag ctcaacaaca caatcatcgc tagctcaaac ctgcttctga tccccaccat   21900
gctaacgccg ctcgacatcg atgaggcact atctacctac cgctacgtca tcgagctgct   21960
gttgagtgaa aatttggcaa ttcctacagc tgttttgcgc caacgcgtcc cggtcggccg   22020
attgacaaca tcgcaacgca ggatgtcaga gacgctagag agccttccag ttgtaccgtc   22080
tcccatgcat gaaagagatg catttgccgc gatgaaagaa cgcggcatgt tgcatcttac   22140
attactaaac acgggaactg atccgacgat gcgcctcata gagaggaatc ttcggattgc   22200
gatggaggaa gtcgtggtca tttcgaaact gatcagcaaa atcttggagg cttgaagatg   22260
gcaattcgca agcccgcatt gtcggtcggc gaagcacggc ggcttgctgg tgctcgaccc   22320
gagatccacc atcccaaccc gacacttgtt ccccagaagc tggacctcca gcacttgcct   22380
gaaaaagccg acgagaaaga ccagcaacgt gagcctctcg tcgccgatca catttacagt   22440
cccgatcgac aacttaagct aactgtggat gcccttagtc cacctccgtc cccgaaaaag   22500
ctccaggttt ttcttttcagc gcgaccgccc gcgcctcaag tgtcgaaaac atatgacaac   22560
ctcgttcggc aatacagtcc ctcgaagtcg ctacaaatga ttttaaggcg cgcgttggac   22620
gatttcgaaa gcatgctggc agatggatca tttcgcgtgg ccccgaaaag ttatccgatc   22680
ccttcaacta cagaaaaatc cgttctcgtt cagacctcac gcatgttccc ggttgcgttg   22740
ctcgaggtcg ctcgaagtca ttttgatccg ttggggttgg agaccgctcg agctttcggc   22800
cacaagctgg ctaccgccgc gctcgcgtca ttctttgctg agagaagcc atcgagcaat   22860
tggtgaagag ggacctatcg gaaccctca ccaaatattg agtgtaggtt tgaggccgct   22920
ggccgcgtcc tcagtcacct tttgagccag ataattaaga gccaaatgca attggctcag   22980
```

```
gctgccatcg tccccccgtg cgaaacctgc acgtccgcgt caaagaaata accggcacct   23040
cttgctgttt ttatcagttg agggcttgac ggatccgcct caagtttgcg gcgcagccgc   23100
aaaatgagaa catctatact cctgtcgtaa acctcctcgt cgcgtactcg actggcaatg   23160
agaagttgct cgcgcgatag aacgtcgcgg ggtttctcta aaaacgcgag gagaagattg   23220
aactcacctg ccgtaagttt cacctcaccg ccagcttcgg acatcaagcg acgttgcctg   23280
agattaagtg tccagtcagt aaaacaaaaa gaccgtcggt ctttggagcg gacaacgttg   23340
gggcgcacgc gcaaggcaac ccgaatgcgt gcaagaaact ctctcgtact aaacggctta   23400
gcgataaaat cacttgctcc tagctcgagt gcaacaactt tatccgtctc ctcaaggcgg   23460
tcgccactga taattatgat tggaatatca gactttgccg ccagatttcg aacgatctca   23520
agcccatctt cacgacctaa atttagatca acaaccacga catcgaccgt cgcggaagag   23580
agtactctag tgaactgggt gctgtcggct accgcggtca ctttgaaggc gtggatcgta   23640
aggtattcga taataagatg ccgcatacgc acatcgtcat cgataagaag aacgtgtttc   23700
aacggctcac ctttcaatct aaaatctgaa cccttgttca cagcgcttga gaaattttca   23760
cgtgaaggat gtacaatcat ctccagctaa atgggcagtt cgtcagaatt gcggctgacc   23820
gcggatgacg aaaatgcgaa ccaagtattt caattttatg acaaaagttc tcaatcgttg   23880
ttacaagtga aacgcttcga ggttacagct actattgatt aaggagatcg cctatggtct   23940
cgccccggcg tcgtgcgtcc gccgcgagcc agatctcgcc tacttcataa acgtcctcat   24000
aggcacggaa tggaatgatg acatcgatcg ccgtagagag catgtcaatc agtgtgcgat   24060
cttccaagct agcaccttgg gcgctacttt tgacaaggga aaacagtttc ttgaatcctt   24120
ggattggatt cgcgccgtgt attgttgaaa tcgatcccgg atgtcccgag acgacttcac   24180
tcagataagc ccatgctgca tcgtcgcgca tctcgccaag caatatccgg tccggccgca   24240
tacgcagact tgcttggagc aagtgctcgg cgctcacagc acccagccca gcaccgttct   24300
tggagtagag tagtctaaca tgattatcgt gtggaatgac gagttcgagc gtatcttcta   24360
tggtgattag cctttcctgg gggggatgg cgctgatcaa ggtcttgctc attgttgtct   24420
tgccgcttcc ggtagggcca catagcaaca tcgtcagtcg gctgacgacg catgcgtgca   24480
gaaacgcttc caaatccccg ttgtcaaaat gctgaaggat agcttcatca tcctgatttt   24540
ggcgtttcct tcgtgtctgc cactggttcc acctcgaagc atcataacgg gaggagactt   24600
ctttaagacc agaaacacgc gagcttggcc gtcgaatggt caagctgacg gtgcccgagg   24660
gaacggtcgg cggcagacag atttgtagtc gttcaccacc aggaagttca gtggcgcaga   24720
gggggttacg tggtccgaca tcctgctttc tcagcgcgcc cgctaaaata gcgatatctt   24780
caagatcatc ataagagacg ggcaaaggca tcttggtaaa aatgccggct tggcgcacaa   24840
atgcctctcc aggtcgattg atcgcaattt cttcagtctt cgggtcatcg agccattcca   24900
aaatcggctt cagaagaaag cgtagttgcg gatccacttc catttacaat gtatcctatc   24960
tctaagcgga aatttgaatt cattaagagc ggcggttcct ccccgcgtg gcgccgccag   25020 tcaggcggag ctggtaaaca ccaaagaaat cgaggtcccg tgctacgaaa atggaaacgg   25080
tgtcaccctg attcttcttc agggttggcg gtatgttgat ggttgcctta agggctgtct   25140
cagttgtctg ctcaccgtta ttttgaaagc tgttgaagct catcccgcca cccgagctgc   25200
cggcgtaggt gctagctgcc tggaaggcgc cttgaacaac actcaagagc atagctccgc   25260
taaaacgctg ccagaagtgg ctgtcgaccg agcccggcaa tcctgagcga ccgagttcgt   25320
```

```
ccgcgcttgg cgatgttaac gagatcatcg catggtcagg tgtctcggcg cgatcccaca    25380
acacaaaaac gcgcccatct ccctgttgca agccacgctg tatttcgcca acaacggtgg    25440
tgccacgatc aagaagcacg atattgttcg ttgttccacg aatatcctga ggcaagacac    25500
actttacata gcctgccaaa tttgtgtcga ttgcggtttg caagatgcac ggaattattg    25560
tcccttgcgt taccataaaa tcggggtgcg gcaagagcgt ggcgctgctg ggctgcagct    25620
cggtgggttt catacgtatc gacaaatcgt tctcgccgga cacttcgcca ttcggcaagg    25680
agttgtcgtc acgcttgcct tcttgtcttc ggcccgtgtc ccctgaatg gcgcgtttgc     25740
tgaccccttg atcgccgctg ctatatgcaa aaatcggtgt ttcttccggc cgtggctcat    25800
gccgctccgg ttcgcccctc ggcggtagag gagcagcagg ctgaacagcc tcttgaaccg    25860
ctggaggatc cggcggcacc tcaatcgag ctggatgaaa tggcttggtg tttgttgcga    25920
tcaaagttga cggcgatgcg ttctcattca ccttcttttg gcgcccacct agccaaatga    25980
ggcttaatga taacgcgaga acgacacctc cgacgatcaa tttctgagac cccgaaagac    26040
gccggcgatg tttgtcggag accagggatc cagatgcatc aacctcatgt gccgcttgct    26100
gactatcgtt attcatccct tcgcccccctt caggacgcgt ttcacatcgg gcctcaccgt    26160
gcccgtttgc ggcttttggc caacgggatc gtaagcggtg ttccagatac atagtactgt    26220
gtggccatcc ctcagacgcc aacctcggga accgaagaa atctcgacat cgctcccttt    26280
aactgaatag ttggcaacag cttccttgcc atcaggatta atggtgtaga tggagggtat    26340
gcgtacattg cccggaaagt ggaataccgt cgtaaatcca ttgtcgaaga cttcgagtgg    26400
caacagcgaa cgatcgcctt gggcgacgta gtgccaatta ctgtccgccg caccaagggc    26460
tgtgacaggc tgatccaata aattctcagc tttccgttga tattgtgctt ccgcgtgtag    26520
tctgtccaca acagccttct gttgtgcctc ccttcgccga gccgccgcat cgtcggcggg    26580
gtaggcgaat tggacgctgt aatagagatc gggctgctct ttatcgaggt gggacagagt    26640
cttgaactt atactgaaaa cataacggcg catcccggag tcgcttgcgg ttagcacgat     26700
tactggctga ggcgtgagga cctggcttgc cttgaaaaat agataatttc cccgcggtag    26760
ggctgctaga tctttgctat ttgaaacggc aaccgctgtc accgtttcgt tcgtggcgaa    26820
tgttacgacc aaagtagctc caaccgccgt cgagaggcgc accacttgat cgggattgta    26880
agccaaataa cgcatgcgcg gatctagctt gcccgccatt ggagtgtctt cagcctccgc    26940
accagtcgca gcggcaaata acatgctaa atgaaaagt gcttttctga tcatggttcg     27000
ctgtggccta cgtttgaaac ggtatcttcc gatgtctgat aggaggtgac aaccagacct    27060
gccgggttgg ttagtctcaa tctgccgggc aagctggtca ccttttcgta gcgaactgtc    27120
gcggtccacg tactcaccac aggcattttg ccgtcaacga cgagggtcct tttatagcga    27180
atttgctgcg tgcttggagt tacatcattt gaagcgatgt gctcgacctc caccctgccg    27240
cgtttgccaa gaatgacttg aggcgaactg ggattgggat agttgaagaa ttgctggtaa    27300
tcctggcgca ctgttgggggc actgaagttc gataccaggt cgtaggcgta ctgagcggtg   27360
tcggcatcat aactctcgcg caggcgaacg tactcccaca atgaggcgtt aacgacggcc    27420
tcctcttgag ttgcaggcaa tcgcgagaca gacacctcgc tgtcaacggt gccgtccggc    27480
cgtatccata gatatacggg cacaagcctg ctcaacggca ccattgtggc tatagcgaac    27540
gcttgagcaa catttcccaa aatcgcgata gctgcgacag ctgcaatgag tttggagaga    27600
cgtcgcgccg atttcgctcg cgcggtttga aaggcttcta cttccttata gtgctcggca    27660
aggctttcgc gcgccactag catggcatat tcaggccccg tcatagcgtc caccccgaatt   27720
```

```
gccgagctga agatctgacg gagtaggctg ccatcgcccc acattcagcg ggaagatcgg   27780
gcctttgcag ctcgctaatg tgtcgtttgt ctggcagccg ctcaaagcga caactaggca   27840
cagcaggcaa tacttcatag aattctccat tgaggcgaat ttttgcgcga cctagcctcg   27900
ctcaacctga gcgaagcgac ggtacaagct gctggcagat tgggttgcgc cgctccagta   27960
actgcctcca atgttgccgg cgatcgccgg caaagcgaca atgagcgcat cccctgtcag   28020
aaaaaacata tcgagttcgt aaagaccaat gatcttggcc gcggtcgtac cggcgaaggt   28080
gattacacca agcataaggg tgagcgcagt cgcttcggtt aggatgacga tcgttgccac   28140
gaggtttaag aggagaagca agagaccgta ggtgataagt tgcccgatcc acttagctgc   28200
gatgtcccgc gtgcgatcaa aaatatatcc gacgaggatc agaggcccga tcgcgagaag   28260
cactttcgtg agaattccaa cggcgtcgta aactccgaag gcagaccaga gcgtgccgta   28320
aaggacccac tgtgcccctt ggaaagcaag gatgtcctgg tcgttcatcg gaccgatttc   28380
ggatgcgatt ttctgaaaaa cggcctgggt cacggcgaac attgtatcca actgtgccgg   28440
aacagtctgc agaggcaagc cggttacact aaactgctga acaaagtttg gaccgtctt    28500
ttcgaagatg gaaccacat agtcttggta gttagcctgc ccaacaatta gcaacaac      28560
gatggtgacc gtgatcaccc gagtgatacc gctacgggta tcgacttcgc cgcgtatgac   28620
taaaataccc tgaacaataa tccaaagagt gacacaggcg atcaatggcg cactcaccgc   28680
ctcctggata gtctcaagca tcgagtccaa gcctgtcgtg aaggctacat cgaagatcgt   28740
atgaatggcc gtaaacggcg ccggaatcgt gaaattcatc gattggacct gaacttgact   28800
ggtttgtcgc ataatgttgg ataaaatgag ctcgcattcg gcgaggatgc gggcggatga   28860
acaaatcgcc cagccttagg ggagggcacc aaagatgaca gcggtctttt gatgctcctt   28920
gcgttgagcg gccgcctctt ccgcctcgtg aaggccggcc tgcgcggtag tcatcgttaa   28980
taggcttgtc gcctgtacat tttgaatcat tgcgtcatgg atctgcttga gaagcaaacc   29040
attggtcacg gttgcctgca tgatattgcg agatcgggaa agctgagcag acgtatcagc   29100
attcgccgtc aagcgtttgt ccatcgtttc cagattgtca gccgcaatgc cagcgctgtt   29160
tgcggaaccg gtgatctgcg atcgcaacag gtccgcttca gcatcactac ccacgactgc   29220
acgatctgta tcgctggtga tcgcacgtgc cgtggtcgac attggcattc gcggcgaaaa   29280
catttcattg tctaggtcct tcgtcgaagg atactgattt ttctggttga gcaagtcag    29340
tagtccagta acgccgtagg ccgacgtcaa catcgtaacc atcgctatag tctgagtgag   29400
attctccgca gtcgcgagcg cagtcgcgag cgtctcagcc tccgttgccg ggtcgctaac   29460
aacaaactgc gcccgcgcgg gctgaatata tagaaagctg caggtcaaaa ctgttgcaat   29520
aagttgcgtc gtcttcatcg tttcctacct tatcaatctt ctgcctcgtg gtgacgggcc   29580
atgaattcgc tgagccagcc agatgagttg ccttcttgtg cctcgcgtag tcgagttgca   29640
aagcgcaccg tgttggcacg ccccgaaagc acgcgacat attcacgcat atcccgcaga   29700
tcaaattcgc agatgacgct tccactttct cgtttaagaa gaaacttacg gctgccgacc   29760
gtcatgtctt cacgatcgc ctgaaattcc ttttcggtac atttcagtcc atcgacataa   29820
gccgatcgat ctgcggttgg tgatggatag aaaatcttcg tcatacattg cgcaaccaag   29880
ctggctccta gcggcgattc cagaacatgc tctggttgct gcgttgccag tattagcatc   29940
ccgttgtttt ttcgaacggt caggaggaat ttgtcgacga cagtcgaaaa tttagggttt   30000
aacaaatagg cgcgaaactc atcgcagctc atcacaaaac ggcggccgtc gatcatggct   30060
```

```
ccaatccgat gcaggagata tgctgcagcg ggagcgcata cttcctcgta ttcgagaaga   30120
tgcgtcatgt cgaagccggt aatcgacgga tctaactttta cttcgtcaac ttcgccgtca   30180
aatgcccagc caagcgcatg gccccggcac cagcgttgga gccgcgctcc tgcgccttcg   30240
gcgggcccat gcaacaaaaa ttcacgtaac cccgcgattg aacgcatttg tggatcaaac   30300
gagagctgac gatggatacc acggaccaga cggcggttct cttccggaga atcccaccc   30360
cgaccatcac tctcgatgag agccacgatc cattcgcgca gaaaatcgtg tgaggctgct   30420
gtgttttcta ggccacgcaa cggcgccaac ccgctgggtg tgcctctgtg aagtgccaaa   30480
tatgttcctc ctgtggcgcg aaccagcaat tcgccacccc ggtccttgtc aaagaacacg   30540
accgtacctg cacggtcgac catgctctgt tcgagcatgg ctagaacaaa catcatgagc   30600
gtcgtcttac ccctcccgat aggcccgaat attgccgtca tgccaacatc gtgctcatgc   30660
gggatatagt cgaaaggcgt tccgccattg gtacgaaatc gggcaatcgc gttgccccag   30720
tggcctgagc tggcgccctc tggaaagttt tcgaaagaga caaaccctgc gaaattgcgt   30780
gaagtgattg cgccagggcg tgtgcgccac ttaaaattcc ccggcaattg ggaccaatag   30840
gccgcttcca taccaatacc ttcttggaca accacggcac ctgcatccgc cattcgtgtc   30900
cgagcccgcg cgcccctgtc cccaagacta ttgagatcgt ctgcatagac gcaaaggctc   30960
aaatgatgtg agcccataac gaattcgttg ctcgcaagtg cgtcctcagc ctcggataat   31020
ttgccgattt gagtcacggc tttatcgccg gaactcagca tctggctcga tttgaggcta   31080
agtttcgcgt gcgcttgcgg gcgagtcagg aacgaaaaac tctgcgtgag aacaagtgga   31140
aaatcgaggg atagcagcgc gttgagcatg cccggccgtg tttttgcagg gtattcgcga   31200
aacgaataga tggatccaac gtaactgtct tttggcgttc tgatctcgag tcctcgcttg   31260
ccgcaaatga ctctgtcggt ataaatcgaa gcgccgagtg agccgctgac gaccggaacc   31320
ggtgtgaacc gaccagtcat gatcaaccgt agcgcttcgc caatttcggt gaagagcaca   31380
ccctgcttct cgcggatgcc aagacgatgc aggccatacg cttttaagaga gccagcgaca   31440
acatgccaaa gatcttccat gttcctgatc tggcccgtga gatcgttttc ccttttttccg   31500
cttagcttgg tgaacctcct ctttaccttc cctaaagccg cctgtgggta gacaatcaac   31560
gtaaggaagt gttcattgcg gaggagttgg ccggagagca cgcgctgttc aaaagcttcg   31620
ttcaggctag cggcgaaaac actacggaag tgtcgcggcg ccgatgatgg cacgtcggca   31680
tgacgtacga ggtgagcata tattgacaca tgatcatcag cgatattgcg caacagcgtg   31740
ttgaacgcac gacaacgcgc attgcgcatt tcagtttcct caagctcgaa tgcaacgcca   31800
tcaattctcg caatggtcat gatcgatccg tcttcaagaa ggacgatatg gtcgctgagg   31860
tggccaatat aagggagata gatctcaccg gatctttcgg tcgttccact cgcgccgagc   31920
atcacaccat tcctctccct cgtggggaa ccctaattgg atttgggcta acagtagcgc   31980
ccccccaaac tgcactatca atgcttcttc ccgcggtccg caaaaatagc aggacgacgc   32040
tcgccgcatt gtagtctcgc tccacgatga gccgggctgc aaaccataac ggcacgagaa   32100
cgacttcgta gagcgggttc tgaacgataa cgatgacaaa gccggcgaac atcatgaata   32160
accctgccaa tgtcagtggc accccaagaa acaatgcggg ccgtgtggct gcgaggtaaa   32220
gggtcgattc ttccaaacga tcagccatca actaccgcca gtgagcgttt ggccgaggaa   32280
gctcgcccca aacatgataa caatgccgcc gacgacgccg gcaaccagcc caagcgaagc   32340
ccgcccgaac atccaggaga tcccgatagc gacaatgccg agaacagcga gtgactggcc   32400
gaacggacca aggataaacg tgcatatatt gttaaccatt gtggcggggt cagtgccgcc   32460
```

```
acccgcagat tgcgctgcgg cgggtccgga tgaggaaatg ctccatgcaa ttgcaccgca    32520
caagcttggg gcgcagctcg atatcacgcg catcatcgca ttcgagagcg agaggcgatt    32580
tagatgtaaa cggtatctct caaagcatcg catcaatgcg cacctcctta gtataagtcg    32640
aataagactt gattgtcgtc tgcggatttg ccgttgtcct ggtgtggcgg tggcggagcg    32700
attaaaccgc cagcgccatc ctcctgcgag cggcgctgat atgaccccca aacatcccac    32760
gtctcttcgg atttttagcgc ctcgtgatcg tcttttggag gctcgattaa cgcgggcacc    32820
agcgattgag cagctgtttc aacttttcgc acgtagccgt ttgcaaaacc gccgatgaaa    32880
ttaccggtgt tgtaagcgga gatcgcccga cgaagcgcaa attgcttctc gtcaatcgtt    32940
tcgccgcctg cataacgact tttcagcatg tttgcagcgg cagataatga tgtgcacgcc    33000
tggagcgcac cgtcaggtgt cagaccgagc atagaaaaat ttcgagagtt tatttgcatg    33060
aggccaacat ccagcgaatg ccgtgcatcg agacggtgcc tgacgacttg ggttgcttgg    33120
ctgtgatctt gccagtgaag cgtttcgccg gtcgtgttgt catgaatcgc taaaggatca    33180
aagcgactct ccaccttagc tatcgccgca agcgtagatg tcgcaactga tggggcacac    33240
ttgcgagcaa catggtcaaa ctcagcagat gagagtggcg tggcaaggct cgacgaacag    33300
aaggagacca tcaaggcaag agaaagcgac cccgatctct taagcatacc ttatctcctt    33360
agctcgcaac taacaccgcc tctcccgttg gaagaagtgc gttgttttat gttgaagatt    33420
atcgggaggg tcggttactc gaaaattttc aattgcttct ttatgatttc aattgaagcg    33480
agaaacctcg cccggcgtct tggaacgcaa catggaccga gaaccgcgca tccatgacta    33540
agcaaccgga tcgacctatt caggccgcag ttggtcaggt caggctcaga acgaaaatgc    33600
tcggcgaggt tacgctgtct gtaaacccat tcgatgaacg ggaagcttcc ttccgattgc    33660
tcttggcagg aatattggcc catgcctgct tgcgctttgc aaatgctctt atcgcgttgg    33720
tatcatatgc cttgtccgcc agcagaaacg cactctaagc gattatttgt aaaaatgttt    33780
cggtcatgcg gcggtcatgg gcttgacccg ctgtcagcgc aagacggatc ggtcaaccgt    33840
cggcatcgac aacagcgtga atcttggtgg tcaaaccgcc acgggaacgt cccatacagc    33900
catcgtcttg atcccgctgt ttcccgtcgc cgcatgttgg tggacgcgga cacaggaact    33960
gtcaatcatg acgacattct atcgaaagcc ttggaaatca cactcagaat atgatcccag    34020
acgtctgcct cacgccatcg tacaaagcga ttgtagcagg ttgtacagga accgtatcga    34080
tcaggaacgt ctgcccaggg cgggcccgtc cggaagcgcc acaagatgac attgatcacc    34140
cgcgtcaacg cgcggcacgc gacgcggctt atttgggaac aaaggactga acaacagtcc    34200
attcgaaatc ggtgacatca aagcggggac gggttatcag tggcctccaa gtcaagcctc    34260
aatgaatcaa aatcagaccg atttgcaaac ctgatttatg agtgtgcggc ctaaatgatg    34320
aaatcgtcct tctagatcgc ctccgtggtg tagcaacacc tcgcagtatc gccgtgctga    34380
ccttggccag ggaattgact ggcaagggtg cttttcacatg accgctcttt tggccgcgat    34440
agatgatttc gttgctgctt tgggcacgta gaaggagaga agtcatatcg gagaaattcc    34500
tcctggcgcg agagcctgct ctatcgcgac ggcatcccac tgtcgggaac agaccggatc    34560
attcacgagg cgaaagtcgt caacacatgc gttataggca tcttcccttg aaggatgatc    34620
ttgttgctgc caatctggag gtgcggcagc cgcaggcaga tgcgatctca gcgcaacttg    34680
cggcaaaaca tctcactcac ctgaaaacca ctagcgagtc tcgcgatcag acgaaggcct    34740
tttacttaac gacacaatat ccgatgtctg catcacaggc gtcgctatcc cagtcaatac    34800
```

```
taaagcggtg caggaactaa agattactga tgacttaggc gtgccacgag gcctgagacg   34860
acgcgcgtag acagttttt gaaatcatta tcaaagtgat ggcctccgct gaagcctatc   34920
acctctgcgc cggtctgtcg gagagatggg caagcattat tacggtcttc gcgcccgtac  34980
atgcattgga cgattgcagg gtcaatggat ctgagatcat ccagaggatt gccgccctta  35040
ccttccgttt cgagttggag ccagcccta aatgagacga catagtcgac ttgatgtgac   35100
aatgccaaga gagagatttg cttaacccga ttttttgct caagcgtaag cctattgaag   35160
cttgccggca tgacgtccgc gccgaaagaa tatcctacaa gtaaacatt ctgcacaccg    35220 aaatgcttgg tgtagacatc gattatgtga ccaagatcct tagcagttc gcttggggac    35280 cgctccgacc agaaataccg aagtgaactg acgccaatga caggaatccc ttccgtctgc   35340
agataggtac catcgataga tctgctgcct cgcgcgtttc ggtgatgacg gtgaaaacct   35400
ctgacacatg cagctcccgg agacggtcac agcttgtctg taagcggatg ccgggagcag   35460
acaagcccgt cagggcgcgt cagcgggtgt tggcgggtgt cggggcgcag ccatgaccca   35520
gtcacgtagc gatagcggag tgtatactgg cttaactatg cggcatcaga gcagattgta   35580
ctgagagtgc accatatgcg gtgtgaaata ccgcacagat gcgtaaggag aaaataccgc   35640
atcaggcgct cttccgcttc ctcgctcact gactcgctgc gctcggtcgt tcggctgcgg   35700
cgagcggtat cagctcactc aaaggcggta atacggttat ccacagaatc aggggataac   35760
gcaggaaaga acatgtgagc aaaaggccag caaaaggcca ggaaccgtaa aaaggccgcg   35820
ttgctggcgt ttttccatag gctccgcccc cctgacgagc atcacaaaaa tcgacgctca   35880
agtcagaggt ggcgaaaccc gacaggacta taaagatacc aggcgtttcc ccctggaagc   35940
tccctcgtgc gctctcctgt tccgaccctg ccgcttaccg gatacctgtc gcctttctc   36000 ccttcgggaa gcgtggcgct ttctcatagc tcacgctgta ggtatctcag ttcggtgtag   36060
gtcgttcgct ccaagctggg ctgtgtgcac gaaccccccg ttcagcccga ccgctgcgcc   36120
ttatccggta actatcgtct tgagtccaac ccggtaagac acgacttatc gccactggca   36180
gcagccactg gtaacaggat tagcagagcg aggtatgtag gcggtgctac agagttcttg   36240
aagtggtggc ctaactacgg ctacactaga aggacagtat ttggtatctg cgctctgctg   36300
aagccagtta ccttcggaaa aagagttggt agctcttgat ccggcaaaca aaccaccgct   36360
ggtagcggtg gtttttttgt ttgcaagcag cagattacgc gcagaaaaaa aggatctcaa   36420
gaagatcctt tgatcttttc tacggggtct gacgctcagt ggaacgaaaa ctcacgttaa   36480
gggattttgg tcatgagatt atcaaaaagg atcttcacct agatcctttt aaattaaaaa   36540
tgaagtttta aatcaatcta agtatatat gagtaaactt ggtctgacag ttaccaatgc   36600
ttaatcagtg aggcacctat ctcagcgatc tgtctatttc gttcatccat agttgcctga   36660
ctccccgtcg tgtagataac tacgatacgg gagggcttac catctggccc cagtgctgca   36720
atgataccgc gagacccacg ctcaccggct ccagatttat cagcaataaa ccagccagcc   36780
ggaagggccg agcgcagaag tggtcctgca actttatccg cctccatcca gtctattaat   36840
tgttgccggg aagctagagt aagtagttcg ccagttaata gtttgcgcaa cgttgttgcc   36900
attgctgcag ggggggggg ggggggggac ttccattgtt cattccacgg acaaaaacag   36960
agaaaggaaa cgacagaggc caaaaagcct cgctttcagc acctgtcgtt cctttctttt   37020
tcagagggta ttttaaataa aaacattaag ttatgacgaa gaagaacgga aacgccttaa   37080
accggaaaat tttcataaat agcgaaaacc cgcgaggtcg ccgccccgta acctgtcgga   37140
tcaccggaaa ggacccgtaa agtgataatg attatcatct acatatcaca acgtgcgtgg   37200
```

```
aggccatcaa accacgtcaa ataatcaatt atgacgcagg tatcgtatta attgatctgc   37260
atcaacttaa cgtaaaaaca acttcagaca atacaaatca gcgacactga atacggggca   37320
acctcatgtc ccccccccccc ccccccctgc aggcatcgtg gtgtcacgct cgtcgtttgg   37380
tatggcttca ttcagctccg gttcccaacg atcaaggcga gttacatgat cccccatgtt   37440
gtgcaaaaaa gcggttagct ccttcggtcc tccgatcgtt gtcagaagta agttggccgc   37500
agtgttatca ctcatggtta tggcagcact gcataattct cttactgtca tgccatccgt   37560
aagatgcttt tctgtgactg gtgagtactc aaccaagtca ttctgagaat agtgtatgcg   37620
gcgaccgagt tgctcttgcc cggcgtcaac acgggataat accgcgccac atagcagaac   37680
tttaaaagtg ctcatcattg gaaaacgttc ttcggggcga aaactctcaa ggatcttacc   37740
gctgttgaga tccagttcga tgtaacccac tcgtgcaccc aactgatctt cagcatcttt   37800
tactttcacc agcgtttctg ggtgagcaaa aacaggaagg caaaatgccg caaaaaaggg   37860
aataagggcg acacggaaat gttgaatact catactcttc cttttttcaat attattgaag   37920 catttatcag ggttattgtc tcatgagcgg atacatattt gaatgtattt agaaaaataa   37980
acaaataggg gttccgcgca catttccccg aaaagtgcca cctgacgtct aagaaaccat   38040
tattatcatg acattaacct ataaaaatag gcgtatcacg aggccctttc gtcttcaaga   38100
attggtcgac gatcttgctg cgttcggata ttttcgtgga gttcccgcca cagacccgga   38160
ttgaaggcga gatccagcaa ctcgcgccag atcatcctgt gacggaactt tggcgcgtga   38220
tgactggcca ggacgtcggc cgaaagagcg acaagcagat cacgcttttc gacagcgtcg   38280
gatttgcgat cgaggatttt tcggcgctgc gctacgtccg cgaccgcgtt gagggatcaa   38340
gccacagcag cccactcgac cttctagccg acccagacga gccaagggat cttttttggaa   38400 tgctgctccg tcgtcaggct ttccgacgtt tgggtggttg aacagaagtc attatcgtac   38460
ggaatgccaa gcactcccga ggggaacccct gtggttggca tgcacataca aatgacgaa   38520 cggataaacc ttttcacgcc cttttaaata tccgttattc taataaacgc tcttttctct   38580
taggtttacc cgccaatata tcctgtcaaa cactgatagt ttaaactgaa ggcgggaaac   38640
gacaatctga tcatgagcgg agaattaagg gagtcacgtt atgaccccccg ccgatgacgc   38700 gggacaagcc gttttacgtt tggaactgac agaaccgcaa cgttgaagga gccactcagc   38760
aagctggtac gattgtaata cgactcacta tagggcgaat tgagcgctgt ttaaacgctc   38820
ttcaactgga agagcggtta cccggaccga agcttgaagt tcctattccg aagttcctat   38880
tctctagaaa gtataggaac ttcagatctc gatgctcacc ctgttgtttg gtgttacttc   38940
tgcaggtcga ctctagagga tccaccatga gcccagaacg acgcccggcc gacatccgcc   39000
gtgccaccga ggcggacatg ccggcggtct gcaccatcgt caaccactac atcgagacaa   39060
gcacggtcaa cttccgtacc gagccgcagg aaccgcagga ctggacggac gacctcgtcc   39120
gtctgcggga gcgctatccc tggctcgtcg ccgaggtgga cggcgaggtc gccggcatcg   39180
cctacgcggg cccctggaag gcacgcaacg cctacgactg gacggccgag tcgaccgtgt   39240
acgtctcccc ccgccaccag cggacgggac tgggctccac gctctacacc cacctgctga   39300
agtccctgga ggcacagggc ttcaagagcg tggtcgctgt catcgggctg cccaacgacc   39360
cgagcgtgcg catgcacgag gcgctcggat atgccccccg cggcatgctg cgggcggccg   39420
gcttcaagca cgggaactgg catgacgtgg gtttctggca gctggacttc agcctgccgg   39480
taccgccccg tccggtcctg cccgtcaccg agatctgatc cgtcgaccaa cctagacttg   39540
```

```
tccatcttct ggattggcca acttaattaa tgtatgaaat aaaaggatgc acacatagtg    39600
acatgctaat cactataatg tgggcatcaa agttgtgtgt tatgtgtaat tactagttat    39660
ctgaataaaa gagaaagaga tcatccatat ttcttatcct aaatgaatgt cacgtgtctt    39720
tataattctt tgatgaacca gatgcatttc attaaccaaa tccatataca tataaatatt    39780
aatcatatat aattaatatc aattgggtta gcaaaacaaa tctagtctag gtgtgttttg    39840
cgaattgcgg ccgcgatctg ggaattccc atggacaccg gtaattccca tgatcttctc    39900
tccttcatca atggatgcca tgtttcataa caataacacc aaatgtttga tgagctacca    39960
acaattgcgc aaagactatg gctaagctcg agctcgctcg ctacaagttg ttgactttca    40020
aatacaagtt tgttttggga acaccaaata ttctacatga tctttcacta agttgcgcac    40080
cactatcaaa agattatcta ggccattatt caagtaaaga gtgaacacgt ctaagaccca    40140
caaccacacc aaatagaata cgcatacatg caacatattg tgcaagaagt atccaactgg    40200
actcccatgt attctaaaac tattttcgta gagttaaagt tatgacaaac ttatcaaata    40260
aaaatttgaa cgctggacca aaactttcat ctttcaaatc caccatcgtc tatcctcata    40320
aattgttttg attataacac atctacgtaa atcatttgtt ttgaacaata ctaatttaat    40380
tttattaagt caaataaccct gcttagaaaa taatccctcc acctcattta acaatttctt    40440
gtcaaacaca caccaagaaa aaattaatg aaagagaaaa gaaatgaaaa ggacatggag    40500
ttgaatacta gcaaaattga ttgaaggaag attcacaatt gaaattgaaa ccatttaatt    40560
tattttcggg tccataataa taaattggta agaataaaaa cccgatcaag tccggtacag    40620
tacaattcca ctccaccaac tccttactta aaccctatt tatacccact ctcatcctca    40680
ctcttccttc acctctcaca ctctcttctc tctctcaaaa ccctcacaca aacgctgcgt    40740
ttagtgtaag aaattcaatc cggcgccttg gcgcgccgat catccacaag tttgtacaaa    40800
aaagctgaac gagaaacgta aatgatata aatatcaata tattaaatta gattttgcat    40860
aaaaaacaga ctacataata ctgtaaaaca caacatatcc agtcactatg gcggccgcat    40920
taggcacccc aggctttaca ctttatgctt ccggctcgta atgtgtgg attttgagtt    40980 aggatttaaa tacgcgttga tccggcttac taaaagccag ataacagtat gcgtatttgc    41040
gcgctgattt ttgcggtata agaatatata ctgatatgta tacccgaagt atgtcaaaaa    41100
gaggtatgct atgaagcagc gtattacagt gacagttgac agcgacagct atcagttgct    41160
caaggcatat atgatgtcaa tatctccggt ctggtaagca caaccatgca gaatgaagcc    41220
cgtcgtctgc gtgccgaacg ctggaaagcg gaaaatcagg aagggatggc tgaggtcgcc    41280
cggtttattg aaatgaacgg ctcttttgct gacgagaaca ggggctggtg aaatgcagtt    41340
taaggtttac acctataaaa gagagagccg ttatcgtctg tttgtggatg tacagagtga    41400
tatcattgac acgcccggtc gacggatggt gatccccctg gccagtgcac gtctgctgtc    41460
agataaagtc tcccgtgaac tttacccggt ggtgcatatc ggggatgaaa gctggcgcat    41520
gatgaccacc gatatggcca gtgtgccggt ctccgttatc ggggaagaag tggctgatct    41580
cagccaccgc gaaaatgaca tcaaaaacgc cattaacctg atgttctggg aatataaat    41640 gtcaggctcc cttatacaca gccagtctgc aggtcgacca tagtgactgg atatgttgtg    41700
ttttacagta ttatgtagtc tgtttttta t gcaaatcta atttaatata ttgatattta    41760 tatcattttta cgtttctcgt tcagctttct tgtacaaagt ggtgttaacc tagacttgtc    41820
catcttctgg attggccaac ttaattaatg tatgaaataa aaggatgcac acatagtgac    41880
atgctaatca ctataatgtg ggcatcaaag ttgtgtgtta tgtgtaatta ctagttatct    41940
```

-continued

```
gaataaaaga gaaagagatc atccatattt cttatcctaa atgaatgtca cgtgtcttta   42000
taattctttg atgaaccaga tgcatttcat taaccaaatc catatacata taaatattaa   42060
tcatatataa ttaatatcaa ttgggttagc aaaacaaatc tagtctaggt gtgttttgcg   42120
aattgcggcc gccaccgcgg tggagctcga attccggtcc gggtcacctt tgtccaccaa   42180
gatggaactg cggccgctca ttaattaagt caggcgcgcc tctagttgaa gacacgttca   42240
tgtcttcatc gtaagaagac actcagtagt cttcggccag aatggccatc tggattcagc   42300
aggcctagaa ggccatttaa atcctgagga tctggtcttc ctaaggaccc gggatatcgg   42360
accgattaaa ctttaattcg gtccgaagct tgaagttcct attccgaagt tcctattctc   42420
cagaaagtat aggaacttcg catgcctgca gtgcagcgtg acccggtcgt gcccctctct   42480
agagataatg agcattgcat gtctaagtta taaaaaatta ccacatattt ttttttgtcac   42540 acttgtttga agtgcagttt atctatcttt atacatatat ttaaacttta ctctacgaat   42600
aatataatct atagtactac aataatatca gtgttttaga gaatcatata aatgaacagt   42660
tagacatggt ctaaaggaca attgagtatt ttgacaacag gactctacag ttttatcttt   42720
ttagtgtgca tgtgttctcc ttttttttttg caaatagctt cacctatata atacttcatc   42780
cattttatta gtacatccat ttagggttta gggttaatgg ttttttataga ctaattttttt   42840 tagtacatct attttattct attttagcct ctaaattaag aaaactaaaa ctctatttta   42900 gttttttttat ttaataattt agatataaaa tagaataaaa taaagtgact aaaaattaaa   42960 caaatacccct ttaagaaatt aaaaaaacta aggaaacatt tttcttgttt cgagtagata   43020
atgccagcct gttaaacgcc gtcgacgagt ctaacggaca ccaaccagcg aaccagcagc   43080
gtcgcgtcgg gccaagcgaa gcagacggca cggcatctct gtcgctgcct ctggaccccct   43140 ctcgagagtt ccgctccacc gttggacttg ctccgctgtc ggcatccaga aattgcgtgg   43200
cggagcggca gacgtgagcc ggcacggcag gcggcctcct cctcctctca cggcaccggc   43260
agctacgggg gattcctttc ccaccgctcc ttcgctttcc cttcctcgcc cgccgtaata   43320
aatagacacc ccctccacac cctctttccc caacctcgtg ttgttcggag cgcacacaca   43380
cacaaccaga tctcccccaa atccacccgt cggcacctcc gcttcaaggt acgccgctcg   43440
tcctcccccc ccccctctc taccttctct agatcggcgt tccggtccat gcatggttag   43500
ggcccggtag ttctacttct gttcatgttt gtgttagatc cgtgtttgtg ttagatccgt   43560
gctgctagcg ttcgtacacg gatgcgacct gtacgtcaga cacgttctga ttgctaactt   43620
gccagtgttt ctctttgggg aatcctggga tggctctagc cgttccgcag acgggatcga   43680
tttcatgatt ttttttgttt cgttgcatag ggtttggttt gcccttttcc tttatttcaa   43740
tatatgccgt gcacttgttt gtcgggtcat cttttcatgc ttttttttgt cttggttgtg   43800
atgatgtggt ctggttgggc ggtcgttcta gatcggagta gaattctgtt tcaaactacc   43860
tggtggattt attaattttg gatctgtatg tgtgtgccat acatattcat agttacgaat   43920
tgaagatgat ggatggaaat atcgatctag gataggtata catgttgatg cgggtttttac   43980 tgatgcatat acagagatgc ttttttgttcg cttggttgtg atgatgtggt gtggttgggc   44040
ggtcgttcat tcgttctaga tcggagtaga atactgtttc aaactacctg gtgtatttat   44100
taattttgga actgtatgtg tgtgtcatac atcttcatag ttacgagttt aagatggatg   44160
gaaatatcga tctaggatag gtatacatgt tgatgtgggt tttactgatg catatacatg   44220
atggcatatg cagcatctat tcatatgctc taaccttgag tacctatcta ttataataaa   44280
```

| | |
|---|---|
| caagtatgtt ttataattat tttgatcttg atatacttgg atgatggcat atgcagcagc | 44340 |
| tatatgtgga ttttttagc cctgccttca tacgctattt atttgcttgg tactgtttct | 44400 |
| tttgtcgatg ctcaccctgt tgtttggtgt tacttctgca ggtcgacttt aacttagcct | 44460 |
| aggatccaca cgacaccatg atagaggtga aaccgattaa cgcagaggat acctatgaac | 44520 |
| taaggcatag aatactcaga ccaaaccagc cgatagaagc gtgtatgttt gaaagcgatt | 44580 |
| tacttcgtgg tgcatttcac ttaggcggct attacgggg caaactgatt tccatagctt | 44640 |
| cattccacca ggccgagcac tcagaactcc aaggccagaa acagtaccag ctccgaggta | 44700 |
| tggctacctt ggaaggttat cgtgagcaga aggcgggatc gagtctaatt aaacacgctg | 44760 |
| aagaaattct tcgtaagagg ggggcggact tgctttggtg taatgcgcgg acatccgcct | 44820 |
| caggctacta caaaaagtta ggcttcagcg agcaggaga ggtattcgac acgccgccag | 44880 |
| taggacctca catcctgatg tataaaagga tcacataact agctagtcag ttaacctaga | 44940 |
| cttgtccatc ttctggattg gccaacttaa ttaatgtatg aaataaaagg atgcacacat | 45000 |
| agtgacatgc taatcactat aatgtgggca tcaaagttgt gtgttatgtg taattactag | 45060 |
| ttatctgaat aaaagagaaa gagatcatcc atatttctta tcctaaatga atgtcacgtg | 45120 |
| tctttataat tctttgatga accagatgca tttcattaac caaatccata tacatataaa | 45180 |
| tattaatcat atataattaa tatcaattgg gttagcaaaa caaatctagt ctaggtgtgt | 45240 |
| tttgcgaatt cagagctcga attcattccg attaatcgtg gcctcttgct cttcaggatg | 45300 |
| aagagctatg tttaaacgtg caagcgctac tagacaattc agtacattaa aaacgtccgc | 45360 |
| aatgtgttat taagttgtct aagcgtcaat ttgtttacac cacaatatat cctgccacca | 45420 |
| gccagccaac agctccccga ccggcagctc ggcacaaaat caccactcga tacaggcagc | 45480 |
| ccatcagtcc gggacggcgt cagcgggaga gccgttgtaa ggcggcagac tttgctcatg | 45540 |
| ttaccgatgc tattcggaag aacggcaact aagctgccgg gtttgaaaca cggatgatct | 45600 |
| cgcggagggt agcatgttga ttgtaacgat gacagagcgt tgctgcctgt gatcaaatat | 45660 |
| catctccctc gcagagatcc gaattatcag ccttcttatt catttctcgc ttaaccgtga | 45720 |
| caggctgtcg atcttgagaa ctatgccgac ataataggaa atcgctggat aaagccgctg | 45780 |
| aggaagctga gtggcgctat ttctttagaa gtgaacgttg acgatcgtcg accgtacccc | 45840 |
| gatgaattaa ttcggacgta cgttctgaac acagctggat acttacttgg gcgattgtca | 45900 |
| tacatgacat caacaatgta cccgtttgtg taaccgtctc ttggaggttc gtatgacact | 45960 |
| agtggttccc ctcagcttgc gactagatgt tgaggcctaa cattttatta gagagcaggc | 46020 |
| tagttgctta gatacatgat cttcaggccg ttatctgtca gggcaagcga aaattggcca | 46080 |
| tttatgacga ccaatgcccc gcagaagctc ccatctttgc cgccatagac gccgcgcccc | 46140 |
| ccttttgggg tgtagaacat ccttttgcca gatgtggaaa agaagttcgt tgtcccattg | 46200 |
| ttggcaatga cgtagtagcc ggcgaaagtg cgagacccat ttgcgctata tataagccta | 46260 |
| cgatttccgt tgcgactatt gtcgtaattg gatgaactat tatcgtagtt gctctcagag | 46320 |
| ttgtcgtaat ttgatggact attgtcgtaa ttgcttatgg agttgtcgta gttgcttgga | 46380 |
| gaaatgtcgt agtggatgg ggagtagtca tagggaagac gagcttcatc cactaaaaca | 46440 |
| attggcaggt cagcaagtgc ctgccccgat gccatcgcaa gtacgaggct tagaaccacc | 46500 |
| ttcaacagat cgcgcatagt cttccccagc tctctaacgc ttgagttaag ccgcgccgcg | 46560 |
| aagcggcgtc ggcttgaacg aattgttaga cattatttgc cgactacctt ggtgatctcg | 46620 |
| cctttcacgt agtgaacaaa ttcttccaac tgatctgcgc gcgaggccaa gcgatcttct | 46680 |

```
tgtccaagat aagcctgcct agcttcaagt atgacgggct gatactgggc cggcaggcgc   46740
tccattgccc agtcggcagc gacatccttc ggcgcgattt tgccggttac tgcgctgtac   46800
caaatgcggg acaacgtaag cactacattt cgctcatcgc cagcccagtc gggcggcgag   46860
ttccatagcg ttaaggtttc atttagcgcc tcaaatagat cctgttcagg aaccggatca   46920
aagagttcct ccgccgctgg acctaccaag gcaacgctat gttctcttgc ttttgtcagc   46980
aagatagcca gatcaatgtc gatcgtggct ggctcgaaga tacctgcaag aatgtcattg   47040
cgctgccatt ctccaaattg cagttcgcgc ttagctggat aacgccacgg aatgatgtcg   47100
tcgtgcacaa caatggtgac ttctacacgc ggagaatct cgctctctcc aggggaagcc    47160
gaagtttcca aaggtcgtt gatcaaagct cgccgcgttg tttcatcaag ccttacagtc    47220
accgtaacca gcaaatcaat atcactgtgt ggcttcaggc cgccatccac tgcggagccg   47280
tacaaatgta cggccagcaa cgtcggttcg agatggcgct cgatgacgcc aactacctct   47340
gatagttgag tcgatacttc ggcgatcacc gcttccctca tgatgtttaa ctcctgaatt   47400
aagccgcgcc gcgaagcggt gtcggcttga atgaattgtt aggcgtcatc ctgtgctccc   47460
gagaaccagt accagtacat cgctgtttcg ttcgagactt gaggtctagt tttatacgtg   47520
aacaggtcaa tgccgccgag agtaaagcca cattttgcgt acaaattgca ggcaggtaca   47580
ttgttcgttt gtgtctctaa tcgtatgcca aggagctgtc tgcttagtgc ccactttttc   47640
gcaaattcga tgagactgtg cgcgactcct ttgcctcggt gcgtgtgcga cacaacaatg   47700
tgttcgatag aggctagatc gttccatgtt gagttgagtt caatcttccc gacaagctct   47760
tggtcgatga atgcgccata gcaagcagag tcttcatcag agtcatcatc cgagatgtaa   47820
tccttccggt aggggctcac acttctggta gatagttcaa agccttggtc ggataggtgc   47880
acatcgaaca cttcacgaac aatgaaatgg ttctcagcat ccaatgtttc cgccacctgc   47940
tcagggatca ccgaaatctt catatgacgc ctaacgcctg gcacagcgga tcgcaaacct   48000
ggcgcggctt ttggcacaaa aggcgtgaca ggtttgcgaa tccgttgctg ccacttgtta   48060
acccttttgc cagatttggt aactataatt tatgttagag gcgaagtctt gggtaaaaac   48120
tggcctaaaa ttgctgggga tttcaggaaa gtaaacatca ccttccggct cgatgtctat   48180
tgtagatata tgtagtgtat ctacttgatc gggggatctg ctgcctcgcg cgtttcggtg   48240
atgacggtga aaacctctga cacatgcagc tcccggagac ggtcacagct tgtctgtaag   48300
cggatgccgg gagcagacaa gcccgtcagg gcgcgtcagc gggtgttggc gggtgtcggg   48360
gcgcagccat gacccagtca cgtagcgata gcggagtgta tactggctta actatgcggc   48420
atcagagcag attgtactga gagtgcacca tatgcggtgt gaaataccgc acagatgcgt   48480
aaggagaaaa taccgcatca ggcgctcttc cgcttcctcg ctcactgact cgctgcgctc   48540
ggtcgttcgg ctgcggcgag cggtatcagc tcactcaaag gcggtaatac ggttatccac   48600
agaatcaggg gataacgcag gaaagaacat gtgagcaaaa ggccagcaaa aggccaggaa   48660
ccgtaaaaag gccgcgttgc tggcgttttt ccataggctc cgcccccctg acgagcatca   48720
caaaaatcga cgctcaagtc agaggtggcg aaacccgaca ggactataaa gataccaggc   48780
gtttccccct ggaagctccc tcgtgcgctc tcctgttccg accctgccgc ttaccggata   48840
cctgtccgcc tttctccctt cgggaagcgt ggcgctttct catagctcac gctgtaggta   48900
tctcagttcg gtgtaggtcg ttcgctccaa gctgggctgt gtgcacgaac cccccgttca   48960
gcccgaccgc tgcgccttat ccggtaacta tcgtcttgag tccaacccgg taagacacga   49020
```

| | | | | | |
|---|---|---|---|---|---|
| cttatcgcca | ctggcagcag | ccactggtaa | caggattagc | agagcgaggt | atgtaggcgg | 49080 |
| tgctacagag | ttcttgaagt | ggtggcctaa | ctacggctac | actagaagga | cagtatttgg | 49140 |
| tatctgcgct | ctgctgaagc | cagttacctt | cggaaaaaga | gttggtagct | cttgatccgg | 49200 |
| caaacaaacc | accgctggta | gcggtggttt | ttttgtttgc | aagcagcaga | ttacgcgcag | 49260 |
| aaaaaaagga | tctcaagaag | atcctttgat | cttttctacg | gggtctgacg | ctcagtggaa | 49320 |
| cgaaaactca | cgttaaggga | ttttggtcat | gagattatca | aaaaggatct | tcacctagat | 49380 |
| ccttttaaat | taaaaatgaa | gttttaaatc | aatctaaagt | atatatgagt | aaacttggtc | 49440 |
| tgacagttac | caatgcttaa | tcagtgaggc | acctatctca | gcgatctgtc | tatttcgttc | 49500 |
| atccatagtt | gcctgactcc | ccgtcgtgta | gataactacg | atacgggagg | gcttaccatc | 49560 |
| tggccccagt | gctgcaatga | taccgcgaga | cccacgctca | ccggctccag | atttatcagc | 49620 |
| aataaaccag | ccagccggaa | gggccgagcg | cagaagtggt | cctgcaactt | tatccgcctc | 49680 |
| catccagtct | attaattgtt | gccgggaagc | tagagtaagt | agttcgccag | ttaatagttt | 49740 |
| gcgcaacgtt | gttgccattg | ctgca | | | | 49765 |

<210> SEQ ID NO 14
<211> LENGTH: 4222
<212> TYPE: DNA
<213> ORGANISM: Zea Mays

<400> SEQUENCE: 14

| | | | | | |
|---|---|---|---|---|---|
| ggcaccaacc | aagagaaaag | tagcaactca | cacacagtag | gagaggagag | gaaagaaccc | 60 |
| agcgatagat | cagagtcgga | gagaaaattt | tgcctcctcc | catcggaatc | tagctaatta | 120 |
| ttttccagtc | cttctccccc | atgtaagtct | ccctctccca | tccccgtcgc | ctgcacctac | 180 |
| cggaagcgaa | gccttctaca | gttcaggtcc | atatccgggt | cgccgccgtc | ggctagctct | 240 |
| aggcggacat | ggtggccgct | tgccggagca | cggcctccac | ctacgcgttt | ctgctgctct | 300 |
| tgctgtttgc | cgctgcggtc | gccgtctctt | cttcctccgg | gttgcgccgt | gtccaggacc | 360 |
| aggacagatc | ggcgctgctc | cagatcaaga | acgccttccc | tgccgtagac | ctgctccagc | 420 |
| agtggtcccc | ggactctagc | ggccgtaacc | actgctcctg | gctgggggta | acatgcgact | 480 |
| caagctcccg | ggtcgtcgct | ctggaggtgc | tctccccttc | acggcgtttc | ggacccggcc | 540 |
| aggagcttgc | cggcgagctt | cctgcggcgg | ttgggctcct | caccgagttg | aaagtggtct | 600 |
| cttttccgct | ccacggcctc | cggggcgaga | tccccggtga | gatctggcgg | ttggaagatc | 660 |
| tcgaggtggt | caacctcgct | gggaactctc | tccgggcgc | ccttcctgcc | gccttcccgc | 720 |
| cgcggctgag | ggtgctctcg | ctcgcttcca | acctgcttca | cggtgagatc | ccgtcttccc | 780 |
| tttccacctg | caaagacttg | gagaggttgg | atctttcagg | caaccggttc | actggatcgg | 840 |
| tgccgagagc | acttggcagc | ctgcctaatc | tgaagtggct | tgacttgtct | gcaaaccttc | 900 |
| ttgtcggtgg | catccctct | ggtctgggga | attgcaggca | gctccgctcg | ctgcggttgt | 960 |
| tctccaattc | attacacggt | tcaattccag | cagggattgg | aaagctgagg | aaactacagg | 1020 |
| tgttggacgt | atcaagaaac | agattaagtg | gcctggtgcc | accggagctc | ggaaattgct | 1080 |
| cagatttgtc | agtgctcgta | ttgtctagcc | agtccaattc | agtaaagtca | catgagttca | 1140 |
| atctgtttaa | aggaggaatt | ccagagagtg | tgacagcttt | gccaagactc | cgggtgctat | 1200 |
| gggtgccaag | ggcgggcctg | gaaggaactc | tcccgagcaa | ctggggaagg | tgttctaatt | 1260 |
| tagaaatggt | taatctgggg | ggaaatttac | tttctggagc | aatcccaagg | gatctaggac | 1320 |
| agtgcagtaa | cctcaagttt | ctcaacctca | gctcaaatag | attatctggt | ttactggata | 1380 |

```
aggatctatg tccgcattgt atgactgtat tcgatgtcag cggaaatgaa atttcaggat   1440
caattccagc atgtgtgaat aaagtctgta cttctcatct agtgctggat aaaatgtcat   1500
ccagttattc ttcattcctc atgtccaaaa ctctacaaga actgccatca gttttttgca   1560
actccgggga gtgttctgtt gtgtatcata attttgcaaa gaacaacctt gaaggtcacc   1620
ttacatcctt gccatttagt gctgacaggt ttggaaacaa gacgtcatat gtgtttgtcg   1680
ttgatcacaa taatttcagt ggatcgttgg attcaattct gttggaacag tgtagcaact   1740
tgaaggggtt ggttgtaagc ttccgagaca acaagatatc tggtcagatc acagcagagt   1800
ttagcagaaa atgcagtgct atcagagctt tggatttagc tggcaatcaa atatcaggaa   1860
tgatgcctga taatgttggt ttgttaggag cccttgtcaa gatggacatg agcagaaatt   1920
ttttggaggg tcaaatacct gccagtttca aagatttcaa gagcttgaag tttctctcat   1980
tagctgggaa caacattagt ggcagaatac catcctgttt gggtcagttg agatcactga   2040
gggttttaga tctctcatct aattctcttg ctggtgagat cccaaataac cttgtgacac   2100
taggagacat aactgtgctt ctactcaaca ataataggct ctctggaaac attccaaatt   2160
ttgcctcttc accatcgctg tccatattca atgtttcatt caatgatttg tctgggccac   2220
tgccttcaaa aattcactca ctgacatgca acagtattcg tggaaatcca tcccttcaac   2280
cttgtggact gtcaacgctc tccagtcctt tagtgaatgc tcgagcacta agtgaggcag   2340
acaataatcc accagctgat aatacagccc ctgatgacaa tggtaacggt ggcggattca   2400
gcaaaataga gattgcctcc ataacttcag catcagcaat tgttgcagtt ctcttggctc   2460
tggtcatcct ttatatttac acacgaaaat gtgcatcaag accatcaagg cgttctctaa   2520
gaagggaagt aactgttttt gttgatattg gtgctccctt gacatatgag gctgttttac   2580
gtgccagtgg aagcttcaat gcaagtaatt gcatcggaag tggtggcttc ggagcaacgt   2640
acaaagctga ggtagcacca ggaaaattgg tggcaataaa gagacttgct attggaaggt   2700
tccaaggcat tcagcaattc caagcagagg tcaaaacact tgggaggtgt cgccattcca   2760
atcttgtaac actcatagga taccatctca gcgattcaga gatgtttcta atatataatt   2820
ttctgcctgg tggcaattta gaaagattca tacaagaaag gactaagaga ccaattgatt   2880
ggagaatgct tcataaaatt gctctagatg ttgcgcgtgc acttgcatat cttcatgaca   2940
attgtgtccc ccgcatctta cacagggatg tcaaaccaag taacatcttg cttgataatg   3000
attacactgc ctacctttct gattttggat tagcaaggct gcttggaaat tcagaaacac   3060
atgcaaccac tggtgtggca ggtacttttg gatatgtagc tccagagtat gcgatgacat   3120
gccgcgtttc tgataaggcg gatgtgtata gctatggagt tgtacttctt gaactcattt   3180
cagacaaaaa ggcactggat ccttcttcct ctccttacgg gaatggattc aacatagttg   3240
cctgggcttg catgcttcta caaaagggtc gagctcgtga attctttata gaagggctgt   3300
gggatgtggc cccacatgac gaccttgttg agattctaca cctgggcatc aagtgtacgg   3360
ttgattctct ttcttctagg cccacaatga agcaagttgt tcggcgactt aaggaactca   3420
gaccaccgtc ttactaggaa tagcaagcag agactggctt gcttctgcat aatgagacca   3480
agactgctgg ctgtttgggt gactgcaaca gccagtaatg ttccaaataa actggtggca   3540
actggcaagc aattcaaatg tcatttctca agggatcctc aagcaggaca ttcatggtat   3600
ttaatcattt ggtcgtcatg gtcactgtat ggaacgccga tatcgcttca atgccactgc   3660
aagcaagcat caaggatgcc tgaggaagtt cttctatgcc tgccaaatct gatgactgga   3720
```

```
ttaggctctg ttcgtttagt ccagattgga ggccggaacc attccaactc atcaagctaa    3780
tacaaatttg cgaactattc caatccggaa ccaatccagt aaagcattca ggaagaaccg    3840
aacgggcact taggcattac cgacccagtt aacaggatgc attatatacc ttgctaagca    3900
attattacgg cgtaacggag atcgaccacc ttgactcatt ggaacgtagc catatatctg    3960
gcagttctag catatatctg atcaaagcaa agccatatat ctggcagttc tggggtgatc    4020
cgtccgtgga aaaggcttgg ccactgacct gcgcgaggac aaagcagtag aaacatatca    4080
gccaatcaaa gcaaagccat atgaattcat gttaaacatg tccatacata tagcagtgaa    4140
aagtatcaaa tcactgattt cctttcttgg cctttgtaac tgtatatact gctttcgtgg    4200
cctttgtaaa aaaaaaaaaa aa                                             4222
```

<210> SEQ ID NO 15
<211> LENGTH: 1062
<212> TYPE: PRT
<213> ORGANISM: Zea mays

<400> SEQUENCE: 15

```
Met Val Ala Ala Cys Arg Ser Thr Ala Ser Thr Tyr Ala Phe Leu Leu
1               5                   10                  15

Leu Leu Leu Phe Ala Ala Val Ala Val Ser Ser Ser Gly Leu
                20                  25                  30

Arg Arg Val Gln Asp Gln Asp Arg Ser Ala Leu Leu Gln Ile Lys Asn
                35                  40                  45

Ala Phe Pro Ala Val Asp Leu Leu Gln Gln Trp Ser Pro Asp Ser Ser
        50                  55                  60

Gly Arg Asn His Cys Ser Trp Leu Gly Val Thr Cys Asp Ser Ser
65                  70                  75                  80

Arg Val Val Ala Leu Glu Val Leu Ser Pro Ser Arg Arg Phe Gly Pro
                85                  90                  95

Gly Gln Glu Leu Ala Gly Glu Leu Pro Ala Ala Val Gly Leu Leu Thr
                100                 105                 110

Glu Leu Lys Val Val Ser Phe Pro Leu His Gly Leu Arg Gly Glu Ile
                115                 120                 125

Pro Gly Glu Ile Trp Arg Leu Glu Asp Leu Glu Val Val Asn Leu Ala
        130                 135                 140

Gly Asn Ser Leu Arg Gly Ala Leu Pro Ala Ala Phe Pro Pro Arg Leu
145                 150                 155                 160

Arg Val Leu Ser Leu Ala Ser Asn Leu His Gly Glu Ile Pro Ser
                165                 170                 175

Ser Leu Ser Thr Cys Lys Asp Leu Glu Arg Leu Asp Leu Ser Gly Asn
                180                 185                 190

Arg Phe Thr Gly Ser Val Pro Arg Ala Leu Gly Ser Leu Pro Asn Leu
                195                 200                 205

Lys Trp Leu Asp Leu Ser Ala Asn Leu Leu Val Gly Ile Pro Ser
        210                 215                 220

Gly Leu Gly Asn Cys Arg Gln Leu Arg Ser Leu Arg Leu Phe Ser Asn
225                 230                 235                 240

Ser Leu His Gly Ser Ile Pro Ala Gly Ile Lys Leu Arg Lys Leu
                245                 250                 255

Gln Val Leu Asp Val Ser Arg Asn Arg Leu Ser Gly Leu Val Pro Pro
                260                 265                 270

Glu Leu Gly Asn Cys Ser Asp Leu Ser Val Leu Val Leu Ser Ser Gln
                275                 280                 285
```

-continued

```
Ser Asn Ser Val Lys Ser His Glu Phe Asn Leu Phe Lys Gly Gly Ile
    290                 295                 300

Pro Glu Ser Val Thr Ala Leu Pro Arg Leu Arg Val Leu Trp Val Pro
305                 310                 315                 320

Arg Ala Gly Leu Glu Gly Thr Leu Pro Ser Asn Trp Gly Arg Cys Ser
                325                 330                 335

Asn Leu Glu Met Val Asn Leu Gly Gly Asn Leu Leu Ser Gly Ala Ile
            340                 345                 350

Pro Arg Asp Leu Gly Gln Cys Ser Asn Leu Lys Phe Leu Asn Leu Ser
        355                 360                 365

Ser Asn Arg Leu Ser Gly Leu Leu Asp Lys Asp Leu Cys Pro His Cys
    370                 375                 380

Met Thr Val Phe Asp Val Ser Gly Asn Glu Ile Ser Gly Ser Ile Pro
385                 390                 395                 400

Ala Cys Val Asn Lys Val Cys Thr Ser His Leu Val Leu Asp Lys Met
                405                 410                 415

Ser Ser Ser Tyr Ser Ser Phe Leu Met Ser Lys Thr Leu Gln Glu Leu
            420                 425                 430

Pro Ser Val Phe Cys Asn Ser Gly Glu Cys Ser Val Val Tyr His Asn
        435                 440                 445

Phe Ala Lys Asn Asn Leu Glu Gly His Leu Thr Ser Leu Pro Phe Ser
    450                 455                 460

Ala Asp Arg Phe Gly Asn Lys Thr Ser Tyr Val Phe Val Val Asp His
465                 470                 475                 480

Asn Asn Phe Ser Gly Ser Leu Asp Ser Ile Leu Leu Glu Gln Cys Ser
                485                 490                 495

Asn Leu Lys Gly Leu Val Val Ser Phe Arg Asp Asn Lys Ile Ser Gly
            500                 505                 510

Gln Ile Thr Ala Glu Phe Ser Arg Lys Cys Ser Ala Ile Arg Ala Leu
        515                 520                 525

Asp Leu Ala Gly Asn Gln Ile Ser Gly Met Met Pro Asp Asn Val Gly
    530                 535                 540

Leu Leu Gly Ala Leu Val Lys Met Asp Met Ser Arg Asn Phe Leu Glu
545                 550                 555                 560

Gly Gln Ile Pro Ala Ser Phe Lys Asp Phe Lys Ser Leu Lys Phe Leu
                565                 570                 575

Ser Leu Ala Gly Asn Asn Ile Ser Gly Arg Ile Pro Ser Cys Leu Gly
            580                 585                 590

Gln Leu Arg Ser Leu Arg Val Leu Asp Leu Ser Ser Asn Ser Leu Ala
        595                 600                 605

Gly Glu Ile Pro Asn Asn Leu Val Thr Leu Gly Asp Ile Thr Val Leu
    610                 615                 620

Leu Leu Asn Asn Asn Arg Leu Ser Gly Asn Ile Pro Asn Phe Ala Ser
625                 630                 635                 640

Ser Pro Ser Leu Ser Ile Phe Asn Val Ser Phe Asn Asp Leu Ser Gly
                645                 650                 655

Pro Leu Pro Ser Lys Ile His Ser Leu Thr Cys Asn Ser Ile Arg Gly
            660                 665                 670

Asn Pro Ser Leu Gln Pro Cys Gly Leu Ser Thr Leu Ser Ser Pro Leu
        675                 680                 685

Val Asn Ala Arg Ala Leu Ser Glu Ala Asp Asn Pro Pro Ala Asp
    690                 695                 700
```

Asn Thr Ala Pro Asp Asp Asn Gly Asn Gly Gly Gly Phe Ser Lys Ile
705                 710                 715                 720

Glu Ile Ala Ser Ile Thr Ser Ala Ser Ala Ile Val Ala Val Leu Leu
            725                 730                 735

Ala Leu Val Ile Leu Tyr Ile Tyr Thr Arg Lys Cys Ala Ser Arg Pro
            740                 745                 750

Ser Arg Arg Ser Leu Arg Arg Glu Val Thr Val Phe Val Asp Ile Gly
            755                 760                 765

Ala Pro Leu Thr Tyr Glu Ala Val Leu Arg Ala Ser Gly Ser Phe Asn
            770                 775                 780

Ala Ser Asn Cys Ile Gly Ser Gly Gly Phe Gly Ala Thr Tyr Lys Ala
785                 790                 795                 800

Glu Val Ala Pro Gly Lys Leu Val Ala Ile Lys Arg Leu Ala Ile Gly
            805                 810                 815

Arg Phe Gln Gly Ile Gln Gln Phe Gln Ala Glu Val Lys Thr Leu Gly
            820                 825                 830

Arg Cys Arg His Ser Asn Leu Val Thr Leu Ile Gly Tyr His Leu Ser
            835                 840                 845

Asp Ser Glu Met Phe Leu Ile Tyr Asn Phe Leu Pro Gly Gly Asn Leu
850                 855                 860

Glu Arg Phe Ile Gln Glu Arg Thr Lys Arg Pro Ile Asp Trp Arg Met
865                 870                 875                 880

Leu His Lys Ile Ala Leu Asp Val Ala Arg Ala Leu Ala Tyr Leu His
            885                 890                 895

Asp Asn Cys Val Pro Arg Ile Leu His Arg Asp Val Lys Pro Ser Asn
            900                 905                 910

Ile Leu Leu Asp Asn Asp Tyr Thr Ala Tyr Leu Ser Asp Phe Gly Leu
            915                 920                 925

Ala Arg Leu Leu Gly Asn Ser Glu Thr His Ala Thr Thr Gly Val Ala
            930                 935                 940

Gly Thr Phe Gly Tyr Val Ala Pro Glu Tyr Ala Met Thr Cys Arg Val
945                 950                 955                 960

Ser Asp Lys Ala Asp Val Tyr Ser Tyr Gly Val Val Leu Leu Glu Leu
            965                 970                 975

Ile Ser Asp Lys Lys Ala Leu Asp Pro Ser Phe Ser Pro Tyr Gly Asn
            980                 985                 990

Gly Phe Asn Ile Val Ala Trp Ala Cys Met Leu Leu Gln Lys Gly Arg
            995                1000                1005

Ala Arg Glu Phe Phe Ile Glu Gly Leu Trp Asp Val Ala Pro His
    1010                1015                1020

Asp Asp Leu Val Glu Ile Leu His Leu Gly Ile Lys Cys Thr Val
    1025                1030                1035

Asp Ser Leu Ser Ser Arg Pro Thr Met Lys Gln Val Val Arg Arg
    1040                1045                1050

Leu Lys Glu Leu Arg Pro Pro Ser Tyr
    1055                1060

<210> SEQ ID NO 16
<211> LENGTH: 3534
<212> TYPE: DNA
<213> ORGANISM: Zea mays

<400> SEQUENCE: 16
ccctttcctc tctacaccga cgagaccta acaaggcccc cgccgccgcc gccgcctccg    60

```
cacatggccg ctcgaacctt gctgctcgtg ctgctcttgc ttctgctcgg tgacgccacc    120
tcggcttccg tcagcggcca gcgcgaagcg ttgatgaagt tcaaagcggc cgtgacggcc    180
gacccgggcg gcctgctgcg cggctggtcc ccggcgtccg ggaccactg ccgctggccg     240 ggcgtgtcgt gcgcgcttc cggggaggtg gtcgcgctca acgtcacctc ctcgcccggg     300
cgcgcgctcg cgggcgcgct gtctccggcc gtcgcggcgc tgcgggagct ccgcgtgctc    360
gctctcccgt cccacgcgct ctcgggcccg ctcccgcccg cgatctggac gctgcgccgc    420
ctccgcgtcc tcgacctctc cggcaatcgc ctccagggcg ggatcccccgc agtgctcgtt   480 tgcgtctccc tccagacgct ggaccttgcc tacaaccagc tcaacggctc cgtgcccgcg    540
gccctcggtg cgctccctgt gctacggcgg ctgtcacttg cctgcaaccg cttcggtggc    600
gccatccctg acgagctcgg tggcgccggt tgccgcaacc tgcagttcct cgatgtctct    660
gggaacatgc tcgtcggtgg catacccegg agcctgggga attgtactga gctgcaggcg    720
ctgttattgt cctcgaacaa tctggatgac atcatcccgc cggagattgg tcggctcaag    780
aacctgcgtg cattagatgt gtccaggaac agtttgagtg ggcctgtgcc agcggagctt    840
ggtggttgca ttcagctgtc agtgcttgtt ctgtccaatc cttatgcacc cactgctggt    900
tctgattctt ctgattatgg tgagctcgat gacttcaact acttccaagg agggattccg    960
gatactatcg ctacactgcc aaagctgagg atgttgtggg cgccaagagc cacattggag    1020
ggagagttgc cgggtaattg gagttcttgc cagagcttgg agatgataaa tttggggag   1080 aatctgttct ctggtgggat tcctaagggg ctggtggaat gtgagaattt gaagttcctg    1140
aatttgagca tgaacaagtt tacaggttca gttgattctt cgctgccagt accttgcatg    1200
gacgtgtttg atgtcagtgg aaatcagctg tctggctcgt tgccagtatt tatgtcaaaa    1260
aagaattgtc tttcatccca ggccccacgg gatgacttgg tgtcggagta ttcttccttc    1320
ttcacatatc aagcgcttgc tggctttatg tcatccccat caccccttgga tgcacatttg   1380 acaagctatc atagtttttc caggaacaat tttactggtc cagttacatc cttacctctt    1440
gctactgaaa agttggggat gcaggggtcc tatgcattct ggctgatgg gaatcatctt     1500 ggtggtcagc ttcaacctag tctatttgac aagtgcaaca gctcaagggg cctcgtcgtg    1560
gaaatcagta caacttgat aagtggagct attcccacag acattggctc gcttttgcagt   1620 tctcttcttg ttcttggtgt tgctggtaat cagctttcag gtatgatacc atcaagtatc    1680
ggggagttaa gttaccttat cagcttggat ttgagtagga atcgccttgg tggtgtaatt    1740
cctacttctg tgaagaactt gctgcattta cagcgcctct cttttggctca gaaccttctg    1800 aatggcacaa ttccacctga tattaatcag ttgcatgctc tcaaggtttt ggacctgtca    1860
tcaaacctcc tcatggggat gatccctgat gcccttgctg acttgagaaa tctcactgct    1920
ctcctccttg ataacaataa acttactggg aagattcctt caggatttgc taactcggca    1980
tcccttacca cgtttaatgt gtcattcaac aatttgtctg gtccagtgcc aacgaatggt    2040
aatacggtta gatgtgacag tgttattggg aatccttttgc tgcaatcttg tcatgtgtac    2100
actctggctg tgccatcagc tgctcagcag ggtcgaggtt tgaattcgaa tgacagcaat    2160
gatacaacac cttcaaactc acaaaacgaa ggagcgaaca attcatttaa tgcaattgaa    2220
attgcttcaa taacttctgc aacagccatc gtttccatcc tccttgcact gattgcactc    2280
ttcatataca caaggaagtg cgcgcccegg atgtcagctc ggtcttctgg aaggagagaa    2340
gttacactct tccaagatat tggtgtccca atcacttatg agactgttgt tcgagccact    2400
ggaagtttca atgcaagcaa ttgcatcgga agtggaggct ttggagccac ttacaaggct    2460
```

-continued

```
gaaattgcac ctggagtgtt ggtagctatt aagagactct ctgtcgggag atttcaggga    2520
gcccaacagt ttgacgctga gataaaaact ctagggagat taagacatcc aaatcttgtt    2580
accttggtag gttaccatct aggcgagtct gaaatgtttc tcatatataa ctacttgtct    2640
ggaggaaacc ttgagaggtt tatacaggag agatcgaaga gaccggtaga ctggaaaatg    2700
ctgcacaaga ttgcattgga cgttgccaaa gcacttgctt atctgcatga tacctgtgtt    2760
cctcgcatcc ttcaccggga cgtgaagccg agcaatattt tgttggacac caactatact    2820
gcttacctct cggactttgg actggcgaga ctcttgggaa attcagaaac acatgcaacc    2880
actggtgtag ctggaacatt tggatatgtt gctccagaat atgctatgac ttgtcgtgtt    2940
tcagataaag ctgatgtgta tagctatggt gttgtcctga tggagctaat ctcagacaag    3000
aaggctttgg acccgtcctt ttccccatat ggtaatgggt tcaacatagt tgcttgggct    3060
tgcatgctgc ttcgtcaagg ccgtgctcgg gaattcttta ttgatggtct gtgggatgtt    3120
ggcccgcatg atgacttggt agaaacattg catttagcag tgatatgcac tgctgattca    3180
ctctctatac ggccaactat gaagcaggtc gttcagagat taaagcagct acagcctcca    3240
attcgtgaac atcgatagag atgaataggt ttacaatttc cacatgtaga aggtaaagat    3300
agctgtgacc tgtgctcttg atgattttt tttcctaatc atctgtttga ctaggtttta    3360
tcttgtagat ggcagctttg tgtaatatag ttttctcctg aatctctcac tagtcactaa    3420
tgtatctgct gataagaagt gcaggtgtaa attaacagtt taatgccaaa gatttcagtt    3480
aagattaaaa aaaaaaaaaa aaaaaaaaaa aaaaaaaaaa aaaaaaaaaa aaag          3534
```

<210> SEQ ID NO 17
<211> LENGTH: 1064
<212> TYPE: PRT
<213> ORGANISM: Zea mays

<400> SEQUENCE: 17

```
Met Ala Ala Arg Thr Leu Leu Val Leu Leu Leu Leu Leu Leu Leu Gly
1               5                   10                  15

Asp Ala Thr Ser Ala Ser Val Ser Gly Gln Arg Glu Ala Leu Met Lys
            20                  25                  30

Phe Lys Ala Ala Val Thr Ala Asp Pro Gly Leu Leu Arg Gly Trp
        35                  40                  45

Ser Pro Ala Ser Gly Asp His Cys Arg Trp Pro Val Ser Cys Gly
    50                  55                  60

Ala Ser Gly Glu Val Val Ala Leu Asn Val Thr Ser Ser Pro Gly Arg
65                  70                  75                  80

Ala Leu Ala Gly Ala Leu Ser Pro Ala Val Ala Leu Arg Glu Leu
                85                  90                  95

Arg Val Leu Ala Leu Pro Ser His Ala Leu Ser Gly Pro Leu Pro Pro
            100                 105                 110

Ala Ile Trp Thr Leu Arg Arg Leu Arg Val Leu Asp Leu Ser Gly Asn
        115                 120                 125

Arg Leu Gln Gly Gly Ile Pro Ala Val Leu Val Cys Val Ser Leu Gln
    130                 135                 140

Thr Leu Asp Leu Ala Tyr Asn Gln Leu Asn Gly Ser Val Pro Ala Ala
145                 150                 155                 160

Leu Gly Ala Leu Pro Val Leu Arg Arg Leu Ser Leu Ala Cys Asn Arg
                165                 170                 175

Phe Gly Gly Ala Ile Pro Asp Glu Leu Gly Gly Ala Gly Cys Arg Asn
```

```
            180                 185                 190
Leu Gln Phe Leu Asp Val Ser Gly Asn Met Leu Val Gly Gly Ile Pro
            195                 200                 205

Arg Ser Leu Gly Asn Cys Thr Glu Leu Gln Ala Leu Leu Ser Ser
210                 215                 220

Asn Asn Leu Asp Asp Ile Ile Pro Pro Glu Ile Gly Arg Leu Lys Asn
225                 230                 235                 240

Leu Arg Ala Leu Asp Val Ser Arg Asn Ser Leu Ser Gly Pro Val Pro
                245                 250                 255

Ala Glu Leu Gly Gly Cys Ile Gln Leu Ser Val Leu Val Leu Ser Asn
                260                 265                 270

Pro Tyr Ala Pro Thr Ala Gly Ser Asp Ser Ser Asp Tyr Gly Glu Leu
                275                 280                 285

Asp Asp Phe Asn Tyr Phe Gln Gly Gly Ile Pro Asp Thr Ile Ala Thr
                290                 295                 300

Leu Pro Lys Leu Arg Met Leu Trp Ala Pro Arg Ala Thr Leu Glu Gly
305                 310                 315                 320

Glu Leu Pro Gly Asn Trp Ser Cys Gln Ser Leu Glu Met Ile Asn
                325                 330                 335

Leu Gly Glu Asn Leu Phe Ser Gly Gly Ile Pro Lys Gly Leu Val Glu
                340                 345                 350

Cys Glu Asn Leu Lys Phe Leu Asn Leu Ser Met Asn Lys Phe Thr Gly
                355                 360                 365

Ser Val Asp Ser Ser Leu Pro Val Pro Cys Met Asp Val Phe Asp Val
370                 375                 380

Ser Gly Asn Gln Leu Ser Gly Ser Leu Pro Val Phe Met Ser Lys Lys
385                 390                 395                 400

Asn Cys Leu Ser Ser Gln Ala Pro Arg Asp Asp Leu Val Ser Glu Tyr
                405                 410                 415

Ser Ser Phe Phe Thr Tyr Gln Ala Leu Ala Gly Phe Met Ser Ser Pro
                420                 425                 430

Ser Pro Leu Asp Ala His Leu Thr Ser Tyr His Ser Phe Ser Arg Asn
                435                 440                 445

Asn Phe Thr Gly Pro Val Thr Ser Leu Pro Leu Ala Thr Glu Lys Leu
450                 455                 460

Gly Met Gln Gly Ser Tyr Ala Phe Leu Ala Asp Gly Asn His Leu Gly
465                 470                 475                 480

Gly Gln Leu Gln Pro Ser Leu Phe Asp Lys Cys Asn Ser Ser Arg Gly
                485                 490                 495

Leu Val Val Glu Ile Ser Asn Asn Leu Ile Ser Gly Ala Ile Pro Thr
                500                 505                 510

Asp Ile Gly Ser Leu Cys Ser Ser Leu Leu Val Leu Gly Val Ala Gly
                515                 520                 525

Asn Gln Leu Ser Gly Met Ile Pro Ser Ser Ile Gly Glu Leu Ser Tyr
                530                 535                 540

Leu Ile Ser Leu Asp Leu Ser Arg Asn Arg Leu Gly Gly Val Ile Pro
545                 550                 555                 560

Thr Ser Val Lys Asn Leu Leu His Leu Gln Arg Leu Ser Leu Ala Gln
                565                 570                 575

Asn Leu Leu Asn Gly Thr Ile Pro Pro Asp Ile Asn Gln Leu His Ala
                580                 585                 590

Leu Lys Val Leu Asp Leu Ser Ser Asn Leu Leu Met Gly Met Ile Pro
                595                 600                 605
```

```
Asp Ala Leu Ala Asp Leu Arg Asn Leu Thr Ala Leu Leu Asp Asn
    610             615                 620

Asn Lys Leu Thr Gly Lys Ile Pro Ser Gly Phe Ala Asn Ser Ala Ser
625             630                 635                 640

Leu Thr Thr Phe Asn Val Ser Phe Asn Asn Leu Ser Gly Pro Val Pro
            645                 650                 655

Thr Asn Gly Asn Thr Val Arg Cys Asp Ser Val Ile Gly Asn Pro Leu
            660                 665                 670

Leu Gln Ser Cys His Val Tyr Thr Leu Ala Val Pro Ser Ala Ala Gln
        675                 680                 685

Gln Gly Arg Gly Leu Asn Ser Asn Asp Ser Asn Asp Thr Thr Pro Ser
690                 695                 700

Asn Ser Gln Asn Glu Gly Ala Asn Asn Ser Phe Asn Ala Ile Glu Ile
705             710                 715                 720

Ala Ser Ile Thr Ser Ala Thr Ala Ile Val Ser Ile Leu Leu Ala Leu
            725                 730                 735

Ile Ala Leu Phe Ile Tyr Thr Arg Lys Cys Ala Pro Arg Met Ser Ala
            740                 745                 750

Arg Ser Ser Gly Arg Arg Glu Val Thr Leu Phe Gln Asp Ile Gly Val
        755                 760                 765

Pro Ile Thr Tyr Glu Thr Val Val Arg Ala Thr Gly Ser Phe Asn Ala
770                 775                 780

Ser Asn Cys Ile Gly Ser Gly Phe Gly Ala Thr Tyr Lys Ala Glu
785             790                 795                 800

Ile Ala Pro Gly Val Leu Val Ala Ile Lys Arg Leu Ser Val Gly Arg
            805                 810                 815

Phe Gln Gly Ala Gln Gln Phe Asp Ala Glu Ile Lys Thr Leu Gly Arg
        820                 825                 830

Leu Arg His Pro Asn Leu Val Thr Leu Val Gly Tyr His Leu Gly Glu
        835                 840                 845

Ser Glu Met Phe Leu Ile Tyr Asn Tyr Leu Ser Gly Gly Asn Leu Glu
850                 855                 860

Arg Phe Ile Gln Glu Arg Ser Lys Arg Pro Val Asp Trp Lys Met Leu
865                 870                 875                 880

His Lys Ile Ala Leu Asp Val Ala Lys Ala Leu Ala Tyr Leu His Asp
            885                 890                 895

Thr Cys Val Pro Arg Ile Leu His Arg Asp Val Lys Pro Ser Asn Ile
        900                 905                 910

Leu Leu Asp Thr Asn Tyr Thr Ala Tyr Leu Ser Asp Phe Gly Leu Ala
        915                 920                 925

Arg Leu Leu Gly Asn Ser Glu Thr His Ala Thr Thr Gly Val Ala Gly
930                 935                 940

Thr Phe Gly Tyr Val Ala Pro Glu Tyr Ala Met Thr Cys Arg Val Ser
945                 950                 955                 960

Asp Lys Ala Asp Val Tyr Ser Tyr Gly Val Val Leu Met Glu Leu Ile
            965                 970                 975

Ser Asp Lys Lys Ala Leu Asp Pro Ser Phe Ser Pro Tyr Gly Asn Gly
            980                 985                 990

Phe Asn Ile Val Ala Trp Ala Cys Met Leu Leu Arg Gln Gly Arg Ala
            995             1000                1005

Arg Glu Phe Phe Ile Asp Gly Leu Trp Asp Val Gly Pro His Asp
    1010                1015                1020
```

```
Asp Leu Val Glu Thr Leu His Leu Ala Val Ile Cys Thr Ala Asp
    1025                1030                1035

Ser Leu Ser Ile Arg Pro Thr Met Lys Gln Val Val Gln Arg Leu
    1040                1045                1050

Lys Gln Leu Gln Pro Pro Ile Arg Glu His Arg
    1055                1060

<210> SEQ ID NO 18
<211> LENGTH: 1797
<212> TYPE: DNA
<213> ORGANISM: Zea mays

<400> SEQUENCE: 18
atgggcttcc tccgccgctc cgccaccacc gccgtcctct tcgctctcca cctcctcctc      60
ctcgccaccg cctccgtcgc gtcctcgccg tcatcctccc tgccggagca gcaggacgac     120
gacgtgcagg cgctgctcca cctcaagcgc ggcctcgcct ccggcgccga cgctcctctc     180
cggcagtggt cgctggagtc cggcgcccac cactgctcct ggccgggggt cacctgcgac     240
gcgcggtccg gccgcgtcgt ggccctcgcc ctcgcgctcg gcggtcgcct cggcggggag     300
ctgtccccgg cggtcgctcg cctcaccgag ctcagagcgc tgtccttccc ctcggccggg     360
ctcggcggcg agattccccc gcagctctgg cggctggggc gcctgcaggc gctcaacctc     420
gccggcaact ctctccgcgg ccgcctgccg gccaccttcc cggaggggct caaaagcttg     480
gacctttccg ggaaccggct gagcggggga tcccgccgg gtctggggag ctgcgcgacg     540
ctccggcgcc tgcgcctgtc ctccaactgg ttggctggaa ccatcccgcc gcggatcggg     600
gagctcgcgc ggctccgcgt tctggacctg tccgggaacc ggctcaccgg cggcgtgccg     660
ccggagctcc tccattgcag gggcctcgtc aggatggatc tcagcaggaa cttgctccac     720
ggccggctgc cctcgggcct cgcgcagctc aagaacctga ggtttctctc cctctccggc     780
aacaatttca gcggcgagat accttccgtt gcactcaccc tgtgcatctg cacaaggaaa     840
tggcgtctga accatcaga gcgctccttt gcgagcaaag aagtcaaggt tttcgctgat     900
gttgatattg agcccccct gacatatgag accgtcgttc gcgccactgg gaatttcaac     960
gctagcaact gcattggtaa cggcggcttt ggcgcgacat acagagccga ggtggcacct    1020
ggagttcttg tggcaataaa gaggcttgct attgggaagc agcacggcga caaggagttc    1080
caagcagaag tgaggatcct cgggcaatgc cgtcatcctc atcttgtcac tctgttgggg    1140
taccacatca acgagtccga gatgttcctg atatacaact acctgccagg tggcaatctg    1200
gaaaggttca tacaagagag gggcaggagg ccgatcagct ggagaaggct tcacaagatc    1260
gccctggatg tcgcccgcgc tctcgcttac atgcacgacg aatgcgtgcc ccgcgtcctg    1320
caccgggatg tcaagccaaa caacatactg ctcgacaacg agtgcaacgc ctacctttcc    1380
gatttcggat tggcgaggct cctccggaac tcggaaacgc atgcgacgac ggacgttgcc    1440
ggtactttcg gttatgtggc tcctgagtac gcaatgacgt gccgcgtgtc ggacaaggca    1500
gacgtgtaca gctatggagt ggtgctgctg gagctgattt cggacaagaa ggcgctggac    1560
ccgtcgtttt ctccatacgg aaacggcttc aacatcgtca gctgggctgt gaggcttatc    1620
cagagaggca gggtccgcga gttcttcgtc gagggcttgt gggagaaggc cccgcatgat    1680
gatctggtcg agttcctgaa cctggcggtg cggtgcacgc aggagtcgct cgcttctagg    1740
cccacaatga agcatgtcct tcgatgcttg agggaactcc gtccaccttc gtactag       1797

<210> SEQ ID NO 19
```

<211> LENGTH: 598
<212> TYPE: PRT
<213> ORGANISM: Zea mays

<400> SEQUENCE: 19

```
Met Gly Phe Leu Arg Arg Ser Ala Thr Thr Ala Val Leu Phe Ala Leu
1               5                   10                  15

His Leu Leu Leu Ala Thr Ala Ser Val Ala Ser Ser Pro Ser Ser
            20                  25                  30

Ser Leu Pro Glu Gln Gln Asp Asp Val Gln Ala Leu Leu His Leu
        35                  40                  45

Lys Arg Gly Leu Ala Ser Gly Ala Asp Ala Pro Leu Arg Gln Trp Ser
50                  55                  60

Leu Glu Ser Gly Ala His His Cys Ser Trp Pro Gly Val Thr Cys Asp
65                  70                  75                  80

Ala Arg Ser Gly Arg Val Val Ala Leu Ala Leu Ala Leu Gly Gly Arg
                85                  90                  95

Leu Gly Gly Glu Leu Ser Pro Ala Val Ala Arg Leu Thr Glu Leu Arg
            100                 105                 110

Ala Leu Ser Phe Pro Ser Ala Gly Leu Gly Gly Glu Ile Pro Pro Gln
        115                 120                 125

Leu Trp Arg Leu Gly Arg Leu Gln Ala Leu Asn Leu Ala Gly Asn Ser
130                 135                 140

Leu Arg Gly Arg Leu Pro Ala Thr Phe Pro Glu Gly Leu Lys Ser Leu
145                 150                 155                 160

Asp Leu Ser Gly Asn Arg Leu Ser Gly Gly Ile Pro Pro Gly Leu Gly
                165                 170                 175

Ser Cys Ala Thr Leu Arg Arg Leu Arg Leu Ser Ser Asn Trp Leu Ala
            180                 185                 190

Gly Thr Ile Pro Pro Arg Ile Gly Glu Leu Ala Arg Leu Arg Val Leu
        195                 200                 205

Asp Leu Ser Gly Asn Arg Leu Thr Gly Gly Val Pro Pro Glu Leu Leu
210                 215                 220

His Cys Arg Gly Leu Val Arg Met Asp Leu Ser Arg Asn Leu Leu His
225                 230                 235                 240

Gly Arg Leu Pro Ser Gly Leu Ala Gln Leu Lys Asn Leu Arg Phe Leu
                245                 250                 255

Ser Leu Ser Gly Asn Asn Phe Ser Gly Glu Ile Pro Ser Val Ala Leu
            260                 265                 270

Thr Leu Cys Ile Cys Thr Arg Lys Trp Arg Leu Lys Pro Ser Glu Arg
        275                 280                 285

Ser Phe Ala Ser Lys Glu Val Lys Val Phe Ala Asp Val Asp Ile Gly
290                 295                 300

Ala Pro Leu Thr Tyr Glu Thr Val Val Arg Ala Thr Gly Asn Phe Asn
305                 310                 315                 320

Ala Ser Asn Cys Ile Gly Asn Gly Gly Phe Gly Ala Thr Tyr Arg Ala
                325                 330                 335

Glu Val Ala Pro Gly Val Leu Val Ala Ile Lys Arg Leu Ala Ile Gly
            340                 345                 350

Lys Gln His Gly Asp Lys Glu Phe Gln Ala Glu Val Arg Ile Leu Gly
        355                 360                 365

Gln Cys Arg His Pro His Leu Val Thr Leu Leu Gly Tyr His Ile Asn
370                 375                 380

Glu Ser Glu Met Phe Leu Ile Tyr Asn Tyr Leu Pro Gly Gly Asn Leu
```

```
                385                 390                 395                 400
Glu Arg Phe Ile Gln Glu Arg Gly Arg Pro Ile Ser Trp Arg Arg
                    405                 410                 415
Leu His Lys Ile Ala Leu Asp Val Ala Arg Ala Leu Ala Tyr Met His
                    420                 425                 430
Asp Glu Cys Val Pro Arg Val Leu His Arg Asp Val Lys Pro Asn Asn
                    435                 440                 445
Ile Leu Leu Asp Asn Glu Cys Asn Ala Tyr Leu Ser Asp Phe Gly Leu
450                 455                 460
Ala Arg Leu Leu Arg Asn Ser Glu Thr His Ala Thr Thr Asp Val Ala
465                 470                 475                 480
Gly Thr Phe Gly Tyr Val Ala Pro Glu Tyr Ala Met Thr Cys Arg Val
                    485                 490                 495
Ser Asp Lys Ala Asp Val Tyr Ser Tyr Gly Val Val Leu Leu Glu Leu
                    500                 505                 510
Ile Ser Asp Lys Lys Ala Leu Asp Pro Ser Phe Ser Pro Tyr Gly Asn
                    515                 520                 525
Gly Phe Asn Ile Val Ser Trp Ala Val Arg Leu Ile Gln Arg Gly Arg
        530                 535                 540
Val Arg Glu Phe Phe Val Glu Gly Leu Trp Glu Lys Ala Pro His Asp
545                 550                 555                 560
Asp Leu Val Glu Phe Leu Asn Leu Ala Val Arg Cys Thr Gln Glu Ser
                    565                 570                 575
Leu Ala Ser Arg Pro Thr Met Lys His Val Leu Arg Cys Leu Arg Glu
                    580                 585                 590
Leu Arg Pro Pro Ser Tyr
                    595

<210> SEQ ID NO 20
<211> LENGTH: 2380
<212> TYPE: DNA
<213> ORGANISM: Arabidopsis thaliana

<400> SEQUENCE: 20
aatgtcattt tcttttgag taaagaaact tcttcttttt gcaacttgaa aattttcgat      60
ttcgagagcg aaggaagaga gagagagagg gagagatcaa aaaaatttgt gaaaaagag     120 atttattta gggttttgtt gatttctctt gttcattttg ccgtcgtctc tttctctttc     180
tcttgtgaag aaaaagaaga aaaatgaaac ttctgggttt ggtcttcttg ctgtttaatc     240
tgtttatgtt ttcgttttct cggaaacttt taaccgagag tggtggtggt ctccacgacg     300
aagctgctct gttgaagttg aagagtagtt tcttggatcc aaatggagtt ctgtctagct     360
gggtttccga cagctcatca aaccattgtt cttggtacgg tgtctcttgc aactctgatt     420
cgagagtcgt ttctttaatt ctcagaggct gtgatgagct tgaaggtagt ggtgttcttc     480
atctcccaga tttgtcttct tgttcttcaa gtaaaagaag acttggtggt gtaatctctc     540
ctgttgttgg agatttgtct gaaattaggg ttttatctct gtcttttaat gatcttagag     600
gtgagattcc aaaggagatt tggggggttgg agaaattaga gattcttgat cttaaaggta     660
acaactttat cggtggaatt agggttgttg ataatgttgt tcttaggaaa cttatgagtt     720
ttgaggatga agatgaaatt ggtccaagct cagctgatga tgattctcct ggtaaatctg     780
gattgtatcc gattgagata gcttctattg tgtcagcttc agtgattgtc tttgtgcttc     840
ttgttcttgt gatcttgttc atctacacga ggaaatggaa acgaaactct caggttcagg     900
```

| | |
|---|---|
| tagatgagat caaggagatt aaagtgtttg ttgacattgg tattcctctg acgtatgaga | 960 |
| tcattgttag agctactggt tactttagta actctaactg tatcggtcac ggcggtttcg | 1020 |
| gttcgactta taaagcagag gtgtctccaa cgaatgtgtt tgctgttaaa agactctctg | 1080 |
| ttgggaggtt tcaaggtgat caacagtttc atgctgagat ctctgctctt gagatggtta | 1140 |
| ggcatccgaa tcttgttatg ttaatcggtt accatgcgag cgaaaccgag atgtttctta | 1200 |
| tttacaacta cttatctgga ggaaaccttc aagatttcat taagagaga tcgaaagctg | 1260 |
| ctattgagtg gaaggtactt cacaagattg ctcttgatgt agcgcgtgct ctctcctatc | 1320 |
| ttcacgaaca gtgttctcct aaagtcttgc atagagatat caaaccgagt aacatactct | 1380 |
| tggacaacaa ctacaacgct tatctatctg atttcggact ctcgaaactc ttgggaactt | 1440 |
| cgcagtctca tgtcacaact ggtgtggctg aacattcgg atatgtagct ccagagtacg | 1500 |
| caatgacatg ccgagtctcg gagaaagcag atgtttacag ctatgggata gtcctcttgg | 1560 |
| agctgatatc ggacaaacga gctctggatc cttctttctc atcgcatgag aacgggttca | 1620 |
| acattgtctc gtgggctcat atgatgttga gtcaaggcaa agcgaaagaa gtcttcacca | 1680 |
| caggactatg ggagactggt cctccagacg atttggtcga ggttctgcat ttggcactca | 1740 |
| aatgcaccgt cgatagcctc tcgataaggc cgacaatgaa acaagctgta agactgctga | 1800 |
| aacgaatcca gccttctaga ttgtgataca aagctagaag aaaggtgttt ttagaggatt | 1860 |
| tgtacagcag caaacaagtg cctagccatt agaatctttc tcaagtctgt tttttatatt | 1920 |
| ttcagtgcta gggaggtttt tcatatgcat catcaaaatg ttattctcag tctactctct | 1980 |
| tgaaaactga tataaatgat gtttctttct ccttaattct ctctgtataa agcaggtaaa | 2040 |
| aaatacatat atgacttaaa aattgagaaa tgaccagaga ctcttaaaaa catcttctct | 2100 |
| aaacaagggt tggttagagg gttttggtc tattataaga gattgaaagg agaagaagtg | 2160 |
| ttgacaacaa tgtgtctaag aggatgatct acatgaggac caccggcatg tttaacgaaa | 2220 |
| tccgccggag acaagaaatc gccatggcaa acacacatga tcctaacttc ttctccactg | 2280 |
| ccgtatctat aaagaatccc atcaactctc ttcccatttg gtccatctcc tttggtaaac | 2340 |
| acacatggca tctcactttt tccttctccct tgtggctcca | 2380 |

<210> SEQ ID NO 21
<211> LENGTH: 1623
<212> TYPE: DNA
<213> ORGANISM: Arabidopsis thaliana

<400> SEQUENCE: 21

| | |
|---|---|
| atgaaacttc tgggtttggt cttcttgctg tttaatctgt ttatgttttc gttttctcgg | 60 |
| aaacttttaa ccgagagtgg tggtggtctc cacgacgaag ctgctctgtt gaagttgaag | 120 |
| agtagtttct tggatccaaa tggagttctg tctagctggg tttccgacag ctcatcaaac | 180 |
| cattgttctt ggtacggtgt ctcttgcaac tctgattcga gagtcgtttc tttaattctc | 240 |
| agaggctgtg atgagcttga aggtagtggt gttcttcatc tcccagattt gtcttcttgt | 300 |
| tcttcaagta aaagaagact tggtggtgta atctctcctg ttgttggaga tttgtctgaa | 360 |
| attagggttt tatctctgtc ttttaatgat cttagaggtg agattccaaa ggagatttgg | 420 |
| gggttggaga aattagagat tcttgatctt aaaggtaaca actttatcgg tggaattagg | 480 |
| gttgttgata tgttgttct taggaaactt atgagttttg aggatgaaga tgaaattggt | 540 |
| ccaagctcag ctgatgatga ttcctcctggt aaatctggat tgtatccgat tgagatagct | 600 |
| tctattgtgt cagcttcagt gattgtcttt gtgcttcttg ttcttgtgat cttgttcatc | 660 |

-continued

```
tacacgagga aatggaaacg aaactctcag gttcaggtag atgagatcaa ggagattaaa      720
gtgtttgttg acattggtat tcctctgacg tatgagatca ttgttagagc tactggttac      780
tttagtaact ctaactgtat cggtcacggc ggtttcggtt cgacttataa agcagaggtg      840
tctccaacga atgtgtttgc tgttaaaaga ctctctgttg gaggtttca aggtgatcaa       900 cagtttcatg ctgagatctc tgctcttgag atggttaggc atccgaatct tgttatgtta      960
atcggttacc atgcgagcga aaccgagatg tttcttattt acaactactt atctggagga     1020
aaccttcaag atttcattaa agagagatcg aaagctgcta ttgagtggaa ggtacttcac     1080
aagattgctc ttgatgtagc gcgtgctctc tcctatcttc acgaacagtg ttctcctaaa     1140
gtcttgcata gagatatcaa accgagtaac atactcttgg acaacaacta caacgcttat     1200
ctatctgatt tcggactctc gaaactcttg gaacttcgc agtctcatgt cacaactggt      1260
gtggctggaa cattcggata tgtagctcca gagtacgcaa tgacatgccg agtctcggag     1320
aaagcagatg tttacagcta tgggatagtc ctcttggagc tgtatcgga caaacgagct      1380 ctggatcctt ctttctcatc gcatgagaac gggttcaaca ttgtctcgtg ggctcatatg     1440
atgttgagtc aaggcaaagc gaaagaagtc ttcaccacag gactatggga gactggtcct     1500
ccagacgatt tggtcgaggt tctgcatttg gcactcaaat gcaccgtcga tagcctctcg     1560
ataaggccga caatgaaaca agctgtaaga ctgctgaaac gaatccagcc ttctagattg     1620
tga                                                                   1623
```

<210> SEQ ID NO 22
<211> LENGTH: 540
<212> TYPE: PRT
<213> ORGANISM: Arabidopsis thaliana

<400> SEQUENCE: 22

```
Met Lys Leu Leu Gly Leu Val Phe Leu Leu Phe Asn Leu Phe Met Phe
1               5                   10                  15

Ser Phe Ser Arg Lys Leu Leu Thr Glu Ser Gly Gly Gly Leu His Asp
            20                  25                  30

Glu Ala Ala Leu Leu Lys Leu Lys Ser Ser Phe Leu Asp Pro Asn Gly
        35                  40                  45

Val Leu Ser Ser Trp Val Ser Asp Ser Ser Asn His Cys Ser Trp
    50                  55                  60

Tyr Gly Val Ser Cys Asn Ser Asp Ser Arg Val Val Ser Leu Ile Leu
65                  70                  75                  80

Arg Gly Cys Asp Glu Leu Glu Gly Ser Gly Val Leu His Leu Pro Asp
                85                  90                  95

Leu Ser Cys Ser Ser Ser Lys Arg Arg Leu Gly Gly Val Ile Ser
            100                 105                 110

Pro Val Val Gly Asp Leu Ser Glu Ile Arg Val Leu Ser Leu Ser Phe
        115                 120                 125

Asn Asp Leu Arg Gly Glu Ile Pro Lys Glu Ile Trp Gly Leu Glu Lys
    130                 135                 140

Leu Glu Ile Leu Asp Leu Lys Gly Asn Asn Phe Ile Gly Gly Ile Arg
145                 150                 155                 160

Val Val Asp Asn Val Val Leu Arg Lys Leu Met Ser Phe Glu Asp Glu
                165                 170                 175

Asp Glu Ile Gly Pro Ser Ser Ala Asp Asp Ser Pro Gly Lys Ser
            180                 185                 190
```

```
Gly Leu Tyr Pro Ile Glu Ile Ala Ser Ile Val Ser Ala Ser Val Ile
            195                 200                 205

Val Phe Val Leu Leu Val Leu Val Ile Leu Phe Ile Tyr Thr Arg Lys
210                 215                 220

Trp Lys Arg Asn Ser Gln Val Gln Val Asp Glu Ile Lys Glu Ile Lys
225                 230                 235                 240

Val Phe Val Asp Ile Gly Ile Pro Leu Thr Tyr Glu Ile Ile Val Arg
            245                 250                 255

Ala Thr Gly Tyr Phe Ser Asn Ser Asn Cys Ile Gly His Gly Gly Phe
            260                 265                 270

Gly Ser Thr Tyr Lys Ala Glu Val Ser Pro Thr Asn Val Phe Ala Val
            275                 280                 285

Lys Arg Leu Ser Val Gly Arg Phe Gln Gly Asp Gln Phe His Ala
290                 295                 300

Glu Ile Ser Ala Leu Glu Met Val Arg His Pro Asn Leu Val Met Leu
305                 310                 315                 320

Ile Gly Tyr His Ala Ser Glu Thr Glu Met Phe Leu Ile Tyr Asn Tyr
            325                 330                 335

Leu Ser Gly Gly Asn Leu Gln Asp Phe Ile Lys Glu Arg Ser Lys Ala
            340                 345                 350

Ala Ile Glu Trp Lys Val Leu His Lys Ile Ala Leu Asp Val Ala Arg
            355                 360                 365

Ala Leu Ser Tyr Leu His Glu Gln Cys Ser Pro Lys Val Leu His Arg
            370                 375                 380

Asp Ile Lys Pro Ser Asn Ile Leu Leu Asp Asn Asn Tyr Asn Ala Tyr
385                 390                 395                 400

Leu Ser Asp Phe Gly Leu Ser Lys Leu Leu Gly Thr Ser Gln Ser His
            405                 410                 415

Val Thr Thr Gly Val Ala Gly Thr Phe Gly Tyr Val Ala Pro Glu Tyr
            420                 425                 430

Ala Met Thr Cys Arg Val Ser Glu Lys Ala Asp Val Tyr Ser Tyr Gly
            435                 440                 445

Ile Val Leu Leu Glu Leu Ile Ser Asp Lys Arg Ala Leu Asp Pro Ser
450                 455                 460

Phe Ser Ser His Glu Asn Gly Phe Asn Ile Val Ser Trp Ala His Met
465                 470                 475                 480

Met Leu Ser Gln Gly Lys Ala Lys Glu Val Phe Thr Thr Gly Leu Trp
            485                 490                 495

Glu Thr Gly Pro Pro Asp Asp Leu Val Glu Val Leu His Leu Ala Leu
            500                 505                 510

Lys Cys Thr Val Asp Ser Leu Ser Ile Arg Pro Thr Met Lys Gln Ala
            515                 520                 525

Val Arg Leu Leu Lys Arg Ile Gln Pro Ser Arg Leu
            530                 535                 540

<210> SEQ ID NO 23
<211> LENGTH: 1049
<212> TYPE: PRT
<213> ORGANISM: Oryza sativa

<400> SEQUENCE: 23

Met Val Ala Ala Arg Ser Ala Ala Ser Ser Phe Phe Leu Leu
1               5                   10                  15

Leu Leu Val Leu Ala Val Arg Val Ala Ser Ser Asp Arg Val Gln
            20                  25                  30
```

```
Glu Arg Asp Arg Ser Ala Leu Leu Glu Leu Arg Gly Ala Ala Gly Leu
        35                  40                  45

Leu Gly Arg Trp Pro Thr Gly Ser Ala Val Ala Asp His Cys Ser Trp
 50                  55                  60

Pro Gly Val Thr Cys Asp Ala Ser Arg Val Val Ala Val Ala Val
 65                  70                  75                  80

Ala Ala Pro Pro Ala Ser Gly Ser Ser Glu Leu Ala Gly Glu Leu Ser
                85                  90                  95

Pro Ala Val Gly Leu Leu Thr Glu Leu Arg Glu Leu Ser Leu Pro Ser
                100                 105                 110

Arg Gly Leu Arg Gly Glu Ile Pro Ala Glu Ile Trp Arg Leu Glu Lys
                115                 120                 125

Leu Glu Val Val Asn Leu Ala Gly Asn Ser Leu His Gly Ala Leu Pro
            130                 135                 140

Leu Ala Phe Pro Pro Arg Met Arg Val Leu Asp Leu Ala Ser Asn Arg
145                 150                 155                 160

Leu His Gly Glu Ile Gln Gly Thr Leu Ser Asp Cys Lys Ser Leu Met
                165                 170                 175

Arg Leu Asn Leu Ser Gly Asn Arg Leu Thr Gly Ser Val Pro Gly Val
                180                 185                 190

Leu Gly Ser Leu Pro Lys Leu Lys Leu Leu Asp Leu Ser Arg Asn Leu
            195                 200                 205

Leu Thr Gly Arg Ile Pro Ser Glu Leu Gly Asp Cys Arg Glu Leu Arg
        210                 215                 220

Ser Leu Gln Leu Phe Ser Asn Leu Leu Glu Gly Ser Ile Pro Pro Glu
225                 230                 235                 240

Ile Gly Arg Leu Arg Arg Leu Gln Val Leu Asp Ile Ser Ser Asn Arg
                245                 250                 255

Leu Asn Gly Pro Val Pro Met Glu Leu Gly Asn Cys Met Asp Leu Ser
                260                 265                 270

Val Leu Val Leu Thr Ser Gln Phe Asp Ala Val Asn Leu Ser Glu Phe
            275                 280                 285

Asn Met Phe Ile Gly Gly Ile Pro Glu Ser Val Thr Ala Leu Pro Lys
        290                 295                 300

Leu Arg Met Leu Trp Ala Pro Arg Ala Gly Phe Glu Gly Asn Ile Pro
305                 310                 315                 320

Ser Asn Trp Gly Arg Cys His Ser Leu Glu Met Val Asn Leu Ala Glu
                325                 330                 335

Asn Leu Leu Ser Gly Val Ile Pro Arg Glu Leu Gly Gln Cys Ser Asn
                340                 345                 350

Leu Lys Phe Leu Asn Leu Ser Ser Asn Lys Leu Ser Gly Ser Ile Asp
            355                 360                 365

Asn Gly Leu Cys Pro His Cys Ile Ala Val Phe Asp Val Ser Arg Asn
        370                 375                 380

Glu Leu Ser Gly Thr Ile Pro Ala Cys Ala Asn Lys Gly Cys Thr Pro
385                 390                 395                 400

Gln Leu Leu Asp Asp Met Pro Ser Arg Tyr Pro Ser Phe Phe Met Ser
                405                 410                 415

Lys Ala Leu Ala Gln Pro Ser Ser Gly Tyr Cys Lys Ser Gly Asn Cys
                420                 425                 430

Ser Val Val Tyr His Asn Phe Ala Asn Asn Leu Gly Gly His Leu
            435                 440                 445
```

-continued

```
Thr Ser Leu Pro Phe Ser Ala Asp Arg Phe Gly Asn Lys Ile Leu Tyr
    450                 455                 460

Ala Phe His Val Asp Tyr Asn Asn Phe Thr Gly Ser Leu His Glu Ile
465                 470                 475                 480

Leu Leu Ala Gln Cys Asn Asn Val Glu Gly Leu Ile Val Ser Phe Arg
                485                 490                 495

Asp Asn Lys Ile Ser Gly Gly Leu Thr Glu Glu Met Ser Thr Lys Cys
            500                 505                 510

Ser Ala Ile Arg Ala Leu Asp Leu Ala Gly Asn Arg Ile Thr Gly Val
        515                 520                 525

Met Pro Gly Asn Ile Gly Leu Leu Ser Ala Leu Val Lys Met Asp Ile
    530                 535                 540

Ser Arg Asn Leu Leu Glu Gly Gln Ile Pro Ser Ser Phe Lys Glu Leu
545                 550                 555                 560

Lys Ser Leu Lys Phe Leu Ser Leu Ala Glu Asn Asn Leu Ser Gly Thr
                565                 570                 575

Ile Pro Ser Cys Leu Gly Lys Leu Arg Ser Leu Glu Val Leu Asp Leu
            580                 585                 590

Ser Ser Asn Ser Leu Ser Gly Lys Ile Pro Arg Asn Leu Val Thr Leu
        595                 600                 605

Thr Tyr Leu Thr Ser Leu Leu Leu Asn Asn Asn Lys Leu Ser Gly Asn
    610                 615                 620

Ile Pro Asp Ile Ala Pro Ser Ala Ser Leu Ser Ile Phe Asn Ile Ser
625                 630                 635                 640

Phe Asn Asn Leu Ser Gly Pro Leu Pro Leu Asn Met His Ser Leu Ala
                645                 650                 655

Cys Asn Ser Ile Gln Gly Asn Pro Ser Leu Gln Pro Cys Gly Leu Ser
            660                 665                 670

Thr Leu Ala Asn Thr Val Met Lys Ala Arg Ser Leu Ala Glu Gly Asp
        675                 680                 685

Val Pro Pro Ser Asp Ser Ala Thr Val Asp Ser Gly Gly Gly Phe Ser
    690                 695                 700

Lys Ile Glu Ile Ala Ser Ile Thr Ser Ala Ser Ala Ile Val Ala Val
705                 710                 715                 720

Leu Leu Ala Leu Ile Ile Leu Tyr Ile Tyr Thr Arg Lys Cys Ala Ser
                725                 730                 735

Arg Gln Ser Arg Arg Ser Ile Arg Arg Arg Glu Val Thr Val Phe Val
            740                 745                 750

Asp Ile Gly Ala Pro Leu Thr Tyr Glu Thr Val Val Arg Ala Thr Gly
        755                 760                 765

Ser Phe Asn Ala Ser Asn Cys Ile Gly Ser Gly Gly Phe Gly Ala Thr
    770                 775                 780

Tyr Lys Ala Glu Ile Ala Pro Gly Val Leu Val Ala Ile Lys Arg Leu
785                 790                 795                 800

Ala Ile Gly Arg Phe Gln Gly Ile Gln Gln Phe Gln Ala Glu Val Lys
                805                 810                 815

Thr Leu Gly Arg Cys Arg His Pro Asn Leu Val Thr Leu Ile Gly Tyr
            820                 825                 830

His Leu Ser Asp Ser Glu Met Phe Leu Ile Tyr Asn Phe Leu Pro Gly
        835                 840                 845

Gly Asn Leu Glu Arg Phe Ile Gln Glu Arg Ala Lys Arg Pro Ile Asp
    850                 855                 860

Trp Arg Met Leu His Lys Ile Ala Leu Asp Ile Ala Arg Ala Leu Gly
```

```
                865                 870                 875                 880
        Phe Leu His Asp Ser Cys Val Pro Arg Ile Leu His Arg Asp Val Lys
                            885                 890                 895
        Pro Ser Asn Ile Leu Asp Asn Glu Tyr Asn Ala Tyr Leu Ser Asp
                        900                 905                 910
        Phe Gly Leu Ala Arg Leu Leu Gly Asn Ser Glu Thr His Ala Thr Thr
                        915                 920                 925
        Gly Val Ala Gly Thr Phe Gly Tyr Val Ala Pro Glu Tyr Ala Met Thr
                        930                 935                 940
        Cys Arg Val Ser Asp Lys Ala Asp Val Tyr Ser Tyr Gly Val Val Leu
        945                 950                 955                 960
        Leu Glu Leu Ile Ser Asp Lys Lys Ala Leu Asp Pro Ser Phe Ser Pro
                        965                 970                 975
        Tyr Gly Asn Gly Phe Asn Ile Val Ala Trp Ala Cys Met Leu Leu Gln
                        980                 985                 990
        Lys Gly Arg Ala Arg Glu Phe Phe  Ile Glu Gly Leu Trp Asp Val Ala
                        995                1000                1005
        Pro His Asp Asp Leu Val Glu  Ile Leu His Leu Gly  Ile Lys Cys
                   1010                1015                1020
        Thr Val Asp Ser Leu Ser Ser Arg Pro Thr Met Lys Gln Val Val
                   1025                1030                1035
        Arg Arg Leu Lys Glu Leu Arg Pro Pro Ser Tyr
                   1040                1045

<210> SEQ ID NO 24
<211> LENGTH: 1070
<212> TYPE: PRT
<213> ORGANISM: Oryza sativa

<400> SEQUENCE: 24

Met Ala Thr Leu Asn Thr Gln Thr Leu Leu Thr Leu Phe Leu Leu Leu
1               5                  10                  15
Leu Leu Ala Ala Ala Ala Ala Ala Asp Ala Gly Gly Gly Gly Glu
                20                  25                  30
Arg Glu Ala Leu Leu Arg Phe Lys Ala Gly Val Ala Ser Asp Pro Gly
            35                  40                  45
Gly Leu Leu Arg Gly Trp Thr Thr Ala Ala Ser Pro Asp His Cys Ala
        50                  55                  60
Trp Pro Gly Val Ser Cys Gly Gly Asn Gly Glu Val Val Ala Leu Asn
65                  70                  75                  80
Val Ser Ser Ser Pro Gly Arg Arg Leu Ala Gly Ala Leu Ser Pro Ala
                85                  90                  95
Val Ala Ala Leu Arg Gly Leu Arg Val Leu Ala Leu Pro Ser His Ala
                100                 105                 110
Leu Ser Gly Gln Leu Pro Ala Ala Ile Trp Ser Leu Arg Arg Leu Leu
            115                 120                 125
Val Leu Asp Leu Ser Gly Asn Arg Leu Gln Gly Glu Ile Pro Pro Ala
        130                 135                 140
Leu Ala Cys Ala Gly Leu Gln Thr Leu Asp Leu Ser Tyr Asn Gln Leu
145                 150                 155                 160
Asn Gly Ser Val Pro Ala Ser Leu Gly Ala Leu Pro Gly Leu Arg Arg
                165                 170                 175
Leu Ser Leu Ala Ser Asn Arg Leu Gly Gly Ala Ile Pro Asp Glu Leu
                180                 185                 190
```

-continued

```
Gly Gly Ala Gly Cys Arg Ser Leu Gln Tyr Leu Asp Leu Ser Gly Asn
            195                 200                 205

Leu Leu Val Gly Gly Ile Pro Arg Ser Leu Gly Asn Cys Ser Lys Leu
210                 215                 220

Glu Ala Leu Leu Leu Ser Ser Asn Leu Leu Asp Asp Val Ile Pro Pro
225                 230                 235                 240

Glu Ile Gly Arg Leu Arg Asn Leu Arg Ala Leu Asp Val Ser Arg Asn
                245                 250                 255

Ser Leu Ser Gly Ser Val Pro Ala Glu Leu Gly Gly Cys Val Glu Leu
            260                 265                 270

Ser Val Leu Val Leu Ser Asn Pro Tyr Thr Pro Ile Gly Gly Ser Asn
            275                 280                 285

Ser Ser Asp Tyr Gly Asp Val Asp Asp Phe Asn Tyr Phe Gln Gly Gly
    290                 295                 300

Ile Pro Asp Ala Val Ala Leu Pro Lys Leu Arg Val Leu Trp Ala
305                 310                 315                 320

Pro Arg Ala Thr Leu Glu Gly Glu Leu Pro Arg Asn Trp Ser Ala Cys
                325                 330                 335

Gln Ser Leu Glu Met Ile Asn Leu Gly Glu Asn Leu Phe Ser Gly Gly
            340                 345                 350

Ile Pro Asn Gly Leu Val Glu Cys Ser His Leu Lys Phe Leu Asn Leu
        355                 360                 365

Ser Ser Asn Lys Leu Thr Gly Ala Ile Asp Pro Ser Leu Thr Val Pro
    370                 375                 380

Cys Met Asp Val Phe Asp Val Ser Gly Asn Arg Phe Ser Gly Ala Met
385                 390                 395                 400

Pro Val Phe Glu Gln Lys Gly Cys Pro Ser Ser Gln Leu Pro Phe Asp
                405                 410                 415

Asp Leu Val Ser Glu Tyr Ser Ser Phe Phe Ser Tyr Gln Ala Leu Ala
            420                 425                 430

Gly Phe Arg Ser Ser Ser Phe Val Leu Gly Thr Asp Leu Thr Ser Tyr
        435                 440                 445

His Ser Phe Ala Gln Asn Asn Phe Thr Gly Pro Val Lys Ser Leu Pro
    450                 455                 460

Leu Ala Ala Asp Lys Leu Gly Met Gln Gly Ser Tyr Ala Phe Leu Ala
465                 470                 475                 480

Asp Gly Asn Asn Ile Ala Gly Gln Leu Gln Pro Asp Leu Phe Ser Lys
                485                 490                 495

Cys Asn Ser Ser Arg Gly Phe Ile Val Asp Val Ser Asn Asn Leu Ile
            500                 505                 510

Thr Gly Gly Ile Pro Val Glu Ile Gly Ser Leu Cys Ser Ser Leu Val
        515                 520                 525

Val Leu Gly Val Ala Gly Asn Gln Leu Ser Gly Leu Ile Pro Thr Ser
    530                 535                 540

Ile Gly Gln Leu Asn Tyr Leu Ile Ser Leu Asp Leu Ser Arg Asn His
545                 550                 555                 560

Leu Gly Gly Glu Ile Pro Thr Ser Val Lys Asn Leu Pro Asn Leu Glu
                565                 570                 575

Arg Leu Ser Leu Gly His Asn Phe Leu Asn Gly Thr Ile Pro Thr Glu
            580                 585                 590

Ile Asn Gln Leu Tyr Ser Leu Lys Val Leu Asp Leu Ser Ser Asn Leu
        595                 600                 605

Leu Thr Gly Glu Ile Pro Gly Ala Leu Ala Asp Leu Arg Asn Leu Thr
```

-continued

```
            610                 615                 620
Ala Leu Leu Leu Asp Asn Asn Lys Leu Thr Gly Lys Ile Pro Ser Ala
625                 630                 635                 640

Phe Ala Lys Ser Met Ser Leu Thr Met Phe Asn Leu Ser Phe Asn Asn
                    645                 650                 655

Leu Ser Gly Pro Val Pro Ala Asn Ser Asn Thr Val Arg Cys Asp Ser
                660                 665                 670

Val Ile Gly Asn Pro Leu Leu Gln Ser Cys His Met Tyr Thr Leu Ala
            675                 680                 685

Val Pro Ser Ala Ala Gln Gln Gly Arg Gly Leu Asn Ser Asn Asp Tyr
        690                 695                 700

Asn Asp Thr Ser Ser Ala Asp Ser Gln Asn Gln Gly Gly Ser Asn Ser
705                 710                 715                 720

Phe Asn Ala Ile Glu Ile Ala Ser Ile Thr Ser Ala Thr Ala Ile Val
                    725                 730                 735

Ser Val Leu Leu Ala Leu Ile Val Leu Phe Ile Tyr Thr Arg Lys Cys
                740                 745                 750

Ala Pro Arg Met Ser Ser Arg Ser Ser Arg Arg Glu Val Ile Thr
            755                 760                 765

Phe Gln Asp Ile Gly Val Pro Ile Thr Tyr Glu Thr Val Val Arg Ala
        770                 775                 780

Thr Gly Ser Phe Asn Ala Ser Asn Cys Ile Gly Ser Gly Gly Phe Gly
785                 790                 795                 800

Ala Thr Tyr Lys Ala Glu Ile Ser Pro Gly Val Leu Val Ala Ile Lys
                    805                 810                 815

Arg Leu Ser Val Gly Arg Phe Gln Gly Val Gln Gln Phe His Ala Glu
                820                 825                 830

Ile Lys Thr Leu Gly Arg Leu Arg His Pro Asn Leu Val Thr Leu Val
            835                 840                 845

Gly Tyr His Leu Gly Glu Ser Glu Met Phe Leu Ile Tyr Asn Tyr Leu
        850                 855                 860

Pro Gly Gly Asn Leu Glu Arg Phe Ile Gln Glu Arg Ser Lys Arg Pro
865                 870                 875                 880

Val Asp Trp Lys Met Leu His Lys Ile Ala Leu Asp Ile Ala Lys Ala
                    885                 890                 895

Leu Ala Tyr Leu His Asp Thr Cys Val Pro Arg Ile Leu His Arg Asp
                900                 905                 910

Val Lys Pro Ser Asn Ile Leu Leu Asp Thr Glu Tyr Asn Ala Tyr Leu
            915                 920                 925

Ser Asp Phe Gly Leu Ala Arg Leu Leu Gly Asn Ser Glu Thr His Ala
        930                 935                 940

Thr Thr Gly Val Ala Gly Thr Phe Gly Tyr Val Ala Pro Glu Tyr Ala
945                 950                 955                 960

Met Thr Cys Arg Val Ser Asp Lys Ala Asp Val Tyr Ser Tyr Gly Val
                    965                 970                 975

Val Leu Met Glu Leu Ile Ser Asp Lys Lys Ala Leu Asp Pro Ser Phe
                980                 985                 990

Ser Pro Tyr Gly Asn Gly Phe Asn Ile Val Ala Trp Ala Cys Met Leu
            995                 1000                1005

Leu Arg Gln Gly Arg Ala Arg Glu Phe Phe Ile Asp Gly Leu Trp
        1010                1015                1020

Asp Val Gly Pro His Asp Asp Leu Val Glu Thr Leu His Leu Ala
        1025                1030                1035
```

Val Met Cys Thr Val Asp Ser Leu Ser Val Arg Pro Thr Met Lys
    1040                1045                1050

Gln Val Val Gln Arg Leu Lys Gln Leu Gln Pro Pro Ile Arg Glu
    1055                1060                1065

His Arg
    1070

<210> SEQ ID NO 25
<211> LENGTH: 29
<212> TYPE: DNA
<213> ORGANISM: artificial sequences
<220> FEATURE:
<223> OTHER INFORMATION: primer

<400> SEQUENCE: 25
ggggacaagt ttgtacaaaa aagcaggct                                    29

<210> SEQ ID NO 26
<211> LENGTH: 29
<212> TYPE: DNA
<213> ORGANISM: artificial sequence
<220> FEATURE:
<223> OTHER INFORMATION: primer

<400> SEQUENCE: 26
ggggaccact ttgtacaaga aagctgggt                                    29

<210> SEQ ID NO 27
<211> LENGTH: 54
<212> TYPE: DNA
<213> ORGANISM: artificial sequence
<220> FEATURE:
<223> OTHER INFORMATION: primer

<400> SEQUENCE: 27
ttaaacaagt ttgtacaaaa aagcaggctg caattaaccc tcactaaagg gaac        54

<210> SEQ ID NO 28
<211> LENGTH: 53
<212> TYPE: DNA
<213> ORGANISM: artificial sequence
<220> FEATURE:
<223> OTHER INFORMATION: primer

<400> SEQUENCE: 28
ttaaaccact ttgtacaaga aagctgggtg cgtaatacga ctcactatag ggc         53

<210> SEQ ID NO 29
<211> LENGTH: 12856
<212> TYPE: DNA
<213> ORGANISM: artificial sequence
<220> FEATURE:
<223> OTHER INFORMATION: vector

<400> SEQUENCE: 29
cgccttggcg cgccgatcat ccacaagttt gtacaaaaaa gctgaacgag aaacgtaaaa    60
tgatataaat atcaatatat taaattagat tttgcataaa aaacagacta cataatactg   120
taaaacacaa catatccagt cactatggcg gccgcattag caccccagg ctttacactt    180 tatgcttccg gctcgtataa tgtgtggatt ttgagttagg atttaaatac gcgttgatcc   240
ggcttactaa aagccagata acagtatgcg tatttgcgcg ctgattttg cggtataaga    300 atatatactg atatgtatac ccgaagtatg tcaaaaagag gtatgctatg aagcagcgta   360

```
ttacagtgac agttgacagc gacagctatc agttgctcaa ggcatatatg atgtcaatat    420
ctccggtctg gtaagcacaa ccatgcagaa tgaagcccgt cgtctgcgtg ccgaacgctg    480
gaaagcggaa aatcaggaag ggatggctga ggtcgcccgg tttattgaaa tgaacggctc    540
ttttgctgac gagaacaggg gctggtgaaa tgcagtttaa ggtttacacc tataaaagag    600
agagccgtta tcgtctgttt gtggatgtac agagtgatat cattgacacg cccggtcgac    660
ggatggtgat cccctggcc agtgcacgtc tgctgtcaga taaagtctcc cgtgaacttt    720
acccggtggt gcatatcggg gatgaaagct ggcgcatgat gaccaccgat atggccagtg    780
tgccggtctc cgttatcggg gaagaagtgg ctgatctcag ccaccgcgaa aatgacatca    840
aaaacgccat taacctgatg ttctggggaa tataaatgtc aggctcccctt atacacagcc    900 agtctgcagg tcgaccatag tgactggata tgttgtgttt tacagtatta tgtagtctgt    960
tttttatgca aaatctaatt taatatattg atatttatat cattttacgt ttctcgttca   1020
gctttcttgt acaaagtggt gttaacctag acttgtccat cttctggatt ggccaactta   1080
attaatgtat gaaataaaag gatgcacaca tagtgacatg ctaatcacta taatgtgggc   1140
atcaaagttg tgtgttatgt gtaattacta gttatctgaa taaaagaaaa agagatcatc   1200
catatttctt atcctaaatg aatgtcacgt gtctttataa ttctttgatg aaccagatgc   1260
atttcattaa ccaaatccat atacatataa atattaatca tatataatta atatcaattg   1320
ggttagcaaa acaaatctag tctaggtgtg ttttgcgaat tgcggccgcc accgcggtgg   1380
agctcgaatt ccggtccggg tcacctttgt ccaccaagat ggaactgcgg ccgctcatta   1440
attaagtcag gcgcgcctct agttgaagac acgttcatgt cttcatcgta agaagacact   1500
cagtagtctt cggccagaat ggccatctgg attcagcagg cctagaaggc catttaaatc   1560
ctgaggatct ggtcttccta aggacccggg atatcggacc gattaaactt taattcggtc   1620
cgaagcttga agttcctatt ccgaagttcc tattctccag aaagtatagg aacttcgcat   1680
gcctgcagtg cagcgtgacc cggtcgtgcc cctctctaga gataatgagc attgcatgtc   1740
taagttataa aaaattacca catatttttt ttgtcacact tgtttgaagt gcagtttatc   1800
tatctttata catatattta aactttactc tacgaataat ataatctata gtactacaat   1860
aatatcagtg ttttagagaa tcatataaat gaacagttag acatggtcta aaggacaatt   1920
gagtattttg acaacaggac tctacagttt tatcttttta gtgtgcatgt gttctccttt   1980 tttttttgcaa atagcttcac ctatataata cttcatccat tttattagta catccattta   2040
gggtttaggg ttaatggttt ttatagacta atttttttag tacatctatt ttattctatt   2100
ttagcctcta aattaagaaa actaaaactc tattttagtt ttttttattta ataatttaga   2160 tataaaatag aataaaataa agtgactaaa aattaaacaa ataccctttt agaaaattaaa   2220 aaaactaagg aaacattttt cttgtttcga gtagataatg ccagcctgtt aaacgccgtc   2280
gacgagtcta acgacaccaa ccagcgaacc agcagcgtc gcgtcgggcc aagcgaagca   2340
gacggcacgg catctctgtc gctgcctctg gaccctctc gagagttccg ctccaccgtt   2400
ggacttgctc cgctgtcggc atccagaaat tgcgtggcgg agcggcagac gtgagccggc   2460
acggcaggcg gcctcctcct cctctcacgg caccggcagc tacgggggat ccttttccca   2520
ccgctccttc gctttccctt cctcgcccgc cgtaataaat agacaccccc tccacaccct   2580
ctttccccaa cctcgtgttg ttcggagcgc acacacacac aaccagatct cccccaaatc   2640
cacccgtcgg cacctccgct tcaaggtacg ccgctcgtcc tcccccccccc ccctctctac   2700
```

```
cttctctaga tcggcgttcc ggtccatgca tggttagggc ccggtagttc tacttctgtt    2760
catgtttgtg ttagatccgt gtttgtgtta gatccgtgct gctagcgttc gtacacggat    2820
gcgacctgta cgtcagacac gttctgattg ctaacttgcc agtgtttctc tttggggaat    2880
cctgggatgg ctctagccgt tccgcagacg ggatcgattt catgattttt tttgtttcgt    2940 tgcataggt ttggtttgcc cttttccttt atttcaatat atgccgtgca cttgtttgtc     3000
gggtcatctt ttcatgcttt tttttgtctt ggttgtgatg atgtggtctg gttgggcggt    3060
cgttctagat cggagtagaa ttctgtttca aactacctgg tggatttatt aattttggat    3120
ctgtatgtgt gtgccataca tattcatagt tacgaattga agatgatgga tggaaatatc    3180
gatctaggat aggtatacat gttgatgcgg gttttactga tgcatataca gagatgcttt    3240
ttgttcgctt ggttgtgatg atgtggtgtg gttgggcggt cgttcattcg ttctagatcg    3300
gagtagaata ctgtttcaaa ctacctggtg tatttattaa ttttggaact gtatgtgtgt    3360
gtcatacatc ttcatagtta cgagtttaag atggatggaa atatcgatct aggataggta    3420
tacatgttga tgtgggtttt actgatgcat atacatgatg gcatatgcag catctattca    3480
tatgctctaa ccttgagtac ctatctatta taataaacaa gtatgtttta taattatttt    3540
gatcttgata tacttggatg atggcatatg cagcagctat atgtggatttt ttttagccct   3600 gccttcatac gctatttatt tgcttggtac tgtttctttt gtcgatgctc accctgttgt    3660
ttggtgttac ttctgcaggt cgactttaac ttagcctagg atccacacga caccatgata    3720
gaggtgaaac cgattaacgc agaggatacc tatgaactaa ggcatagaat actcagacca    3780
aaccagccga tagaagcgtg tatgtttgaa agcgattac ttcgtggtgc atttcactta     3840
ggcggctatt acggggcaa actgattttcc atagcttcat tccaccaggc cgagcactca    3900
gaactccaag gccagaaaca gtaccagctc cgaggtatgg ctaccttgga aggttatcgt    3960
gagcagaagg cgggatcgag tctaattaaa cacgctgaag aaattcttcg taagaggggg   4020
gcggacttgc tttggtgtaa tgcgcggaca tccgcctcag gctactacaa aaagttaggc    4080
ttcagcgagc agggagaggt attcgacacg ccgccagtag gacctcacat cctgatgtat    4140
aaaaggatca cataactagc tagtcagtta acctagactt gtccatcttc tggattggcc    4200
aacttaatta atgtatgaaa taaaaggatg cacacatagt gacatgctaa tcactataat    4260
gtgggcatca aagttgtgtg ttatgtgtaa ttactagtta tctgaataaa agagaaagag    4320
atcatccata tttcttatcc taaatgaatg tcacgtgtct ttataattct ttgatgaacc    4380
agatgcattt cattaaccaa atccatatac atataaatat taatcatata taattaatat    4440
caattgggtt agcaaaacaa atctagtcta ggtgtgtttt gcgaattcag agctcgaatt    4500
cattccgatt aatcgtggcc tcttgctctt caggatgaag agctatgttt aaacgtgcaa    4560
gcgctactag acaattcagt acattaaaaa cgtccgcaat gtgttattaa gttgtctaag    4620
cgtcaatttg tttacaccac aatatatcct gccaccagcc agccaacagc tcccgaccg     4680 gcagctcggc acaaaatcac cactcgatac aggcagccca tcagtccggg acggcgtcag    4740
cgggagagcc gttgtaaggc ggcagacttt gctcatgtta ccgatgctat tcggaagaac    4800
ggcaactaag ctgccgggtt tgaaacacg atgatctcgc ggagggtagc atgttgattg     4860
taacgatgac agagcgttgc tgcctgtgat caaatatcat ctccctcgca gagatccgaa    4920
ttatcagcct tcttattcat ttctcgctta accgtgacag gctgtcgatc ttgagaacta    4980
tgccgacata ataggaaatc gctggataaa gccgctgagg aagctgagtg gcgctatttc    5040
tttagaagtg aacgttgacg atcgtcgacc gtaccccgat gaattaattc ggacgtacgt    5100
```

```
tctgaacaca gctggatact tacttgggcg attgtcatac atgacatcaa caatgtaccc    5160
gtttgtgtaa ccgtctcttg gaggttcgta tgacactagt ggttcccctc agcttgcgac    5220
tagatgttga ggcctaacat tttattagag agcaggctag ttgcttagat acatgatctt    5280
caggccgtta tctgtcaggg caagcgaaaa ttggccattt atgacgacca atgcccccgca   5340 gaagctccca tctttgccgc catagacgcc gcgcccccct tttggggtgt agaacatcct    5400
tttgccagat gtggaaaaga agttcgttgt cccattgttg gcaatgacgt agtagccggc    5460
gaaagtgcga gacccatttg cgctatatat aagcctacga tttccgttgc gactattgtc    5520
gtaattggat gaactattat cgtagttgct ctcagagttg tcgtaatttg atggactatt    5580
gtcgtaattg cttatggagt tgtcgtagtt gcttggagaa atgtcgtagt tggatgggga    5640
gtagtcatag gaagacgag cttcatccac taaaacaatt gcaggtcag caagtgcctg       5700 ccccgatgcc atcgcaagta cgaggcttag aaccaccttc aacagatcgc gcatagtctt    5760
ccccagctct ctaacgcttg agttaagccg cgccgcgaag cggcgtcggc ttgaacgaat    5820
tgttagacat tatttgccga ctaccttggt gatctcgcct ttcacgtagt gaacaaattc    5880
ttccaactga tctgcgcgcg aggccaagcg atcttcttgt ccaagataag cctgcctagc    5940
ttcaagtatg acgggctgat actgggccgg caggcgctcc attgcccagt cggcagcgac    6000
atccttcggc gcgattttgc cggttactgc gctgtaccaa atgcgggaca acgtaagcac    6060
tacatttcgc tcatcgccag cccagtcggg cggcgagttc catagcgtta aggtttcatt    6120
tagcgcctca aatagatcct gttcaggaac cggatcaaag agttcctccg ccgctggacc    6180
taccaaggca acgctatgtt ctcttgcttt tgtcagcaag atagccagat caatgtcgat    6240
cgtggctggc tcgaagatac ctgcaagaat gtcattgcgc tgccattctc caaattgcag    6300
ttcgcgctta gctggataac gccacggaat gatgtcgtcg tgcacaacaa tggtgacttc    6360
tacagcgcgg agaatctcgc tctctccagg ggaagccgaa gttccaaaa ggtcgttgat      6420 caaagctcgc cgcgttgttt catcaagcct tacagtcacc gtaaccagca atcaatatc     6480 actgtgtggc ttcaggccgc catccactgc ggagccgtac aaatgtacgg ccagcaacgt    6540
cggttcgaga tggcgctcga tgacgccaac tacctctgat agttgagtcg atacttcggc    6600
gatcaccgct tccctcatga tgtttaactc ctgaattaag ccgcgccgcg aagcggtgtc    6660
ggcttgaatg aattgttagg cgtcatcctg tgctcccgag aaccagtacc agtacatcgc    6720
tgtttcgttc gagacttgag gtctagtttt atacgtgaac aggtcaatgc cgccgagagt    6780
aaagccacat tttgcgtaca aattgcaggc aggtacattg ttcgtttgtg tctctaatcg    6840
tatgccaagg agctgtctgc ttagtgccca cttttttcgca aattcgatga gactgtgcgc    6900
gactcctttg cctcggtgcg tgtgcgacac aacaatgtgt tcgatagagg ctagatcgtt    6960
ccatgttgag ttgagttcaa tcttcccgac aagctcttgg tcgatgaatg cgccatagca    7020
agcagagtct tcatcagagt catcatccga gatgtaatcc ttccggtagg ggctcacact    7080
tctggtagat agttcaaagc cttggtcgga taggtgcaca tcgaacactt cacgaacaat    7140
gaaatggttc tcagcatcca atgtttccgc cacctgctca gggatcaccg aaatcttcat    7200
atgacgccta acgcctggca cagcggatcg caaacctggc gcggcttttg cacaaaagg     7260 cgtgacaggt ttgcgaatcc gttgctgcca cttgttaacc cttttgccag atttggtaac    7320
tataatttat gttagaggcg aagtcttggg taaaaactgg cctaaaattg ctggggattt    7380
caggaaagta aacatcacct tccggctcga tgtctattgt agatatatgt agtgtatcta    7440
```

```
cttgatcggg ggatctgctg cctcgcgcgt ttcggtgatg acggtgaaaa cctctgacac    7500
atgcagctcc cggagacggt cacagcttgt ctgtaagcgg atgccggag cagacaagcc    7560 cgtcagggcg cgtcagcggg tgttggcggg tgtcggggcg cagccatgac ccagtcacgt    7620
agcgatagcg gagtgtatac tggcttaact atgcggcatc agagcagatt gtactgagag    7680
tgcaccatat gcggtgtgaa ataccgcaca gatgcgtaag gagaaaatac cgcatcaggc    7740
gctcttccgc ttcctcgctc actgactcgc tgcgctcggt cgttcggctg cggcgagcgg    7800
tatcagctca ctcaaaggcg gtaatacggt tatccacaga atcaggggat aacgcaggaa    7860
agaacatgtg agcaaaaggc cagcaaaagg ccaggaaccg taaaaaggcc gcgttgctgg    7920 cgttttttcca taggctccgc cccctgacg agcatcacaa aaatcgacgc tcaagtcaga    7980
ggtggcgaaa cccgacagga ctataaagat accaggcgtt tccccctgga agctccctcg    8040
tgcgctctcc tgttccgacc ctgccgctta ccggatacct gtccgccttt ctcccttcgg    8100
gaagcgtggc gctttctcat agctcacgct gtaggtatct cagttcggtg taggtcgttc    8160
gctccaagct gggctgtgtg cacgaacccc ccgttcagcc cgaccgctgc gccttatccg    8220
gtaactatcg tcttgagtcc aacccggtaa gacacgactt atcgccactg gcagcagcca    8280
ctggtaacag gattagcaga gcgaggtatg taggcggtgc tacagagttc ttgaagtggt    8340
ggcctaacta cggctacact agaaggacag tatttggtat ctgcgctctg ctgaagccag    8400
ttaccttcgg aaaaagagtt ggtagctctt gatccggcaa acaaaccacc gctggtagcg    8460
gtggtttttt tgtttgcaag cagcagatta cgcgcagaaa aaaaggatct caagaagatc    8520
ctttgatctt ttctacgggg tctgacgctc agtggaacga aaactcacgt taagggattt    8580
tggtcatgag attatcaaaa aggatcttca cctagatcct tttaaattaa aaatgaagtt    8640
ttaaatcaat ctaaagtata tatgagtaaa cttggtctga cagttaccaa tgcttaatca    8700
gtgaggcacc tatctcagcg atctgtctat ttcgttcatc catagttgcc tgactccccg    8760
tcgtgtagat aactacgata cgggagggct taccatctgg ccccagtgct gcaatgatac    8820
cgcgagaccc acgctcaccg gctccagatt tatcagcaat aaaccagcca gccggaaggg    8880
ccgagcgcag aagtggtcct gcaactttat ccgcctccat ccagtctatt aattgttgcc    8940
gggaagctag agtaagtagt tcgccagtta atagtttgcg caacgttgtt gccattgctg    9000 caggggggggg gggggggggg gacttccatt gttcattcca cggacaaaaa cagagaaagg    9060
aaacgacaga ggccaaaaag cctcgctttc agcacctgtc gtttcctttc ttttcagagg    9120
gtattttaaa taaaaacatt aagttatgac gaagaagaac ggaaacgcct taaaccggaa    9180
aattttcata aatagcgaaa acccgcgagg tcgccgcccc gtaacctgtc ggatcaccgg    9240
aaaggacccg taaagtgata atgattatca tctacatatc acaacgtgcg tggaggccat    9300
caaaccacgt caaataatca attatgacgc aggtatcgta ttaattgatc tgcatcaact    9360
taacgtaaaa acaacttcag acaatacaaa tcagcgacac tgaatacggg gcaacctcat    9420 gtccccccccc cccccccccc tgcaggcatc gtggtgtcac gctcgtcgtt tggtatggct    9480
tcattcagct ccggttccca acgatcaagg cgagttacat gatcccccat gttgtgcaaa    9540
aaagcggtta gctccttcgg tcctccgatc gttgtcagaa gtaagttggc cgcagtgtta    9600
tcactcatgg ttatggcagc actgcataat tctcttactg tcatgccatc cgtaagatgc    9660
ttttctgtga ctggtgagta ctcaaccaag tcattctgag aatagtgtat gcggcgaccg    9720
agttgctctt gcccgcgtc aacacgggat aataccgcgc cacatagcag aactttaaaa    9780
gtgctcatca ttggaaaacg ttcttcgggg cgaaaactct caaggatctt accgctgttg    9840
```

```
agatccagtt cgatgtaacc cactcgtgca cccaactgat cttcagcatc ttttactttc   9900
accagcgttt ctgggtgagc aaaaacagga aggcaaaatg ccgcaaaaaa gggaataagg   9960
gcgacacgga aatgttgaat actcatactc ttccttttc aatattattg aagcatttat  10020
cagggttatt gtctcatgag cggatacata tttgaatgta tttagaaaaa taaacaaata  10080
ggggttccgc gcacatttcc ccgaaaagtg ccacctgacg tctaagaaac cattattatc  10140
atgacattaa cctataaaaa taggcgtatc acgaggccct ttcgtcttca agaattggtc  10200
gacgatcttg ctgcgttcgg atattttcgt ggagttcccg ccacagaccc ggattgaagg  10260
cgagatccag caactcgcgc cagatcatcc tgtgacggaa ctttggcgcg tgatgactgg  10320
ccaggacgtc ggccgaaaga gcgacaagca gatcacgctt ttcgacagcg tcggatttgc  10380
gatcgaggat ttttcggcgc tgcgctacgt ccgcgaccgc gttgagggat caagccacag  10440
cagcccactc gaccttctag ccgacccaga cgagccaagg gatctttttg gaatgctgct  10500
ccgtcgtcag gctttccgac gtttgggtgg ttgaacagaa gtcattatcg tacgaatgc  10560 caagcactcc cgaggggaac cctgtggttg gcatgcacat acaaatggac gaacggataa  10620
accttttcac gcccttttaa atatccgtta ttctaataaa cgctcttttc tcttaggttt  10680
acccgccaat atatcctgtc aaacactgat agtttaaact gaaggcggga aacgacaatc  10740
tgatcatgag cggagaatta agggagtcac gttatgaccc ccgccgatga cgcgggacaa  10800
gccgttttac gtttggaact gacagaaccg caacgttgaa ggagccactc agcaagctgg  10860
tacgattgta atacgactca ctatagggcg aattgagcgc tgtttaaacg ctcttcaact  10920
ggaagagcgg ttacccggac cgaagcttga agttcctatt ccgaagttcc tattctctag  10980
aaagtatagg aacttcagat ctcgatgctc accctgttgt ttggtgttac ttctgcaggt  11040
cgactctaga ggatccacca tgagcccaga acgacgcccg ccgacatcc gccgtgccac  11100 cgaggcggac atgccggcgg tctgcaccat cgtcaaccac tacatcgaga caagcacggt  11160
caacttccgt accgagccgc aggaaccgca ggactggacg gacgacctcg tccgtctgcg  11220
ggagcgctat ccctggctcg tcgccgaggt ggacggcgag gtcgccggca tcgcctacgc  11280
gggcccctgg aaggcacgca acgcctacga ctggacggcc gagtcgaccg tgtacgtctc  11340
cccccgccac cagcggacgg gactgggctc cacgctctac acccacctgc tgaagtccct  11400
ggaggcacag ggcttcaaga gcgtggtcgc tgtcatcggg ctgcccaacg acccgagcgt  11460
gcgcatgcac gaggcgctcg gatatgcccc ccgcggcatg ctgcgggcgg ccggcttcaa  11520
gcacgggaac tggcatgacg tgggtttctg gcagctggac ttcagcctgc cggtaccgcc  11580
ccgtccggtc ctgcccgtca ccgagatctg atccgtcgac caacctagac ttgtccatct  11640
tctggattgg ccaacttaat taatgtatga aataaaagga tgcacacata gtgacatgct  11700
aatcactata atgtgggcat caaagttgtg tgttatgtgt aattactagt tatctgaata  11760
aaagagaaag agatcatcca tatttcttat cctaaatgaa tgtcacgtgt ctttataatt  11820
ctttgatgaa ccagatgcat ttcattaacc aaatccatat acatataaat attaatcata  11880
tataattaat atcaattggg ttagcaaaac aaatctagtc taggtgtgtt ttgcgaattg  11940
cggccgcgat ctgggaatt cccatggaca ccggtaattc ccatgatctt ctctccttca  12000
tcaatggatg ccatgtttca taacaataac accaaatgtt tgatgagcta ccaacaattg  12060
cgcaaagact atggctaagc tcgagctcgc tcgctacaag ttgttgactt tcaaatacaa  12120
gtttgttttt ggaacaccaa atattctaca tgatctttca ctaagttgcg caccactatc  12180
```

| | |
|---|---:|
| aaaagattat ctaggccatt attcaagtaa agagtgaaca cgtctaagac ccacaaccac | 12240 |
| accaaataga atacgcatac atgcaacata ttgtgcaaga agtatccaac tggactccca | 12300 |
| tgtattctaa aactattttc gtagagttaa agttatgaca aacttatcaa ataaaaattt | 12360 |
| gaacgctgga ccaaaacttt catctttcaa atccaccatc gtctatcctc ataaattgtt | 12420 |
| ttgattataa cacatctacg taaatcattt gttttgaaca atactaattt aattttatta | 12480 |
| agtcaaataa cctgcttaga aaataatccc tccacctcat ttaacaattt cttgtcaaac | 12540 |
| acacaccaag aaaaaaatta tgaaagaga aaagaaatga aaggacatg gagttgaata | 12600 |
| ctagcaaaat tgattgaagg aagattcaca attgaaattg aaaccattta atttattttc | 12660 |
| gggtccataa taataaattg gtaagaataa aaacccgatc aagtccggta cagtacaatt | 12720 |
| ccactccacc aactccttac ttaaacccct atttataccc actctcatcc tcactcttcc | 12780 |
| ttcacctctc acactctctt ctctctctca aaaccctcac acaaacgctg cgtttagtgt | 12840 |
| aagaaattca atccgg | 12856 |

<210> SEQ ID NO 30
<211> LENGTH: 825
<212> TYPE: DNA
<213> ORGANISM: Zea mays

<400> SEQUENCE: 30

| | |
|---|---:|
| aaatccttac agaattgctg tagtttcata gtgctagatg tggacagcaa agcgccgctg | 60 |
| tatgcttctg ctttctttt tggtgtgtg tagccacatc ctttgttcct gcccggcgcc | 120 |
| atcccacttg gttgttttt tttatgattg aaagccttca tgcttcctcg gtcaatcacc | 180 |
| ggtgcgcact gggagcatcg ccggaaaaaa aattcttcgg ctaagagtaa cttctttctc | 240 |
| cttttcttct ctgatctcgc gagcagtgct gataacgtgt tgtaatctac ttagcggtaa | 300 |
| cgagattgag agagacaaaa tgacagaact attgtcttta ttgcagagtg tcatgtattt | 360 |
| atacagggga tacaaagtct cccaggggt gtgtcccttg ggagtaactg ccagttgatc | 420 |
| acaggacaat attttgtaac aaaacgtaca catcgtcaaa atagcgaggc atgaaactgg | 480 |
| ccttggccat ggacgcgtga agcgcgccat gcgttggata tgtggtcaat aagtatatac | 540 |
| aatacaatgt ttaacagagc tgatagtact gctttggcac attttttgtcc acgcttcatg | 600 |
| agagataaaa cacctgcacg taaattcaca tgctgcactg aaggcccgat cactgaggag | 660 |
| cgaactgccg taactcccctt ctatatatac ccccagtccc tgtttcagtt ttcgtcaagc | 720 |
| tagcagcacc aagttgtcga tcacttgcct gctcttgagc tcgattaagc tatcatcagc | 780 |
| tacagcatcc gatcccaaac tgcaactgta gcagcgacaa ctgcc | 825 |

<210> SEQ ID NO 31
<211> LENGTH: 860
<212> TYPE: DNA
<213> ORGANISM: Zea mays

<400> SEQUENCE: 31

| | |
|---|---:|
| ctggtaatta ttggctgtag gattctaaac agagcctaaa tagctggaat agctctagcc | 60 |
| ctcaatccaa actaatgata tctatactta tgcaactcta atttttatt ctaaaagtaa | 120 |
| tatttcattt ttgtcaacga gattctctac tctattccac aatcttttga agcaatattt | 180 |
| accttaaatc tgtactctat accaataatc atatattcta ttatttattt ttatctctct | 240 |
| cctaaggagc atcccctat gtctgcatgg ccccgcctc gggtcccaat ctcttgctct | 300 |
| gctagtagca cagaagaaaa cactagaaat gacttgcttg acttagagta tcagataaac | 360 |

```
atcatgttta cttaacttta atttgtatcg gtttctacta ttttttataat attttttgtct    420 ctatagatac tacgtgcaac agtataatca acctagttta atccagagcg aaggattttt    480
tactaagtac gtgactccat atgcacagcg ttccttttat ggttcctcac tgggcacagc    540
ataaacgaac cctgtccaat gttttcagcg cgaacaaaca gaaattccat cagcgaacaa    600
acaacataca tgcgagatga aaataaataa taaaaaaagc tccgtctcga taggccggca    660
cgaatcgaga gcctccatag ccagttttt ccatcggaac ggcggttcgc gcacctaatt    720
atatgcacca cacgcctata aagccaacca acccgtcgga ggggcgcaag ccagacagaa    780
gacagcccgt cagcccctct cgttttcat ccgccttcgc ctccaaccgc gtgcgctcca    840
cgcctcctcc aggaaagcga                                                 860
```

<210> SEQ ID NO 32
<211> LENGTH: 899
<212> TYPE: DNA
<213> ORGANISM: Zea mays

<400> SEQUENCE: 32

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg    300 caaatagctt cacctatata atacttcatc cattttatta gtacatccat ttagggttta    360
gggttaatgg ttttatagaa ctaatttttt tagtacatct attttattct attttagcct    420
ctaaattaag aaaactaaaa ctctatttta gtttttttat ttaataattt agatataaaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccccct ctcgagagtt ccgctccacc gttggacttg    720
ctccgctgtc ggcatccaga aattgcgtgg cggagcggca gacgtgagcc ggcacggcag    780
gcggcctcct cctcctctca cggcacggca gctacggggg attcctttcc caccgctcct    840
tcgctttccc ttcctcgccc gccgtaataa atagacaccc cctccacacc ctctttccc     899
```

<210> SEQ ID NO 33
<211> LENGTH: 879
<212> TYPE: DNA
<213> ORGANISM: Medicago sativa

<400> SEQUENCE: 33

```
aattcccatg atcttctctc cttcatcaat ggatgccatg tttcataaca ataacaccaa     60
atgtttgatg agctaccaac aattgcgcaa agactatggc taagctcgag ctcgctcgct    120
acaagttgtt gactttcaaa tacaagtttg ttttttggaac accaaatatt ctacatgatc    180
tttcactaag ttgcgcacca ctatcaaaag attatctagg ccattattca agtaaagagt    240
gaacacgtct aagacccaca accacaccaa atagaatacg catacatgca acatattgtg    300
caagaagtat ccaactggac tcccatgtat tctaaaacta ttttcgtaga gttaaagtta    360
tgacaaactt atcaaataaa aatttgaacg ctggaccaaa actttcatct ttcaaatcca    420
```

```
ccatcgtcta tcctcataaa ttgttttgat tataacacat ctacgtaaat catttgtttt      480
gaacaatact aatttaattt tattaagtca aataacctgc ttagaaaata atccctccac      540
ctcatttaac aatttcttgt caaacacaca ccaagaaaaa aattaatgaa agagaaaaga      600
aatgaaaagg acatggagtt gaatactagc aaaattgatt gaaggaagat tcacaattga      660
aattgaaacc atttaattta ttttcgggtc cataataata aattggtaag aataaaaacc      720
cgatcaagtc cggtacagta caattccact ccaccaactc cttacttaaa cccctattta      780
tacccactct catcctcact cttccttcac ctctcacact ctcttctctc tctcaaaacc      840
ctcacacaaa cgctgcgttt agtgtaagaa attcaatcc                            879
```

```
<210> SEQ ID NO 34
<211> LENGTH: 318
<212> TYPE: DNA
<213> ORGANISM: Solanum tuberosum

<400> SEQUENCE: 34
agacttgtcc atcttctgga ttggccaact taattaatgt atgaaataaa aggatgcaca       60
catagtgaca tgctaatcac tataatgtgg gcatcaaagt tgtgtgttat gtgtaattac      120
tagttatctg aataaaagag aaagagatca tccatatttc ttatcctaaa tgaatgtcac      180
gtgtctttat aattctttga tgaaccagat gcatttcatt aaccaaatcc atatacatat      240
aaatattaat catatataat taatatcaat tgggttagca aaacaaatct agtctaggtg      300
tgttttgcga attgcggc                                                   318
```

```
<210> SEQ ID NO 35
<211> LENGTH: 2228
<212> TYPE: DNA
<213> ORGANISM: Zea mays

<400> SEQUENCE: 35
gtttctcttt tgtttcgcac ccctccatcc ttcactcctc gctggtccag ccattaatgc       60
caccacctgc tatacatcac taccttcctc ttccctcccg cagtctccga cctctctctc      120
tcctctctct ttcttttttct ctctctccct cgctttttct gctgtctatc cccgcgccgc     180
gcgaggttgc tgccttggcc ttgctggttc tttgcttgtg ggatgagtgg aaggaaggcc      240
ggtcctcgct gcagaaagag ggagaagact tcatctgcac gtgctgctga tgtgcattag      300
aggatccgtg ctgataatat acagctgaca cccacaagat cgactggata agttcgagcc      360
tgacggcatc atgggttccg gcgatttgag ctcggagatg gagaggacgg ttcttggcct      420
gacgctgtgg gtctggattg ccatcggcgt ggtcgcgctt ctcgtggcaa tcctgctgat      480
gatctgcatt tgggtggcgt cccgcctgag gaccaagaga accatggaca gcctgaggca      540
gacgcagatc cccatctact ccaaggagat ccccatcgac cgggtcggcg gcgcagcct       600 ggcacagaca atgcatgagc gcgagcagcc gagcttgccg ccgccggaca agtacgcgaa      660
ccgggagccg gccggggcgg ctgtggggca cctggcactc agcaagtcct cggatcatga      720
caacatgagc caggggagct cggtttgcaa tgctgaccgt gctggcactg gcagcatgca      780
ctccggtgag gatgggagct caggacctcg gaggaaaccc aactctcctg cggcgttcgt      840
gtcagcttcg cccttggttg gccttccgga gttctcgcat cttggttggg gtcactggtt      900
tactcagcgt gaccttgaac ttgctaccaa ccgcttctct aaggagaatg tgctcgggga      960
gggtggttat ggagttgtgt accgtggacg tctggtgaat ggaactgaag tcgcaataaa     1020
aaagatcttt aacaacatgg ggcaggcaga aaaagaattc agagtggaag ttgaggctat     1080
```

-continued

```
tggccatgtc cgacataaga atttggttcg gctgttggga tattgtgttg agggcgtaaa    1140
caggatgcta gtatatgagt tcgtgaacaa tggtaattta gagcagtggc ttcatggagc    1200
tatgcatcag cgtggtgttt ttagctggga aaatcgcatg aaggttgtaa caggcactgc    1260
aaaagcgctt gcttaccttc atgaagctat tgagccaaaa gttgtacatc gagatataaa    1320
atcaagcaac atattgattg atgatgaatt taatggcaaa gtatctgact ttggattggc    1380 taaactttg ggatcagaca aaagccacat tactactaga gtgatgggaa catttggata    1440
tgttgcacct gaatatgcta atactggaat gttaaatgaa aagagtgacg tttacagttt    1500
tggcgttctc ttgttagaaa ctgtgacagg aaggaatcct gttgactaca gccgatcttc    1560
caatgaggtc aatcttgttg aatggcttaa acaatggtg gccaatcgga gggcagagga    1620
agtggctgat ccaagcttag aggctagacc cagtatccgg gctctcaagc gggctctttt    1680
ggtggcactg aggtgtgttg atcctgactc tgaaaagaga cctaagatgg gccaggttgt    1740
taggatgctt gagtcagaag aagtaccata ccgggaggat cggagaaatc gtagaagtcg    1800
cactggaagc atggatattg agtccattgc agagggttcc aactctgcgg agtttggaaa    1860
gaaggtagaa aggactggaa gctctatatc tgacagatct caaccatgag gcctggaaat    1920
ctaagctata tcaggaactg tctcagaaac gatgttaatc accaaggtga ttgctgtcct    1980
gataggggat gctggtaggt gacagaggca aggcaggccc aggtattact gcctaagtat    2040
taggctttag ttttcaggtg cagtagaagc attcttggat gaggaacctc ctggtctcct    2100
cttatttgta taggtatatg ttggtgcctg aggaattcct cttggtttgg gtgtttaaca    2160
tttgttcggt tcttttattt cttgcattgt tgccttctta aaaaaaaaaa aaaaaaaaa    2220 aaaaaaag                                                             2228
```

<210> SEQ ID NO 36
<211> LENGTH: 512
<212> TYPE: PRT
<213> ORGANISM: Zea mays

<400> SEQUENCE: 36

```
Met Gly Ser Gly Asp Leu Ser Ser Glu Met Glu Arg Thr Val Leu Gly
1               5                   10                  15

Leu Thr Leu Trp Val Trp Ile Ala Ile Gly Val Val Ala Leu Leu Val
            20                  25                  30

Ala Ile Leu Leu Met Ile Cys Ile Trp Val Ala Ser Arg Leu Arg Thr
        35                  40                  45

Lys Arg Thr Met Asp Ser Leu Arg Gln Thr Gln Ile Pro Ile Tyr Ser
    50                  55                  60

Lys Glu Ile Pro Ile Asp Arg Val Gly Arg Ser Leu Ala Gln Thr
65                  70                  75                  80

Met His Glu Arg Glu Gln Pro Ser Leu Pro Pro Asp Lys Tyr Ala
                85                  90                  95

Asn Arg Glu Pro Ala Gly Ala Ala Val Gly His Leu Ala Leu Ser Lys
            100                 105                 110

Ser Ser Asp His Asp Asn Met Ser Gln Gly Ser Val Cys Asn Ala
        115                 120                 125

Asp Arg Ala Gly Thr Gly Ser Met His Ser Gly Glu Asp Gly Ser Ser
    130                 135                 140

Gly Pro Arg Arg Lys Pro Asn Ser Pro Ala Ala Phe Val Ser Ala Ser
145                 150                 155                 160
```

-continued

Pro Leu Val Gly Leu Pro Glu Phe Ser His Leu Gly Trp Gly His Trp
            165                 170                 175

Phe Thr Gln Arg Asp Leu Glu Leu Ala Thr Asn Arg Phe Ser Lys Glu
            180                 185                 190

Asn Val Leu Gly Glu Gly Gly Tyr Gly Val Val Tyr Arg Gly Arg Leu
            195                 200                 205

Val Asn Gly Thr Glu Val Ala Ile Lys Lys Ile Phe Asn Asn Met Gly
            210                 215                 220

Gln Ala Glu Lys Glu Phe Arg Val Glu Val Ala Ile Gly His Val
225                 230                 235                 240

Arg His Lys Asn Leu Val Arg Leu Leu Gly Tyr Cys Val Glu Gly Val
            245                 250                 255

Asn Arg Met Leu Val Tyr Glu Phe Val Asn Asn Gly Asn Leu Glu Gln
            260                 265                 270

Trp Leu His Gly Ala Met His Gln Arg Gly Val Phe Ser Trp Glu Asn
            275                 280                 285

Arg Met Lys Val Val Thr Gly Thr Ala Lys Ala Leu Ala Tyr Leu His
            290                 295                 300

Glu Ala Ile Glu Pro Lys Val Val His Arg Asp Ile Lys Ser Ser Asn
305                 310                 315                 320

Ile Leu Ile Asp Asp Glu Phe Asn Gly Lys Val Ser Asp Phe Gly Leu
            325                 330                 335

Ala Lys Leu Leu Gly Ser Asp Lys Ser His Ile Thr Thr Arg Val Met
            340                 345                 350

Gly Thr Phe Gly Tyr Val Ala Pro Glu Tyr Ala Asn Thr Gly Met Leu
            355                 360                 365

Asn Glu Lys Ser Asp Val Tyr Ser Phe Gly Val Leu Leu Leu Glu Thr
            370                 375                 380

Val Thr Gly Arg Asn Pro Val Asp Tyr Ser Arg Ser Ser Asn Glu Val
385                 390                 395                 400

Asn Leu Val Glu Trp Leu Lys Thr Met Val Ala Asn Arg Arg Ala Glu
            405                 410                 415

Glu Val Ala Asp Pro Ser Leu Glu Ala Arg Pro Ser Ile Arg Ala Leu
            420                 425                 430

Lys Arg Ala Leu Leu Val Ala Leu Arg Cys Val Asp Pro Asp Ser Glu
            435                 440                 445

Lys Arg Pro Lys Met Gly Gln Val Val Arg Met Leu Glu Ser Glu Glu
            450                 455                 460

Val Pro Tyr Arg Glu Asp Arg Arg Asn Arg Arg Ser Arg Thr Gly Ser
465                 470                 475                 480

Met Asp Ile Glu Ser Ile Ala Glu Gly Ser Asn Ser Ala Glu Phe Gly
            485                 490                 495

Lys Lys Val Glu Arg Thr Gly Ser Ser Ile Ser Asp Arg Ser Gln Pro
            500                 505                 510

<210> SEQ ID NO 37
<211> LENGTH: 509
<212> TYPE: PRT
<213> ORGANISM: Oryza sativa

<400> SEQUENCE: 37

Met Gly Ser Ser Asp Leu Ser Ser Glu Met Arg Arg Thr Val Leu Gly
1               5                   10                  15

Leu Thr Leu Trp Val Trp Ile Ala Ile Gly Val Val Ala Leu Leu Val
            20                  25                  30

```
Ala Ile Leu Leu Met Ile Cys Ile Trp Met Ala Ser Arg Arg Lys Thr
             35                  40                  45

Lys Arg Thr Met Asp Asn Leu Arg Gln Thr Gln Ile Pro Ile Phe Ser
 50                  55                  60

Lys Glu Ile Pro Val Asp Arg Val Gly Arg Ser Leu Ala Gln Thr
65                   70                  75                  80

Met His Glu Arg Glu Gln Pro Ser Phe Pro Pro Gln Asp Lys His Thr
                 85                  90                  95

Asn Arg Glu Pro Gly Lys Thr Leu Gly His Met Ala Leu Ser Lys Ser
                100                 105                 110

Ser Glu Pro Asp Asn Met Ser Gln Gly Ser Ser Val Cys Asn Val Asp
            115                 120                 125

Arg Ala Gly Ser Val His Ser Gly Glu Asp Gly Ser Thr Gly His Gly
130                 135                 140

Arg Lys Pro Tyr Ser Pro Ala Ala Phe Val Ser Ala Ser Pro Leu Val
145                 150                 155                 160

Gly Leu Pro Glu Phe Ser His Leu Gly Trp Gly His Trp Phe Thr Leu
                165                 170                 175

Arg Asp Leu Glu Leu Ala Thr Asn Arg Phe Ser Arg Glu Asn Val Leu
            180                 185                 190

Gly Glu Gly Gly Tyr Gly Val Val Tyr Arg Gly Arg Leu Val Asn Gly
            195                 200                 205

Thr Glu Val Ala Ile Lys Lys Ile Phe Asn Asn Met Gly Gln Ala Glu
210                 215                 220

Lys Glu Phe Arg Val Glu Val Glu Ala Ile Gly His Val Arg His Lys
225                 230                 235                 240

Asn Leu Val Arg Leu Leu Gly Tyr Cys Val Glu Gly Val Asn Arg Met
                245                 250                 255

Leu Val Tyr Glu Phe Val Asn Asn Gly Asn Leu Glu Gln Trp Leu His
            260                 265                 270

Gly Ala Met Arg Gln His Gly Val Phe Ser Trp Glu Asn Arg Met Lys
            275                 280                 285

Val Val Ile Gly Thr Ala Lys Ala Leu Ala Tyr Leu His Glu Ala Ile
290                 295                 300

Glu Pro Lys Val Val His Arg Asp Ile Lys Ser Ser Asn Ile Leu Ile
305                 310                 315                 320

Asp Glu Glu Phe Asn Gly Lys Val Ser Asp Phe Gly Leu Ala Lys Leu
                325                 330                 335

Leu Gly Ser Asp Lys Ser His Ile Thr Thr Arg Val Met Gly Thr Phe
            340                 345                 350

Gly Tyr Val Ala Pro Glu Tyr Ala Asn Thr Gly Met Leu Asn Glu Lys
            355                 360                 365

Ser Asp Val Tyr Ser Phe Gly Val Leu Leu Leu Glu Thr Val Thr Gly
370                 375                 380

Arg Glu Pro Val Asp Tyr Ser Arg Ser Gly Asn Glu Val Asn Leu Val
385                 390                 395                 400

Glu Trp Leu Lys Ile Met Val Ala Asn Arg Arg Ala Glu Glu Val Val
                405                 410                 415

Asp Pro Ile Leu Glu Val Arg Pro Thr Val Arg Ala Ile Lys Arg Ala
            420                 425                 430

Leu Leu Val Ala Leu Arg Cys Val Asp Pro Asp Ser Glu Lys Arg Pro
            435                 440                 445
```

```
                                    -continued
Lys Met Gly Gln Val Val Arg Met Leu Glu Ser Glu Glu Val Pro Tyr
    450                 455             460

Arg Glu Asp Arg Arg Asn Arg Arg Ser Arg Thr Gly Ser Met Asp Ile
465             470             475             480

Glu Ser Ile Ala Glu Gly Ser Asn Ser Thr Glu Phe Ala Asn Lys Val
                485             490             495

Glu Arg Thr Gly Ser Ser Thr Ser Asp Arg Ser Gln Ser
            500             505
```

PLANTS WITH ALTERED ROOT ARCHITECTURE, RELATED CONSTRUCTS AND METHODS INVOLVING GENES ENCODING LEUCINE RICH REPEAT KINASE (LLRK) POLYPEPTIDES AND HOMOLOGS THEREOF

This application is a continuation of U.S. application Ser. No. 12/274,412 filed Nov. 20, 2008, which claims the benefit of U.S. Provisional Application No. 61/041,281, filed Apr. 1, 2008, and U.S. Provisional Application No. 60/989,161, filed Nov. 20, 2007. The entire contents of these three applications are herein incorporated by reference.

FIELD OF THE INVENTION

The field of invention relates to plant breeding and genetics and, in particular, relates to recombinant DNA constructs useful in plants for altering root architecture.

BACKGROUND OF THE INVENTION

Water and nutrient availability limit plant growth in all but a very few natural ecosystems. They limit yield in most agricultural ecosystems. Plant roots serve important functions such as water and nutrient uptake, anchorage of the plants in the soil and the establishment of biotic interactions at the rhizosphere. Elucidation of the genetic regulation of plant root development and function is therefore the subject of considerable interest in agriculture and ecology.

The root system originates from a primary root that develops during embryogenesis. The primary root produces secondary roots, which in turn produce tertiary roots. All secondary, tertiary, quaternary and further roots are referred to as lateral roots. Many plants, including maize, can also produce shoot borne roots, from consecutive under-ground nodes (crown roots) or above-ground nodes (brace roots). Three major processes affect the overall architecture of the root system. First, cell division at the primary root meristem enables indeterminate growth by adding new cells to the root. Second, lateral root formation increases the exploratory capacity of the root system. Third, root-hair formation increases the total surface of primary and lateral roots (Lopez-Bucio et al., Current Opinion in Plant Biology (2003) 6:280-287). In maize mutants have been isolated that are missing only a subset of root types. In *Arabidopsis*, mutations in root patterning genes such as SHORTROOT and SCARECROW, which show developmental defects in primary and lateral roots, have been identified (J. E. Malamy, Plant, Cell and Environment (2005) 28: 67-77).

A number of maize mutants affected specifically in root development have been identified (Hochholdinger et al 2004, Annals of Botany 93:359-368). The recessive mutants rtcs and rt1 forms no, or fewer, crown and brace roots, while the primary and lateral roots are not affected. In the recessive mutants des21, lateral seminal roots and root hairs are absent. Root hairs are lacking in the recessive mutant rth1-3. The mutants lrt1 and rum1 are affected before lateral root initiation and mutants slr1 and slr2 are impaired in lateral root elongation. Intrinsic response pathways that determine root system architecture include hormones, cell cycle regulators and regulatory genes. Water stress and nutrient availability belong to the environmental response pathways that determine root system architecture.

U.S. Application No. 2005-57473 filed Feb. 14, 2005 (U.S. Patent Publication No. 2005/223429 A1 published Oct. 6, 2005) concerns the use of *Arabidopsis* cytokinin oxidase genes to alter cytokinin levels in plants and stimulate root growth.

U.S. Pat. No. 6,344,601 (issued Feb. 5, 2002) concerns the under- or overexpression of profilin in a plant cell to alter plant growth habit, e.g. a reduced root and root hair system, delay in the onset of flowering.

WO2004/US16432 (filed May 21, 2004 (WO2004/106531 published Dec. 9, 2004) concerns the use of methods to manipulate the growth rate and/or yield and/or architecture by over expression of cis-prenyltransferase.

U.S. Application No. 2004/489500 filed Sep. 30, 2004 (U.S. Patent Publication No. 2005/059154 A1 published Mar. 13, 2005) concerns methods to modify cell number, architecture and yield using over expression of the transcription factor E2F in plants.

Activation tagging can be utilized to identify genes with the ability to affect a trait. This approach has been used in the model plant species *Arabidopsis thaliana* (Weigel et al., 2000, Plant Physiol. 122:1003-1013).

Insertions of transcriptional enhancer elements can dominantly activate and/or elevate the expression of nearby endogenous genes.

SUMMARY OF THE INVENTION

The present invention includes:

In one embodiment, an isolated polynucleotide comprising a nucleic acid sequence encoding a LLRK or LLRK-like polypeptide having an amino acid sequence of at least 80% sequence identity, when compared to SEQ ID NO: 15, or 19, or of at least 85% sequence identity, when compared to SEQ ID NO: 17, based on the Clustal V method of alignment, or a full complement of said nucleic acid sequence.

In a second embodiment, an isolated polynucleotide comprising a nucleic acid sequence encoding a LLRK or LLRK-like polypeptide having an amino acid sequence of at least 85% sequence identity, when compared to SEQ ID NO: 15, or 19, or of at least 90% sequence identity, when compared to SEQ ID NO: 17, based on the Clustal V method of alignment, or a full complement of said nucleic acid sequence.

In a third embodiment, an isolated polynucleotide comprising a nucleic acid sequence encoding a LLRK or LLRK-like polypeptide having an amino acid sequence of at least 90% sequence identity, when compared to SEQ ID NO: 15, or 19, or of at least 95% sequence identity, when compared to SEQ ID NO: 17, based on the Clustal V method of alignment, or a full complement of said nucleic acid sequence.

In a fourth embodiment, an isolated polynucleotide comprising a nucleic acid sequence encoding a LLRK or LLRK-like polypeptide having an amino acid sequence of at least 95% sequence identity, when compared to SEQ ID NO:15, or 19, based on the Clustal V method of alignment, or a full complement of said nucleic acid sequence.

In a fifth embodiment, an isolated polynucleotide comprising a nucleic acid sequence encoding a LLRK or LLRK-like polypeptide, wherein the amino acid sequence of the polypeptide comprises SEQ ID NO: 15, 17, 19, or 22.

In a sixth embodiment, an isolated polynucleotide comprising a nucleic acid sequence encoding a LLRK or LLRK-like polypeptide, wherein the nucleic acid sequence comprises SEQ ID NO: 14, 16, 18, or 20.

In further embodiments, vectors and recombinant constructs comprising any of the foregoing polynucleotides and cells comprising the recombinant constructs.

In additional embodiments, methods for transforming a cell with any of the foregoing polynucleotides and for producing and regenerating a transformed plant comprising any of the foregoing polynucleotides.

In another embodiment, a plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal V method of alignment, when compared to SEQ ID NO: 15, 17, 19, 22, or 36 and wherein said plant exhibits altered root architecture when compared to a control plant not comprising said recombinant DNA construct.

In another embodiment, a plant comprising in its genome a recombinant DNA construct comprising:

(a) a polynucleotide operably linked to at least one regulatory element, wherein said polynucleotide encodes a polypeptide having an amino acid sequence of at least 50% sequence identity, based on the Clustal V method of alignment, when compared to SEQ ID NO: 15, 17, 19, 22, or 36 or (b) a suppression DNA construct comprising at least one regulatory element operably linked to: (i) all or part of: (A) a nucleic acid sequence encoding a polypeptide having an amino acid sequence of at least 50% sequence identity, based on the Clustal V method of alignment, when compared to SEQ ID NO: 15, 17, 19, 22, or 36 or (B) a full complement of the nucleic acid sequence of (b)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a LLRK or LLRK-like polypeptide, and wherein said plant exhibits an alteration of at least one agronomic characteristic when compared to a control plant not comprising said recombinant DNA construct.

In another embodiment, a method of altering root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 22, or 36; and (b) regenerating a transgenic plant from the regenerable plant cell after step (a), wherein the transgenic plant comprises in its genome the recombinant DNA construct and exhibits altered root architecture when compared to a control plant not comprising the recombinant DNA construct; and optionally, (c) obtaining a progeny plant derived from the transgenic plant, wherein said progeny plant comprises in its genome the recombinant DNA construct and exhibits altered root architecture when compared to a control plant not comprising the recombinant DNA construct.

In another embodiment, a method of evaluating root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 22, or 36 (b) regenerating a transgenic plant from the regenerable plant cell after step (a), wherein the transgenic plant comprises in its genome the recombinant DNA construct; and (c) evaluating root architecture of the transgenic plant compared to a control plant not comprising the recombinant DNA construct; and optionally, (d) obtaining a progeny plant derived from the transgenic plant, wherein the progeny plant comprises in its genome the recombinant DNA construct; and optionally, (e) evaluating root architecture of the progeny plant compared to a control plant not comprising the recombinant DNA construct.

In another embodiment, a method of evaluating root architecture in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 22, or 36 (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating root architecture of the progeny plant compared to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 22, or 36 (b) regenerating a transgenic plant from the regenerable plant cell after step (a), wherein the transgenic plant comprises in its genome the recombinant DNA construct; and (c) determining whether the transgenic plant exhibits an alteration of at least one agronomic characteristic when compared to a control plant not comprising the recombinant DNA construct; and optionally, (d) obtaining a progeny plant derived from the transgenic plant, wherein the progeny plant comprises in its genome the recombinant DNA construct; and optionally, (e) determining whether the progeny plant exhibits an alteration of at least one agronomic characteristic when compared to a control plant not comprising the recombinant DNA construct.

In another embodiment, a method of determining an alteration of an agronomic characteristic in a plant, comprising (a) introducing into a regenerable plant cell a recombinant DNA construct comprising a polynucleotide operably linked to at least one regulatory sequence, wherein the polynucleotide encodes a polypeptide having an amino acid sequence of at least 50% sequence identity, based on the Clustal V method of alignment, when compared to SEQ ID NO: 15, 17, 19, 22, or 36 (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct.

In another embodiment, a method of determining an alteration of an agronomic characteristic in a plant, comprising:

(a) introducing into a regenerable plant cell a suppression DNA construct comprising at least one regulatory element operably linked to:
(i) all or part of: (A) a nucleic acid sequence encoding a polypeptide having an amino acid sequence of at least 50% sequence identity, based on the Clustal V method of alignment, when compared to SEQ ID NO: 15, 17, 19, 22, or 36, or (B) a full complement of the nucleic acid sequence of (b)(i)(A); or (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a LLRK or LLRK-like polypeptide;

(b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared to a control plant not comprising the suppression DNA construct;

and optionally, (d) obtaining a progeny plant derived from the transgenic plant, wherein the progeny plant comprises in its genome the suppression DNA construct; and optionally, (e) determining whether the progeny plant exhibits an alteration of at least one agronomic characteristic when compared to a control plant not comprising the suppression DNA construct.

In another embodiment, a method of determining an alteration of an agronomic characteristic in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 22, or 36, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a LLRK or LLRK-like polypeptide;

(b) regenerating a transgenic plant from the regenerable plant cell after step (a), wherein the transgenic plant comprises in its genome the suppression DNA construct and exhibits altered root architecture when compared to a control plant not comprising the suppression DNA construct;

(c) obtaining a progeny plant derived from the transgenic plant, wherein the progeny plant comprises in its genome the suppression DNA construct; and (d) determining whether the progeny plant exhibits an alteration of at least one agronomic characteristic when compared to a control plant not comprising the suppression DNA construct.

In another embodiment, a method of altering root architecture in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 22, or 36; or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a LLRK or LLRK-like polypeptide; and (b) regenerating a transgenic plant from the regenerable plant cell after step (a), wherein the transgenic plant comprises in its genome the suppression DNA construct and wherein the transgenic plant exhibits altered root architecture when compared to a control plant not comprising the suppression DNA construct; and optionally, (c) obtaining a progeny plant derived from the transgenic plant, wherein said progeny plant comprises in its genome the recombinant DNA construct and wherein the progeny plant exhibits altered root architecture when compared to a control plant not comprising the suppression DNA construct.

In another embodiment, a method of evaluating root architecture in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 22, or 36, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a LLRK or LLRK-like polypeptide;

(b) regenerating a transgenic plant from the regenerable plant cell after step (a), wherein the transgenic plant comprises in its genome the suppression DNA construct; and (c) evaluating root architecture of the transgenic plant compared to a control plant not comprising the suppression DNA construct;

and optionally, (d) obtaining a progeny plant derived from the transgenic plant, wherein the progeny plant comprises in its genome the suppression DNA construct; and optionally, (e) evaluating root architecture of the progeny plant compared to a control plant not comprising the suppression DNA construct.

In another embodiment, a method of evaluating root architecture in a plant, comprising:

(a) introducing into a regenerable plant cell a suppression DNA construct comprising at least one regulatory element operably linked to:
  (i) all or part of: (A) a nucleic acid sequence encoding a polypeptide having an amino acid sequence of at least 50% sequence identity, based on the Clustal V method of alignment, when compared to SEQ ID NO: 15, 17, 19, 22, or 36, or (B) a full complement of the nucleic acid sequence of (b)(i)(A); or
  (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a LLRK or LLRK-like polypeptide;

(b) regenerating a transgenic plant from the regenerable plant cell after step (a), wherein the transgenic plant comprises in its genome the suppression DNA construct;

(c) obtaining a progeny plant derived from the transgenic plant, wherein the progeny plant comprises in its genome the suppression DNA construct; and (d) evaluating root architecture of the progeny plant compared to a control plant not comprising the suppression DNA construct.

Also included in the present invention is any progeny of the above plants, any seeds of the above plants, and cells from any of the above plants and progeny.

A method of producing seed that can be sold as a product offering with altered root architecture comprising any of the preceding preferred methods, and further comprising obtaining seeds from said progeny plant, wherein said seeds comprise in their genome said recombinant DNA construct.

In another embodiment, this invention also concerns a method of mapping genetic variations related to controlling embryo/endosperm size during seed development and/or altering oil phenotypes in plants comprising:

(a) crossing two plant varieties; and
(b) evaluating genetic variations with respect to:
  (i) a nucleic acid sequence selected from the group consisting of SEQ ID NO: 14, 16, 18, 21, or 35; or
  (ii) a nucleic acid sequence encoding a polypeptide selected from the group consisting of SEQ ID NO: 15, 17, 19, 22, or 36 in progeny plants resulting from the cross of step (a), wherein the evaluation is made using a method selected from the group consisting of RFLP analysis, SNP analysis, and PCR-based analysis.

In another embodiment, this invention concerns a method of molecular breeding to obtain altered embryo/endosperm size during seed development and/or altered oil phenotypes in plants comprising:

(a) crossing two plant varieties; and
(b) evaluating genetic variations with respect to:
  (i) a nucleic acid sequence selected from the group consisting of SEQ ID NO: 14, 16, 18, 21, or 35; or
  (ii) a nucleic acid sequence encoding a polypeptide selected from the group consisting of SEQ ID NO: 15, 17, 19, 22, or 36; in progeny plants resulting from the cross of step (a), wherein the evaluation is made using a method selected from the group consisting of RFLP analysis, SNP analysis, and PCR-based analysis.

BRIEF DESCRIPTION OF THE FIGURES AND SEQUENCE LISTINGS

The invention can be more fully understood from the following detailed description and the accompanying drawings and Sequence Listing which form a part of this application.

Figure 15A:
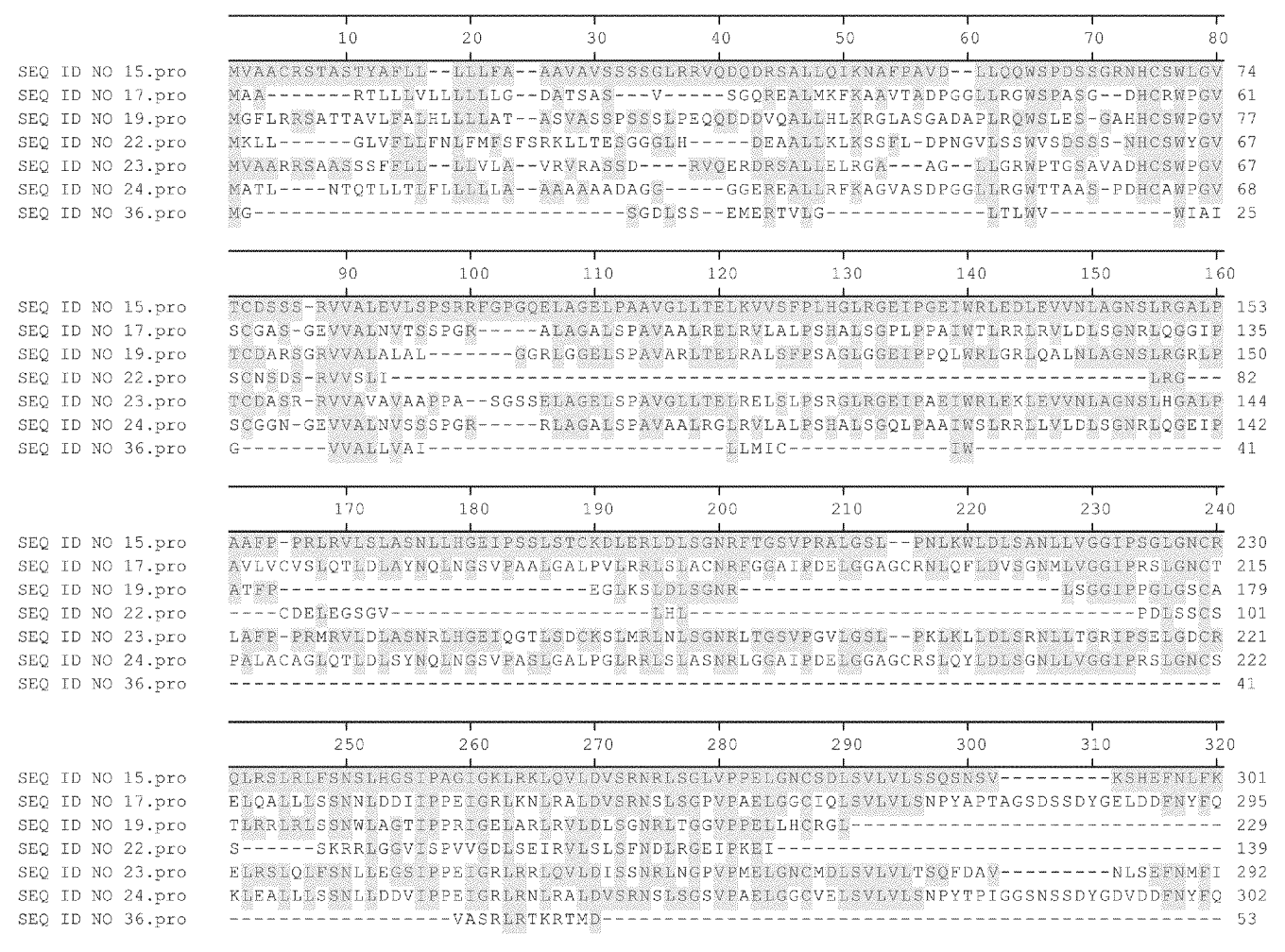
Figure 15C:
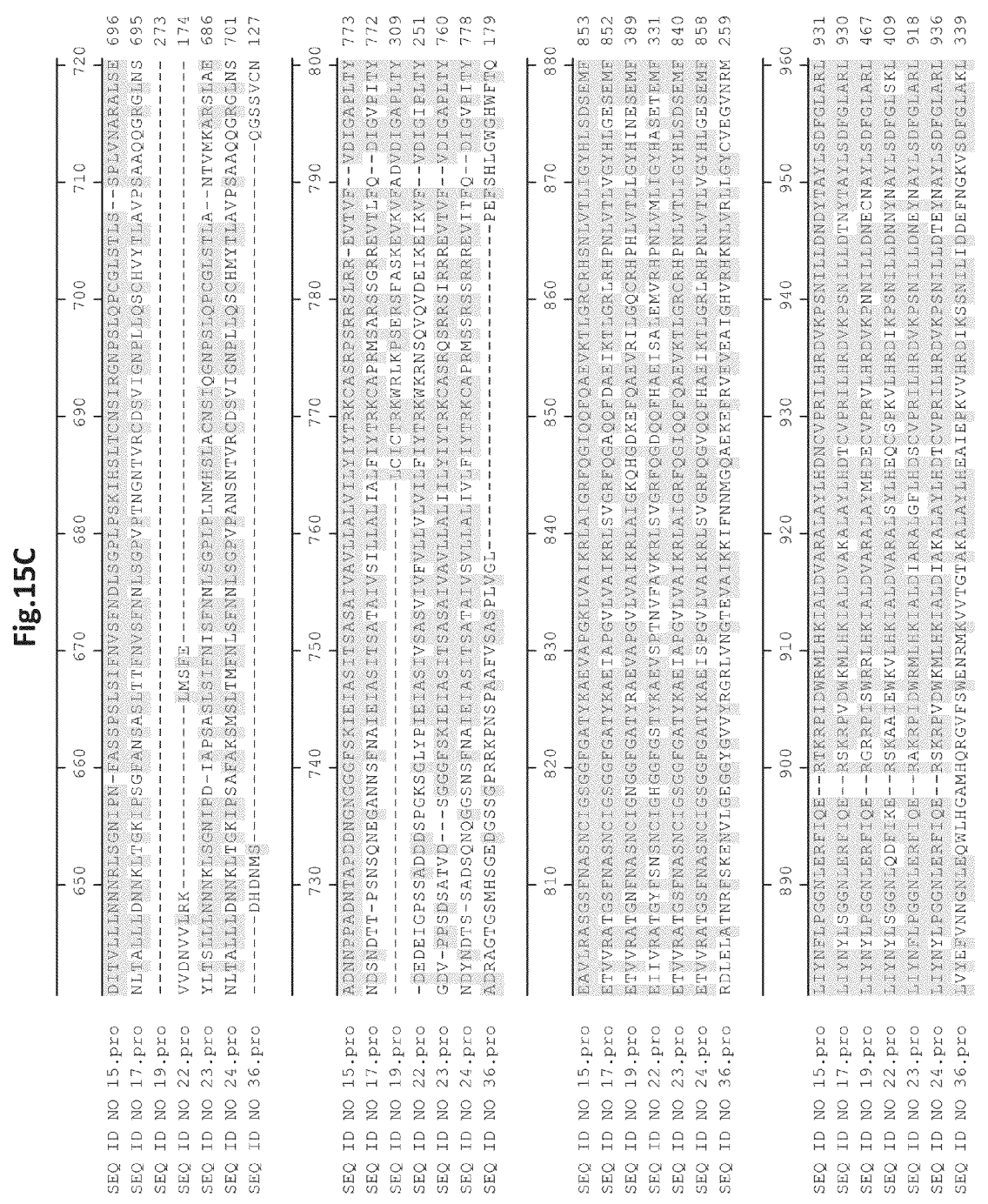

FIGS. 15A-15D show the multiple alignment of the full length amino acid sequences of SEQ ID NOs: 15, 17, 19, 22 and 36, and SEQ ID NOs: 23, and 24. Residues that match the Consensus sequence exactly are shaded. The consensus sequence is shown above each alignment. The consensus residues are determined by a straight majority.

Figure 16:
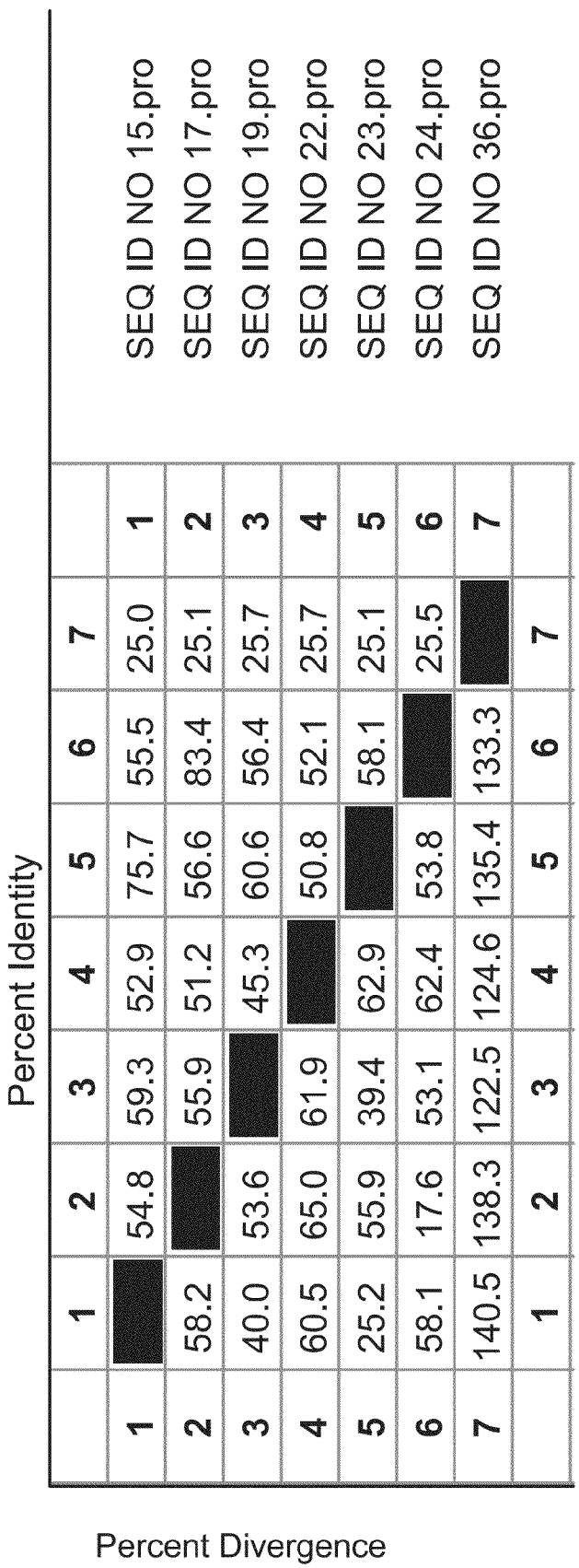

FIG. 16 shows a chart of the percent sequence identity and the divergence values for each pair of amino acid sequences of the LLRK homologs displayed in FIGS. 15A-15D.

FIG. 17 is the growth medium used for semi-hydroponics maize growth in Example 17.

FIG. 18 is a chart setting forth data relating to the effect of different nitrate concentrations on the growth and development of Gaspe Bay Flint derived maize lines in Example 17.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

SEQ ID NO: 1, pHSbarENDs
SEQ ID NO: 2, pDONR™/Zeo
SEQ ID NO: 3, pDONR™221
SEQ ID NO: 4, pBC-yellow
SEQ ID NO: 5, PHP27840
SEQ ID NO: 6, PHP23236
SEQ ID NO: 7, PHP10523
SEQ ID NO: 8, PHP23235
SEQ ID NO: 9, PHP20234
SEQ ID NO: 10, PHP28529
SEQ ID NO: 11, PHP28408
SEQ ID NO: 12, PHP22020
SEQ ID NO: 13, PHP29635

Table 1 and SEQ ID NO: 36 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence listing.

TABLE 1

Leucine Rich Repeat Kinase (LLRK)

| Protein | Clone Designation | SEQ ID NO: (Nucleotide) | SEQ ID NO: (Amino Acid) |
|---------|-------------------|-------------------------|-------------------------|
| LLRK | p0128.cpiae89r:fis | 14 | 15 |
| LLRK | cfp1n.pk018.k5b:fis | 16 | 17 |
| LLRK | Contig of: my.cco1n.pk077.a19 cfp2n.pk056.k23a.f cfp2n.pk056.k23b | 18 | 19 |

SEQ ID NO: 20 corresponds to the *Arabidopsis thaliana* Leucine Rich Repeat Kinase (LLRK) (AT1G69270) locus.

SEQ ID NO: 21 corresponds to the coding sequence of the *Arabidopsis thaliana* LLRK encoded by nucleotides 204-1826 (Stop) of SEQ ID NO:20.

SEQ ID NO: 22 corresponds to the amino acid sequence encoded by SEQ ID NO:21 and is a shorter version of NCBI GI NO: 6730642.

SEQ ID NO: 23 corresponds to NCBI GI NO: 115455429 (Rice)

SEQ ID NO: 24 corresponds to NCBI GI No: 125600990 (Rice)

SEQ ID NO: 25 is the attB1 sequence.
SEQ ID NO: 26 is the attB2 sequence.
SEQ ID NO: 27 is the forward primer VC062 in Example 9.
SEQ ID NO: 28 is the reverse primer VC063 in Example 9.
SEQ ID NO: 29 PIIOXS2a-FRT87(ni)m.
SEQ ID NO: 30 is the maize NAS2 promoter.
SEQ ID NO: 31 is the GOS2 promoter.
SEQ ID NO: 32 is the ubiquitin promoter.
SEQ ID NO: 33 is the S2A promoter.
SEQ ID NO: 34 is the PIN II terminator.
SEQ ID NO: 35 is the DNA sequence of corn clone cfp5n.pk002.f22:fis, a homolog of the *Arabidopsis* LLRK.
SEQ ID NO: 36 is the amino acid sequences encoded by nucleotides 371 through 1909 (STOP) of SEQ ID NO: 35.
SEQ ID NO: 37 corresponds to NCBI GI No: 115438737 (Rice).

DETAILED DESCRIPTION OF PREFERRED EMBODIMENTS

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The term "root architecture" refers to the arrangement of the different parts that comprise the root. The terms "root architecture", "root structure", "root system" or "root system architecture" are used interchangeably herewithin.

In general, the first root of a plant that develops from the embryo is called the primary root. In most dicots, the primary root is called the taproot. This main root grows downward and gives rise to branch (lateral) roots. In monocots the primary root of the plant branches, giving rise to a fibrous root system.

The term "altered root architecture" refers to aspects of alterations of the different parts that make up the root system at different stages of its development compared to a reference or control plant. It is understood that altered root architecture encompasses alterations in one or more measurable parameters, including but not limited to, the diameter, length, number, angle or surface of one or more of the root system parts, including but not limited to, the primary root, lateral or branch root, adventitious root, and root hairs, all of which fall within the scope of this invention. These changes can lead to an overall alteration in the area or volume occupied by the root. The reference or control plant does not comprise in its genome the recombinant DNA construct or heterologous construct.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

The term "V" stage refers to the leaf stages of a corn plant; e.g. V4=four, V5=five leaves with visible leaf collars. The leaf collar is the light-colored collar-like "band" located at the base of an exposed leaf blade, near the spot where the leaf blade comes in contact with the stem of the plant. The leaves are counted beginning with the lowermost, short, rounded-tip true leaf and ending with the uppermost leaf with a visible leaf collar.

"Agronomic characteristics" is a measurable parameter including but not limited to greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length, and harvest index.

"llrk" (leucine rich repeat kinase), rpk1, "at-llrk", "at-rpk1" (*Arabidopsis thaliana*-receptor protein kinase 1) are used interchangeably herewithin and refer to the *Arabidopsis thaliana* locus, AT1G69270 (SEQ ID NO:20).

"LLRK", "RPK1" (Receptor protein Kinase1) or "AT-RPK1" refers to the protein (SEQ ID NO:22) encoded by AT1G69270 (SEQ ID NO:20).

"llrk-like" refers to nucleotide homologs from different species, such as corn, of the *Arabidopsis thaliana* "LLRK" locus, AT1G69270 (SEQ ID NO:20) and includes without limitation any of the nucleotide sequences of SEQ ID NOs: 14, 16, 18, and 35.

"LLRK-like" refers to protein homologs from different species, such as corn, of the *Arabidopsis thaliana* "LLRK" (SEQ ID NO:22) and includes without limitation any of the amino acid sequences of SEQ ID NOs:15, 17, 19, and 36.

"Environmental conditions" refer to conditions under which the plant is grown, such as the availability of water, availability of nutrients (for example nitrogen), or the presence of disease.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation "Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transgenic plant" includes reference to a plant which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Association Mapping of Genes.

The goal of gene mapping is to identify genes which contribute to phenotypes of interest. The first stage of mapping is usually to locate a general region of a chromosome which is associated with transmission of the phenotypes of interest. Next, the gene and ultimately, particular alleles, are identified as having a causative role.

One approach to gene mapping (linkage analysis) uses maize lines with a known pedigree structure. Individuals are genotyped at random markers spread across the genome. If a disease gene is close to one of the markers then, within the pedigree, the inheritance pattern at the marker will mimic the inheritance pattern of the phenotype of interest. Linkage analysis has been highly successful at finding genes for simple genes associated with a phenotype of interest, i.e., those in which a single major gene is responsible for the phenotype in a given pedigree, and environmental factors are not very important.

A second approach to gene mapping (association, or disequilibrium mapping) uses associations at the population level. The idea is that a phenotype of interest arises on a particular haplotype background, and so individuals who inherit the phenotype of interest will also inherit the same alleles at nearby marker loci. This process is complicated by recombination and mutation. In a sense, association mapping is not fundamentally different from linkage analysis, but instead of using a family pedigree, an unknown population genealogy is used. Because the population genealogy is much deeper than a family pedigree, disequilibrium mapping permits much finer-scale mapping than does linkage analysis. An overview of the association mapping strategies and analysis is given in "Association Mapping in Plants," Oraguzie, N. C.; Rikkerink, E. H. A.; Gardiner, S. E.; Silva, H. N. D. Springer, January 2007.

Turning now to preferred embodiments:

Preferred embodiments include isolated polynucleotides and polypeptides, recombinant DNA constructs, compositions (such as plants or seeds) comprising these recombinant DNA constructs, and methods utilizing these recombinant DNA constructs.

Preferred Isolated Polynucleotides and Polypeptides

The present invention includes the following preferred isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36; or (ii) a full complement of the nucleic acid sequence of (i). Any of the foregoing isolated polynucleotides may be utilized in any recombinant DNA constructs (including suppression DNA constructs) of the present invention. The polypeptide is preferably a LLRK or LLRK-like protein.

An isolated polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36. The polypeptide is preferably a LLRK or LLRK-like protein.

An isolated polynucleotide comprising (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 14, 16, 18, or 20, or (ii) a full complement of the nucleic acid sequence of (i). Any of the foregoing isolated polynucleotides may be utilized in any recombinant DNA constructs (including suppression DNA constructs) of the present invention. The isolated polynucleotide encodes a LLRK or LLRK-like protein.

Preferred Recombinant DNA Constructs and Suppression DNA Constructs.

In one aspect, the present invention includes recombinant DNA constructs (including suppression DNA constructs).

In one preferred embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (ii) a full complement of the nucleic acid sequence of (i).

In another preferred embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 14, 16, 18, or 20, or (ii) a full complement of the nucleic acid sequence of (i).

FIGS. 15A-15D show the multiple alignment of the full length amino acid sequences of SEQ ID NOs: 15, 17, 19, 22, and 36 and SEQ ID NOs:23, and 24. The multiple alignment of the sequences was performed using the Megalign® program of the LASERGENE® bioinformatics computing suite (DNASTAR® Inc., Madison, Wis.); in particular, using the Clustal V method of alignment (Higgins and Sharp (1989) *CABIOS*. 5:151-153) with the multiple alignment default parameters of GAP PENALTY=10 and GAP LENGTH PENALTY=10, and the pairwise alignment default parameters of KTUPLE=1, GAP PENALTY=3, WINDOW=5 and DIAGONALS SAVED=5.

FIG. 16 shows the percent sequence identity and the divergence values for each pair of amino acids sequences displayed in FIGS. 15A-15D.

In another preferred embodiment, a recombinant DNA construct comprises a polynucleotide operably linked to at least one regulatory sequence (e.g., a promoter functional in a plant), wherein said polynucleotide encodes a LLRK or LLRK-like protein.

In another aspect, the present invention includes suppression DNA constructs.

A suppression DNA construct preferably comprises at least one regulatory sequence (preferably a promoter functional in a plant) operably linked to (a) all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a LLRK or LLRK-like protein; or (c) all or part of (i) a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 14, 16, 18, or 20, or (ii) a full complement of the nucleic acid sequence of (c)(i). The suppression DNA construct preferably comprises a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the invention encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate or prevent. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al. (1998) Plant J. 16:651-659; and Gura (2000) Nature 404:804-808).

Another variation describes the use of plant viral sequences to direct the suppression of proximal mRNA encoding sequences (PCT Publication WO 98/36083 published on Aug. 20, 1998).

Previously described is the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression see Wesley, S. V. et al. (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication No. WO 99/61632 published on Dec. 2, 1999).

The use of poly-T and poly-A sequences to generate the stem in the stem-loop structure has also been described (PCT Publication No. WO 02/00894 published Jan. 3, 2002).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication No. WO 02/00904, published 3 Jan. 2002.

RNA interference refers to the process of sequence-specific post-transcriptional gene silencing in animals mediated by short interfering RNAs (siRNAs) (Fire et al., Nature 391: 806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., Nature 409:363, 2001). Short interfering RNAs derived from dicer activity are typically about 21 to about 23 nucleotides in length and comprise about 19 base pair duplexes (Elbashir et al., Genes Dev. 15:188, 2001). Dicer has also been implicated in the excision of 21- and 22-nucleotide small temporal RNAs (stRNAs) from precursor RNA of conserved structure that are implicated in translational control (Hutvagner et al., Science 293:834, 2001). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al., Genes Dev. 15:188, 2001). In addition, RNA interference can also involve small RNA (e.g., miRNA) mediated gene silencing, presumably through cellular mechanisms that regulate chromatin structure and thereby prevent transcription of target gene sequences (see, e.g., Allshire, Science 297:1818-1819, 2002; Volpe et al., Science 297:1833-1837, 2002; Jenuwein, Science 297:2215-2218, 2002; and Hall et al., Science 297:2232-2237, 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (Nature 391:806, 1998) were the first to observe RNAi in *C. elegans*. Wianny and Goetz (Nature Cell Biol. 2:70, 1999) describe RNAi mediated by dsRNA in mouse embryos. Hammond et al. (Nature 404:293, 2000) describe RNAi in *Drosophila* cells transfected with dsRNA. Elbashir et al., (Nature 411:494, 2001) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity causes RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., Science 294:853-858 2001, Lagos-Quintana et al., Curr. Biol. 12:735-739, 2002; Lau et al., Science 294:858-862, 2001; Lee and Ambros, Science 294:862-864, 2001; Llave et al., Plant Cell 14:1605-1619, 2002; Mourelatos et al., Genes. Dev. 16:720-728, 2002; Park et al., Curr. Biol. 12:1484-1495, 2002; Reinhart et al., Genes. Dev. 16:1616-1626, 2002). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., Cell 106:23-34, 2001; Hutvagner et al., Science 293:834-838, 2001; Ketting et al., Genes. Dev. 15:2654-2659, 2001). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al., Curr. Biol. 12:1484-1495, 2002; Reinhart et al., Genes. Dev. 16:1616-1626, 2002). Furthermore, it is becoming clear from recent work that at least some miRNA hairpin precursors originate as longer polyadenylated transcripts, and several different miRNAs and associated hairpins can be present in a single transcript (Lagos-Quintana et al., Science 294:853-858, 2001; Lee et al., EMBO J. 21:4663-4670, 2002). Recent work has also examined the selection of the miRNA strand from the dsRNA product arising from processing of the hairpin by DICER (Schwartz, et al., Cell 115:199-208, 2003). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

MicroRNAs appear to regulate target genes by binding to complementary sequences located in the transcripts produced by these genes. In the case of lin-4 and let-7, the target sites are located in the 3' UTRs of the target mRNAs (Lee et al., Cell 75:843-854, 1993; Wightman et al., Cell 75:855-862, 1993; Reinhart et al., Nature 403:901-906, 2000; Slack et al., Mol. Cell. 5:659-669, 2000), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, Dev. Biol. 216:671-680, 1999). On the other hand, recent evidence suggests that miRNAs can in some cases cause specific RNA cleavage of the target transcript within the target site, and this cleavage step appears to require 100% complementarity between the miRNA and the target transcript (Hutvagner and Zamore, Science 297:2056-2060, 2002; Llave et al., Plant Cell 14:1605-1619, 2002). It seems likely that miRNAs can enter at least two pathways of target gene regulation: Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe 1999; Hammond et al., 2000; Zamore et al., 2000; Elbashir et al., 2001), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., Plant Cell 14:1605-1619 2002; Park et al., Curr. Biol. 12:1484-1495 2002; Rhoades et al., Cell 110:513-520 2002), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

A recombinant DNA construct (including a suppression DNA construct) of the present invention preferably comprises at least one regulatory sequence.

A preferred regulatory sequence is a promoter.

A number of promoters can be used in recombinant DNA constructs (and suppression DNA constructs) of the present invention. The promoters can be selected based on the desired outcome, and may include constitutive, tissue-specific, cell specific, inducible, or other promoters for expression in the host organism.

High level, constitutive expression of the candidate gene under control of the 35S or UBI promoter may have pleiotropic effects, although Candidate gene efficacy may be estimated when driven by a constitutive promoter.

Use of tissue-specific and/or stress-specific expression may eliminate undesirable effects but retain the ability to alter root architecture. This effect has been observed in *Arabidopsis* (Kasuga et al. (1999) Nature Biotechnol. 17:287-291).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (UBI) (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), the maize GOS2 promoter (WO0020571 A2, published Apr. 1, 2000) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A preferred tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo specific and may be useful in the invention include soybean Kunitz trysin inhibitor (Kti3, Jofuku and Goldberg, Plant Cell 1:1079-1093 (1989)), patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schernthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)), bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J. 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Preferred promoters include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993)). "Structural characterization, chromosomal localization and phylogenetic evaluation of two pairs of AGAMOUS-like MADS-box genes from maize", Theissen et al., Gene 156(2): 155-166 (1995); NCBI GenBank Accession No. X80206)). Zag2 transcripts can be detected 5 days prior to pollination to 7 to 8 days after pollination (DAP), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Additional preferred promoters for regulating the expression of the nucleotide sequences of the present invention in plants are vascular element specific or stalk-preferred promoters. Such stalk-preferred promoters include the alfalfa S2A promoter (GenBank Accession No. EF030816; Abrahams et al., Plant Mol. Biol. 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B., Biochemistry of Plants 15:1-82 (1989). (Put this with the other constitutive promoter description.)

Preferred promoters may include: RIP2, mLIP15, ZmCOR1, Rab17, CaMV 35S, RD29A, B22E, Zag2, SAM synthetase, ubiquitin (SEQ ID NO:32), CaMV 19S, nos, Adh, sucrose synthase, R-allele, root cell promoter, the vascular tissue specific promoters S2A (Genbank accession number EF030816; SEQ ID NO:33) and S2B (Genbank accession number EF030817) and the constitutive promoter GOS2 (SEQ ID NO:31) from Zea mays. Other preferred promoters include root preferred promoters, such as the maize NAS2 promoter (SEQ ID NO:30), the maize Cyclo promoter (US 2006/0156439, published Jul. 13, 2006), the maize ROOT-MET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790, gi: 1063664).

A "substantial portion" of a nucleotide sequence comprises a nucleotide sequence that is sufficient to afford putative identification of the promoter that the nucleotide sequence comprises. Nucleotide sequences can be evaluated either manually, by one skilled in the art, or using computer-based sequence comparison and identification tools that employ algorithms such as BLAST (Basic Local Alignment Search Tool; Altschul et al. (1993) J. Mol. Biol. 215:403-410). In general, a sequence of thirty or more contiguous nucleotides is necessary in order to putatively identify a promoter nucleic acid sequence as homologous to a known promoter. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

Recombinant DNA constructs (and suppression DNA constructs) of the present invention may also include other regulatory sequences, including but not limited to, translation leader sequences, introns, and polyadenylation recognition sequences. In another preferred embodiment of the present invention, a recombinant DNA construct of the present invention further comprises an enhancer or silencer.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, Mol. Cell. Biol. 8:4395-4405 (1988); Callis et al., Genes Dev. 1:1183-1200 (1987). Such intron enhancement of gene expression is typically greatest when placed near the 5' end of the transcription unit. Use of maize introns Adh1-S intron 1, 2, and 6, the Bronze-1 intron are known in the art. See generally, The Maize Handbook, Chapter 116, Freeling and Walbot, Eds., Springer, New York (1994).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

A translation leader sequence is a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. Molecular Biotechnology 3:225 (1995)).

In another preferred embodiment of the present invention, a recombinant DNA construct of the present invention further comprises an enhancer or silencer.

Any plant can be selected for the identification of regulatory sequences and genes to be used in creating recombinant DNA constructs and suppression DNA constructs of the present invention. Examples of suitable plant targets for the isolation of genes and regulatory sequences would include but are not limited to alfalfa, apple, apricot, Arabidopsis, artichoke, arugula, asparagus, avocado, banana, barley, beans, beet, blackberry, blueberry, broccoli, brussel sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred plants for the identification of regulatory sequences are Arabidopsis, corn, wheat, soybean, and cotton.

Preferred Compositions

A preferred composition of the present invention is a plant comprising in its genome any of the recombinant DNA constructs (including any of the suppression DNA constructs) of the present invention (such as those preferred constructs discussed above). Preferred compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

Preferably, in hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit altered root (or plant) architecture, or used in a breeding program to produce hybrid seed, which can be grown to produce plants that would exhibit altered root (or plant) architecture. Preferably, the seeds are maize.

Preferably, the plant is a monocotyledonous or dicotyledonous plant, more preferably, a maize or soybean plant, even more preferably a maize plant, such as a maize hybrid plant or a maize inbred plant. The plant may also be sunflower, sorghum, castor bean, grape, canola, wheat, alfalfa, cotton, rice, barley or millet.

Preferably, the recombinant DNA construct is stably integrated into the genome of the plant.

Particularly preferred embodiments include but are not limited to the following preferred embodiments:

1. A plant (preferably a maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, and wherein said plant exhibits an altered root architecture when compared to a control plant not comprising said recombinant DNA construct. Preferably, the plant further exhibits an alteration of at least one agronomic characteristic when compared to the control plant.

2. A plant (preferably a maize or soybean plant) comprising in its genome:
   a recombinant DNA construct comprising:
   (a) a polynucleotide operably linked to at least one regulatory element, wherein said polynucleotide encodes a polypeptide having an amino acid sequence of at least 50% sequence identity, based on the Clustal V method of alignment, when compared to SEQ ID NO: 15, 17, 19, 22, or 36, or
   (b) a suppression DNA construct comprising at least one regulatory element operably linked to:
   (i) all or part of: (A) a nucleic acid sequence encoding a polypeptide having an amino acid sequence of at least 50% sequence identity, based on the Clustal V method of alignment, when compared to SEQ ID NO: 15, 17, 19, 22, or 36, or (B) a full complement of the nucleic acid sequence of (b)(i)(A); or
   (ii) a region derived from all or part of a sense strand or antisense strand of a target gene of interest, said region having a nucleic acid sequence of at least 50% sequence identity, based on the Clustal V method of alignment, when compared to said all or part of a sense strand or antisense strand from which said region is derived, and wherein said target gene of interest encodes a LLRK or LLRK-like polypeptide, and wherein said plant exhibits an alteration of at least one agronomic characteristic when compared to a control plant not comprising said recombinant DNA construct.

3. A plant (preferably a maize or soybean plant) comprising in its genome a recombinant DNA construct comprising a polynucleotide operably linked to at least one regulatory sequence, wherein said polynucleotide encodes a LLRK or LLRK-like protein, and wherein said plant exhibits an altered root architecture when compared to a control plant not comprising said recombinant DNA construct. Preferably, the plant further exhibits an alteration of at least one agronomic characteristic.

Preferably, the LLRK protein is from *Arabidopsis thaliana, Zea mays, Glycine max, Glycine tabacina, Glycine soja* or *Glycine tomentella*.

4. A plant (preferably a maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a LLRK or LLRK-like protein, and wherein said plant exhibits an alteration of at least one agronomic characteristic when compared to a control plant not comprising said recombinant DNA construct.

5. A plant (preferably a maize or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (b) a full complement of the nucleic acid sequence of (a), and wherein said plant exhibits an alteration of at least one agronomic characteristic when compared to a control plant not comprising said recombinant DNA construct.

6. Any progeny of the above plants in preferred embodiments 1-5, any seeds of the above plants in preferred embodiments 1-5, any seeds of progeny of the above plants in preferred embodiments 1-5, and cells from any of the above plants in preferred embodiments 1-5 and progeny thereof.

In any of the foregoing preferred embodiments 1-6 or any other embodiments of the present invention, the recombinant DNA construct (or suppression DNA construct) preferably comprises at least a promoter that is functional in a plant as a preferred regulatory sequence.

In any of the foregoing preferred embodiments 1-6 or any other embodiments of the present invention, the alteration of at least one agronomic characteristic is either an increase or decrease, preferably an increase.

In any of the foregoing preferred embodiments 1-6 or any other embodiments of the present invention, the at least one agronomic characteristic is preferably selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length and harvest index. Yield, greenness, biomass and root lodging are particularly preferred agronomic characteristics for alteration (preferably an increase).

In any of the foregoing preferred embodiments 1-6 or any other embodiments of the present invention, the plant preferably exhibits the alteration of at least one agronomic characteristic irrespective of the environmental conditions, for example, water and nutrient availability, when compared to a control plant.

One of ordinary skill in the art is familiar with protocols for determining alteration in plant root architecture. For example, transgenic maize plants can be assayed for changes in root architecture at seedling stage, flowering time or maturity. Alterations in root architecture can be determined by counting the nodal root numbers of the top 3 or 4 nodes of the greenhouse grown plants or the width of the root band. "Root band" refers to the width of the mat of roots at the bottom of a pot at plant maturity. Other measures of alterations in root architecture include, but are not limited to, the number of lateral roots, average root diameter of nodal roots, average root diameter of lateral roots, number and length of root hairs. The extent of lateral root branching (e.g. lateral root number, lateral root length) can be determined by sub-sampling a complete root system, imaging with a flat-bed scanner or a digital camera and analyzing with WinRHIZO™ software (Regent Instruments Inc.).

Data taken on root phenotype are subjected to statistical analysis, normally a t-test to compare the transgenic roots with that of non-transgenic sibling plants. One-way ANOVA may also be used in cases where multiple events and/or constructs are involved in the analysis.

The Examples below describe some representative protocols and techniques for detecting alterations in root architecture.

One can also evaluate alterations in root architecture by the ability of the plant to increase yield in field testing when compared, under the same conditions, to a control or reference plant.

One can also evaluate alterations in root architecture by the ability of the plant to maintain substantial yield (preferably at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under stress conditions (e.g., nutrient over-abundance or limitation, water over-abundance or limitation, presence of disease), when compared to the yield of a control or reference plant under non-stressed conditions.

Alterations in root architecture can also be measured by determining the resistance to root lodging of the transgenic plants compared to reference or control plants.

One of ordinary skill in the art would readily recognize a suitable control or reference plant to be utilized when assessing or measuring an agronomic characteristic or phenotype of a transgenic plant in any embodiment of the present invention in which a control or reference plant is utilized (e.g., compositions or methods as described herein). For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct) (i.e., the progeny not comprising the recombinant DNA construct (or suppression DNA construct) is the control or reference plant).

2. Introgression of a recombinant DNA construct (or suppression DNA construct) into an inbred line, such as in maize, or into a variety, such as in soybean: the introgressed line would typically be measured relative to the parent inbred or variety line (i.e., the parent inbred or variety line is the control or reference plant).

3. Two hybrid lines, where the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the parent inbred or variety line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct (or suppression DNA construct). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

Preferred Methods

Preferred methods include but are not limited to methods for altering root architecture in a plant, methods for evaluating alteration of root architecture in a plant, methods for altering an agronomic characteristic in a plant, methods for determining an alteration of an agronomic characteristic in a plant, and methods for producing seed. Preferably, the plant is a monocotyledonous or dicotyledonous plant, more preferably, a maize or soybean plant, even more preferably a maize plant. The plant may also be sunflower, sorghum, castor bean, canola, wheat, alfalfa, cotton, rice, barley or millet. The seed is preferably a maize or soybean seed, more preferably a maize seed, and even more preferably, a maize hybrid seed or maize inbred seed.

Particularly preferred methods include but are not limited to the following:

A method of altering root architecture of a plant, comprising: (a) introducing into a regenerable plant cell a recombinant DNA construct comprising a polynucleotide operably linked to at least one regulatory sequence (preferably a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36; and (b) regenerating a transgenic plant from the regenerable plant cell after step (a), wherein the transgenic plant comprises in its genome the recombinant DNA construct and exhibits altered root architecture when compared to a control plant not comprising the recombinant DNA construct. The method may further comprise (c) obtaining a progeny plant derived from the transgenic plant, wherein said progeny plant comprises in its genome the recombinant DNA construct and exhibits altered root architecture when compared to a control plant not comprising the recombinant DNA construct.

A method of altering root architecture in a plant, comprising: (a) introducing into a regenerable plant cell a suppression DNA construct comprising at least one regulatory sequence (preferably a promoter functional in a plant) operably linked to:

(i) all or part of: (A) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (B) a full complement of the nucleic acid sequence of (a)(i)(A); or (ii) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a LLRK or LLRK-like polypeptide; and (b) regenerating a transgenic plant from the regenerable plant cell after step (a), wherein the transgenic plant comprises in its genome the recombinant DNA construct and exhibits an altered root architecture when compared to a control plant not comprising the suppression DNA construct. The method may further comprise (c) obtaining a progeny plant derived from the transgenic plant, wherein said progeny plant comprises in its genome the recombinant DNA construct and exhibits altered root architecture when compared to a control plant not comprising the suppression DNA construct.

A method of evaluating altered root architecture in a plant, comprising (a) introducing into a regenerable plant cell a recombinant DNA construct comprising a polynucleotide operably linked to at least on regulatory sequence (preferably a promoter functional in a plant), wherein the polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (b) regenerating a transgenic plant from the regenerable plant cell after step (a), wherein the transgenic plant comprises in its genome the recombinant DNA construct; and (c) evaluating root architecture of the transgenic plant compared to a control plant not comprising the recombinant DNA construct. The method may further comprise (d) obtaining a progeny plant derived from the transgenic plant, wherein the progeny plant comprises in its genome the recombinant DNA construct; and (e) evaluating root architecture of the progeny plant compared to a control plant not comprising the recombinant DNA construct.

A method of evaluating altered root architecture in a plant, comprising (a) introducing into a regenerable plant cell a suppression DNA construct comprising at least one regulatory sequence (preferably a promoter functional in a plant) operably linked to:

(i) all or part of: (A) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (B) a full complement of the nucleic acid sequence of (a)(i)(A); or (ii) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a LLRK or LLRK-like polypeptide; and (b) regenerating a transgenic plant from the regenerable plant cell after step (a), wherein the transgenic plant comprises in its genome the suppression DNA construct; and (c) evaluating the transgenic plant for altered root architecture compared to a control plant not comprising the suppression DNA construct. The method may further comprise (d) obtaining a progeny plant derived from the transgenic plant, wherein the progeny plant comprises in its genome the suppression DNA construct; and (e) evaluating the progeny plant for altered root architecture compared to a control plant not comprising the suppression DNA construct.

A method of evaluating altered root architecture in a plant, comprising (a) introducing into a regenerable plant cell a recombinant DNA construct comprising a polynucleotide operably linked to at least one regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36 (b) regenerating a transgenic plant from the regenerable plant cell after step (a), wherein the transgenic plant comprises in its genome the recombinant DNA construct; (c) obtaining a progeny plant derived from said transgenic plant, wherein the progeny plant comprises in its genome the recombinant DNA construct; and (d) evaluating the progeny plant for altered root architecture compared to a control plant not comprising the recombinant DNA construct.

A method of evaluating root architecture in a plant, comprising:

(a) introducing into a regenerable plant cell a suppression DNA construct comprising at least one regulatory element operably linked to: (i) all or part of: (A) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (B) a full complement of the nucleic acid sequence of (a)(i)(A); or (ii) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a LLRK or LLRK-like polypeptide; (b) regenerating a transgenic plant from the regenerable plant cell after step (a), wherein the transgenic plant comprises in its genome the suppression DNA construct;

(c) obtaining a progeny plant derived from the transgenic plant, wherein the progeny plant comprises in its genome the suppression DNA construct; and (d) evaluating root architecture of the progeny plant compared to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least on regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36 (b) regenerating a transgenic plant from the regenerable plant cell after step (a), wherein the transgenic plant comprises in its genome said recombinant DNA construct; and (c) determining whether the transgenic plant exhibits an alteration of at least one agronomic characteristic when compared to a control plant not comprising the recombinant DNA construct. The method may further comprise (d) obtaining a progeny plant derived from the transgenic plant, wherein the progeny plant comprises in its genome the recombinant DNA construct; and (e) determining whether the progeny plant exhibits an alteration of at least one agronomic characteristic when compared to a control plant not comprising the recombinant DNA construct.

A method of determining an alteration of an agronomic characteristic in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (ii) a full complement of the nucleic acid sequence of (i); (b) regenerating a transgenic plant from the regenerable plant cell after step (a), wherein the transgenic plant comprises in its genome the suppression DNA construct; and (c) determining whether the transgenic plant exhibits an alteration in at least one agronomic characteristic when compared to a control plant not comprising the suppression DNA construct. The method may further comprise (d) obtaining a progeny plant derived from the transgenic plant, wherein the progeny plant comprises in its genome the suppression DNA construct; and (e) determining whether the progeny plant exhibits an alteration in at least one agronomic characteristic when compared to a control plant not comprising the suppression DNA construct.

A method of determining an alteration of an agronomic characteristic in a plant, comprising (a) introducing into a regenerable plant cell a recombinant DNA construct comprising a polynucleotide operably linked to at least one regulatory sequence (preferably a promoter functional in a plant), wherein said polynucleotide encodes a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36 (b) regenerating a transgenic plant from the regenerable plant cell after step (a), wherein the transgenic plant comprises in its genome said recombinant DNA construct; (c) obtaining a progeny plant derived from said transgenic plant, wherein the progeny plant comprises in its genome the recombinant DNA construct; and (d) determining whether the progeny plant exhibits an alteration of at least one agronomic characteristic when compared to a control plant not comprising the recombinant DNA construct. The method of determining an alteration of an agronomic characteristic in a plant may further comprise determining whether the transgenic plant exhibits an alteration of at least one agronomic characteristic when compared, under varying environmental conditions, to a control plant not comprising the recombinant DNA construct.

A method of determining an alteration of an agronomic characteristic in a plant, comprising (a) introducing into a regenerable plant cell a suppression DNA construct comprising at least one regulatory sequence (preferably a promoter functional in a plant) operably linked to all or part of (i) a nucleic acid sequence encoding a polypeptide having an amino acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 15, 17, 19, 22, or 36, or (ii) a full complement of the nucleic acid sequence of (i);

(b) regenerating a transgenic plant from the regenerable plant cell after step (a), wherein the transgenic plant comprises in its genome the suppression DNA construct; (c) obtaining a progeny plant derived from said transgenic plant, wherein the progeny plant comprises in its genome the suppression DNA construct; and (d) determining whether the progeny plant exhibits an alteration in at least one agronomic characteristic when compared to a control plant not comprising the recombinant DNA construct.

A method of determining an alteration of an agronomic characteristic in a plant, comprising: (a) introducing into a regenerable plant cell a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a LLRK or LLRK-like polypeptide; (b) regenerating a transgenic plant from the regenerable plant cell after step (a), wherein the transgenic plant comprises in its genome the suppression DNA construct; and (c) determining whether the transgenic plant exhibits an alteration of at least one agronomic characteristic when compared to a control plant not comprising the suppression DNA construct. The method may further comprise: (d) obtaining a progeny plant derived from the transgenic plant, wherein the progeny plant comprises in its genome the suppression DNA construct; and (e) determining whether the progeny plant exhibits an alteration of at least one agronomic characteristic when compared to a control plant not comprising the suppression DNA construct.

A method of determining an alteration of an agronomic characteristic in a plant, comprising: (a) introducing into a regenerable plant cell a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 56%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to said all or part of a sense strand or antisense strand from which said region is derived, and wherein said target gene of interest encodes a LLRK or LLRK-like polypeptide; (b) regenerating a transgenic plant from the regenerable plant cell after step (a), wherein the transgenic plant comprises in its genome the suppression DNA construct; (c) obtaining a progeny plant derived from the transgenic plant, wherein the progeny plant comprises in its genome the suppression DNA construct; and (d) determining whether the progeny plant exhibits an alteration of at least one agronomic characteristic when compared to a control plant not comprising the suppression DNA construct.

A method of producing seed (preferably seed that can be sold as a product offering with altered root architecture) comprising any of the preceding preferred methods, and further comprising obtaining seeds from said progeny plant, wherein said seeds comprise in their genome said recombinant DNA construct (or suppression DNA construct).

In any of the foregoing preferred methods or any other embodiments of methods of the present invention, the step of determining an alteration of an agronomic characteristic in a transgenic plant, if applicable, may preferably comprise determining whether the transgenic plant exhibits an alteration of at least one agronomic characteristic when compared, under varying environmental conditions, to a control plant not comprising the recombinant DNA construct.

In any of the foregoing preferred methods or any other embodiments of methods of the present invention, the step of determining an alteration of an agronomic characteristic in a progeny plant, if applicable, may preferably comprise determining whether the progeny plant exhibits an alteration of at least one agronomic characteristic when compared, under varying environmental conditions, to a control plant not comprising the recombinant DNA construct.

In any of the preceding preferred methods or any other embodiments of methods of the present invention, in said introducing step said regenerable plant cell preferably comprises a callus cell (preferably embryogenic), a gametic cell, a meristematic cell, or a cell of an immature embryo. The regenerable plant cells are preferably from an inbred maize plant.

In any of the preceding preferred methods or any other embodiments of methods of the present invention, said regenerating step preferably comprises: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding preferred methods or any other embodiments of methods of the present invention, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, preferably as part of a transposable element), and then screen for an event in which the regulatory sequence is operably linked to an endogenous gene encoding a polypeptide of the instant invention.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

In any of the preceding preferred methods or any other embodiments of methods of the present invention, the at least one agronomic characteristic is preferably selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, stalk lodging, plant height, ear length, stalk lodging and harvest index. Yield, greenness, biomass and root lodging are particularly preferred agronomic characteristics for alteration (preferably an increase).

In any of the preceding preferred methods or any other embodiments of methods of the present invention, the plant preferably exhibits the alteration of at least one agronomic characteristic irrespective of the environmental conditions when compared to a control.

The introduction of recombinant DNA constructs of the present invention into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation.

Preferred techniques are set forth below in the Examples below for transformation of maize plant cells and soybean plant cells.

Other preferred methods for transforming dicots, primarily by use of *Agrobacterium tumefaciens*, and obtaining transgenic plants include those published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *Bio/Technology* 6:923 (1988), Christou et al., *Plant Physiol.* 87:671 674 (1988)); *Brassica* (U.S. Pat. No. 5,463,174); peanut (Cheng et al., *Plant Cell Rep.* 15:653 657 (1996), McKently et al., *Plant Cell Rep.* 14:699 703 (1995)); papaya; and pea (Grant et al., *Plant Cell Rep.* 15:254 258, (1995)).

Transformation of monocotyledons using electroporation, particle bombardment, and *Agrobacterium* have also been reported and are included as preferred methods, for example, transformation and plant regeneration as achieved in asparagus (Bytebier et al., *Proc. Natl. Acad. Sci. U.S.A.* 84:5354, (1987)); barley (Wan and Lemaux, *Plant Physiol.* 104:37 (1994)); *Zea mays* (Rhodes et al., *Science* 240:204 (1988), Gordon-Kamm et al., *Plant Cell* 2:603 618 (1990), Fromm et al., *Bio/Technology* 8:833 (1990), Koziel et al., *Bio/Technology* 11:194, (1993), Armstrong et al., *Crop Science* 35:550-557 (1995)); oat (Somers et al., *Bio/Technology* 10:1589 (1992)); orchard grass (Horn et al., *Plant Cell Rep.* 7:469 (1988)); rice (Toriyama et al., *Theor. Appl. Genet.* 205:34, (1986); Part et al., *Plant Mol. Biol.* 32:1135 1148, (1996); Abedinia et al., *Aust. J. Plant Physiol.* 24:133 141 (1997); Zhang and Wu, *Theor. Appl. Genet.* 76:835 (1988); Zhang et al., *Plant Cell Rep.* 7:379, (1988); Battraw and Hall, *Plant Sci.* 86:191 202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)), and wheat (Vasil et al., *Bio/Technology* 10:667 (1992); U.S. Pat. No. 5,631,152).

There are a variety of methods for the regeneration of plants from plant tissue. The particular method of regeneration will depend on the starting plant tissue and the particular plant species to be regenerated.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In another aspect, this invention also concerns a method of mapping genetic variations related to altering root architecture and/or altering at least one agronomic characteristic in plants comprising:
(a) crossing two plant varieties; and
(c) evaluating genetic variations with respect to:
(j) a nucleic acid sequence selected from the group consisting of SEQ ID NO: 14, 16, 18, 20, 22, 24, 26, 28, 30 or 33; or
(iii) a nucleic acid sequence encoding a polypeptide selected from the group consisting of SEQ ID NO: 15; 17, 19, 21, 23, 25, 27, 29, 31 or 34
in progeny plants resulting from the cross of step (a), wherein the evaluation is made using a method selected from the group consisting of RFLP analysis, SNP analysis, and PCR-based analysis.

In another embodiment, this invention concerns a method of molecular breeding to obtain an altered root architecture and/or at least one altered agronomic characteristic in plants comprising:
(a) crossing two plant varieties; and
(b) evaluating genetic variations with respect to:
(i) a nucleic acid sequence selected from the group consisting of SEQ ID NO: 14, 16, 18, 20, 22, 24, 26, 28, 30 or 33; or
(iii) a nucleic acid sequence encoding a polypeptide selected from the group consisting of SEQ ID NO: 15; 17, 19, 21, 23, 25, 27, 29, 31 or 34;
in progeny plants resulting from the cross of step (a), wherein the evaluation is made using a method selected from the group consisting of RFLP analysis, SNP analysis, and PCR-based analysis.

The terms "mapping genetic variation" or "mapping genetic variability" are used interchangeably and define the process of identifying changes in DNA sequence, whether from natural or induced causes, within a genetic region that differentiates between different plant lines, cultivars, varieties, families, or species. The genetic variability at a particular locus (gene) due to even minor base changes can alter the pattern of restriction enzyme digestion fragments that can be generated. Pathogenic alterations to the genotype can be due to deletions or insertions within the gene being analyzed or even single nucleotide substitutions that can create or delete a restriction enzyme recognition site. RFLP analysis takes advantage of this and utilizes Southern blotting with a probe corresponding to the isolated nucleic acid fragment of interest.

Thus, if a polymorphism (i.e., a commonly occurring variation in a gene or segment of DNA; also, the existence of several forms of a gene (alleles) in the same species) creates or destroys a restriction endonuclease cleavage site, or if it results in the loss or insertion of DNA (e.g., a variable nucleotide tandem repeat (VNTR) polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms ("RFLPs"). RFLPs have been widely used in human and plant genetic analyses (Glassberg, UK Patent Application 2135774; Skolnick et al, *Cytogen. Cell Genet.* 32:58-67 (1982); Botstein et al, *Ann. J. Hum. Genet.* 32:314-331

(1980); Fischer et al (PCT Application WO 90/13668; Uhlen, PCT Application WO 90/11369).

A central attribute of "single nucleotide polymorphisms" or "SNPs" is that the site of the polymorphism is at a single nucleotide. SNPs have certain reported advantages over RFLPs or VNTRs. First, SNPs are more stable than other classes of polymorphisms. Their spontaneous mutation rate is approximately $10^{-9}$ (Kornberg, DNA Replication, W.H. Freeman & Co., San Francisco, 1980), approximately, 1,000 times less frequent than VNTRs (U.S. Pat. No. 5,679,524). Second, SNPs occur at greater frequency, and with greater uniformity than RFLPs and VNTRs. As SNPs result from sequence variation, new polymorphisms can be identified by sequencing random genomic or cDNA molecules. SNPs can also result from deletions, point mutations and insertions. Any single base alteration, whatever the cause, can be a SNP. The greater frequency of SNPs means that they can be more readily identified than the other classes of polymorphisms.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or by other biochemical interpretation. SNPs can be sequenced by a number of methods. Two basic methods may be used for DNA sequencing, the chain termination method of Sanger et al, *Proc. Natl. Acad. Sci.* (U.S.A.) 74:5463-5467 (1977), and the chemical degradation method of Maxam and Gilbert, *Proc. Natl. Acad. Sci.* (U.S.A.) 74: 560-564 (1977).

Furthermore, single point mutations can be detected by modified PCR techniques such as the ligase chain reaction ("LCR") and PCR-single strand conformational polymorphisms ("PCR-SSCP") analysis. The PCR technique can also be used to identify the level of expression of genes in extremely small samples of material, e.g., tissues or cells from a body. The technique is termed reverse transcription-PCR ("RT-PCR").

The term "molecular breeding" defines the process of tracking molecular markers during the breeding process. It is common for the molecular markers to be linked to phenotypic traits that are desirable. By following the segregation of the molecular marker or genetic trait, instead of scoring for a phenotype, the breeding process can be accelerated by growing fewer plants and eliminating assaying or visual inspection for phenotypic variation. The molecular markers useful in this process include, but are not limited to, any marker useful in identifying mapable genetic variations previously mentioned, as well as any closely linked genes that display synteny across plant species. The term "synteny" refers to the conservation of gene placement/order on chromosomes between different organisms. This means that two or more genetic loci, that may or may not be closely linked, are found on the same chromosome among different species. Another term for synteny is "genome colinearity."

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Creation of an *Arabidopsis* Population with Activation-Tagged Genes

Figure 1:
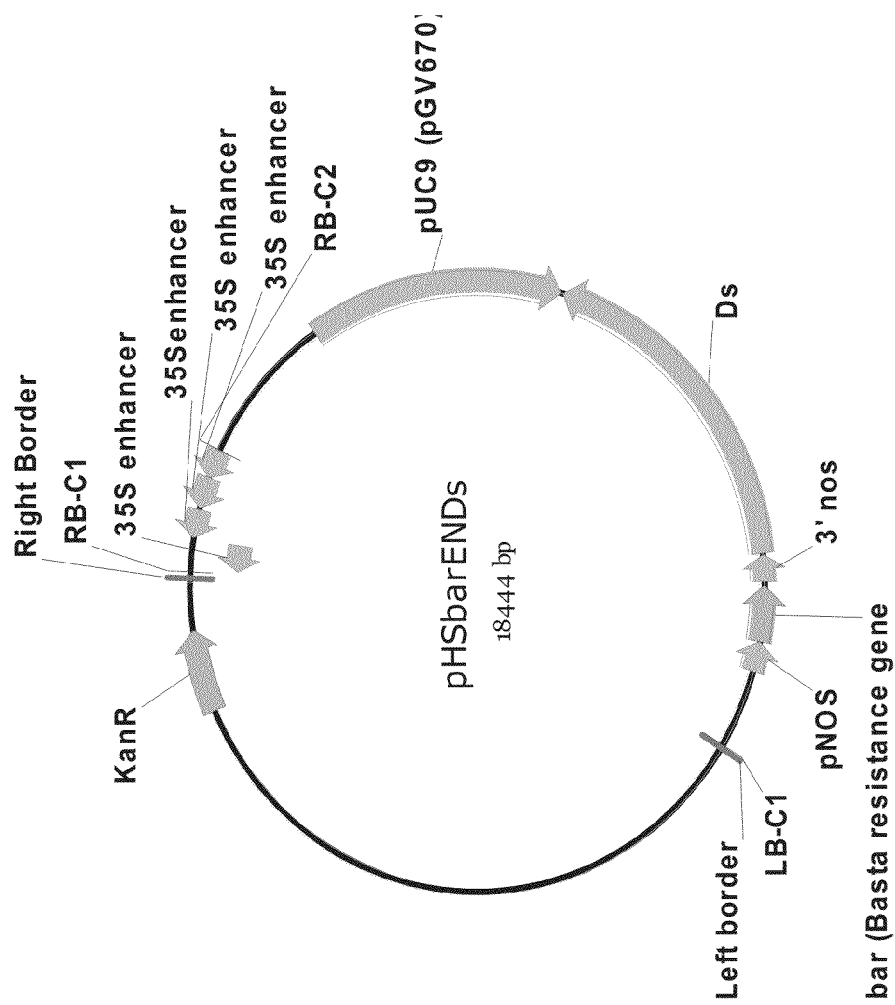
FIG. 1 shows a map of the pHSbarENDs activation tagging construct (SEQ ID NO:1) used to make the *Arabidopsis* populations.

A 18.4 kb T-DNA based binary construct was created, pHSbarENDs (FIG. 1; SEQ ID NO:1) containing four multimerized enhancer elements derived from the Cauliflower Mosaic Virus 35S promoter, corresponding to sequences −341 to −64, as defined by Odell et al. (1985) *Nature* 313: 810-812. The construct also contains vector sequences (pUC9) to allow plasmid rescue, transposon sequences (Ds) to remobilize the T-DNA, and the bar gene to allow for glufosinate selection of transgenic plants. Only the 10.8 kb segment from the right border (RB) to left border (LB) inclusive will be transferred into the host plant genome. Since the enhancer elements are located near the RB, they can induce cis-activation of genomic loci following T-DNA integration.

The pHSbarENDs construct was transformed into *Agrobacterium tumefaciens* strain C58, grown in LB at 25° C. to OD600 ~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting $T_1$ seed were sown on soil, and transgenic seedlings were selected by spraying with glufosinate (Finale® AgrEvo; Bayer Environmental Science). $T_2$ seed was collected from approximately 35,000 individual glufosinate resistant $T_1$ plants. $T_2$ plants were grown and equal volumes of $T_3$ seed from 96 separate $T_2$ lines were pooled. This constituted 360 sub-populations.

The *Agrobacterium* strain and whole plant transformation was performed as described above.

A total of 100,000 glufosinate resistant $T_1$ seedlings were selected. $T_2$ seed from each line was kept separate.

Example 2A

Screens to Identify Lines with Altered Root Architecture (Non-Limiting Nitrogen Conditions)

Activation-tagged *Arabidopsis* seedlings, grown under non-limiting nitrogen conditions, can be analyzed for altered root system architecture when compared to control seedlings during early development from the population described in Example 1.

From each of 96,000 separate T1 activation-tagged lines, ten T2 seeds can be sterilized with chlorine gas and planted on petri plates containing the following medium: 0.5×N-Free Hoagland's, 60 mM $KNO_3$, 0.1% sucrose, 1 mM MES and 1% Phytagel™. Typically 10 plates are placed in a rack. Plates are kept for three days at 4° C. to stratify seeds and then held vertically for 11 days at 22° C. light and 20° C. dark. Photoperiod is 16 h; 8 h dark, average light intensity was ~180 μmol/m²/s. Racks (typically holding 10 plates each) are rotated daily within each shelf. At day 14, plates are evaluated for seedling status, whole plate digital images were taken, and analyzed for root area. Plates are arbitrarily divided in 10 horizontal areas. The root area in each of 10 horizontal zones on the plate is expressed as a percentage of the total area. Only areas in zones 3 to 9 are used to calculate the total root area of the line. Rootbot image analysis tool (proprietary) developed by ICORIA can be used to assess root area. Total root area is expressed in $mm^2$.

Lines with enhanced root growth characteristics are expected to lie at the upper extreme of the root area distributions. A sliding window approach can be used to estimate the variance in root area for a given rack with the assumption that there could be up to two outliers in the rack. Environmental variations in various factors including growth media, temperature, and humidity can cause significant variation in root growth, especially between sow dates. Therefore the lines are grouped by sow date and shelf for the data analysis. The racks in a particular sow date/shelf group are then sorted by mean root area. Root area distributions for sliding windows is performed by combining data for a rack, $r_i$, with data from the rack with the next lowest, ($r_{i-1}$, and the next highest mean root area, $r_{i+1}$. The variance of the combined distribution is then analyzed to identify outliers in $r_i$ using a Grubbs-type approach (Barnett et al., Outliers in Statistical Data, John Wiley & Sons, $3^{rd}$ edition (1994).

Lines with significant enhanced root growth as determined by the method outlined above, are designated as Phase 1 hits. Phase 1 hits are re-screened in duplicate under the same assay conditions. When either or both of the Phase 2 replicates shows a significant difference from the mean, the line is then considered a validated root architecture line.

Those lines that were again found to be outliers in at least one plate in Phase 2 were subjected to a Phase 3 screening performed in house, to validate the results obtained in Phase 1 and Phase 2. The results were validated in Phase 3 using both the Rootboot image analysis (as described above) and WinRHIZO® as described below. The confirmation was performed in the same fashion as in the first round of screening. T2 seeds were sterilized using 50% household bleach 0.01% triton X-100 solution and plated onto the same plate medium as described in the first round of screening at a density of 10 seeds/plate. Plates were kept for three days at 4° C. to stratify seeds, and grown in the same temperature and photoperiod as the first experiment with the light intensity ~160 µmol/m²/s. Plates were placed vertically into the eight center positions of a 10 plate rack with the first and last position holding blank plates. The racks and the plates within a rack were rotated every other day. Two sets of pictures were taken for each plate. The first set taking place at day 14-16 when the primary roots for most lines had reached the bottom of the plate, the second set of pictures two days later after more lateral roots had developed. The latter set of picture was usually used for data analysis. These seedlings grown on vertical plates were analyzed for root growth with the software WinRHIZO® (Regent Instruments Inc), an image analysis system specifically designed for root measurement. WinRHIZO® uses the contrast in pixels to distinguish the light root from the darker background. To identify the maximum amount of roots without picking up background, the pixel classification was 150-170 and the filter feature was used to remove objects that have a length/width ratio less then 10.0. The area on the plates analyzed was from the edge of the plant's leaves to about 1 cm from the bottom of the plate. The exact same WinRHIZO® settings and area of analysis were used to analyze all plates within a batch. The total root length score given by WinRHIZO® for a plate was divided by the number of plants that had germinated and had grown halfway down the plate. Three plates for every line were grown and their scores were averaged. This average was then compared to the average of three plates containing wild type seeds that were grown at the same time.

*Arabidopsis* activation tagged lines re-confirmed by having a higher value of root growth compared to wild type were then used for the molecular identification of the DNA flanking the T-DNA insertion.

Example 2B

Identification of Mutant Lines with an Altered Root Phenotype in a Mutant Population (Limiting Nitrogen Conditions)

A Two-Step Screening Procedure can be Used, Comprising:
(1) Identification of an altered root growth phenotype in a vertical plate assay;
(2) Confirm herbicide resistance and root phenotype in rescued mutant lines;

The primary screen is based on vertical plates containing Nitrogen-free Hoagland salts, 0.3% sucrose and 1 mM $KNO_3$. The media also contains 0.8%-1.0% PhytaGel as a gelling agent. Media with Phytagel at 1.0% is sometimes difficult to pour as it solidifies quickly, however, at below 0.8% the media will slide off plates when placed vertically. Mutants from an activation-tagged population where pools of 100 lines each are available for a total of 36000 lines are being screened. On each plate, 12 mutant and 2 wild type Columbia seeds are seeded. Plates are placed in a growth room with a constant temperature of 26° C., 16 hr-day cycle with an average of 110 µE/m²s light intensity at the top of the plates. These plates are photographed 3-4 times in a 2.5 week time frame. Individual seedlings are rescued when a clear root phenotype is observed. Rescued seedlings are grown to maturity in a growth chamber (24° C., 16 hr day, 250-300 µE/m²s) for seed collection.

For the secondary screening, seeds from putative hits identified in the primary screen are sowed on plates containing the same media as above plus 6 mg/L bialaphos. Wild type Columbia seeds are sown at the same time on the same media but without bialaphos. Each plate has 10 seeds. There are 3 plates for each mutant line, and 2 plates for wild type Columbia, as replication. These plates are placed under the same growth conditions as described above in a growth room. Those lines that do not have herbicide resistance or no obvious root phenotype are discarded as false positives. Lines validated by the second screen are saved for further study.

Example 3

Identification of Activation-Tagged Genes

Genes flanking the T-DNA insert in lines with altered root architecture are identified using one, or both, of the following two standard procedures: (1) thermal asymmetric interlaced (TAIL) PCR (Liu et al., (1995), *Plant J.* 8:457-63); and (2) SAIFF PCR (Siebert et al., (1995) *Nucleic Acids Res.* 23:1087-1088). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence.

Once a tag of genomic sequence flanking a T-DNA insert is obtained, candidate genes are identified by alignment to publicly available *Arabidopsis* genome sequence.

Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged llrk Gene

The llrk gene was obtained by the screening procedure as described in Example 2B and subsequently subjected to a phase 3 (in house) screening as described in Example 2A. Identification of the activation-tagged gene was performed as described in Example 3.

One line (5-7) displaying altered root architecture was further analyzed. DNA from the line was extracted and the T-DNA insertion was found by ligation mediated PCR (Siebert et al., (1995) *Nucleic Acids Res.* 23:1087-1088) using primers within the LeftBorder of the T-DNA. Once a tag of genomic sequence flanking a T-DNA insert was obtained, the candidate gene was identified by sequence alignment to the completed *Arabidopsis* genome. One of the insertion sites identified was identified as a chimeric insertion; Left Border T-DNA sequence was determined to be at both ends of the T-DNA insertion. It is still possible that the enhancer elements located near the Right Border of the T-DNA are close enough to have an effect on the nearby candidate gene. In this case the location of the Right Border was assumed to be present at the insertion site, and the two genes that flank the insertion site were chosen as candidates. One of the genes nearest the 35S enhancers of the chimeric insertion was AT1G69270 (SEQ ID NO:20); *Arabidopsis thaliana* leucine rich repeat kinase), encoding the LLRK protein (SEQ ID NO:22), referred herein as leucine rich repeat kinase, or LLRK.

Example 5A

Validation of a Candidate *Arabidopsis* Gene (AT1G69270) for its Ability to Enhance Root Architecture in Plants Via Transformation into *Arabidopsis*

Candidate genes can be transformed into *Arabidopsis* and overexpressed under the 35S promoter. If the same or similar phenotype is observed in the transgenic line as in the parent activation-tagged line, then the candidate gene is considered to be a validated "lead gene" in *Arabidopsis*. The *Arabidopsis* AT1G69270 Gene can be directly tested for its ability to enhance Root Architecture in *Arabidopsis*.

The *Arabidopsis* AT1G69270 cDNA was PCR amplified with oligos that introduce the attB1 (SEQ ID NO:25) sequence, a consensus start sequence (CAACA) upstream of the ATG start codon and the first 21 nucleotides of the protein coding-region of the AT1G69270 cDNA (nucleotides 51-764 (Stop) of SEQ ID NO:50) and the attB2 (SEQ ID NO:26) sequence and the last 23 nucleotides of the protein-coding region including the stop codon of said cDNA. Using Invitrogen™ Gateway® technology a MultiSite Gateway® BP Recombination Reaction was performed with pDONR™/Zeo (Invitrogen™, FIG. 2; SEQ ID NO:2). This process removes the bacteria lethal ccdB gene, as well as the chloramphenicol resistance gene (CAM) from pDONR™/Zeo and directionally clones the PCR product with flanking attB1 (SEQ ID NO:25) and attB2 (SEQ ID NO:26) sites creating entry clone PHP28738.

Figure 4:
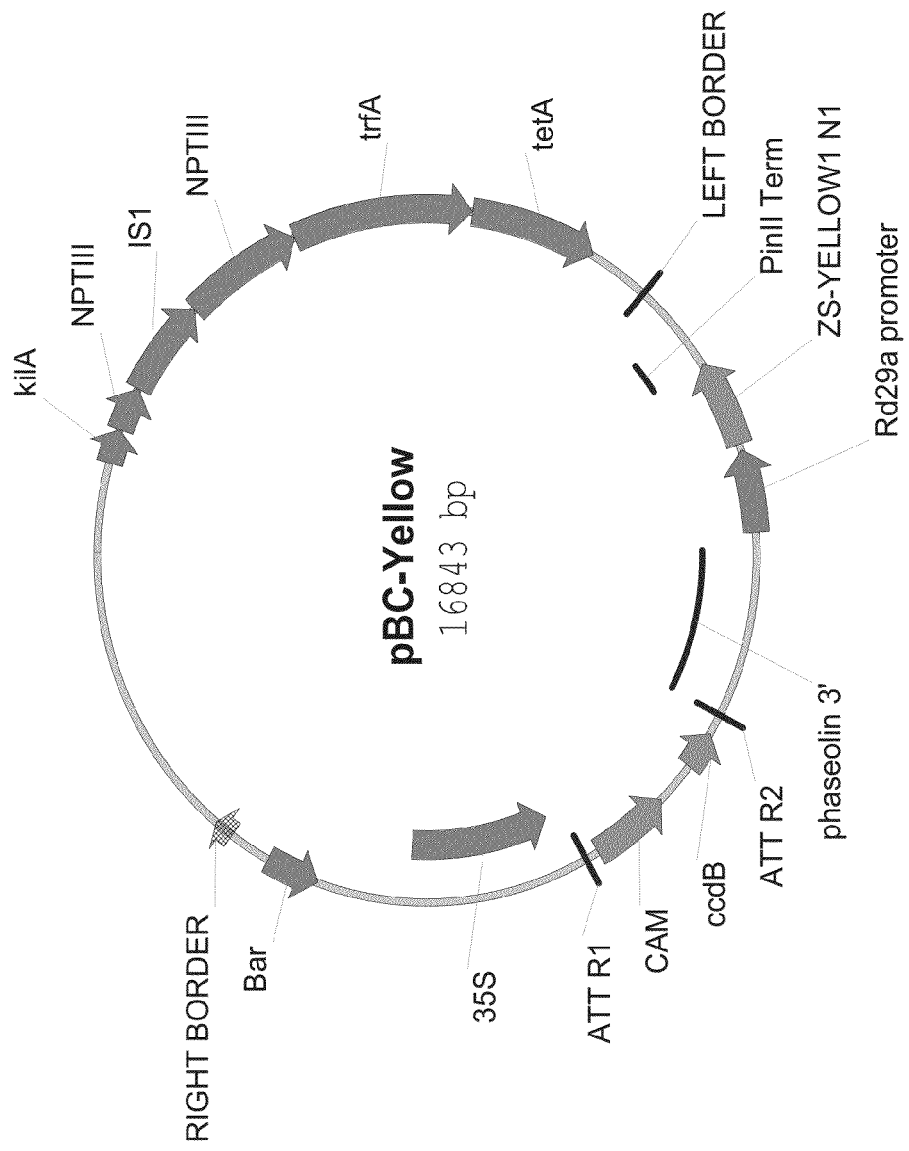
FIG. 4 shows a map of the vector pBC-yellow (SEQ ID NO:4), a destination vector for use in construction of expression vectors for *Arabidopsis*. The attR1 site is at nucleotides 11276-11399 (complementary strand); the attR2 site is at nucleotides 9695-9819 (complementary strand).

A 16.8-kb T-DNA based binary vector, called pBC-yellow (FIG. 4, SEQ ID NO:4), was constructed with the 1.3-kb 35S promoter immediately upstream of the Invitrogen™ Gateway® C1 conversion insert containing the ccdB gene and the chloramphenicol resistance gene (CAM) flanked by attR1 and attR2 sequences. The vector also contains a YFP marker under the control of the Rd29a promoter for the selection of transformed seeds.

Using Invitrogen™ Gateway® technology a MultiSite Gateway® LR Recombination Reaction was performed on the entry clone containing the directionally cloned PCR product and pBC-yellow. This allowed rapid and directional cloning of the AT1G69270 gene behind the 35S promoter in pBC-yellow.

The 35S-AT1G69270 gene construct was introduced into wild-type *Arabidopsis* ecotype Col-0, using the same *Agrobacterium*-mediated transformation procedure described in Example 1.

Transgenic T1 seeds were selected by the presence of the fluorescent YFP marker. Fluorescent seeds were subjected to the Root Architecture Assay following the procedure described in Example 2A. Transgenic T1 seeds were re-screened using 6 plates per construct. Two plates per rack containing non-transformed Columbia seed discarded from fluorescent seed sorting served as a control.

Six plates per construct were analyzed statistically and a trend was detected between the number of plants growing on a plate and their average WinRHIZO® score. WinRHIZO® scores were normalized for this trend and the root score corresponding to the construct was divided by the wild-type root score.

Example 5B

Screen of Candidate Genes Under Nitrogen Limiting Conditions

Transgenic T1 seed selected by the presence of the fluorescent marker YFP as described above in Example 5A can also be screened for their tolerance to grow under nitrogen limiting conditions. For this purpose 32 transgenic individuals can be grown next to 32 wild-type individuals on one plate with either 0.4 mM $KNO_3$ or 60 mM $KNO_3$. If a line shows a statistically significant difference from the controls, the line is considered a validated nitrogen-deficiency tolerant line. After masking the plate image to remove background color, two different measurements are collected for each individual: total rosetta area, and the percentage of color that falls into a green color bin. Using hue, saturation and intensity data (HIS), the green color bin consists of hues 50-66. Total rosetta area is used as a measure of plant biomass, whereas the green color bin has been shown by dose-response studies to be an indicator of nitrogen assimilation.

Example 5C

Validation of a Candidate *Arabidopsis* Gene (AT1G69270) for its Ability to Improve Nitrogen Utilization in Plants Via Transformation into *Arabidopsis*

Transgenic seeds were screened for their ability to grow under nitrogen limiting conditions as described in Example 5B.

Plants were evaluated at 10, 11, 12 and 13 days. Transgenic individuals expressing the *Arabidopsis* Candidate gene (AT1G69270) validated under low (0.4 mM $KNO_3$) and non-limiting nitrogen conditions (60 mM $KNO_3$) compared to the wild type plants; e.g. the transgenic plants had increased biomass under both conditions.

Example 5D

Screen to Identify Lines with Improved Nitrate Uptake

For each overexpressor line, twelve T2 plants are sown on 96 well micro titer plates containing 2 mM $MgSO_4$, 0.5 mM $KH_2PO_4$, 1 mM $CaCl_2$, 2.5 mM KCl, 0.15 mM Sprint 330, 0.06 mM $FeSO_4$, 1 µM $MnCl_2$ $4H_2O$, 1 µM $ZnSO_4$ $7H_2O$, 3 µM $H_3BO_3$, 0.1 µM $NaMoO_4$, 0.1 µM $CuSO_4$ $5H_2O$, 0.8 mM potassium nitrate, 0.1% sucrose, 1 mM MES, 200 µM bromophenol red and 0.40% Phytagel™ (pH assay medium). The pH of the medium is so that the color of bromophenol is red, the pH indicator dye, is yellow.

Four lines are plated per plate, and the inclusion of 12 wild-type individuals and 12 individuals from a line that has shown an improvement in nitrate uptake (positive control) on each plate makes for a total of 72 individuals on each 96 well micro titer plate A web-based random sequence generator can be used to determine the order of the lines on each plate. Seeds are not plated in Row A or Row H on the 96 well micro titer plate. Four plates are plated for each experiment, resulting in a maximum of 48 plants per line analyzed. Plates are kept for three days in the dark at 4° C. to stratify seeds, and then placed horizontally for six days at 22° C. light and dark. Photoperiod is sixteen hours light; eight hours dark, with an average light intensity of ~200 mmol/m²/s. Plates are rotated and shuffled within each shelf. At day eight or nine (five or six days of growth), seedling status is evaluated by recording the color of the medium as pink, peach, yellow or no germination. Then the plants and/or seeds are removed from each well. Each medium plug is transferred to 1.2 ml micro titer tubes and placed in the corresponding well in a 96 well deep micro titer plate. An equal volume of water containing 2 µM flourescein is added to each 1.2 ml micro titer tube. The plate is covered with foil and autoclaved on liquid cycle. Each tube is mixed well, and an aliquot is removed from each tube and analyzed for amount of nitrate remaining in the medium. If the t-test shows that a line is significantly different (p<0.05) from wild-type control, the line is then considered a validated improved nitrate uptake line.

Example 5E

Validation of Increased Nitrate Uptake by Transgenic Lines Containing the Candidate *Arabidopsis* Gene (AT1G69270)

Transgenic seeds were screened for increased nitrate uptake as described in Example 5D.

Transgenic individuals overexpressing the *Arabidopsis* Candidate gene (AT1G69270) did not validate as an improved nitrate uptake line compared to wild type plants not overexpressing the *Arabidopsis* candidate gene.

Example 6

Composition of cDNA Libraries

Isolation and Sequencing of cDNA Clones cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs," see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred and Phrap (Ewing et al. (1998) *Genome Res.* 8:175-185; Ewing and Green (1998) *Genome*

Res. 8:186-194). Phred is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (Gordon et al. (1998) *Genome Res.* 8:195-202).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen™ (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 7

Identification of cDNA Clones cDNA clones encoding LLRK-like polypeptides were identified by conducting BLAST (Basic Local Alignment Search Tool; Altschul et al. (1993) *J. Mol. Biol.* 215:403-410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained as described in Example 6 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the Genbank database as described above. ESTs that contain sequences more 5- or 3-prime can be found by using the BLASTn algorithm (Altschul et al (1997) *Nucleic Acids Res.* 25:3389-3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 6. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 8

Preparation of cDNA Libraries and Characterization of cDNA Clones Encoding LLRK-like Polypeptides cDNA libraries representing mRNAs from various tissues of Maize, were prepared as described in Example 6. The characteristics of the libraries are described in Table 2.

TABLE 2 cDNA Libraries from, Maize

| Library | Tissue | Clone |
|---|---|---|
| p0128 | Pooled primary and secondary immature ear | p0128.cpiae89r:fis |
| cfp1n | Maize Tassel V7 to V12 pooled, Full-length enriched normalized. | cfp1n.pk018.k5b:fis |
| cfp2n | Maize Silk pollinated and unpollinated, pooled, Full-length enriched, normalized | cfp2n.pk056.k23a.f cfp2n.pk056.k23b |
| my | Myriad project submissions. | my.cco1n.pk077.a19 |
| cfp5n | Maize Kernel, pooled stages, Full-length enriched, normalized | cfp5n.pk002.f22:fis |

The BLASTX search using the EST sequences from clones listed in Table 1 and SEQ ID NO:36 revealed similarity of the polypeptides encoded by the cDNAs to LLRK-like polypeptides from rice (GI No. 115455429, 12500990 and 115438737 corresponding to SEQ ID NOs:23, 24, and 37, respectively). Shown in Table 3 are the BLAST results for the sequences of the entire cDNA inserts ("Full-Insert Sequence" or "FIS") of the clones listed in Table 2. Each cDNA insert encodes an entire functional protein ("Complete Gene Sequence" or "CGS"). Also shown in Tables 3 and 4 are the percent sequence identity values per each pair of amino acid sequences using the Clustal V method of alignment with default parameters.

TABLE 3

BLAST Results and Percent Identity for Sequences Encoding Polypeptides Homologous to LLRK-like Polypeptides

| Sequence | Status | NCBI GI No. | BLAST pLog Score | % identity |
|---|---|---|---|---|
| p0128.cpiae89r:fis SEQ ID NO: 14 | CGS | 115455429 (Rice) SEQ ID NO: 23 | >180 | 75.7 |
| cfp1n.pk018.k5b:fis SEQ ID NO: 16 | CGS | 125600990 (Rice) SEQ ID NO: 24 | >180 | 83.4 |
| Contig of: my.cco1n.pk077.a19 cfp2n.pk056.k23a.f cfp2n.pk056.k23b (SEQ ID NO: 18) | CGS | 115455429 (Rice) SEQ ID NO: 23 | 164 | 60.6 |
| cfp5n.pk002.f22:fis (SEQ ID NO: 35) | CGS | 115438737 (Rice) SEQ ID NO: 37 | >180 | 90.2 |

FIGS. 15A-15D show the multiple alignment of the full length amino acid sequences of SEQ ID NOs: 15, 17, 19, 22, and 36 and SEQ ID NOs:23, and 24. FIG. 16 presents the percent sequence identities and divergence values for each sequence pair presented in FIGS. 15A-15D.

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST scores and probabilities indicate that the nucleic acid fragments comprising the instant cDNA clones encode LLRK-like polypeptides.

TABLE 4

BLAST Results for Sequences Encoding Polypeptides Homologous to LLRK and LLRK-like polypeptides

| Sequence | Status | Reference | Blast pLog Score | % identity |
|---|---|---|---|---|
| p0128.cpiae89r:fis SEQ ID NO: 14 | CGS | SEQ ID NO: 4815 in WO2003008540-A2 | >180 | 74.6 |
| cfp1n.pk018.k5b:fis SEQ ID NO: 16 | CGS | SEQ ID NO: 52915 in JP2005185101 | >180 | 83.4 |
| Contig of: my.cco1n.pk077.a19 cfp2n.pk056.k23a.f cfp2n.pk056.k23b (SEQ ID NO: 18) | CGS | SEQ ID NO: 47357 in US2004034888-A1 | >180 | 60.6 |
| cfp5n.pk002.f22:fis (SEQ ID NO: 35) | CGS | SEQ ID NO: 64281 in US2007011783 | >180 | 99.8 |

Example 9

Preparation of a Plant Expression Vector Containing a Homolog of the *Arabidopsis* Lead Gene (AT1G69270)

Sequences homologous to the lead llrk gene can be identified using sequence comparison algorithms such as BLAST (Basic Local Alignment Search Tool; Altschul et al., J. Mol. Biol. 215:403-410 (1993); see also the explanation of the BLAST algorithm on the world wide web site for the National Center for Biotechnology Information at the National Library of Medicine of the National Institutes of Health). Homologous llrkr-like sequences, such as the ones described in Example 8, can be PCR-amplified by either of the following methods.

Method 1 (RNA-based): If the 5' and 3' sequence information for the protein-coding region of a llrk homolog is available, gene-specific primers can be designed as outlined in Example 5A. RT-PCR can be used with plant RNA to obtain a nucleic acid fragment containing the llrk protein-coding region flanked by attB1 (SEQ ID NO:25) and attB2 (SEQ ID NO:26) sequences. The primer may contain a consensus Kozak sequence (CAACA) upstream of the start codon.

Method 2 (DNA-based): Alternatively, if a cDNA clone is available for a gene encoding a LLRK polypeptide homolog, the entire cDNA insert (containing 5' and 3' non-coding regions) can be PCR amplified. Forward and reverse primers can be designed that contain either the attB1 sequence and vector-specific sequence that precedes the cDNA insert or the attB2 sequence and vector-specific sequence that follows the cDNA insert, respectively. For a cDNA insert cloned into the vector pBluescript SK+, the forward primer VC062 (SEQ ID NO:27) and the reverse primer VC063 (SEQ ID NO:28) can be used.

Methods 1 and 2 can be modified according to procedures known by one skilled in the art. For example, the primers of method 1 may contain restriction sites instead of attB1 and attB2 sites, for subsequent cloning of the PCR product into a vector containing attB1 and attB2 sites. Additionally, method 2 can involve amplification from a cDNA clone, a lambda clone, a BAC clone or genomic DNA.

Figure 2:
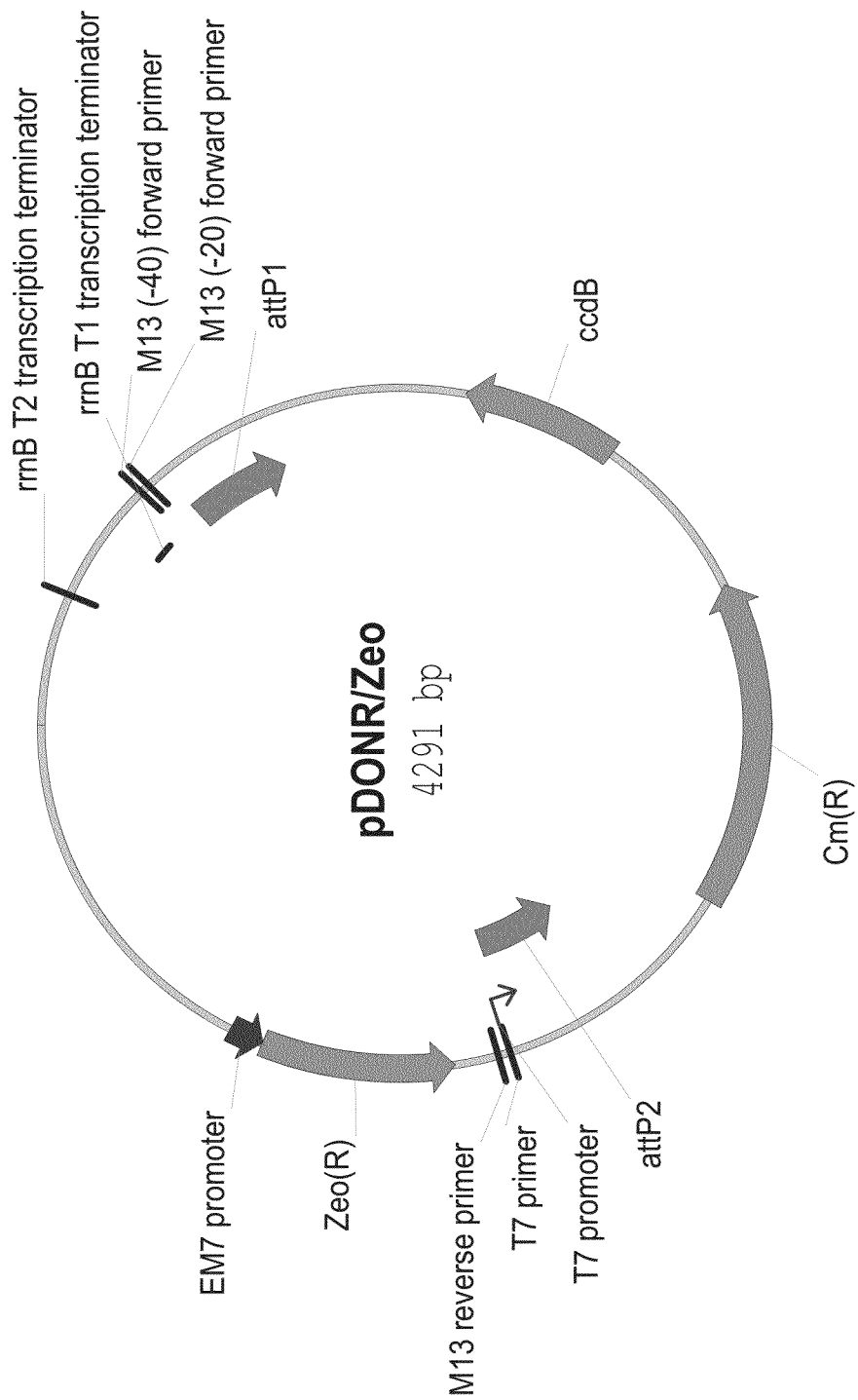
FIG. 2 shows a map of the vector pDONR™/Zeo (SEQ ID NO:2). The attP1 site is at nucleotides 570-801; the attP2 site is at nucleotides 2754-2985 (complementary strand).
Figure 3:
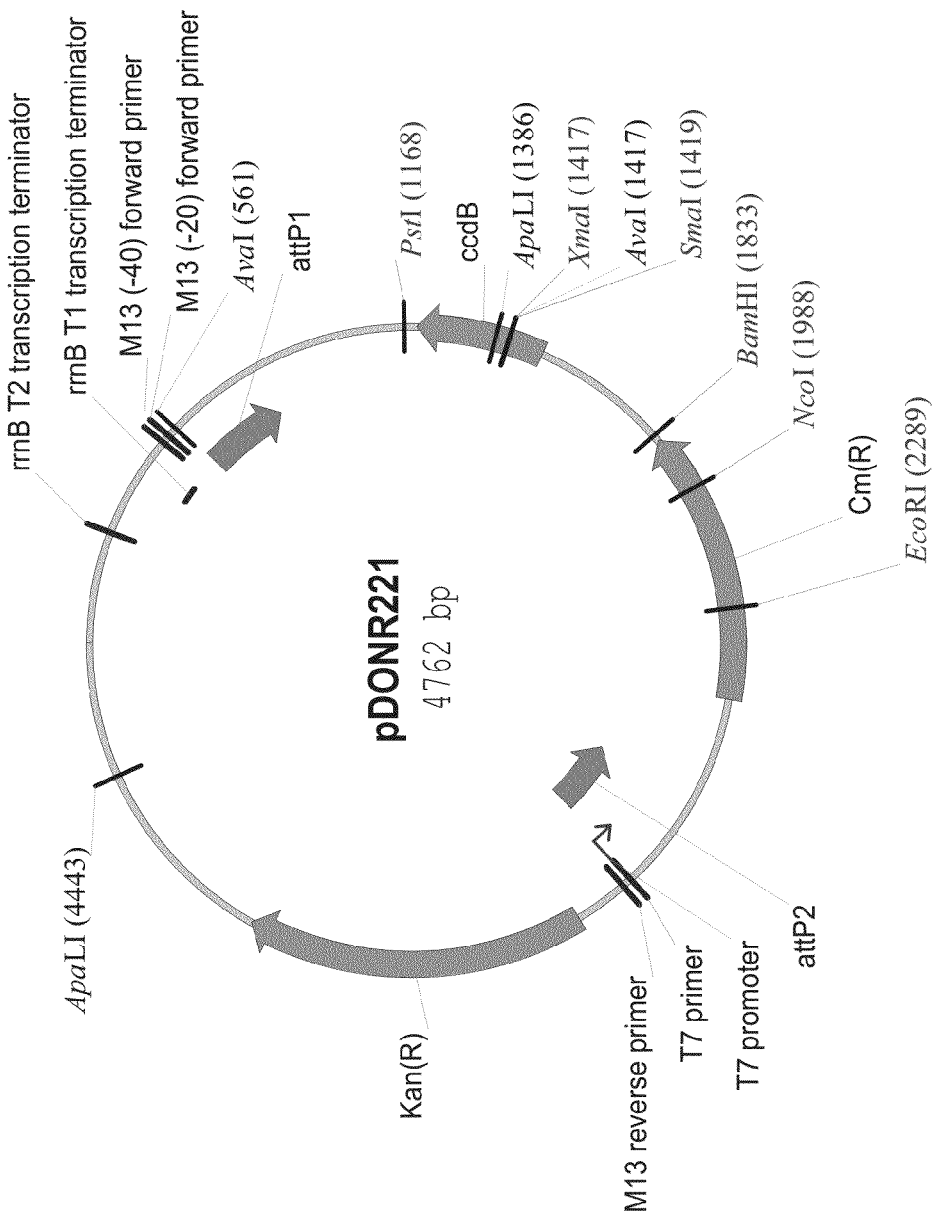
FIG. 3 shows a map of the vector pDONR™221 (SEQ ID NO:3). The attP1 site is at nucleotides 570-801; the attP2 site is at nucleotides 2754-2985 (complementary strand).
Figure 5:
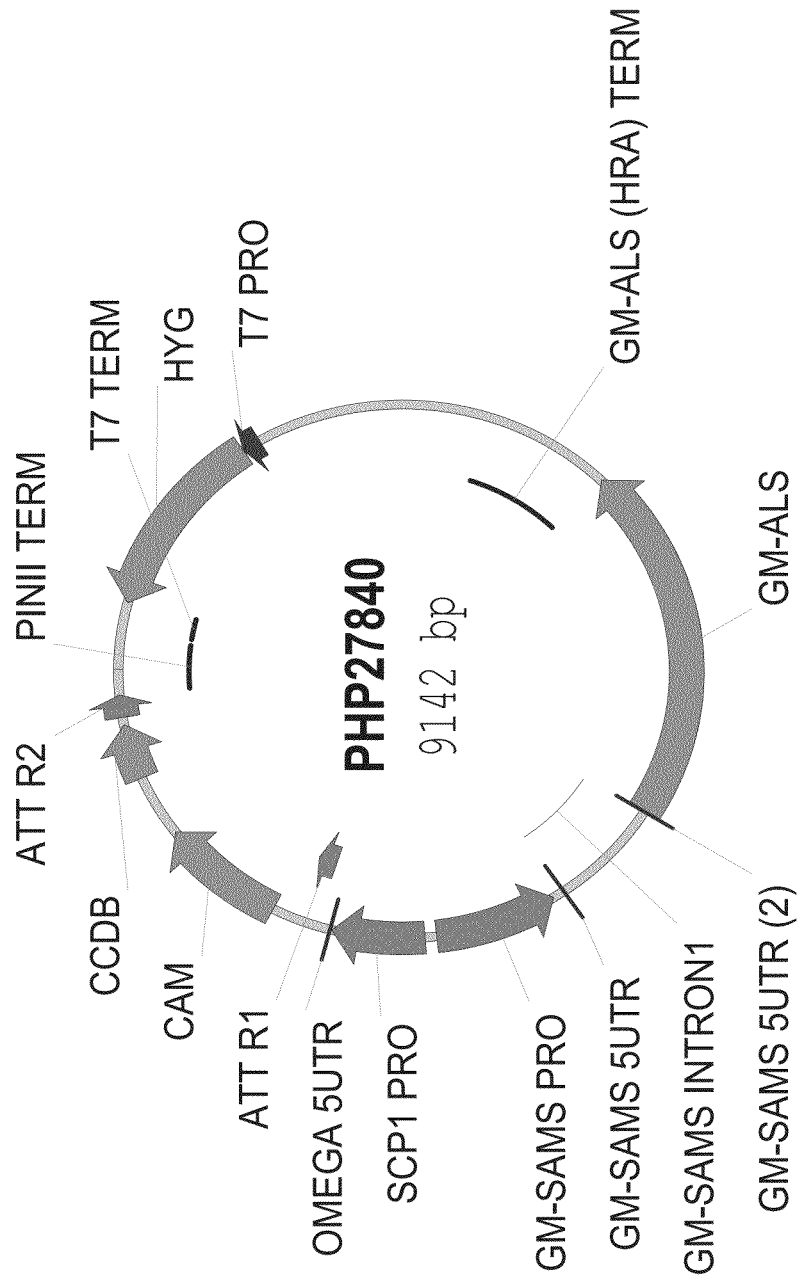
FIG. 5 shows a map of PHP27840 (SEQ ID NO:5), a destination vector for use in construction of expression vectors for soybean. The attR1 site is at nucleotides 7310-7434; the attR2 site is at nucleotides 8890-9014.
Figure 6:
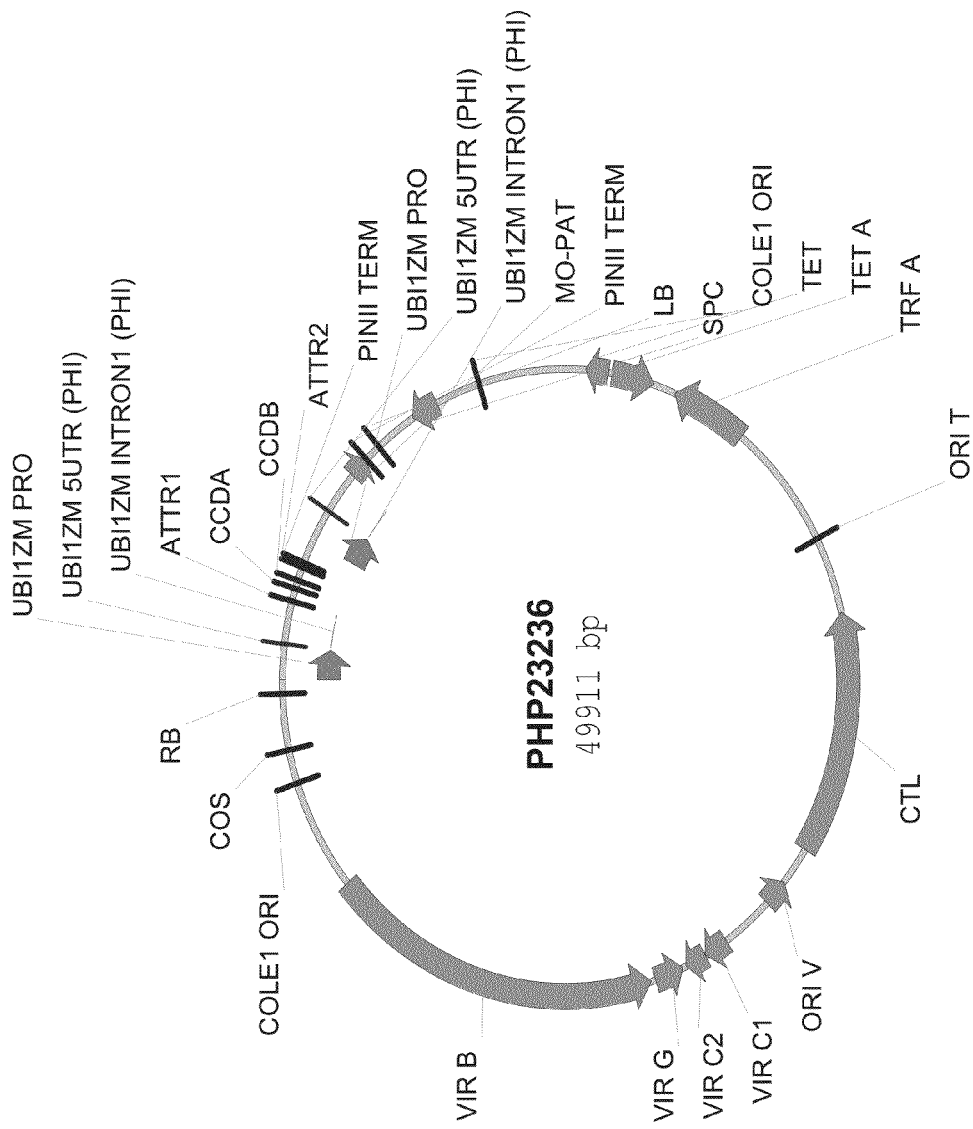
FIG. 6 shows a map of PHP23236 (SEQ ID NO:6), a destination vector for use in construction of expression vectors for Gaspe Bay Flint derived maize lines. The attR1 site is at nucleotides 2006-2130; the attR2 site is at nucleotides 2899-3023.

A PCR product obtained by either method above can be combined with the Gateway® donor vector, such as pDONR™/Zeo (Invitrogen™, FIG. 2; SEQ ID NO:2) or pDONR™221 (Invitrogen™, FIG. 3; SEQ ID NO:3) using a BP Recombination Reaction. This process removes the bacteria lethal ccdB gene, as well as the chloramphenicol resistance gene (CAM) from pDONR™221 and directionally clones the PCR product with flanking attB1 and attB2 sites to create an entry clone. Using the Invitrogen™ Gateway® Clonase™ technology, the homologous llrk-like gene from the entry clone can then be transferred to a suitable destination vector to obtain a plant expression vector for use with *Arabidopsis*, corn and soy, such as pBC-Yellow (FIG. 4; SEQ ID NO:4), PHP27840 (FIG. 5; SEQ ID NO:5) or PHP23236 (FIG. 6; SEQ ID NO:6), to obtain a plant expression vector for use with *Arabidopsis*, soybean and corn, respectively.

Alternatively a MultiSite Gateway® LR recombination reaction between multiple entry clones and a suitable destination vector can be performed to create an expression vector. An Example of this procedure is outlined in Example 14A, describing the construction of maize expression vectors for transformation of maize lines.

Example 10

Preparation of Soybean Expression Vectors and Transformation of Soybean with Validated *Arabidopsis* Lead Genes and Homologs Thereof Soybean plants can be transformed to overexpress the validated *Arabidopsis* gene (AT1G69270) and the corresponding homologs from various species in order to examine the resulting phenotype.

The entry clones described in Example 5A and 9 can be used to directionally clone each gene into PHP27840 vector (FIG. 5, SEQ ID NO:5) such that expression of the gene is under control of the SCP1 promoter.

Soybean embryos may then be transformed with the expression vector comprising sequences encoding the instant polypeptides.

To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos, which produce secondary embryos, are then excised and placed into a suitable liquid medium. After repeated selection for clusters of somatic embryos which multiply as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. Another selectable marker gene which can be used to facilitate soybean transformation is an herbicide-resistant acetolactate synthase (ALS) gene from soybean or *Arabidopsis*. ALS is the first common enzyme in the biosynthesis of the branched-chain amino acids valine, leucine and isoleucine. Mutations in ALS have been identified that convey resistance to some or all of three classes of inhibitors of ALS (U.S. Pat. No. 5,013,659; the entire contents of which are herein incorporated by reference). Expression of the herbicide-resistant ALS gene can be under the control of a SAM synthetase promoter (U.S. Patent Application No. US-2003-0226166-A1; the entire contents of which are herein incorporated by reference).

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Enhanced root architecture can be measured in soybean by growing the plants in soil and wash the roots before analysis of the total root mass with WinRHIZO®.

Soybean plants transformed with validated genes can then be assayed to study agronomic characteristics relative to control or reference plants. For example, nitrogen utilization efficacy, yield enhancement and/or stability under various environmental conditions (e.g. nitrogen limiting conditions, drought etc.).

Example 11

Transformation of Maize with validated *Arabidopsis* Lead Genes Using Particle Bombardment Maize plants can be transformed to overexpress a validated *Arabidopsis* lead gene or the corresponding homologs from various species in order to examine the resulting phenotype.

The Gateway® entry clones described in Example 5A can be used to directionally clone each gene into a maize transformation vector. Expression of the gene in maize can be under control of a constitutive promoter such as the maize ubiquitin promoter (Christensen et al., *Plant Mol. Biol.* 12:619-632 (1989) and Christensen et al., *Plant Mol. Biol.* 18:675-689 (1992))

The recombinant DNA construct described above can then be introduced into maize cells by the following procedure. Immature maize embryos can be dissected from developing caryopses derived from crosses of the inbred maize lines H99 and LH132. The embryos are isolated ten to eleven days after pollination when they are 1.0 to 1.5 mm long. The embryos are then placed with the axis-side facing down and in contact with agarose-solidified N6 medium (Chu et al., *Sci. Sin. Peking* 18:659-668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every two to three weeks.

The plasmid, p35S/Ac (obtained from Dr. Peter Eckes, Hoechst Ag, Frankfurt, Germany) may be used in transformation experiments in order to provide for a selectable marker. This plasmid contains the pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al., *Nature* 313:810-812 (1985)) and the 3' region of the nopaline synthase gene from the T-DNA of the Ti plasmid of *Agrobacterium tumefaciens*.

The particle bombardment method (Klein et al., *Nature* 327:70-73 (1987)) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After ten minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the maize tissue with a Biolistic® PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialaphos (5 mg per liter) and lacks casein or proline. The tissue continues to grow slowly on this medium. After an additional two weeks the tissue can be transferred to fresh N6 medium containing bialaphos. After six weeks, areas of about 1 cm in diameter of actively growing callus can be identified on some of the plates containing the bialaphos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined following HTP procedures. T1 seed can be collected.

T1 plants can be grown and analyzed for phenotypic changes. The following parameters can be quantified using image analysis: plant area, volume, growth rate and color analysis can be collected and quantified. Expression constructs that result in an alteration of root architecture or any one of the agronomic characteristics listed above compared to suitable control plants, can be considered evidence that the *Arabidopsis* lead gene functions in maize to alter root architecture or plant architecture.

Furthermore, a recombinant DNA construct containing a validated *Arabidopsis* gene can be introduced into an maize line either by direct transformation or introgression from a separately transformed line.

Transgenic plants, either inbred or hybrid, can undergo more vigorous field-based experiments to study root or plant architecture, yield enhancement and/or resistance to root lodging under various environmental conditions (e.g. variations in nutrient and water availability).

Subsequent yield analysis can also be done to determine whether plants that contain the validated *Arabidopsis* lead gene have an improvement in yield performance, when compared to the control (or reference) plants that do not contain the validated *Arabidopsis* lead gene. Plants containing the validated *Arabidopsis* lead gene would improved yield relative to the control plants, preferably 50% less yield loss under adverse environmental conditions or would have increased yield relative to the control plants under varying environmental conditions.

Example 12

Electroporation of *Agrobacterium tumefaciens* LBA4404

Electroporation competent cells (40 μl), such as *Agrobacterium tumefaciens* LBA4404 (containing PHP10523), are thawed on ice (20-30 min). PHP10523 contains VIR genes for T-DNA transfer, an *Agrobacterium* low copy number plasmid origin of replication, a tetracycline resistance gene, and a cos site for in vivo DNA biomolecular recombination. Meanwhile the electroporation cuvette is chilled on ice. The electroporator settings are adjusted to 2.1 kV.

A DNA aliquot (0.5 μL JT (U.S. Pat. No. 7,087,812) parental DNA at a concentration of 0.2 μg-1.0 μg in low salt buffer or twice distilled $H_2O$) is mixed with the thawed *Agrobacterium* cells while still on ice. The mix is transferred to the bottom of electroporation cuvette and kept at rest on ice for 1-2 min. The cells are electroporated (Eppendorf electroporator 2510) by pushing "Pulse" button twice (ideally achieving a 4.0 msec pulse). Subsequently 0.5 ml 2xYT medium (or SOC medium) are added to cuvette and transferred to a 15 ml Falcon tube. The cells are incubated at 28-30° C., 200-250 rpm for 3 h.

Aliquots of 250 μl are spread onto #30B (YM+50 μg/mL Spectinomycin) plates and incubated 3 days at 28-30° C. To increase the number of transformants one of two optional steps can be performed:

Option 1: overlay plates with 30 μl of 15 mg/ml Rifampicin. LBA4404 has a chromosomal resistance gene for Rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on AB minimal medium plus 50 mg/mL Spectinomycin plates (#12S medium) for isolation of single colonies. The plated are incubate at 28° C. for 2-3 days.

A single colony for each putative co-integrate is picked and inoculated with 4 ml #60A with 50 mg/l Spectinomycin. The mix is incubated for 24 h at 28° C. with shaking. Plasmid DNA from 4 ml of culture is isolated using Qiagen Miniprep+ optional PB wash. The DNA is eluted in 30 μl. Aliquots of 2 μl are used to electroporate 20 μl of DH10b+20 μl of $ddH_2O$ as per above. Optionally a 15 μl aliquot can be used to transform 75-100 μl of Invitrogen™-Library Efficiency DH5α. The cells are spread on LB medium plus 50 mg/mL Spectinomycin plates (#34T medium) and incubated at 37° C. overnight.

Three to four independent colonies are picked for each putative co-integrate and inoculated 4 ml of 2xYT (#60A) with 50 μg/ml Spectinomycin. The cells are incubated at 37° C. overnight with shaking.

The plasmid DNA is isolated from 4 ml of culture using QIAprep® Miniprep with optional PB wash (elute in 50 μl) and 8 μl are used for digestion with SalI (using JT parent and PHP10523 as controls).

Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Alternatively, for high throughput applications, such as described for Gaspe Bay Flint Derived Maize Lines (Examples 15-17), instead of evaluating the resulting co-integrate vectors by restriction analysis, three colonies can be simultaneously used for the infection step as described in Example 13.

Example 13

*Agrobacterium* Mediated Transformation into Maize

Maize plants can be transformed to overexpress a validated *Arabidopsis* lead gene or the corresponding homologs from various species in order to examine the resulting phenotype.

*Agrobacterium*-mediated transformation of maize is performed essentially as described by Zhao et al., in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium innoculation, co-cultivation, resting, selection and plant regeneration.

1. Immature Embryo Preparation

Immature embryos are dissected from caryopses and placed in a 2 mL microtube containing 2 mL PHI-A medium.

2. *Agrobacterium* Infection and Co-Cultivation of Embryos 2.1 Infection Step

PHI-A medium is removed with 1 mL micropipettor and 1 mL *Agrobacterium* suspension is added. Tube is gently inverted to mix. The mixture is incubated for 5 min at room temperature.

2.2 Co-Culture Step

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for 3 days. L-cysteine can be used in the co-cultivation phase. With the standard binary vector, the co-cultivation medium supplied with 100-400 mg/L L-cysteine is critical for recovering stable transgenic events.

3. Selection of Putative Transgenic Events

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue are expected to be visible in 6-8 weeks. Embryos that produce no events may be brown and necrotic, and little friable tissue growth is evident. Putative transgenic embryonic tissue is subcultured to fresh PHI-D plates at 2-3 week intervals, depending on growth rate. The events are recorded.

4. Regeneration of T0 plants

Embryonic tissue propagated on PHI-D medium is subcultured to PHI-E medium (somatic embryo maturation medium); in 100×25 mm Petri dishes and incubated at 28° C., in darkness, until somatic embryos mature, for about 10-18 days. Individual, matured somatic embryos with well-defined scutellum and coleoptile are transferred to PHI-F embryo germination medium and incubated at 28° C. in the light (about 80 µE from cool white or equivalent fluorescent lamps). In 7-10 days, regenerated plants, about 10 cm tall, are potted in horticultural mix and hardened-off using standard horticultural methods.

Media for Plant Transformation

1. PHI-A: 4 g/L CHU basal salts, 1.0 mL/L 1000× Eriksson's vitamin mix, 0.5 mg/L thiamin HCL, 1.5 mg/L 2,4-D, 0.69 g/L L-proline, 68.5 g/L sucrose, 36 g/L glucose, pH 5.2. Add 100 µM acetosyringone, filter-sterilized before using.
2. PHI-B: PHI-A without glucose, increased 2,4-D to 2 mg/L, reduced sucrose to 30 g/L and supplemented with 0.85 mg/L silver nitrate (filter-sterilized), 3.0 g/L gelrite, 100 µM acetosyringone (filter-sterilized), 5.8.
3. PHI-C:PHI-B without gelrite and acetosyringone, reduced 2,4-D to 1.5 mg/L and supplemented with 8.0 g/L agar, 0.5 g/L Ms-morpholino ethane sulfonic acid (MES) buffer, 100 mg/L carbenicillin (filter-sterilized).
4. PHI-D:PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, cat. no. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (fileter-sterilized), 8 g/L agar, pH 5.6.
6. PHI-F: PHI-E without zeatin, IAA, ABA; sucrose reduced to 40 g/L; replacing agar with 1.5 g/L gelrite; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Phenotypic analysis of transgenic T0 plants and T1 plants can be performed.

T1 plants can be analyzed for phenotypic changes. Using image analysis T1 plants can be analyzed for phenotypical changes in plant area, volume, growth rate and color analysis can be taken at multiple times during growth of the plants. Alteration in root architecture can be assayed as described in Example 20.

Subsequent analysis of alterations in agronomic characteristics can be done to determine whether plants containing the validated *Arabidopsis* lead gene have an improvement of at least one agronomic characteristic, when compared to the control (or reference) plants that do not contain the validated *Arabidopsis* lead gene. The alterations may also be studied under various environmental conditions.

Expression constructs that result in a significant alteration in root architecture will be considered evidence that the *Arabidopsis* gene functions in maize to alter root architecture.

Example 14A

Construction of Maize expression vectors with the *Arabidopsis* Lead Gene (AT1G69270) Using *Agrobacterium* Mediated Transformation Maize expression vectors were prepared with the *Arabidopsis* llrk gene (AT1G69270) under the control of the NAS2 (SEQ ID NO:30) and GOS2 (SEQ ID NO:31) promoter. PINII was the terminator (SEQ ID NO:34)

Figure 9:
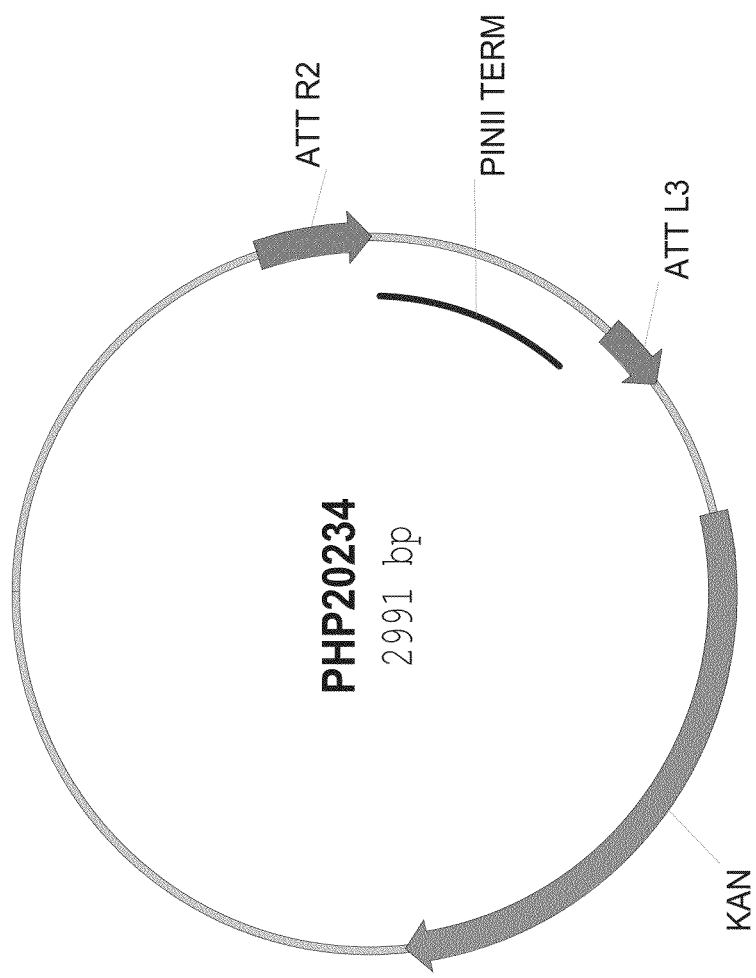
FIG. 9 shows a map of the entry clone PHP20234 (SEQ ID NO: 9), a vector carrying the PINII terminator. The attR2 site is at nucleotides 591-747; the attL3 site is at nucleotides 1100-1195.
Figure 10:
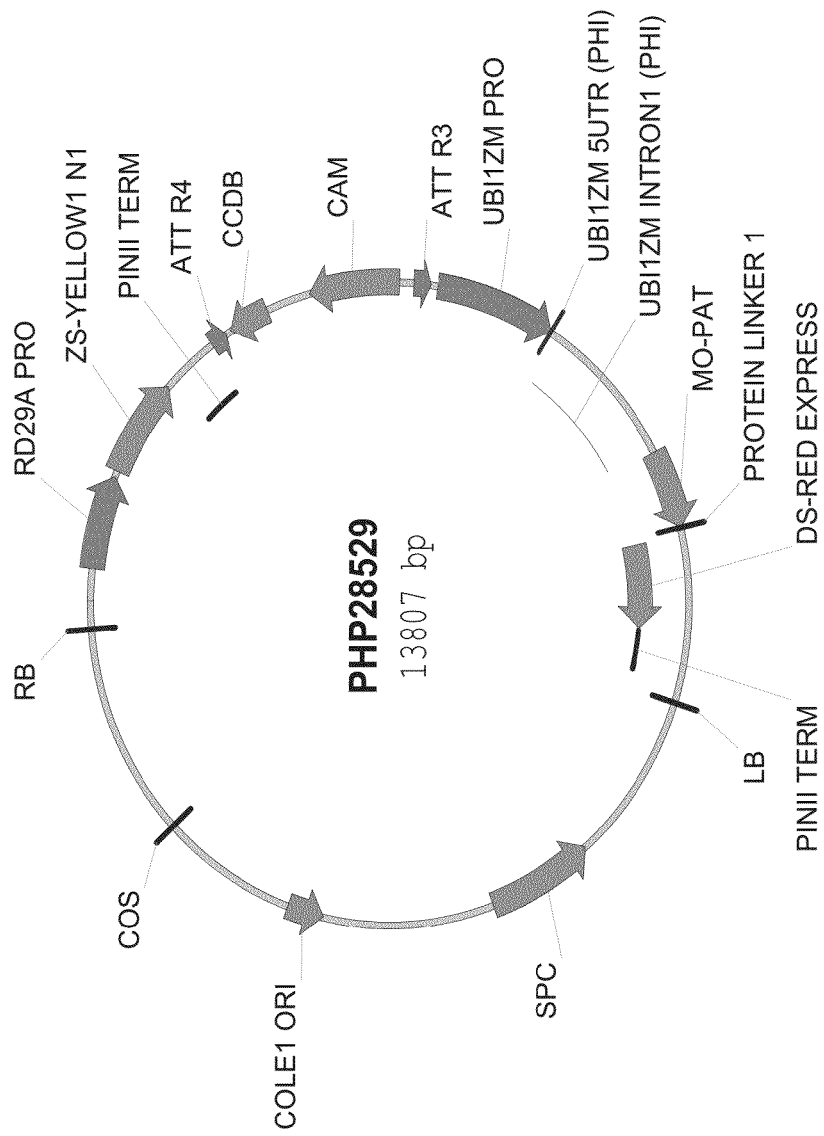
FIG. 10 shows a map of PHP28529 (SEQ ID NO: 10), a destination vector for use in construction of expression vectors for maize lines. The attR3 site is at nucleotides 3613-3737; the attR4 site is at nucleotides 2035-2159.
Figure 11:
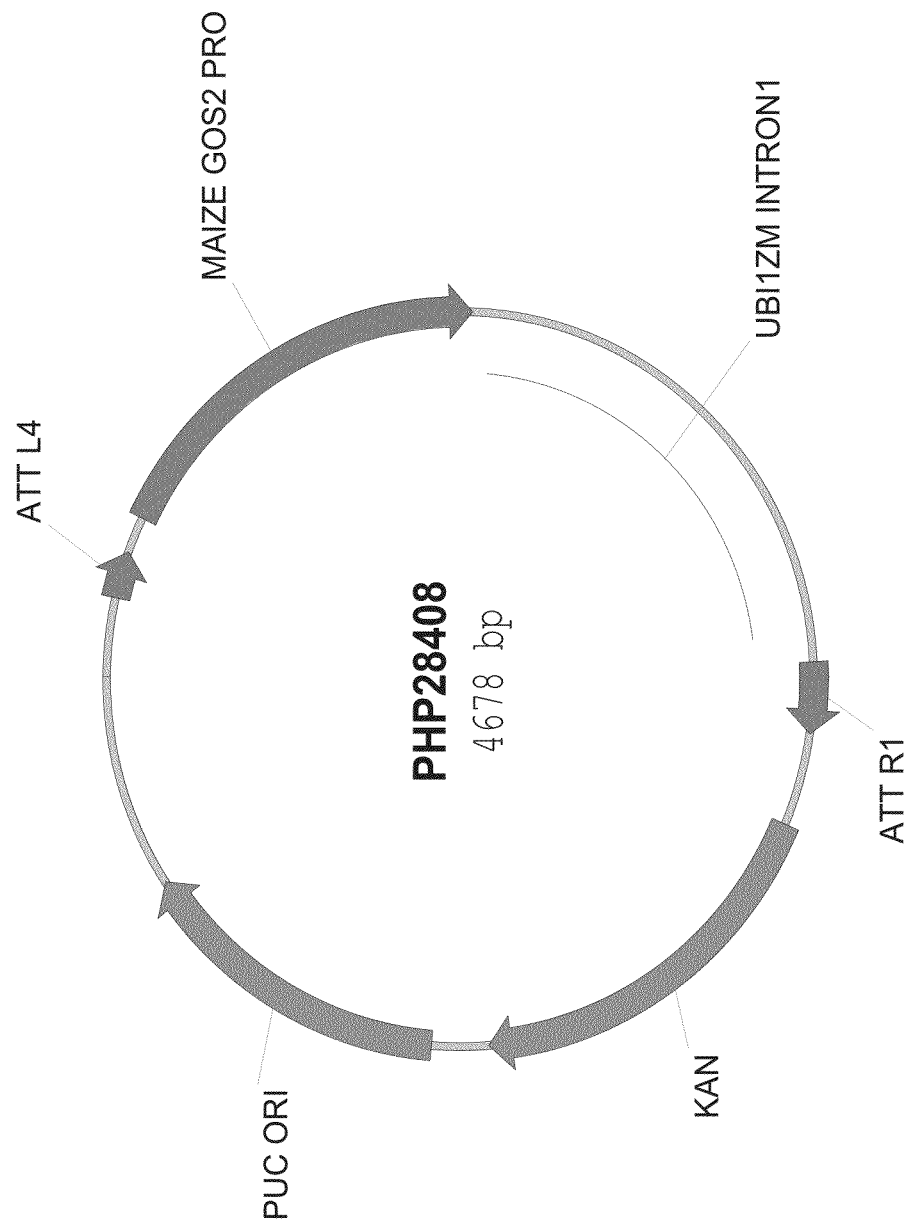
FIG. 11 shows a map of the entry clone PHP28408 (SEQ ID NO: 11), a vector carrying the constitutive maize GOS2 promoter. The attL4 site is at nucleotides 160-255; the attR1 site is at nucleotides 2301-2447.

Using Invitrogen™ Gateway® technology the entry clone, created as described in Example 5A, PHP 28738, containing the *Arabidopsis* llrk gene (AT1G69270) was used in separate Gateway® LR reactions with:

1) the constitutive maize GOS2 promoter entry clone (PHP28408, FIG. 11, SEQ ID NO:11) and the PinII Terminator entry clone (PHP20234, FIG. 9, SEQ ID NO:9) into the destination vector PHP28529 (FIG. 10, SEQ ID NO:10). The resulting vector was named PHP29302.

Figure 12:
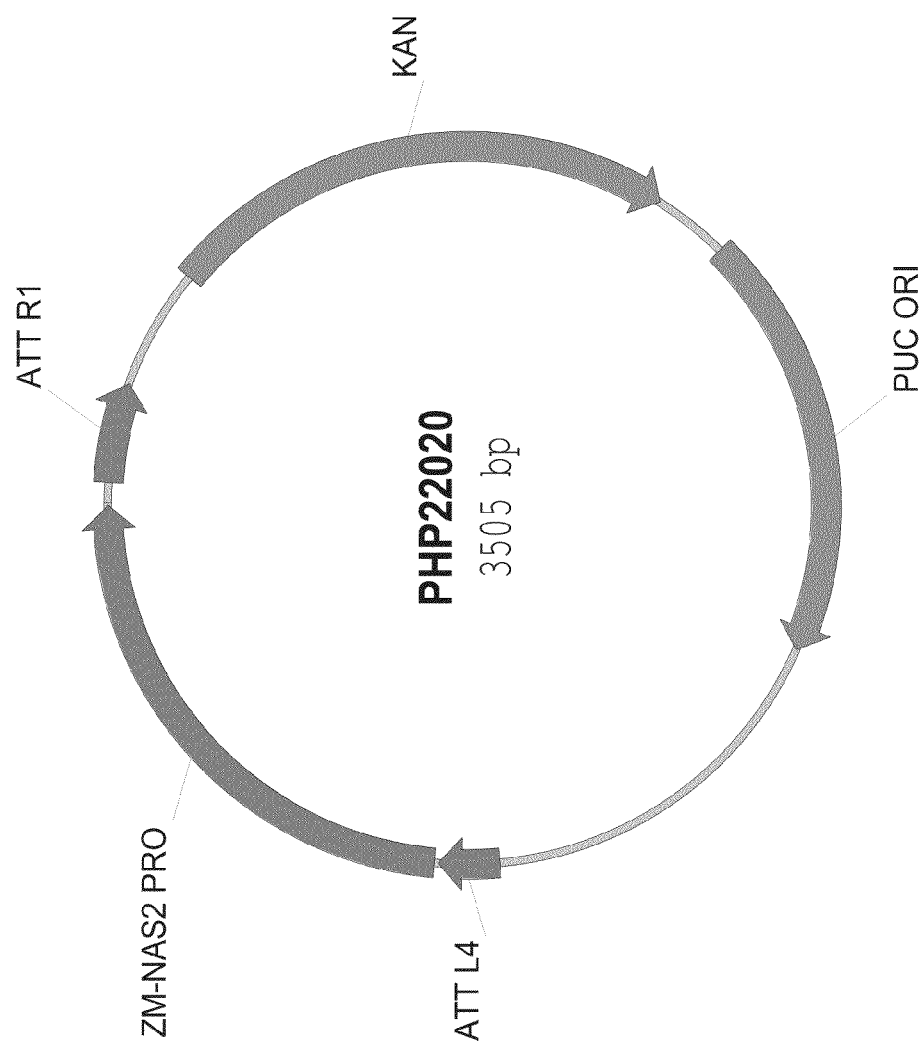
FIG. 12 shows a map of the entry clone PHP22020 (SEQ ID NO:12), a vector carrying the root maize NAS2 promoter. The attR1 site is at nucleotides 31-187; the attL4 site is at nucleotides 2578-2673.

2) the root maize NAS2 promoter entry clone (PHP22020, FIG. 12, SEQ ID NO:12) and the PinII Terminator entry clone (PHP20234, FIG. 9, SEQ ID NO:9) into the destination vector PHP28529 (FIG. 10, SEQ ID NO:10). The resulting vector was named PHP29303.

The destination vector PHP28529 added to each of the final vectors (PHP28911 and PHP28912) also an:
1) RD29A promoter::yellow fluorescent protein::PinII terminator cassette for *Arabidopsis* seed sorting
2) a Ubiquitin promoter::moPAT/red fluorescent protein fusion::PinII terminator cassette for transformation selection and *Z. mays* seed sorting.

Example 14B

Preparation of Maize Expression Constructs Containing the *Arabidopsis* llrk Gene and Homologs Thereof The *Arabidopsis* llrk gene and the corresponding homologs from maize and other species (Table 1 and SEQ ID NO: 35) can be transformed into maize lines using the procedures outlined in Examples 5A and 14A. Maize expression vectors with *Arabidopsis* llrk gene and the corresponding homologs from maize and other species (Table 1 and SEQ ID NO:35) can be prepared as outlined in Examples 5A and 14A. In addition to the GOS2 or NAS2 promoter, other promoters such as, but not limited to the ubiquitin promoter, the S2A and S2B promoter, the maize ROOTMET2 promoter, the maize Cyclo, the CR1BIO, the CRWAQ81 and the maize ZRP2.4447 are useful for directing expression of llrk and llrk-like genes in maize. Furthermore, a variety of terminators, such as, but not limited to the PINII terminator, could be used to achieve expression of the gene of interest in maize.

Example 14C

Figure 7:
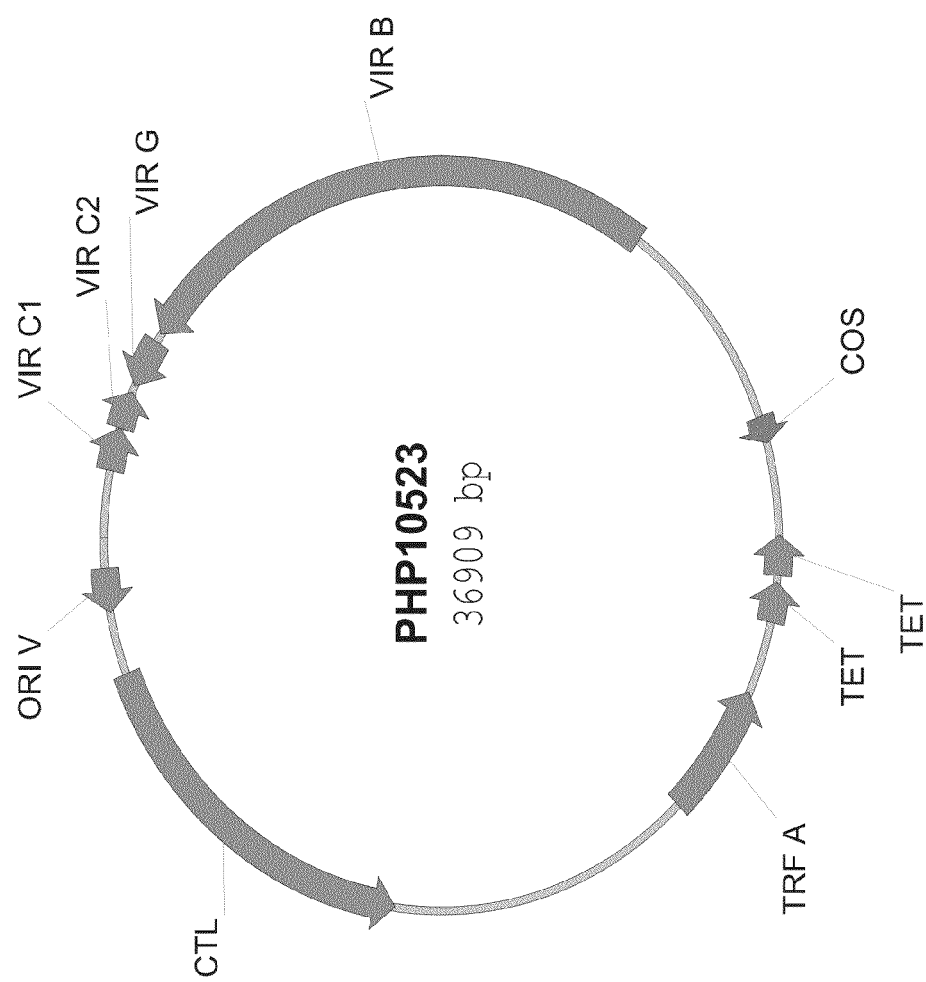
FIG. 7 shows a map of PHP10523 (SEQ ID NO: 7), a plasmid DNA present in *Agrobacterium* strain LBA4404.

Transformation of Maize Lines with the *Arabidopsis* Lead Gene (AT1G69270) and Corresponding Homologs from Other Species Using *Agrobacterium* Mediated Transformation The final vectors (vectors for expression in Maize, Example 14A, and B) can be then electroporated separately into LBA4404 *Agrobacterium* containing PHP10523 (FIG. 7; SEQ ID NO: 7, Komari et al. Plant J 10:165-174 (1996), NCBI GI: 59797027) to create the co-integrate vectors for maize transformation. The co-integrate vectors are formed by recombination of the final vectors (maize expression vectors) with PHP10523, through the COS recombination sites contained on each vector. The co-integrate vectors contain in addition to the expression cassettes described in Examples 14A-B, also genes needed for the *Agrobacterium* strain and the *Agrobacterium* mediated transformation, (TET, TET, TRFA, ORI terminator, CTL, ORI V, VIR C1, VIR C2, VIR G, VIR B). Transformation into a maize line can be performed as described in Example 13.

Example 15

Figure 8:
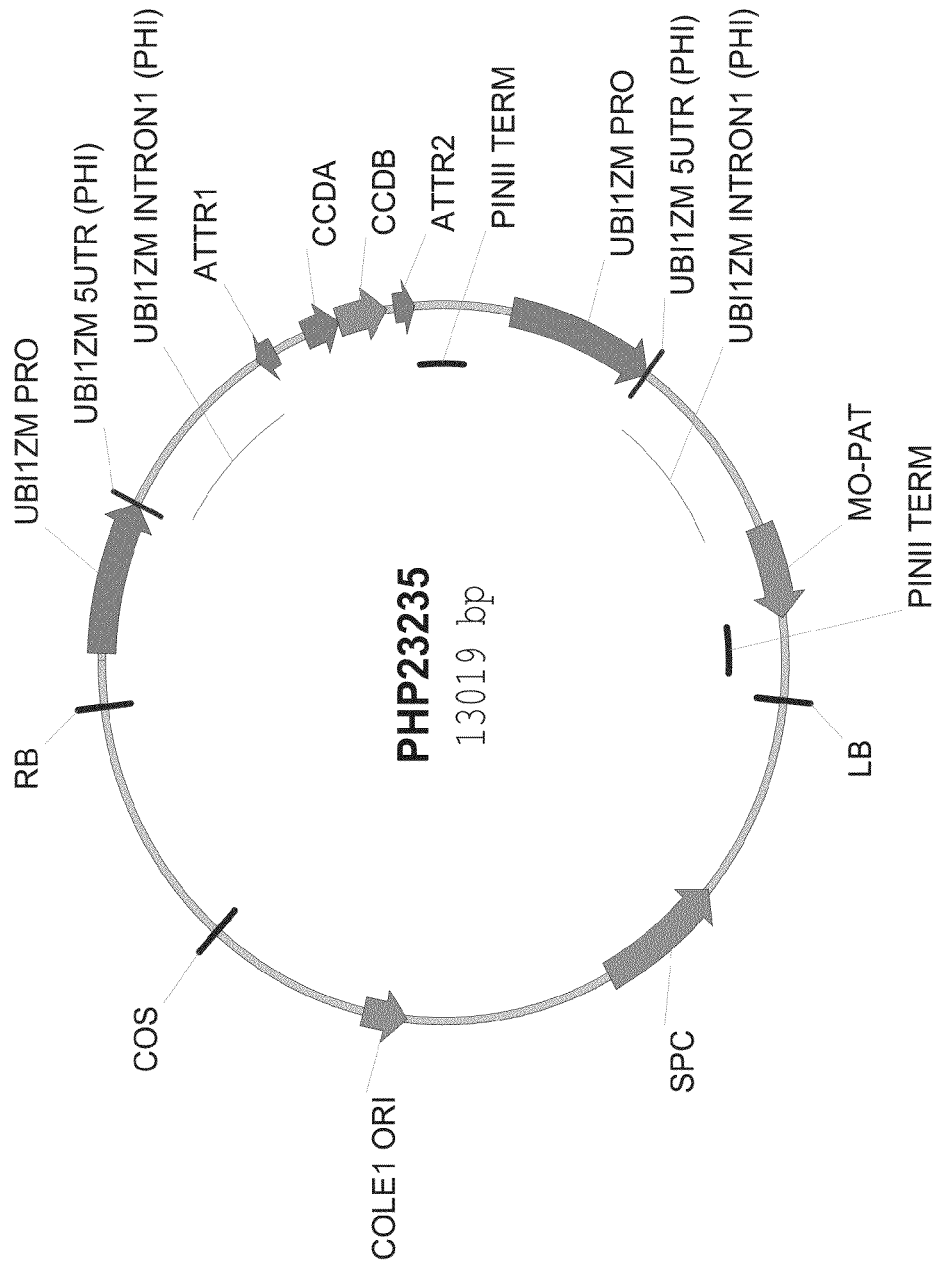
FIG. 8 shows a map of PHP23235 (SEQ ID NO: 8), a vector used to construct the destination vector PHP23236.

Preparation of the Destination Vectors PHP23236 and PHP29635 for Transformation of Gaspe Bay Flint Derived Maize Lines Destination vector PHP23236 (FIG. 6, SEQ ID NO:6) was obtained by transformation of *Agrobacterium* strain LBA4404 containing plasmid PHP10523 (FIG. 7, SEQ ID NO:7) with plasmid PHP23235 (FIG. 8, SEQ ID NO:8) and isolation of the resulting co-integration product. Destination vector PHP23236, can be used in a recombination reaction with an entry clone as described in Example 16 to create a maize expression vector for transformation of Gaspe Bay Flint derived maize lines. Expression of the gene of interest is under control of the ubiquitin promoter (SEQ ID NO:32).

Figure 13:
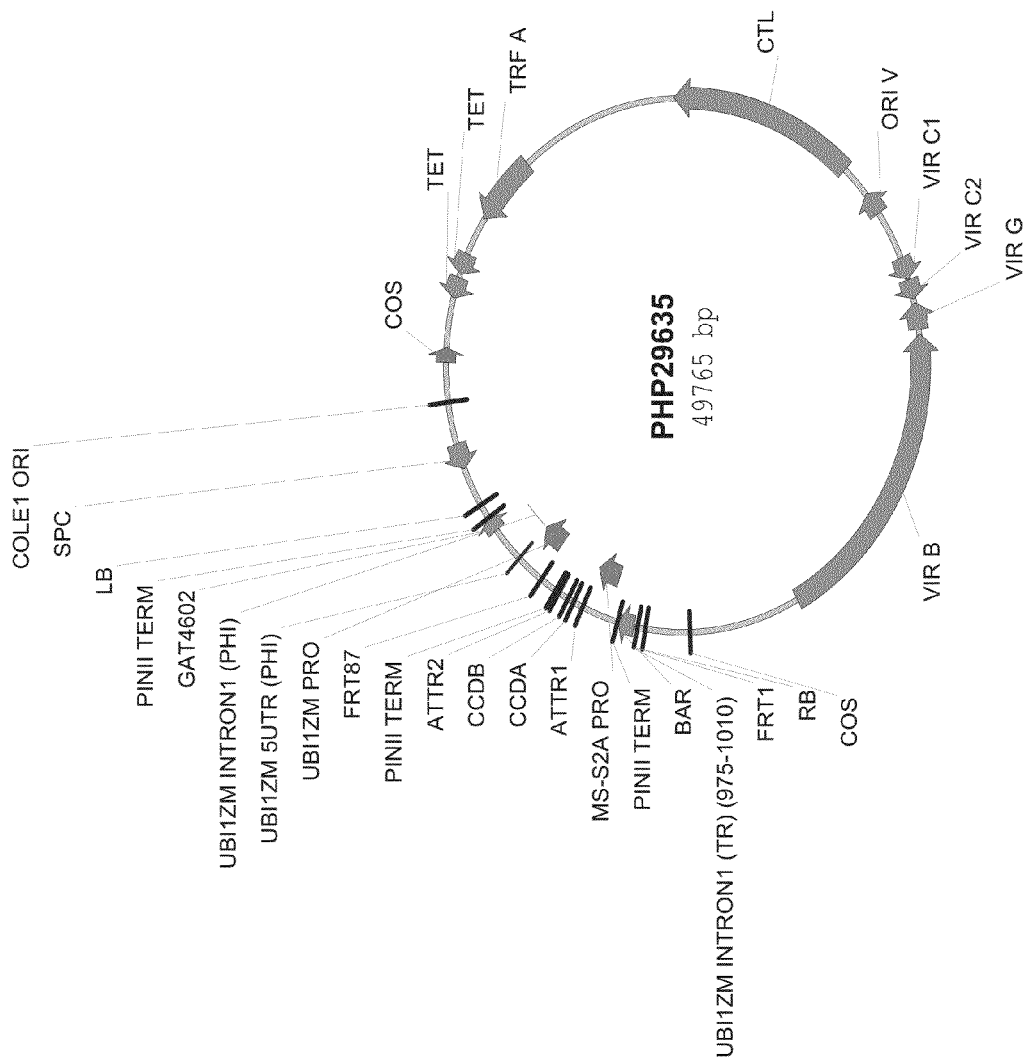
FIG. 13 shows a map of PHP29635 (SEQ ID NO: 13), a destination vector for use in construction of expression vectors for Gaspe Bay Flint derived maize lines. The attR1 site is at nucleotides 40786-40910; the attR2 site is at nucleotides 41679-41803.
Figure 14:
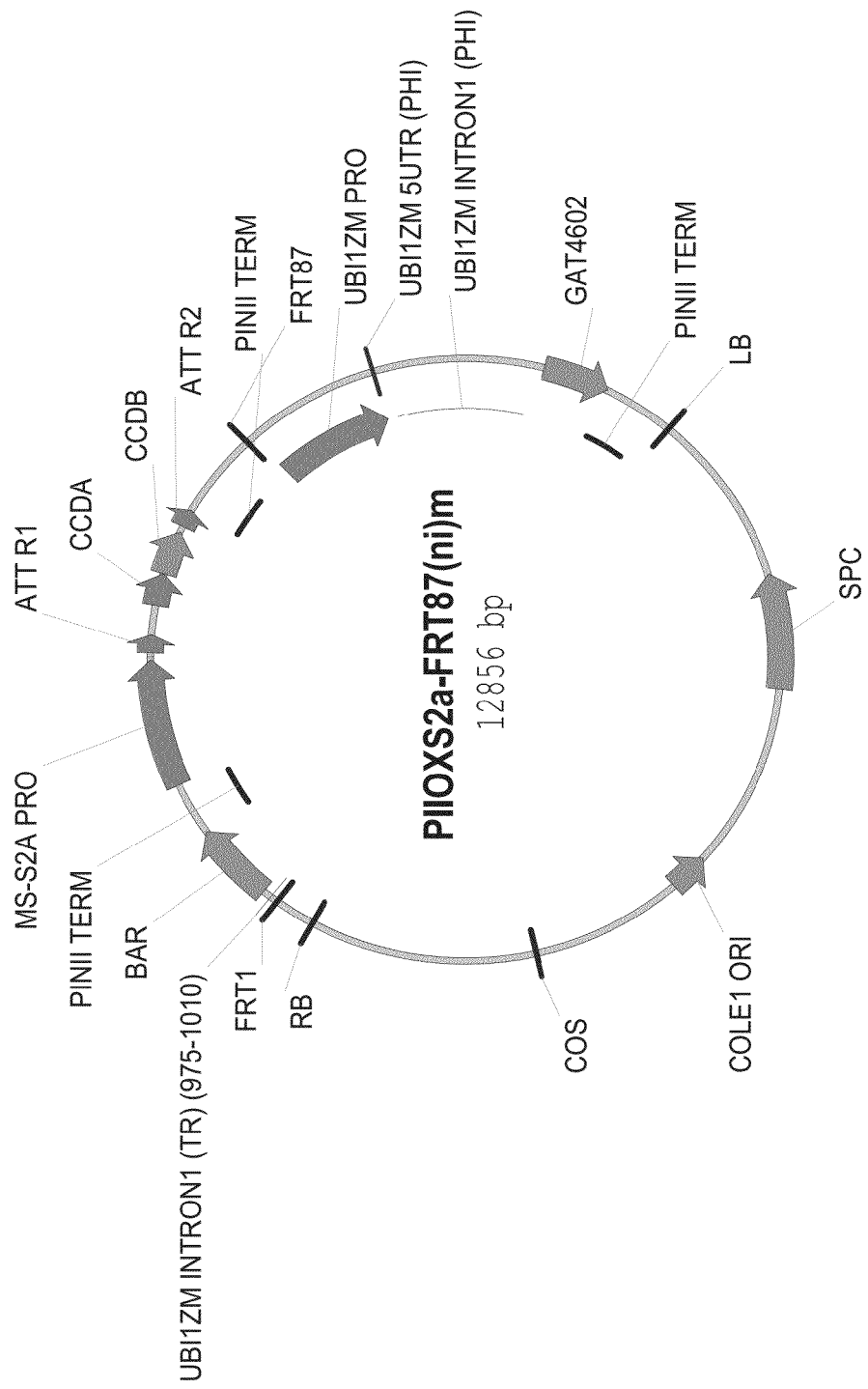
FIG. 14 shows a map of PHOXS2a-FRT87(ni)m (SEQ ID NO: 29), a vector used to construct the destination vector PHP29635.

PHP29635 (FIG. 13, SEQ ID NO: 13) was obtained by transformation of *Agrobacterium* strain LBA4404 containing plasmid PHP10523 with plasmid PIIOXS2a-FRT87(ni)m (FIG. 14, SEQ ID NO:29) and isolation of the resulting co-integration product. Destination vector PHP29635 can be used in a recombination reaction with an entry clone as described in Example 16 to create a maize expression vector for transformation of Gaspe Bay Flint derived maize lines. Expression of the gene of interest is under control of the S2A promoter (SEQ ID NO: 33).

Example 16

Preparation of Plasmids for Transformation of Gaspe Bay Flint Derived Maize Lines Using Invitrogen™ Gateway® Recombination technology, entry clones containing the *Arabidopsis* llrk gene (AT1G69270) or a maize llrk-like homolog can be created, as described in Examples 5A and 9 and used to directionally clone each gene into destination vector PHP23236 (Example 15) for expression under the ubiquitin promoter or into destination vector PHP29635 (Example 15) for expression under the S2A promoter. Each of the expression vectors are T-DNA binary vectors for *Agrobacterium*-mediated transformation into corn.

Gaspe Bay Flint Derived Maize Lines can be transformed with the expression constructs as described in Example 17.

Example 17

Transformation of Gaspe Bay Flint Derived Maize Lines with Validated *Arabidopsis* Lead Genes and Corresponding Homologs from Other Species Maize plants can be transformed as described in Example 16 to overexpress the *Arabidopsis* AT1G69270 gene and the corresponding homologs from other species, such as the ones listed in Table 1 and SEQ ID NO:35, in order to examine the resulting phenotype. In addition to the promoters described in Example 16 other promoters such the S2B promoter, the maize ROOTMET2 promoter, the maize Cyclo, the CR1BIO, the CRWAQ81 and the maize ZRP2.4447 are useful for directing expression of llrk and llrk-like genes in maize. Furthermore, a variety of terminators, such as, but not limited to the PINII terminator, can be used to achieve expression of the gene of interest in Gaspe Bay Flint Derived Maize Lines.

Recipient Plants

Recipient plant cells can be from a uniform maize line having a short life cycle ("fast cycling"), a reduced size, and high transformation potential. Typical of these plant cells for maize are plant cells from any of the publicly available Gaspe Bay Flint (GBF) line varieties. One possible candidate plant line variety is the F1 hybrid of GBF×QTM (Quick Turnaround Maize, a publicly available form of Gaspe Bay Flint selected for growth under greenhouse conditions) disclosed in Tomes et al. U.S. Patent Application Publication No. 2003/0221212. Transgenic plants obtained from this line are of such a reduced size that they can be grown in four inch pots (¼ the space needed for a normal sized maize plant) and mature in less than 2.5 months. (Traditionally 3.5 months is required to obtain transgenic T0 seed once the transgenic plants are acclimated to the greenhouse.) Another suitable line is a double haploid line of GS3 (a highly transformable line) X Gaspe Flint. Yet another suitable line is a transformable elite inbred line carrying a transgene which causes early flowering, reduced stature, or both.

Transformation Protocol

Any suitable method may be used to introduce the transgenes into the maize cells, including but not limited to inoculation type procedures using *Agrobacterium* based vectors as described in Example 9. Transformation may be performed on immature embryos of the recipient (target) plant.

Precision Growth and Plant Tracking

The event population of transgenic (T0) plants resulting from the transformed maize embryos is grown in a controlled greenhouse environment using a modified randomized block design to reduce or eliminate environmental error. A randomized block design is a plant layout in which the experimental plants are divided into groups (e.g., thirty plants per group), referred to as blocks, and each plant is randomly assigned a location with the block.

For a group of thirty plants, twenty-four transformed, experimental plants and six control plants (plants with a set phenotype) (collectively, a "replicate group") are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of thirty plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

An alternative to the addition of a specific control group is to identify those transgenic plants that do not express the gene of interest. A variety of techniques such as RT-PCR can be applied to quantitatively assess the expression level of the introduced gene. T0 plants that do not express the transgene can be compared to those which do.

Each plant in the event population is identified and tracked throughout the evaluation process, and the data gathered from that plant is automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor. See U.S. Published Patent Application No. 2004/0122592, incorporated herein by reference.

Phenotypic Analysis Using Three-Dimensional Imaging

Each greenhouse plant in the T0 event population, including any control plants, is analyzed for agronomic characteristics of interest, and the agronomic data for each plant is recorded or stored in a manner so that it is associated with the identifying data (see above) for that plant. Confirmation of a phenotype (gene effect) can be accomplished in the T1 generation with a similar experimental design to that described above.

The T0 plants are analyzed at the phenotypic level using quantitative, non-destructive imaging technology throughout the plant's entire greenhouse life cycle to assess the traits of interest. Preferably, a digital imaging analyzer is used for automatic multi-dimensional analyzing of total plants. The imaging may be done inside the greenhouse. Two camera systems, located at the top and side, and an apparatus to rotate the plant, are used to view and image plants from all sides. Images are acquired from the top, front and side of each plant. All three images together provide sufficient information to evaluate the biomass, size and morphology of each plant.

Due to the change in size of the plants from the time the first leaf appears from the soil to the time the plants are at the end of their development, the early stages of plant development are best documented with a higher magnification from the top. This may be accomplished by using a motorized zoom lens system that is fully controlled by the imaging software.

In a single imaging analysis operation, the following events occur: (1) the plant is conveyed inside the analyzer area, rotated 360 degrees so its machine readable label can be read, and left at rest until its leaves stop moving; (2) the side image is taken and entered into a database; (3) the plant is rotated 90 degrees and again left at rest until its leaves stop moving, and (4) the plant is transported out of the analyzer.

Plants are allowed at least six hours of darkness per twenty four hour period in order to have a normal day/night cycle.

Imaging Instrumentation

Any suitable imaging instrumentation may be used, including but not limited to light spectrum digital imaging instrumentation commercially available from LemnaTec GmbH of Wurselen, Germany. The images are taken and analyzed with a LemnaTec Scanalyzer HTS LT-0001-2 having a ½" IT Progressive Scan IEE CCD imaging device. The imaging cameras may be equipped with a motor zoom, motor aperture and motor focus. All camera settings may be made using LemnaTec software. Preferably, the instrumental variance of the imaging analyzer is less than about 5% for major components and less than about 10% for minor components.

Software

The imaging analysis system comprises a LemnaTec HTS Bonit software program for color and architecture analysis and a server database for storing data from about 500,000 analyses, including the analysis dates. The original images and the analyzed images are stored together to allow the user to do as much reanalyzing as desired. The database can be connected to the imaging hardware for automatic data collection and storage. A variety of commercially available software systems (e.g., Matlab and others) can be used for quantitative interpretation of the imaging data, and any of these software systems can be applied to the image data set.

Conveyor System

A conveyor system with a plant rotating device may be used to transport the plants to the imaging area and rotate them during imaging. For example, up to four plants, each with a maximum height of 1.5 m, are loaded onto cars that travel over the circulating conveyor system and through the imaging measurement area. In this case the total footprint of the unit (imaging analyzer and conveyor loop) is about 5 m×5 m.

The conveyor system can be enlarged to accommodate more plants at a time. The plants are transported along the conveyor loop to the imaging area and are analyzed for up to 50 seconds per plant. Three views of the plant are taken. The conveyor system, as well as the imaging equipment, should be capable of being used in greenhouse environmental conditions.

Illumination

Any suitable mode of illumination may be used for the image acquisition. For example, a top light above a black background can be used. Alternatively, a combination of top- and backlight using a white background can be used. The illuminated area should be housed to ensure constant illumination conditions. The housing should be longer than the measurement area so that constant light conditions prevail without requiring the opening and closing or doors. Alternatively, the illumination can be varied to cause excitation of either transgene (e.g., green fluorescent protein (GFP), red fluorescent protein (RFP)) or endogenous (e.g. Chlorophyll) fluorophores.

Biomass Estimation Based on Three-Dimensional Imaging

For best estimation of biomass the plant images should be taken from at least three axes, preferably the top and two side (sides 1 and 2) views. These images are then analyzed to separate the plant from the background, pot and pollen control bag (if applicable). The volume of the plant can be estimated by the calculation:

$$\text{Volume(voxels)} = \sqrt{\text{TopArea(pixels)}} \times \sqrt{\text{Side1Area(pixels)}} \times \sqrt{\text{Side2Area(pixels)}}$$

In the equation above the units of volume and area are "arbitrary units". Arbitrary units are entirely sufficient to detect gene effects on plant size and growth in this system because what is desired is to detect differences (both positive-larger and negative-smaller) from the experimental mean, or control mean. The arbitrary units of size (e.g. area) may be trivially converted to physical measurements by the addition of a physical reference to the imaging process. For instance, a physical reference of known area can be included in both top and side imaging processes. Based on the area of these physical references a conversion factor can be determined to allow conversion from pixels to a unit of area such as square centimeters ($cm^2$). The physical reference may or may not be an independent sample. For instance, the pot, with a known diameter and height, could serve as an adequate physical reference.

Color Classification

The imaging technology may also be used to determine plant color and to assign plant colors to various color classes. The assignment of image colors to color classes is an inherent feature of the LemnaTec software. With other image analysis software systems color classification may be determined by a variety of computational approaches.

For the determination of plant size and growth parameters, a useful classification scheme is to define a simple color scheme including two or three shades of green and, in addition, a color class for chlorosis, necrosis and bleaching, should these conditions occur. A background color class which includes non plant colors in the image (for example pot and soil colors) is also used and these pixels are specifically excluded from the determination of size. The plants are analyzed under controlled constant illumination so that any change within one plant over time, or between plants or different batches of plants (e.g. seasonal differences) can be quantified.

In addition to its usefulness in determining plant size growth, color classification can be used to assess other yield component traits. For these other yield component traits additional color classification schemes may be used. For instance, the trait known as "staygreen," which has been associated with improvements in yield, may be assessed by a color classification that separates shades of green from shades of yellow and brown (which are indicative of senescing tissues). By applying this color classification to images taken toward the end of the T0 or T1 plants' life cycle, plants that have increased amounts of green colors relative to yellow and brown colors (expressed, for instance, as Green/Yellow Ratio) may be identified. Plants with a significant difference in this Green/Yellow ratio can be identified as carrying transgenes which impact this important agronomic trait.

The skilled plant biologist will recognize that other plant colors arise which can indicate plant health or stress response (for instance anthocyanins), and that other color classification schemes can provide further measures of gene action in traits related to these responses.

Plant Architecture Analysis

Transgenes which modify plant architecture parameters may also be identified using the present invention, including such parameters as maximum height and width, internodal distances, angle between leaves and stem, number of leaves starting at nodes and leaf length. The LemnaTec system software may be used to determine plant architecture as follows. The plant is reduced to its main geometric architecture in a first imaging step and then, based on this image, parameterized identification of the different architecture parameters can be performed. Transgenes that modify any of these architecture parameters either singly or in combination can be identified by applying the statistical approaches previously described.

Pollen Shed Date

Pollen shed date is an important parameter to be analyzed in a transformed plant, and may be determined by the first appearance on the plant of an active male flower. To find the male flower object, the upper end of the stem is classified by color to detect yellow or violet anthers. This color classification analysis is then used to define an active flower, which in turn can be used to calculate pollen shed date.

Alternatively, pollen shed date and other easily visually detected plant attributes (e.g. pollination date, first silk date) can be recorded by the personnel responsible for performing plant care. To maximize data integrity and process efficiency this data is tracked by utilizing the same barcodes utilized by the LemnaTec light spectrum digital analyzing device. A computer with a barcode reader, a palm device, or a notebook PC may be used for ease of data capture recording time of observation, plant identifier, and the operator who captured the data.

Orientation of the Plants

Mature maize plants grown at densities approximating commercial planting often have a planar architecture. That is, the plant has a clearly discernable broad side, and a narrow side. The image of the plant from the broadside is determined. To each plant a well defined basic orientation is assigned to obtain the maximum difference between the broadside and edgewise images. The top image is used to determine the main axis of the plant, and an additional rotating device is used to turn the plant to the appropriate orientation prior to starting the main image acquisition.

Example 18

Screening of Gaspe Bay Flint Derived Maize Lines Under Nitrogen Limiting Conditions Some transgenic plants will contain two or three doses of Gaspe Flint-3 with one dose of GS3 (GS3/(Gaspe-3)2X or GS3/(Gaspe-3)3X) and will segregate 1:1 for a dominant transgene. Other transgenic plants will be regular inbreds and will be used in top crosses to generate test hybrids. Plants will be planted in Turface, a commercial potting medium, and watered four times each day with 1 mM $KNO_3$ growth medium and with 2 mM $KNO_3$, or higher, growth medium (see FIG. 17). Control plants grown in 1 mM $KNO_3$ medium will be less green, produce less biomass and have a smaller ear at anthesis. Gaspe-derived lines will be grown to flowering stage whereas regular inbreds and hybrids will be grown to V4 to V5 stages.

Statistics are used to decide if differences seen between treatments are significantly different. FIG. 18 illustrates one method which places letters after the values. Those values in the same column that have the same letter (not group of letters) following them are not significantly different. Using this method, if there are no letters following the values in a column, then there are no significant differences between any of the values in that column or, in other words, all the values in that column are equal. Expression of a transgene will result in plants with improved plant growth in 1 mM $KNO_3$ when compared to a transgenic null. Thus biomass and greenness data (as described in Example 17) will be collected at time of sampling (anthesis for Gaspe and V4-V5 for others) and compared to a transgenic null. In addition, total nitrogen in the plants will be analyzed in ground tissues. Improvements in growth, greenness, nitrogen accumulation and ear size at anthesis will be indications of increased nitrogen use efficiency.

Example 19

Yield Analysis of Maize Lines with Validated *Arabidopsis* Lead Gene (AT1G69270)

A recombinant DNA construct containing a validated *Arabidopsis* gene can be introduced into a maize line either by direct transformation or introgression from a separately transformed line.

Transgenic plants, either inbred or hybrid, can undergo more vigorous field-based experiments to study yield enhancement and/or stability under various environmental conditions, such as variations in water and nutrient availability.

Subsequent yield analysis can be done to determine whether plants that contain the validated *Arabidopsis* lead gene have an improvement in yield performance under various environmental conditions, when compared to the control plants that do not contain the validated *Arabidopsis* lead gene. Reduction in yield can be measured for both. Plants containing the validated *Arabidopsis* lead gene have less yield loss relative to the control plants, preferably 50% less yield loss.

Example 20

Assays to Determine Alterations of Root Architecture in Maize

Transgenic maize plants are assayed for changes in root architecture at seedling stage, flowering time or maturity. Assays to measure alterations of root architecture of maize plants include, but are not limited to the methods outlined below. To facilitate manual or automated assays of root architecture alterations, corn plants can be grown in clear pots.

1) Root mass (dry weights). Plants are grown in Turface, a growth media that allows easy separation of roots. Oven-dried shoot and root tissues are weighed and a root/shoot ratio calculated.

2) Levels of lateral root branching. The extent of lateral root branching (e.g. lateral root number, lateral root length) is determined by sub-sampling a complete root system, imaging with a flat-bed scanner or a digital camera and analyzing with WinRHIZO™ software (Regent Instruments Inc.).

3) Root band width measurements. The root band is the band or mass of roots that forms at the bottom of greenhouse pots as the plants mature. The thickness of the root band is measured in mm at maturity as a rough estimate of root mass.

4) Nodal root count. The number of crown roots coming off the upper nodes can be determined after separating the root from the support medium (e.g. potting mix). In addition the angle of crown roots and/or brace roots can be measured. Digital analysis of the nodal roots and amount of branching of nodal roots form another extension to the aforementioned manual method.

All data taken on root phenotype are subjected to statistical analysis, normally a t-test to compare the transgenic roots with that of non-transgenic sibling plants. One-way ANOVA may also be used in cases where multiple events and/or constructs are involved in the analysis.

Example 21

Nitrogen Utilization Efficiency Seedling Assay

Seed of transgenic events are separated into transgene (heterozygous) and null seed using a seed color marker. Two different random assignments of treatments are made to each block of 54 pots arranged 6 rows by 9 columns using 9 replicates of all treatments.

Two seed of each treatment are planted in 4 inch, square pots containing Turface on 8 inch, staggered centers and watered four times each day with a solution containing the following nutrients:

| | | | |
|---|---|---|---|
| 1 mM $CaCl_2$ | 2 mM $MgSO_4$ | 0.5 mM $KH_2PO_4$ | 83 ppm Sprint330 |
| 3 mM KCl | 1 mM $KNO_3$ | 1 µM $ZnSO_4$ | 1 µM $MnCl_2$ |
| 3 µM $H_3BO_4$ | 1 µM $MnCl_2$ | 0.1 µM $CuSO_4$ | 0.1 µM $NaMoO_4$ |

After emergence the plants are thinned to one seed per pot. At harvest, plants are removed from the pots and the Turface is washed from the roots. The roots are separated from the shoot, placed in a paper bag and dried at 70° C. for 70 hr. The dried plant parts (roots and shoots) are weighed and placed in a 50 ml conical tube with approximately 20 5/32 inch steel balls and ground by shaking in a paint shaker. Approximately, 30 mg of the ground tissue (weight recorded for later adjustment) is hydrolyzed in 2 ml of 20% $H_2O_2$ and 6M $H_2SO_4$ for 30 min at 170° C. After cooling, water is added to 20 ml, mixed thoroughly, and a 50 µl aliquot is removed and added to 950 µl 1 M $Na_2CO_3$. The ammonia in this solution is used to estimate total reduced plant nitrogen by placing 100 µl of this solution into individual wells of a 96 well plate followed by adding 50 µl of OPA solution. Fluorescence, excitation=360 nM/emission=530 nM, is determined and compared to $NH_4Cl$ standards dissolved in a similar solution and treated with OPA solution.

OPA solution—5 µl Mercaptoethanol+1 ml OPA stock solution

OPA stock—50 mg o-phthadialdehyde (OPA—Sigma #P0657) dissolved in 1.5 ml methanol+4.4 ml 1 M Borate buffer pH9.5 (3.09 g $H_3BO_4$+1 g NaOH in 50 ml water)+0.55 ml 20% SDS Using these data the following parameters are measured and means compared to null mean parameters using a Student's t test:
Total Plant Biomass
Root Biomass
Shoot Biomass
Root/Shoot Ratio
Plant N concentration
Total Plant N Variance is calculated within each block using a nearest neighbor calculation as well as by Analysis of Variance (ANOVA) using a completely random design (CRD) model. An overall treatment effect for each block is calculated using an F statistic by dividing overall block treatment mean square by the overall block error mean square. The probability of a greater Student's t test is calculated for each transgenic mean compared to the appropriate null (either construct bulked or individual event null mean) mean. A minimum (P<t) of 0.1 is used as a cut off.

Example 22

Analysis of Roots of Maize Seedlings Containing the *Arabidopsis* llrk Gene Compared to Roots from Seedlings not Containing the llrk Gene Maize expression vectors, containing the maize NAS2 promoter (SEQ ID NO: 30) or the maize GOS2 promoter (SEQ ID NO: 31) and the *Arabidopsis* llrk gene (AT1G69270) were prepared as described in Example 14A.

Transformation of maize was achieved via *Agrobacterium* mediated transformation as described in Example 14C by creating a cointegrate vector (PHP29405 and PHP29414, respectively) and roots were assayed as described in Example 20 using a seedling assay.

All 10 events from construct PHP29405 (ZM-NAS2::AT-RPK1) were assayed in a greenhouse experiment, where 9 plants per each event were grown in Turface media to V4 stage. Seeds were from the top cross hybrid seeds. The control in the experiment was 9 plants of bulked nulls (non-transgenic segregates) grown to the same stage. Seeds were planted using a complete random block design. Plants were harvested 3 weeks after planting, when they reached about V4 stage. Roots were washed and collected separately from shoots. All samples were oven-dried before dry weights were taken on balance.

Three (3) events were found to have significant changes in root dry weights, 3 events in shoot dry weights, and 3 events in overall plant dry weights, when compared to the bulked null control, at a P-value less than 0.1. Table 5 shows the significance of a t-Test analysis between each transgenic event and the control. The p-values are shown for each trait, root dry weights, shoot dry weights, and root-to-shoot ratios. Bold face fonts indicate the transgenic had a higher value than the control, also indicated with an asterisk (*). Those events with a P-value greater than 0.1 when compared to control are shown as "NS" (not significant).

TABLE 5

| EVENT | Root Dry Weight | Shoot Dry Weight | Plant Dry Weight |
|---|---|---|---|
| 1 | 0.038 | NS | NS |
| 2 | NS | NS | NS |
| 3 | NS | NS | NS |
| 4 | 0.076* | 0.076* | 0.070* |
| 5 | 0.063* | NS | NS |
| 6 | NS | NS | NS |
| 7 | <0.001* | <0.001* | <0.001* |
| 8 | NS | NS | NS |
| 9 | NS | NS | NS |
| 10 | NS | 0.047* | 0.094* |

Example 23

Yield Testing of Transgenic Hybrids Under Normal and Under Nitrogen Depleted Conditions in the Field A field experiment was carried out on a farm in Johnston, Iowa for 2008 season. Ten (10) transgenic events carrying maize NAS2 promoter controlling the *Arabidopsis* rpk1 gene (AT1G69270), and the control were tested. The control is a non-transgenic null with nulls bulked across all 10 events. All of the events were top cross hybrids of IntroEF09B ETX line generated from a common inbred tester.

Two treatments were performed, one being normal nitrogen, the other, a stress environment with depleted nitrogen. In the normal treatment, nitrogen fertilizer was applied at a rate of 2601 b per acre. The nitrogen depletion treatment was carried out in a field where soil nitrogen levels had been drawn down by crops grown previous years without fertilization. The depleted nitrogen treatment received a 60 to 801b per acre nitrogen fertilization that led to 6% yield reduction when compared to the normal nitrogen treatment. The experiment was set up as 2-row plots with a density of 32000 plants per acre. There were 4 replications in normal nitrogen treatment and 6 replications in depleted nitrogen treatment. The experiments were planted on May 15, 2008 and combine harvested on Oct. 18, 2008.

The grain yield data in bushels per acre from the experiments are summarized as percent increases over the null control, in Table 6 below. Overall, there were 4 events under depleted nitrogen and 5 events under normal nitrogen that had significant increase in yield over the bulked null control (alpha=0.2, 2 tail analysis). All events tested showed a positive trend in yield increase over nulls.

TABLE 6

| Event | Yield increase over null | Significance | Treatment |
|---|---|---|---|
| 1 | 8.18% | * | Low nitrogen |
| 2 | 3.65% |  | Low nitrogen |
| 3 | 3.67% |  | Low nitrogen |
| 4 | 2.82% |  | Low nitrogen |
| 5 | 5.64% |  | Low nitrogen |
| 6 | 5.36% |  | Low nitrogen |
| 7 | 7.79% | * | Low nitrogen |
| 8 | 4.91% |  | Low nitrogen |
| 9 | 11.28% | * | Low nitrogen |
| 10 | 9.88% | * | Low nitrogen |
| 1 | 11.09% | * | Normal nitrogen |
| 2 | 1.59% |  | Normal nitrogen |
| 3 | 15.22% | * | Normal nitrogen |
| 4 | 14.06% | * | Normal nitrogen |
| 5 | 10.64% | * | Normal nitrogen |
| 6 | 3.43% |  | Normal nitrogen |
| 7 | 13.24% | * | Normal nitrogen |
| 8 | 0.52% |  | Normal nitrogen |
| 9 | 4.01% |  | Normal nitrogen |
| 10 | 7.85% |  | Normal nitrogen |

Example 24

Association Mapping Analysis

An association mapping strategy can be undertaken to identify markers associated with alterations in root architecture in maize.

Phenotypic scores for an alteration in root architecture or in at least one agronomic characteristic will be obtained. Lines with extreme phenotypes will be tested against genotypes in a whole genome association test (using 2×2 contingency tables with Fisher's exact test). A structure-based association analysis will be used, where the population structure is controlled using marker data. The model-based cluster analysis software, Structure, developed by Pritchard et al., (Genetics 155:945-959 (2000)) will be used with haplotype data for hundreds of elite maize inbreds at several hundred markers to estimate admixture coefficients and assign the inbreds to a number of subpopulations. This reduces the occurrence of false positives that can arise due to the effect of population structure on association mapping statistics. Kuiper's statistic for testing whether two distributions are the same was used to test a given marker for association between haplotype and phenotype in a given subpopulation (Press et al., Numerical Recipes in C, second edition, Cambridge University Press, NY (2002)).

At least one strong peak in at least one subpopulation is indicative of significant marker-trait associations (e.g. p<0.001). Marker positions are given in cM, with position zero being the first (most distal from the centromere) marker known at the beginning of a chromosome. These map positions are not absolute, and represent an estimate of map position based on the internally derived genetic map.

What is claimed is:

1. A method of selecting a plant with an increase in root dry weight, comprising:
   (a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO:22; and
   (b) regenerating a transgenic plant from the regenerable plant cell after step (a), wherein the transgenic plant comprises in its genome the recombinant DNA construct;
   (c) measuring root dry weight of the transgenic plant compared to a control plant not comprising the recombinant DNA construct; and
   (d) selecting a plant from step (c) that has an increase in root dry weight; or
   (a') introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO:22; and
   (b') regenerating a transgenic plant from the regenerable plant cell after step (a'), wherein the transgenic plant comprises in its genome the recombinant DNA construct;
   (c') obtaining a progeny plant derived from the transgenic plant, wherein the progeny plant comprises in its genome the recombinant DNA construct;
   (d') measuring root dry weight of the progeny plant compared to a control plant not comprising the recombinant DNA construct; and
   (e') selecting a progeny plant from step (d') that has an increase in root dry weight.

2. A method of selecting a plant with an increase in yield, comprising:
   (a) introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO:22; and
   (b) regenerating a transgenic plant from the regenerable plant cell after step (a), wherein the transgenic plant comprises in its genome the recombinant DNA construct; and
   (c) measuring whether the transgenic plant exhibits an increase in yield when compared, under low nitrogen conditions, to a control plant not comprising the recombinant DNA construct; and
   (d) selecting a plant from step (c) that has an increase in yield; or
   (a') introducing into a regenerable plant cell a recombinant DNA construct comprising a polynucleotide operably linked to at least one heterologous regulatory sequence, wherein the polynucleotide encodes a polypeptide having an amino acid sequence of at least 95% sequence identity, based on the Clustal V method of alignment, when compared to SEQ ID NO:22;
   (b') regenerating a transgenic plant from the regenerable plant cell after step (a'), wherein the transgenic plant comprises in its genome the recombinant DNA construct;
   (c') obtaining a progeny plant derived from the transgenic plant, wherein the progeny plant comprises in its genome the recombinant DNA construct;
   (d') measuring whether the progeny plant exhibits an increase in yield when compared, under low nitrogen conditions, to a control plant not comprising the recombinant DNA construct; and
   (e') selecting a progeny plant from step (d') that has an increase in yield.

3. The method of claim 1, wherein said plant is a maize plant.

4. The method of claim 2, wherein said plant is a maize plant.

* * * * *